United States Patent
Cooper et al.

(10) Patent No.: US 10,688,470 B2
(45) Date of Patent: Jun. 23, 2020

(54) SEPARATIONS WITH ORGANIC MOLECULAR SOLIDS

(71) Applicant: The University of Liverpool, Liverpool (GB)

(72) Inventors: Andrew Cooper, Liverpool (GB); Thomas Hasell, Liverpool (GB); Daniel Holden, Liverpool (GB); Michael Briggs, Liverpool (GB); Linjiang Chen, Liverpool (GB)

(73) Assignee: University of Liverpool, Liverpool (GB)

( * ) Notice: Subject to any disclaimer, the term of this patent is extended or adjusted under 35 U.S.C. 154(b) by 213 days.

(21) Appl. No.: 15/321,886

(22) PCT Filed: Jun. 26, 2015

(86) PCT No.: PCT/GB2015/051874
§ 371 (c)(1),
(2) Date: Dec. 23, 2016

(87) PCT Pub. No.: WO2015/198070
PCT Pub. Date: Dec. 30, 2015

(65) Prior Publication Data
US 2017/0128910 A1     May 11, 2017

(30) Foreign Application Priority Data

Jun. 27, 2014 (GB) .................. 1411515.8

(51) Int. Cl.
*B01J 20/282* (2006.01)
*C01B 23/00* (2006.01)
*B01D 15/38* (2006.01)
*C07D 307/20* (2006.01)
*C07C 7/12* (2006.01)
*B01D 53/02* (2006.01)
*B01J 20/22* (2006.01)
*C07C 29/76* (2006.01)
*B01J 20/28* (2006.01)

(52) U.S. Cl.
CPC ........ *B01J 20/282* (2013.01); *B01D 15/3833* (2013.01); *B01D 53/02* (2013.01); *B01D 53/025* (2013.01); *B01J 20/22* (2013.01); *B01J 20/2808* (2013.01); *C01B 23/0057* (2013.01); *C07C 7/12* (2013.01); *C07C 29/76* (2013.01); *C07D 307/20* (2013.01); *B01D 2253/20* (2013.01); *B01D 2257/11* (2013.01); *B01J 2220/52* (2013.01); *B01J 2220/58* (2013.01); *B01J 2220/80* (2013.01); *C01B 2210/0015* (2013.01); *C01B 2210/0037* (2013.01); *C01B 2210/0039* (2013.01)

(58) Field of Classification Search
None
See application file for complete search history.

(56) References Cited

FOREIGN PATENT DOCUMENTS

WO     2013063368 A1     5/2013

OTHER PUBLICATIONS

Alexandra F. Bushell et al: "Nanoporous Organic Polymer/Cage Composite Membranes", Angewandte Chemie International Edition, vol. 52, No. 4, Dec. 6, 2012 (Dec. 6, 2012), pp. 1253-1256, XP055212454, ISSN: 1433-7851, DOI: 10.1002/anie.201206339 (Year: 2012).*
Tozawa et al. "Porous organic cages" Nature Materials, vol. 8, Oct. 25, 2009, p. 973-978, "Supplementary Information", p. 1-46. (Year: 2009).*
Bushell et al., "Nanoporous Organic Polymer/Cage Composite Membranes," Angew. Chem. Int. Ed. (2013); 52(4):1253-1256 (plus supporting information 16 pages).
Liu et al., "Metal-Organic Frameworks for Removal of Xe and Kr from Nuclear Fuel Reprocessing Plants," Langmuir (Jul. 26, 2012): 28(31):11584-11589.
Tozawa et al., "Porous Organic Cages," Nature Materials (Dec. 2009); 8:973-978.
Li et al., "Multiscale Simulation of Pollution Gases Adsorption in Porous Organic Cage CC3," Journal of Computational Chemistry (2014); 35(2):174-180.

* cited by examiner

*Primary Examiner* — Ryan B Huang
(74) *Attorney, Agent, or Firm* — Fox Rothschild LLP

(57) ABSTRACT

A host material may be used for the separation of elements or compounds, wherein the host material is an organic molecular solid with suitable cavities for accommodating a guest material to be separated, and with interconnections between the cavities to allow the guest material to diffuse through the host material, and wherein said interconnections are closed for a proportion of the time or have a static pore limiting diameter which is smaller than the static dimension of the guest material. Applications include separations of rare gases, chiral molecules, and alkanes. One class of suitable host materials may be made by imine condensation.

27 Claims, 52 Drawing Sheets

SEPARATIONS WITH ORGANIC MOLECULAR SOLIDS

CROSS REFERENCE TO RELATED APPLICATION

This application is the U.S. National Phase of International Application No. PCT/GB2015/051874, filed Jun. 26, 2015, which claims priority to British Patent Application No. 1411515.8, filed Jun. 27, 2014, the contents of which are incorporated herein by reference.

The present invention relates to chemical separations using porous materials.

In chemistry and materials science, separation processes are used for various purposes including analysis, identification, isolation, purification, decontamination and recovery.

In many applications, the selectivity of separation is important. For example it can be important to separate one component cleanly from another or from a mixture. This can become more challenging when the properties of the components are similar, for example in terms of size, chemical characteristics, or physical characteristics, such as boiling point.

Several types of material have the ability to separate one element or compound from another element(s) or compound(s). These include zeolites and metal-organic frameworks (MOFs). Zeolites are naturally occurring or industrially produced solid aluminosilicate porous materials, with a regular pore structure that enables them to selectively absorb, filter or separate molecules of specific sizes. MOFs contain organic moieties, or linkers, bonded to metal or metal-containing centres, or 'nodes', and certain types of MOFs are porous. For example, *Langmuir* 2012, 28, 11584-11589, Liu et al. discloses MOFs for removal of xenon and krypton from nuclear fuel reprocessing plants.

The principle of "host-guest" chemistry is well known and relevant to the present invention. A "host" material provides a space (which may for example be a cavity or channel) for a corresponding "guest" material. The space may be within a rigid structure or may be formed reversibly. The guest is not covalently bound within the host, but may be bound by non-covalent interactions. The strength and reversible nature of the bonding can vary.

Amongst many examples of host materials are zeolites and MOFs as referred to above, and cryptophane structures such as those disclosed in for example *J. Am. Chem. Soc.* 2007, 129, 10332-10333, Fogarty et al., *J. Am. Chem. Soc.* 2010, 132, 15505-15507, Fairchild et al. and *Nature Communications*, 1:148, DOI:10.1038/NCOMMS 1151, 2010, Taratula et al.

There is a need for materials that can exhibit improved separation properties and in particular improved selectivity.

Figure 1:
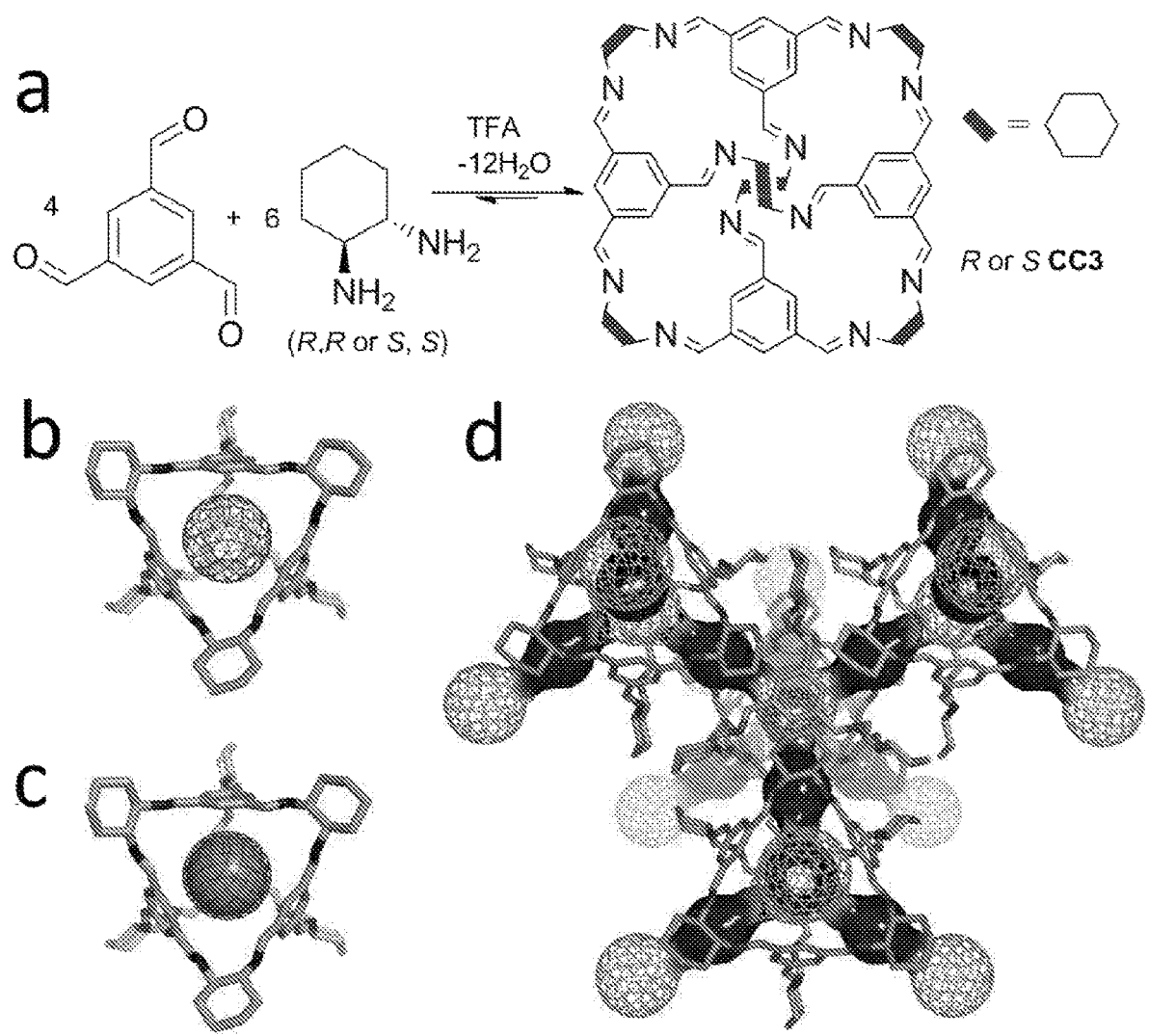
FIGS. 1a, 1b and 1c: (a) shows the structure, and a reaction scheme for the synthesis of, CC3. (b and c) each show a single molecule of CC3.
FIG. 1d shows the extended crystal packing of individual CC3 cage molecules adjacent to each other in the solid state.

The present invention will now be described in further detail by way of non-limiting examples and figures.

From a first aspect the present invention provides the use of a host material for the separation of elements or compounds,
wherein the host material is an organic molecular solid with suitable cavities for accommodating a guest material to be separated, and with interconnections between the cavities to allow the guest material to diffuse through the host material,
and wherein said interconnections are closed for a proportion of the time.

The invention relates to molecular solids, where the molecular components of the host are not interconnected by covalent or metal-ligand coordination bonding, as opposed to extended frameworks or networks, such as MOFs, covalent organic frameworks (COFs), zeolites, activated carbons, or porous organic polymers.

The porous materials of the present invention are non-metallic, in contrast to MOFs and zeolites. Furthermore the porous materials of the present invention comprise discrete organic molecules assembled together in the solid state, such organic molecules of course being relatively small in comparison to porous polymers or extended COFs.

We have found that solid-state organic molecular materials wherein interconnections are only open for a fraction of the time are particularly effective in selectively separating guest materials. Static molecular models or single crystal X-ray structures of a host material might indicate that the interconnections between cavities are too narrow to allow guest materials to pass through; that is, that they are "closed". However, vibrational motion of the atoms in the cage molecules means that such interconnections may be "open" for part of the time. In effect, therefore, the present invention allows dynamic molecular passage of guest materials into and through the solid organic molecular host. The similarity between the dimensions of the host cavities, the dimensions of the host interconnections, and the dimensions of the guest, allows the separations of guest mixtures with similar molecular dimensions and physical properties.

Some of the host materials we have made are described in further detail below. We did not expect host materials with narrow interconnections to allow sufficient diffusion of guest materials to give effective, practical separations, and were surprised to observe that the host materials could function as separation media for a range of achiral and chiral guests. To rationalise our results, detailed molecular modelling analysis was carried out, and this has led us to believe that the dynamic properties of the host are particularly important. Simulations reveal time-averaged, pore-limiting envelopes. Surprisingly, even when pore windows are open for only a small percentage of the time, our results show that guest materials can pass through and that this leads to effective separations, in some cases at faster guest flow rates than are possible with MOFs. This was by no means obvious to us.

In particular the present invention can be effective when the interconnections are only "open" for a relatively small percentage of the time, e.g. less than 20% of the time, e.g. less than 10% of the time, e.g. less than 5% of the time, as defined by molecular dynamics simulations that reflect the conditions (in particular, temperature) of the separation. Conveniently, these conditions may be standard ambient temperature and pressure. As demonstrated, for example, by experiments on xenon adsorption, it is not necessary for the static pore-limiting diameter, which is defined as the smallest interconnection between host cavities, to be larger than the minimum dimension of the guest in order for good separations to be obtained.

Optionally, the interconnections or pores may be deemed to be closed when the narrowest diameter, or limiting diameter, of the interconnections between the host cavities is smaller, e.g. significantly smaller, than the narrowest diameter of the guest, as determined from the van der Waals radii of the atom or atoms comprising the guest.

The narrowest or limiting diameter of the interconnections in the host may be determined by analytical techniques such as single crystal X-ray diffraction or powder X-ray diffraction, or this diameter can be calculated using atomistic simulations. Optionally, the range of limiting diameters can be defined using molecular dynamics simulations for the host, thus taking into account the flexibility of the host and the ability of the interconnections to expand or contract as a result of molecular vibrations in the host.

Molecular dynamics simulations are useful for understanding these processes, but they are not essential for the deployment of this technology in all cases.

From a further aspect the present invention provides the use of a host material for the separation of elements or compounds,
wherein the host material is an organic molecular solid with suitable cavities for accommodating a guest material to be separated, and with interconnections between the cavities to allow the guest material to diffuse through the host material,
and wherein said interconnections have a static pore limiting diameter which is smaller than the static dimension of the guest material.

For example, the static pore limiting diameter, measured from the associated van der Waals contacts, may be between about 35% and about 5% smaller than the minimum dimension of the guest as measured from the van der Waals radii of its constituent atoms, e.g. between about 30% and 10%, e.g. between about 20% and 15%, e.g. about 30%, 20% or 15% smaller than the minimum dimension of the guest.

The cavities in the host material are suitable for accommodating a guest material. This suitability can arise due to the cavity being of a suitable size and shape, and/or due to the cavity having suitable chemical property for binding to the host.

The cavity can be suitably sized when it is for example slightly larger than the guest material. Optionally the diameter of the cavity, as measured by the corresponding van der Waals surface, is up to 25%, e.g. about 25% larger than the dimension of the guest as measured from the van der Waals radii of its constituent atoms, or up to 60%, e.g. about 55% larger than the dimension of the guest, or up to 90%, e.g. about 80% larger than the dimension of the guest. Optionally the sizes may be very similar e.g. the diameter of the cavity may be only up to 10%, 15% or 20% larger than the guest.

The host may have a limited number of types of cavity, for example one or two repeating cavities, to enhance the selectivity of the host towards binding one guest material or a limited number or a subset of guest materials.

A combination of good fit for specific guest materials with partially restricted access or bottleneck permeability through the host, as provided by the present invention, can be contrasted with some prior art methods which focus on capacity, large surface areas, and/or relatively large pores.

Whilst various papers relate to theoretical considerations of molecular simulations, we believe that effective separation as disclosed herein has not been previously achieved in practice. As shown in further detail below, the kinetic behaviour of the host-guest interactions means that separation can be carried out in a practically effective manner, sometimes with greater selectivity and adsorption capacity, while simultaneously operating at higher flow rates. Fast flow rates may be an advantage in accelerating separation times, and might in some cases be necessary: for example, when a contaminated gas stream is released from a chemical operation at a rate which necessitates rapid separation processes.

The host material has a cage structure and may be prepared by various methods and using various chemistries including reversible covalent bond-forming reactions and irreversible direct carbon-carbon bond-forming reactions. For example, cages may be formed by imine condensation, boronate ester formation, disulphide formation, hemithioacetal formation, hydrazine formation, olefin metathesis, alkyne metathesis, thiol-enone exchange, alkyne homocoupling, Sonogashira coupling, ester formation, amide formation, and click-chemistry techniques. Cages may also be formed by one type of process, e.g. imine condensation, and then transformed into other functionality, for example such that the cages show better stability to water, acids, and bases, as disclosed in for example Liu et al., *J. Am. Chem. Soc.* 2014, 136, 7583-7586.

The present invention is flexible in allowing the structure to be tailored by varying the type and number of monomers and the structure of the monomers, and hence the size and shape of the cavities. The assembly of the host molecules can be controlled using the principles of crystal engineering, for example by introducing dominant host-host interactions, such as chiral recognition motifs, that induce the host molecules to assemble in a particular fashion: for example, to produce a 3-dimensional interconnected pore structure that is particularly effective for rapid separations.

Optionally the number of interconnections to each cavity may be at least three, or at least four, or four, for example in a generally tetrahedral arrangement or with tetrahedral symmetry. These numbers of interconnections can bring about a useful and effective three dimensional structure.

One convenient method for host synthesis involves the condensation of aldehydes and amines in a cycloimination reaction. For example, a monomer having two, three or four carbonyl (e.g., aldehyde) groups may be reacted with a monomer having two, three or four amine groups. The stoichiometry may be chosen to tailor the size and geometry of the cage, and may for example be [4+6], [2+3], [4+4] or [8+12]. Preferably, within this group of compounds, one monomer has at least three aldehyde groups or at least three amine groups so as to facilitate the formation of a three-dimensional architecture.

One subset of useful materials includes those formed by reaction of tri-aldehydes with di-amines in a [4+6] cycloimination. Another subset of useful materials includes those formed by reaction of tri-amines with di-aldehydes in a [4+6]cycloimination.

For example, one suitable cage molecule, denoted CC3, is that made from four 1,3,5-triformylbenzene molecules and six 1, 2-diaminocyclohexane molecules. The preparation and structure of CC3 is described in for example *Nature Materials* 2009, 8, 973-978, Tozawa et al.

The solid form of the host material may be crystalline or amorphous. Cavities may be present intrinsically within the cage structure and may also be present between molecules due to the way the cages stack in the solid state.

The organic nature, and the discrete molecular nature, of the host materials of the present invention, bring advantages compared to other host materials. They are more easily processable, and in particular they can be solution-processed from true molecular solutions to create either crystalline or amorphous materials, depending on the processing conditions. This introduces advantages over other materials such as polymers, MOFs, and zeolites. Also, the organic nature of the host could allow application in some fields where metals are undesirable or incompatible, in contrast to MOFs.

The present invention is applicable to a wide variety of guest materials. For example, and as exemplified below, the present invention can be used to separate each of the following: rare gases, chiral molecules, and alkanes. These are however merely examples, and the concepts of the present invention are applicable to other separations.

Rare gases can pose either an economic opportunity or an environmental hazard and the present invention allows the separation of these spherical molecules selectively at low concentrations in air.

With the exception of argon, which makes up almost 1% of air, the rare or 'noble' gases are all commonly encountered in low concentrations: xenon (Xe) occurs naturally in the atmosphere at 0.087 parts per million by volume (ppmv); krypton (Kr) at 1.14 ppmv.

As an alternative to the present invention, cryogenic methods may be used to extract commercially valuable rare gases such as xenon from air, but this is costly because of the low concentrations involved.

Noble gases are valuable: high purity xenon, for example, has uses including commercial lighting, medical imaging, anesthesia, and neuroprotection, and it sells for more than $5,000 per kilogram.

Other noble gas isotopes can be harmful. Radon gas, which occurs naturally in a radioactive form ($^{222}$Rn), can accumulate in buildings and is a leading cause of lung cancer, accounting for around 21,000 deaths per year in the USA alone. Likewise, unstable, hazardous radioisotopes of krypton and xenon, such as $^{85}$Kr and $^{133}$Xe, are produced in nuclear fission and can enter the atmosphere during the reprocessing of spent nuclear fuel or via nuclear accidents, such as the Fukushima Daiichi Nuclear Power Plant catastrophe in Japan. Cryogenic processes have been suggested for the removal of radioactive rare gases from off-gas streams in future nuclear reprocessing plants, but again this is energy intensive and expensive because of the low rare gas concentrations.

The present invention is therefore an important step forward in terms of saving energy, protecting the environment, and producing valuable resources: for example, the reduction of $^{85}$Kr concentrations to permissible levels in xenon-rich nuclear reprocessing streams provides an entirely new source of xenon for industrial use.

The present invention meets the challenge of efficiently separating gas molecules that are present in low concentrations (<500 ppmv) from the principal components in the gas mixture, despite their lack of chemical reactivity and the small size difference between the higher-mass noble gases such as Kr (diameter=3.69 Å), Xe (4.10 Å), Rn (4.17 Å), and the common constituents of air. The present invention is effective despite the spherical nature of the rare gases, which precludes strategies based on shape selectivity.

Although some porous MOFs show promise for Xe/Kr separations, few known materials provide effective separations of noble gases at low concentrations of just a few parts per million in air. As discussed in more details below, the present invention performs better than the leading MOF material (a nickel-based MOF, Ni/DOBDC) disclosed in *Langmuir* 2012, 28, 11584-11589, Liu et al.

The present invention is also useful for the separation of organic molecules. The host material may comprise chiral cages and therefore is useful for the separation of chiral enantiomers. Enantioselective separation is important for several purposes, including the preparation of building blocks for pharmaceutical and other biologically active products. As discussed further below, the present invention is useful in analytical enantiomeric separation.

Other materials that are useful to separate include alkanes, for example different alkanes or different isomers of alkanes, e.g. structural isomers of hexane. As shown in the examples below, the present invention allows the analytical separation of these isomers.

Organic Cage Molecules

We reported previously an organic cage molecule, CC3 [Tozawa, T. et al. Porous organic cages. *Nat. Mater.* 8, 973-978, (2009)].

Notes on Cage Nomenclature, Chirality, and Cage Synthesis

Helicity, or axial chirality, is an intrinsic property of the organic cage CC3. In this study, a homochiral diamine, either (R, R)-1,2-cyclohexanediamine or (S, S)-1,2-cyclohexanediamine, was used in the cage synthesis. The cage used throughout the rare gas study was the homochiral form, CC3-R. Identical results would, presumably, be obtained with the opposite enantiomer, CC3-S. Gas adsorption measurements suggested that the racemic equivalent, CC3-(R, S), also has similar properties with respect to the rare gases Xe and Kr. This latter cage would be less expensive to produce on a large scale because it can be prepared from the racemic cyclohexanediamine. However, the chiral forms, CC3-R and CC3-S, can form large single crystals with enhanced long-range order with respect to the less expensive racemic cage, CC3-(R, S). This is because the racemic form is much less soluble than the homochiral form and precipitates rapidly, preventing the growth of large, high-quality single crystals. For this reason, the homochiral form of CC3 was used for these studies, in particular because it allows direct comparison of experiments with atomistic simulations, which assume an idealized 3-dimensional crystal structure with no defects.

CC3-R (and CC3-S) were synthesised as reported previously.[1] In a 250 mL round bottom flask, dichloromethane (DCM, 100 mL) was added slowly onto solid 1,3,5-triformylbenzene (5.0 g, 30.86 mmol) at room temperature without stirring to avoid mixing and hence to prevent rapid dissolution of the aldehyde. Trifluoroacetic acid (100 μL) was added directly to this solution as a catalyst for imine bond formation. Next, a solution of (R, R)-1,2-diaminocyclohexane (5.0 g, 44.64 mmol) in dichloromethane (100 mL) was slowly layered onto this solution, again being careful to avoid mixing. The unmixed reaction was then covered and left to stand at room temperature. The white, crystalline product was removed by filtration and washed with 95% ethanol/5% dichloromethane. Isolated yield: 6.5 g, 83%.

Rare Gas Separation

We show here that CC3 has an internal cavity that is precisely the right size to accommodate a single xenon or radon atom.

FIG. 1a shows the structure, and a reaction scheme for the synthesis of, CC3, by a one-pot [4+6] cycloimination reaction involving 4 trialdehyde and 6 diamine molecules, catalysed by trifluoroacetic acid (TFA).

FIGS. 1b and 1c each show a single molecule of CC3.

The largest inclusion sphere [Willems, T. F. et al. Algorithms and tools for high-throughput geometry-based analysis of crystalline porous materials. Microporous Mesoporous Mater. 149, 134-141, (2012)] in this cavity (d=4.4 Å; shown as a mesh sphere in FIGS. 1b and 1c) is very close to the diameters of xenon (4.10 Å; shown as a solid sphere in FIG. 1c) and radon (4.17 Å; not shown).

FIG. 1d shows the extended crystal packing and in particular the arrangement of individual CC3 cage molecules adjacent to each other in the solid state. Two pore cavities exist in the 3-dimensional pore structure: a cage cavity inside the molecule itself (lighter, mesh) and a window cavity between adjacent cage windows (darker, solid).

Thus, the cage packs in the crystalline state to give a robust 3-dimensional pore structure. In a static view, however, the narrowest point in the pore channels, the pore-limiting diameter [Haldoupis, E., Nair, S. & Sholl, D. S. Pore size analysis of >250,000 hypothetical zeolites. *Phys. Chem. Chem. Phys.* 13, 5053-5060, (2011)], lies between the cage and the window cavities and has dimensions of just 3.6 Å (vertical solid line in FIG. 2a). This is slightly smaller than the diameter of Kr (3.69 Å), and in principle too narrow to permit the diffusion of either xenon or radon.

Figure 2A:
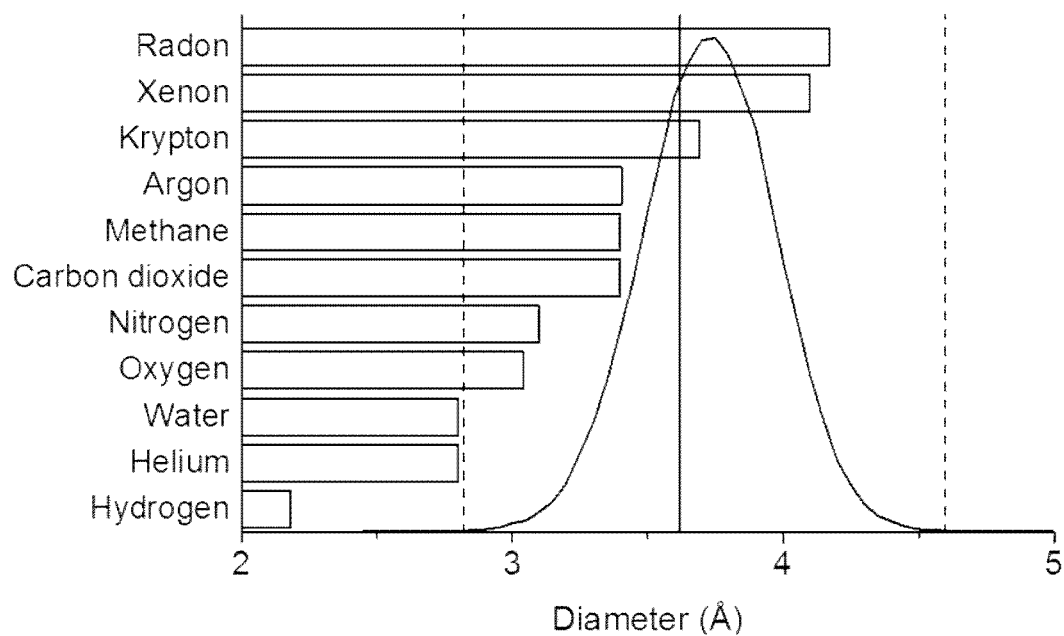
FIG. 2a shows a graph of pre size distribution generated using molecular dynamics simulations.

However, molecular dynamics simulations allow for vibrational motion of the atoms in the cage molecules. FIG. 2a shows a graph of pore size distribution generated using molecular dynamics simulations, plotted against the diameters of hydrogen, helium, water, oxygen, nitrogen, carbon dioxide, methane, argon, krypton, xenon, and radon. Molecular dynamics simulations (298K, 1 atm) reveal a time-averaged, pore-limiting envelope (FIG. 2a) between 3 Å and 4.5 Å in crystalline CC3 that encompasses the diameters of all noble gases, up to radon. This is therefore broad enough to permit diffusion of both xenon and radon. Calculations suggest that the pore windows are 'open' for only 7% and 3% of the simulation time for xenon and radon, respectively, but this is enough to allow opportunistic hopping of these gases through the pores.

Figure 2B:
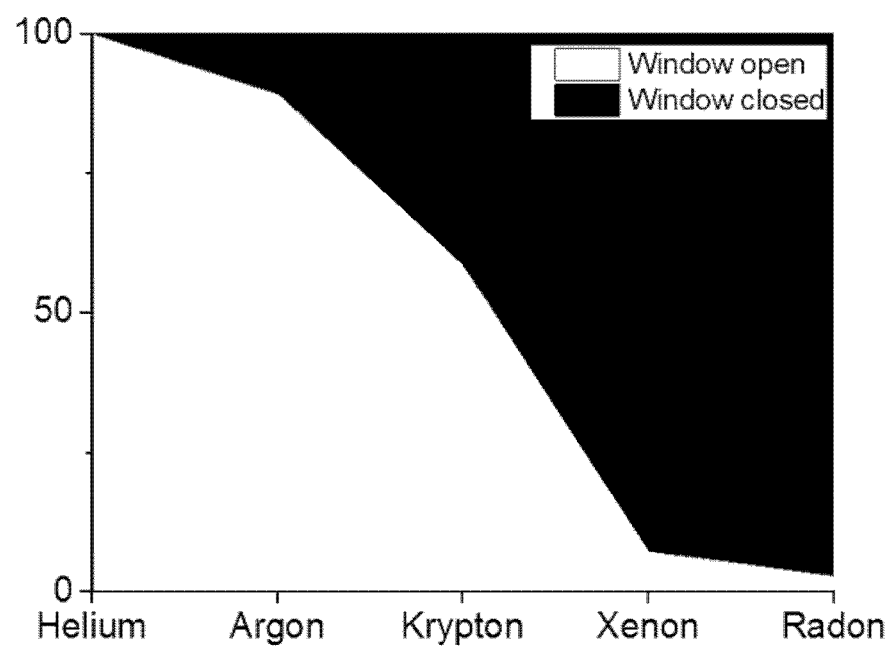
FIG. 2b shows the percentage of time for which the window is open, according to the simulation.

FIG. 2b shows the percentage of time for which the window is open, according to the simulation, for various gases.

Figure 2C:
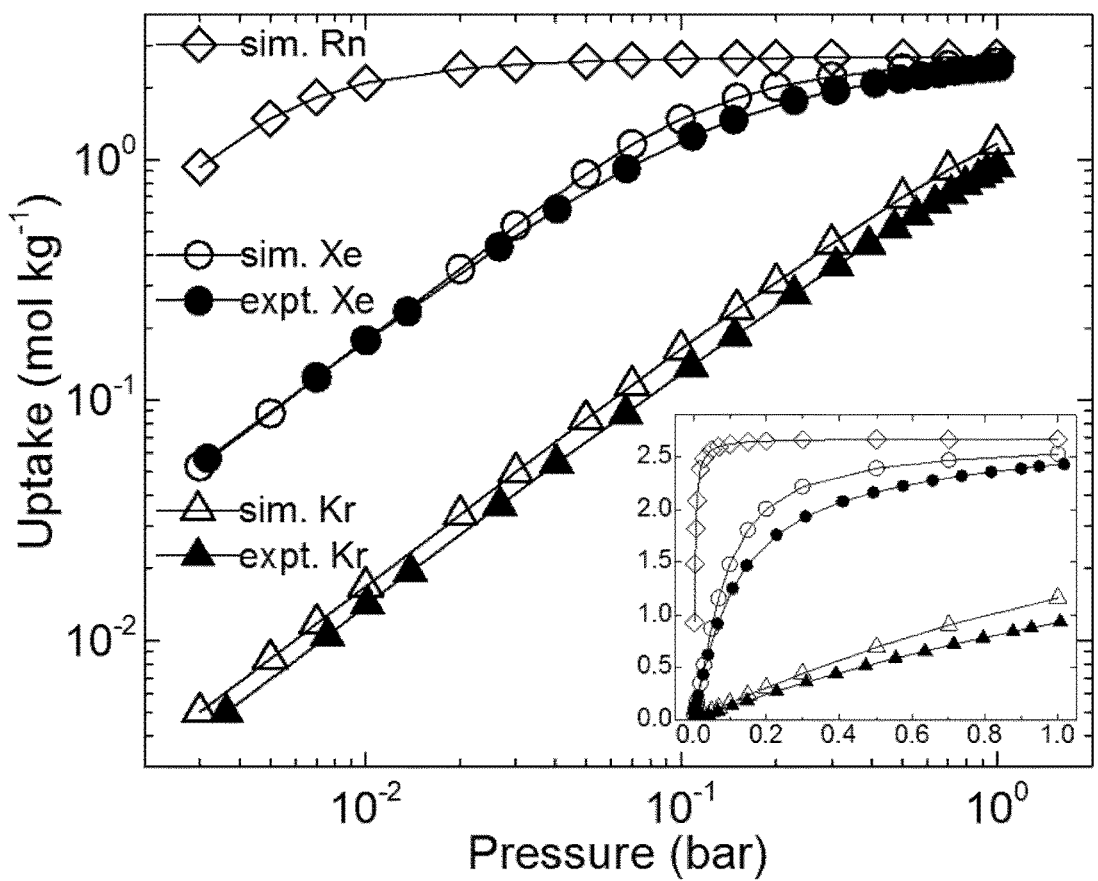
FIG. 2c shows predicted single-component log-log gas adsorption plotted against calculated gas uptakes from a hypothetical equimolar, 11-component competitive adsorption simulations and calculated Henry's coefficients at 298 K.

FIG. 2c shows predicted single-component log-log gas adsorption isotherms (Kr, Xe and Rn; open symbols) and experimental equivalents (Kr, Xe; filled symbols) at 298 K for CC3 (inset shows linear-linear plot). Simulated isotherms were obtained from grand-canonical Monte Carlo (GCMC) simulations. Both simulated and experimental gas adsorption isotherms demonstrate substantial uptake of both krypton and xenon in CC3. We also simulated the radon adsorption isotherm, which we could not measure experimentally because, to our knowledge, no laboratory worldwide is equipped with a suitable gas sorption apparatus that is configured for such radioisotopes. The xenon isotherm and the simulated radon isotherm both approach saturation at 1 bar (298 K) at a gas uptake of around 2.69 mol kg$^{-1}$, corresponding to three gas molecules per CC3 cage. This can be rationalized by one gas molecule occupying each cage cavity, plus four more gas molecules shared between two cages in the surrounding window cavities. The smaller noble gas, krypton, is less strongly adsorbed and is much further from saturation at 1 bar (FIG. 2c, linear inset plot).

Figure 2D:
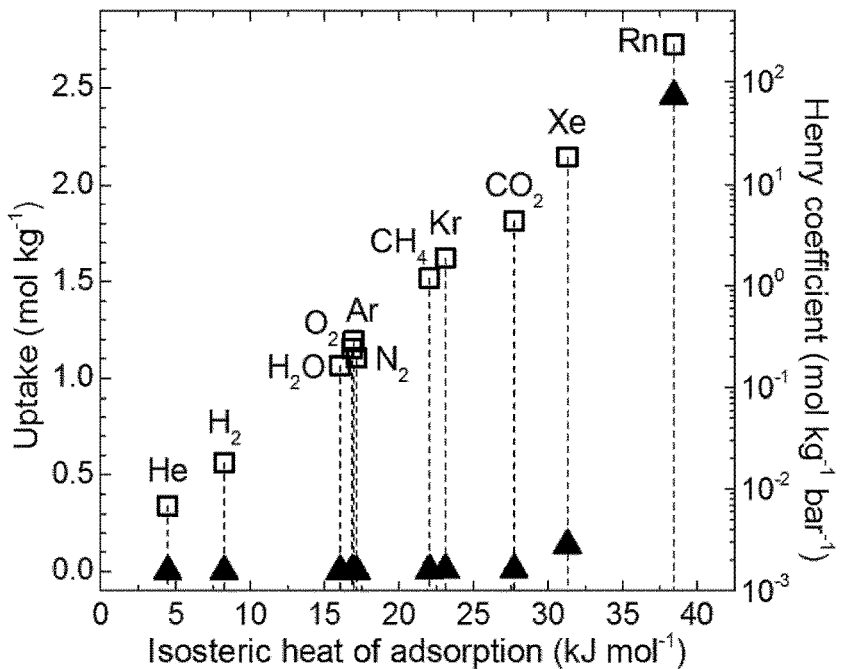

FIG. 2d shows calculated zero-coverage heats of adsorption plotted against calculated gas uptakes from a hypothetical equimolar, 11-component competitive adsorption simulations (triangles) and calculated Henry's coefficients (squares), all at 298 K. We predict highly selective Rn uptake for this equimolar mixture. At equilibrium, the guest occupancy in the CC3 pores (298 K, 1 bar total pressure) is calculated to be: Rn=91.66%; Xe=5.03%; Kr=0.32%; $CO_2$=0.30%; $CH_4$=0.20%; Ar+He+$N_2$+$O_2$+$H_2$+$H_2O$=0.10%. These Henry's coefficients, supported by binary GCMC simulations, suggest that CC3 has potential for separating various gas mixtures, in addition to the rare gases.

The calculations show enhanced zero-coverage heats of adsorption for xenon (31.3 kJ mol$^{-1}$) with respect to krypton (23.1 kJ mol$^{-1}$) and the more common gases that are the main constituents of air (4.5-27.7 kJ mol$^{-1}$). These calculations for krypton and xenon agree reasonably with measured heats of adsorption. Radon is predicted to have an even higher heat of adsorption of 38.4 kJ mol$^{-1}$. The computed Henry's coefficients scale with both the heats of adsorption and with the gas uptakes calculated from the equimolar 11-component competitive adsorption simulation. In the hypothetical 11-component mixture, we predict that 91.7% of the available sorption sites in the crystalline cage solid would be occupied by Rn at equilibrium, even though Rn constitutes just 9.1 mol. % of the gas mixture and has a diameter, 4.17 Å, which is only 0.07 Å larger than that of Xe. These simulation data suggest selectivity for xenon and radon adsorption in this concentration range that far exceeds other reported materials [Liu, J., Thallapally, P. K. & Strachan, D. Metal-organic frameworks for removal of Xe and Kr from nuclear fuel reprocessing plants. *Langmuir* 28, 11584-11589, (2012)].

Computational Methods.

Largest Inclusion Sphere.

The largest inclusion sphere, as shown in FIG. 1b, is the diameter of the largest spherical probe that can be inserted within the void structure of a material. This was calculated for CC3 using Zeo++,[2] with van der Waals radii for the host atoms taken from the CCDC database.[3]

Gas Diameters.

Figure 3:
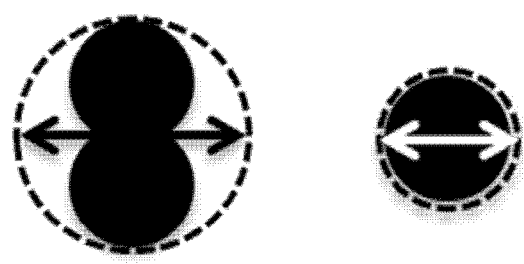
FIG. 3 shows a nitrogen molecule in a side-on orientation (left) and in an end-on orientation (right).

When considering whether a particular sorbate will diffuse through a pore, we used the minimum molecular diameter of that sorbate. For non-spherical molecules, such as diatomic gases, this is not typically equal to the kinetic diameter. For example, the kinetic radius for nitrogen, $N_2$, is 1.82 Å, but the minimum molecular diameter is the van der Waals radius of a single nitrogen atom, 1.55 Å. This difference is illustrated in FIG. 3. The values used for the diameters of the eleven different common gases in air are listed in Table 1.

FIG. 3 shows a nitrogen molecule in a side-on orientation (left), where the kinetic diameter is 1.82 Å, and in an end-on orientation (right), for which the minimum molecular dimension is 1.55 Å.

TABLE 1

Van der Waal diameters and consideration of the molecular geometry were used to calculate the minimum molecular diameter for each molecule.[3] The Shrake-Rupley model was used to represent water,[4] with values reported by Sholl et al. used for the four largest rare gases.[5] Methane was based on the model proposed by Martin and Siepmann.[6] The kinetic diameter of each gas is also included.[7]

| Gas | Minimum molecular dimension (Å) | Molecular dimension reference | Kinetic diameter (Å) |
| --- | --- | --- | --- |
| Hydrogen | 2.18 | 3 | 2.89 |
| Helium | 2.80 | 3 | 2.60 |
| Water | 2.80 | 4 | 2.65 |
| Oxygen | 3.04 | 3 | 3.46 |
| Nitrogen | 3.10 | 3 | 3.64 |
| Carbon Dioxide | 3.40 | 3 | 3.30 |
| Argon | 3.40 | 5 | 3.40 |
| Krypton | 3.69 | 5 | 3.60 |
| Methane | 3.73 | 6 | 3.80 |

TABLE 1-continued

Van der Waal diameters and consideration of the molecular geometry were used to calculate the minimum molecular diameter for each molecule.[3] The Shrake-Rupley model was used to represent water,[4] with values reported by Sholl et al. used for the four largest rare gases.[5] Methane was based on the model proposed by Martin and Siepmann.[6] The kinetic diameter of each gas is also included.[7]

| Gas | Minimum molecular dimension (Å) | Molecular dimension reference | Kinetic diameter (Å) |
|---|---|---|---|
| Xenon | 4.10 | 5 | 3.96 |
| Radon | 4.17 | 5 | — |

Comparison of Gas Size with the Pore Limiting Diameter (PLD).

Figure 4:
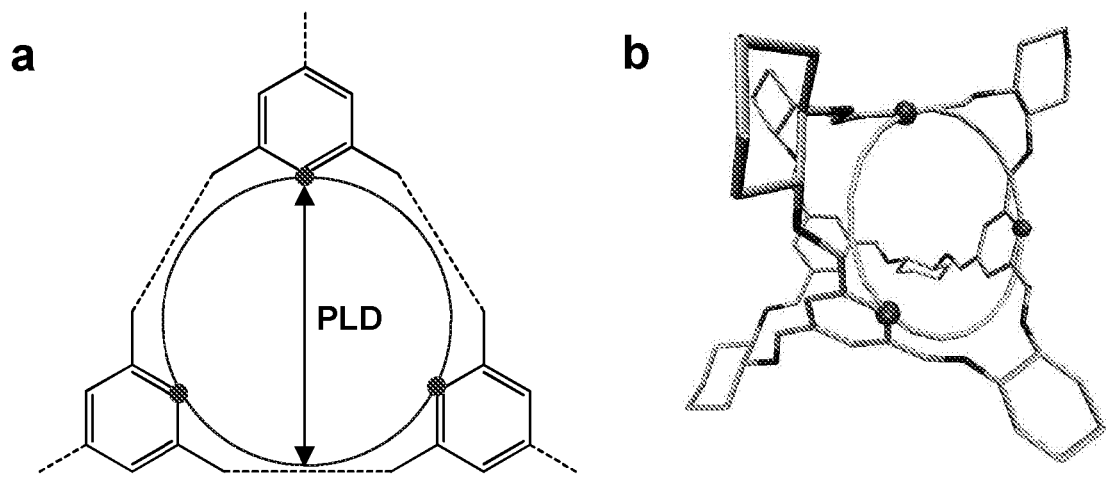
FIG. 4a shows (Left): Scheme showing how the pore limiting diameter (PLD) for CC3 was measured from the circumcircle prescribed by the three phenyl carbons on the open cage face.
FIG. 4b shows (Right:) Relative sizes of various gases and spheres respresenting their minimum molecular diameters.

The narrowest point in the pore network for CC3, the pore limiting diameter (PLD), is in the windows of the cage molecule. The surrounding phenyl carbon atoms define this window size, as shown in FIG. 4 (left panel). It was shown previously that the windows in these tetrahedral cage molecules can be described geometrically as a circumcircle.[8] A circumcircle, or circumscribed circle, is a circle that passes through all the vertices of a given polygon. Here, this circle passes through the three phenyl carbons located around each cage window, which prescribe a triangle. The diameter of this circle, with the van der Waals diameter of the carbon atom subtracted (1.7 Å), was used as the PLD. The PLD can be used to gauge the potential of a particular gas molecule to diffuse through the pore structure. Gases such as hydrogen and helium, for example, with a minimum molecular dimension that is smaller than the PLD, should be able to traverse the pores in CC3 even if one takes a simple 'static' view of the structure. However, gases with minimum molecular dimensions larger than the PLD can, in fact, also diffuse through the pores as a result of molecular motion in the organic crystal. This cooperative diffusion mechanism can be captured by defining a 'pore limiting envelope', as shown in FIG. 2a, rather than a single PLD.

FIGS. 4a and 4b. FIG. 4a shows (Left): Scheme showing how the pore limiting diameter (PLD) for CC3 was measured from the circumcircle prescribed by the three phenyl carbons on the open cage face. This was calculated using an in-house code, developed by Dr David Willock.[9] Carbon and nitrogen atoms are shown; all hydrogen atoms are omitted for clarity.

FIG. 4b shows (Right:) Relative sizes of various gases and spheres representing their minimum molecular diameters.

Generating the Pore Limiting Envelope (PLE).

The cage molecules in the CC3 crystal have a degree of flexibility, and thus simple comparisons of gas diameters with a PLD generated from a static structure can underestimate the potential for diffusion of larger guests. Such approximations are particularly poor when the dimension of the sorbate approaches the PLD, which is likely to be true, by definition, in most porous materials with high gas separation selectivity. We therefore generated a time-averaged pore limiting envelope (PLE) for the CC3 host to reflect the distribution of PLDs in the flexible organic crystal. This was calculated by monitoring the PLD as a function of time over a molecular dynamics (MD) simulation. The MD simulation was carried out using DL_POLY_2.20,[10] with a 2×2×2 supercell generated from the single-crystal structure of the desolvated CC3 host.[11] The supercell dimension had initial cell dimensions a=b=c=49.59 Å, α=β=γ=90°. We used CSFF, a force field that we have previously parameterized for porous imine cages, including CC3.[8] A potential cutoff of 10 Å was used and electrostatic interactions were calculated using the partial charges from the FF. An NPT ensemble (constant number of moles, pressure and temperature) at 1 atm and 298 K was used with the Hoover barostat and thermostat,[12] both had a time constant of 0.5 ps. A timestep of 0.5 fs was used, with the system was first equilibrated for 50 ps with temperature scaling every 5 fs, followed by a production run of 10 ns, with a frame output every 1 ps. An in-house script was used to calculate the window diameter for each window in the cage for each frame. There are 4 windows per cage, and 64 cages per supercell. This corresponds to 256 cage windows in the supercell, and all of these were used to generate a histogram of time-averaged window diameters, which we refer to here as the pore limiting envelope (FIG. 2a). The PLE was used to determine the proportion of time that the cage windows were open for each gas during the 10 ns simulation (FIG. 2b). This was achieved by calculating the percentage of time for which the diameter of each window was larger than the minimum molecular diameter of the gas in question—that is, "open". For the rest of the simulation time, the window was deemed "closed", because its diameter was smaller than the minimum molecular diameter of the gas. These values are tabulated in Table 2.

TABLE 2

Proportion of time that the cage windows are "open" and "closed" for each gas. In essence, $H_2$, He, $H_2O$, $O_2$, $N_2$, $CO_2$, and Ar do not require molecular flexibility in CC3 to rationalize their diffusion. For Kr, $CH_4$, Xe, and Rn, however, the static window diameter is smaller than the minimum molecular diameter, and diffusion is a dynamic process that involves transient opening of the cage windows. This is particularly true for Xe and Rn.

| Gas | Minimum molecular diameter (Å) | Proportion Open (%) | Proportion Closed (%) |
|---|---|---|---|
| Hydrogen | 2.18 | 100.0 | 0.0 |
| Helium | 2.80 | 100.0 | 0.0 |
| Water | 2.80 | 100.0 | 0.0 |
| Oxygen | 3.04 | 99.8 | 0.2 |
| Nitrogen | 3.10 | 99.6 | 0.4 |
| Carbon Dioxide | 3.40 | 92.5 | 7.5 |
| Argon | 3.41 | 89.2 | 10.8 |
| Krypton | 3.69 | 58.7 | 41.3 |
| Methane | 3.73 | 50.6 | 49.4 |
| Xenon | 4.10 | 7.3 | 92.7 |
| Radon | 4.17 | 2.9 | 97.1 |

Binding Energies for Rare Gases with the CC3 Host.

Host-guest binding energies were determined (Table 3) for a single rare gas atom interacting with a single, isolated CC3 cage molecule, and also for a single rare gas atom interacting with the bulk CC3 crystal (Table 4). Calculations were performed employing density functional theory (DFT) with periodic boundary conditions and P1 symmetry, as implemented in the QUICKSTEP[13] module of the CP2K simulation package (http://www.cp2k.org/). Energies were calculated with the Gaussian plane-wave scheme,[13,14] which uses a dual basis set method wherein a linear combination of Gaussian-type orbitals is used to describe the Kohn-Sham (KS) molecular orbitals while the electron density is described by an auxiliary plane-wave basis set. The MOLOPT basis set,[15] in conjunction with the relativistic, norm-conserving Goedecker-Teter-Hutter pseudopotentials,[16-18] was used for all elements. Both the DZVP and TZVP variants of the MOLOPT basis set were tested for the CC3 host, while the DZVP basis set was used throughout for the rare gases (for which TZVP is not available). The auxiliary plane-wave basis set was defined by an energy cutoff of 700 Ry, accompanied by a relative cutoff of 50 Ry for the Gaussian basis set collocation. During each self-consistent-field cycle, the electronic structure was explicitly minimized to a tolerance of $10^{-7}$ Hartree. Dispersion (van der Waals or vdW) interactions play a dominant role in the binding of the rare gas . . . CC3 systems studied here. Standard KS-DFT functionals, however, by construction account poorly for such long-range correlation effects.[19] Therefore, two methods were used to determine binding energies that explicitly take account of dispersion interactions within the KS-DFT framework. The first dispersion-correction scheme employed is Grimme's DFT-D3 method,[20] in which the conventional self-consistent KS-DFT energy is augmented by a semi-empirical dispersion potential ($\sim\Sigma_n C_n R^{-n}$). All DFT-D3 calculations made use of the Perdew-Burke-Ernzerhof (PBE)[21] exchange-correlation functional, together with a cutoff radius of 24.0 Å adopted for dispersion calculations and the three-body contribution to dispersion evaluated explicitly. The second approach, accounting explicitly for dispersion interactions, is a revised version of the nonlocal vdW density functional proposed by Vydrov and Van Voorhis, which is hereafter referred to as rVV10.[22,23] Such nonlocal correlation functionals, including rVV10, allow for a first-principles description of dispersion interactions using only the electron density as an input: dispersion interactions are not included by means of any (semi)empirical potentials or parameters.

Figure 22:
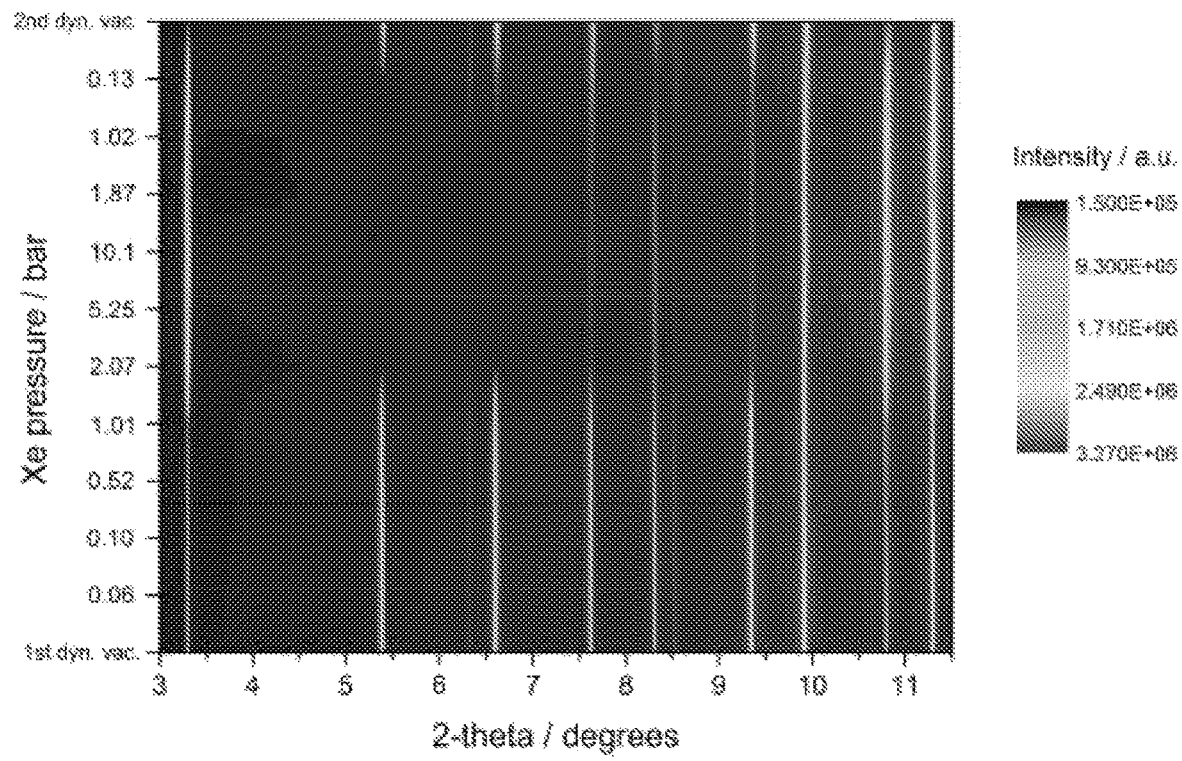
FIG. 22 shows in situ powder diffraction data for loading and removal of xenon into a sample of CC3.

Two sets of host-guest binding energies were determined for the CC3 host. Both sets used coordinates taken from the single crystal X-ray diffraction structure, and these coordinates were kept fixed at their original positions for all calculations. That is, we did not allow for expansion of the unit cell upon gas sorption, which is a reasonable approximation given the constant peak positions observed in powder X-ray diffraction experiments in the presence of xenon (FIG. 22). The first set of calculations, concerning the binding of a single rare gas atom with a single, isolated CC3 cage molecule (Table 3), were performed by placing the rare gas atom at the centre of the void of a CC3 cage. The cage was centred in an empty, cubic box having the dimensions of 40 Å×40 Å×40 Å. The other set of binding energies (Table 4) was obtained by placing a single rare gas atom in one unit cell of the CC3 bulk crystal structure, comprising eight cage molecules. For each rare gas species, two binding sites inside the bulk CC3 crystal structure were characterized: the cage-cavity site and the window-cavity site. For both sites, the gas atom was placed at the centre of the cavity. All of the host-guest binding energies are given by:

$$E_{binding} = E(\text{host} \ldots \text{guest}) - E(\text{host}) - E(\text{guest})$$

where E(host . . . guest), E(host), and E(guest) are the total energies of the guest-loaded CC3 host, empty CC3 host, and isolated guest atom, respectively. E(guest) was calculated by placing a single guest atom in a 40 Å×40 Å×40 Å box (for gas-phase binding) or in a box the same size as the unit cell of the CC3 crystal structure (for solid-state binding). Corrections for basis set superposition error were applied to all of the binding energy calculations, through the full counterpoise procedure.[24]

Table 3 reports (gas-phase) cage . . . gas binding energies obtained using four different models, resulting from the combinations of two basis sets and two DFT methods. It is clear that, irrespective of the model, the binding strength of the CC3 cage with the rare gases increases in the order Ar<Kr<Xe<Rn. Moreover, the discrepancies between the different models are small and are within the accuracies of these methods (typically ca. 2 kJ mol$^{-1}$). In light of this, only the PBE-D3/DZVP approach, which is computationally most efficient for the systems studied here, was used to determine rare gas binding with the solid-state CC3 structure. Binding energies for Ar, Kr, Xe, and Rn with the CC3 bulk crystal are summarized in Table 4. The CC3$_{bulk}$ . . . gas binding strengths, for both cage-cavity and window-cavity sites scale, again, with the atomic weights of the rare gases, as for rare gases interacting with an isolated CC3 cage (Table 3). Furthermore, for the larger Xe and Rn atoms, the cage-cavity site appeared to be more attractive than the window-cavity site, whereas the reverse trend applied for the smaller Ar and Kr atoms. The differences in binding energy between the two sites are, however, very small for all four rare gases.

TABLE 3

Gas-phase host-guest binding energies for a single rare gas atom at the centre of an isolated CC3 cage molecule.

| | model chemistries | | | $E_{binding}$ for cage . . . gas (kJ mol$^{-1}$) | | | |
|---|---|---|---|---|---|---|---|
| basis set$^a$ | functional | exchange | correlation | Ar | Kr | Xe | Rn |
| DZVP | PBE-D3 | PBE | PBE + D3 | −15.699 | −21.732 | −29.527 | −34.233 |
| TZVP | PBE-D3 | PBE | PBE + D3 | −15.813 | −21.832 | −29.788 | −34.616 |
| DZVP | rVV10 | rPW86 | PBE + rVV10 | −15.248 | −21.120 | −29.491 | −32.679 |
| TZVP | rVV10 | rPW86 | PBE + rVV10 | −15.424 | −21.341 | −30.175 | −33.624 |

$^a$For the cage both the DZVP- and TZVP-MOLOPT basis sets were investigated, while only the DZVP-MOLOPT basis set was available for the rare gases.

TABLE 4

Solid-state host-guest binding energies (in kJ mol$^{-1}$) of one rare gas atom per unit cell of the bulk CC3 crystal structure for the cage-cavity and window-cavity binding sites, as determined by the DFT (PBE-D3/DZVP) calculations and by different classical force fields.$^a$

| Site | CC3$_{bulk}$ . . . Ar | CC3$_{bulk}$ . . . Kr | CC3$_{bulk}$ . . . Xe | CC3$_{bulk}$ . . . Rn |
|---|---|---|---|---|
| | | PBE-D3/DZVP | | |
| cage-cavity | −16.325 | −22.710 | −31.119 | −36.210 |
| window-cavity | −17.402 | −23.417 | −30.874 | −36.091 |

TABLE 4-continued

Solid-state host-guest binding energies (in kJ mol⁻¹) of one rare gas atom per unit cell of the bulk CC3 crystal structure for the cage-cavity and window-cavity binding sites, as determined by the DFT (PBE-D3/DZVP) calculations and by different classical force fields.[a]

| Site | $CC3_{bulk}$ . . . Ar | $CC3_{bulk}$ . . . Kr | $CC3_{bulk}$ . . . Xe | $CC3_{bulk}$ . . . Rn |
|---|---|---|---|---|
| DREIDING[b] | | | | |
| cage-cavity | −18.617 (*14.0%*) | −26.856 (*18.3%*) | −37.666 (*21.0%*) | −46.414 (*28.2%*) |
| window-cavity | −18.763 (*7.8%*) | −27.017 (*15.4%*) | −37.521 (*21.5%*) | −46.101 (*27.7%*) |
| OPLS-AA[b] | | | | |
| cage-cavity | −17.469 (*7.0%*) | −25.177 (*10.9%*) | −35.265 (*13.3%*) | −43.447 (*20.0%*) |
| window-cavity | −18.490 (*6.2%*) | −26.983 (*15.2%*) | −38.461 (*24.6%*) | −47.520 (*31.7%*) |
| UFF[b] | | | | |
| cage-cavity | −19.502 (*19.5%*) | −28.329 (*24.7%*) | −40.219 (*29.2%*) | −49.684 (*37.2%*) |
| window-cavity | −20.636 (*18.6%*) | −30.038 (*28.3%*) | −42.463 (*37.5%*) | −52.352 (*45.1%*) |
| CAFF[b] | | | | |
| cage-cavity | −15.453 (*−5.3%*) | −22.291 (*−1.8%*) | −31.263 (*0.5%*) | −38.524 (*6.4%*) |
| window-cavity | −15.573 (*−10.5%*) | −22.424 (*−4.2%*) | −31.143 (*0.9%*) | −38.264 (*6.0%*) |

[a]Relative errors of the force-field-based binding energies, with respect to the corresponding PBE-D3 ones, are given in italic in parentheses.
[b]Force fields used for the CC3 host. For the rare gases, see Table 5 for the force-field parameters used and references therein.

Grand-Canonical Monte Carlo (GCMC) Simulations.

Gas sorption in CC3 was studied using the GCMC method,[25] and the simulations were performed with the RASPA code developed by D. Dubbeldam, S. Calero, D. E. Ellis, and R. Q. Snurr. In the GCMC method, the chemical potential, volume, and temperature are kept fixed while the number of gas molecules in the adsorbed phase is allowed to fluctuate so that the chemical potentials of the adsorbed phase and the bulk gas reservoir are equal. The input of a GCMC simulation includes the temperature and chemical potential of the gas molecules in the reservoir, and the output of the simulation is the average number of adsorbed molecules. This is analogous to an adsorption experiment, in which the temperature and bulk pressure of a gas are specified and the corresponding uptake is measured. The chemical potential, as used in GCMC simulations, can be related to the gas-phase pressure, as specified in experiments, by an equation of state. The Peng-Robinson equation was used here. The GCMC simulations performed in this work included a 300,000-cycle equilibration period and a 500,000-cycle production run. One cycle consisted of n Monte Carlo (MC) steps, with n being equal to the number of adsorbate molecules (i.e., n fluctuated during the simulation). The trial MC moves-including insertion, deletion, translation, rotation, and reinsertion-were randomly selected with equal probabilities. In the cases of mixtures, an identity-change move was also used. The Henry coefficients and isosteric heats of adsorption at zero coverage (infinite dilution) were obtained from MC simulations in the NVT ensemble using the Widom test particle method.[25,26]

The atomistic representation of the CC3 crystal structure was constructed from the experimental crystallographic data, with all the cage atoms kept fixed at their positions during the simulation (see comments above about lack of cell expansion as a function of Xe adsorption observed in gas cell experiments; also FIG. 22). In order to ensure statistical meaningfulness and numerical accuracy, a 2×2×2 unit-cell representation of the CC3 crystal structure was used in the GCMC simulations; that is, a cubic simulation box (49.6 Å in length) with periodic boundary conditions exerted in three dimensions. When the adsorbate of interest had a very low concentration (e.g., 400 ppmv Xe), an even larger 3×3×3 CC3 supercell was used. The large simulation boxes were used primarily to guarantee that at least one Xe (and/or Rn) atom was (almost) always present in the simulation box at each MC step. Moreover, very low concentrations of Xe and Rn, which would lead to zero adsorbate uptake in an appreciable proportion of the total simulation cycles, were not considered, ensuring that the results are statistically meaningful. The guest atoms/molecules investigated included radon, xenon, krypton, argon, helium, nitrogen, oxygen, carbon dioxide, methane, hydrogen, and water.

The host-guest and guest-guest interaction energies were determined according to the Lennard-Jones (U) and Coulomb potentials, given as:

$$V_{ij} = 4\varepsilon_{ij}\left[\left(\frac{\sigma_{ij}}{r_{ij}}\right)^{12} - \left(\frac{\sigma_{ij}}{r_{ij}}\right)^6\right] + \frac{z_i z_j e^2}{4\pi\varepsilon_0 r_{ij}}$$

where $\varepsilon_{ij}$ and $\sigma_{ij}$ are the ⊔ potential-well depth and hard-sphere diameter, respectively; $r_{ij}$ is the distance between atoms i and j; z; $z_i$ and $z_j$ are the fractional charges; e is the elementary charge; and Eo is the vacuum permittivity. A cut-off radius of 21.0 Å was used for all ⊔ interactions (simple truncation), while all Coulomb interactions were computed using the Ewald summation technique with a relative precision of $10^{-6}$. The Lorentz-Berthelot combining rules were used to calculate the U cross-parameters.

The force-field parameters used for the adsorbates were taken from the literature and are summarized in Table 5, together with references to the sources. The LJ parameters for the CC3 atoms were assigned based on the DREIDING force field,[27] with one modification applied. The ε values for all of the host atoms were multiplied by 0.69, resulting in, for all adsorbates, the host-guest interactions being uniformly reduced to 83% of those given by DREIDING. The original DREIDING σ values were used unaltered. The ⊔ parameters used for the CC3 atoms are presented in Table 5 and are referred to hereafter as CAFF (Cage Adsorption Force Field). Further discussion on the force-field modification is given below. To obtain partial atomic charges for the CC3 host, an isolated cage molecule in gas phase was used for calculations, performed at the B3LYP/6-31++G(d, p) level of theory with the Gaussian 09 programme.[28] The Merz-Kollman scheme was used to fit partial charges to the first-principles electrostatic potential of the cage on a grid having ca. 2,000 sampling points per atom. The vdW exclusion radii of the H, C, and N atoms are 1.10, 1.70, and 1.55 Å, respectively. The resulting charges are reported in Table 5.

TABLE 5

Force-field parameters for the adsorbates investigated and the CC3 host atoms.[a]

| adsorbate | ref. | atom type | $\varepsilon/k_B$ (K) | $\sigma$ (Å) | q (e) |
|---|---|---|---|---|---|
| radon | 29 | Rn | 300.000 | 4.170 | 0.000 |
| xenon | 30 | Xe | 211.000 | 4.100 | 0.000 |
| krypton | 30 | Kr | 170.000 | 3.690 | 0.000 |
| argon | 30 | Ar | 120.000 | 3.405 | 0.000 |
| helium | 31 | He | 10.220 | 2.580 | 0.000 |
| methane | 6 | $CH_4$(UA) | 148.000 | 3.730 | 0.000 |
| nitrogen | 32 | $N(N_2)$ | 36.000 | 3.310 | −0.482 |
|  |  | N(com) | 0.000 | 0.000 | 0.964 |
| oxygen | 33 | $O(O_2)$ | 49.000 | 3.020 | −0.113 |
|  |  | O(com) | 0.000 | 0.000 | 0.226 |
| carbon dioxide | 32 | $O(CO_2)$ | 79.000 | 3.050 | −0.350 |
|  |  | $C(CO_2)$ | 27.000 | 2.800 | 0.700 |
| hydrogen | 34 | $H(H_2)$ | 0.000 | 0.000 | 0.468 |
|  |  | H(com) | 36.700 | 2.958 | −0.936 |
| water | 35 | $O(H_2O)$ | 89.633 | 3.097 | 0.000 |
|  |  | $H(H_2O)$ | 0.000 | 0.000 | 0.241 |
|  |  | $L(H_2O)$ | 0.000 | 0.000 | −0.241 |

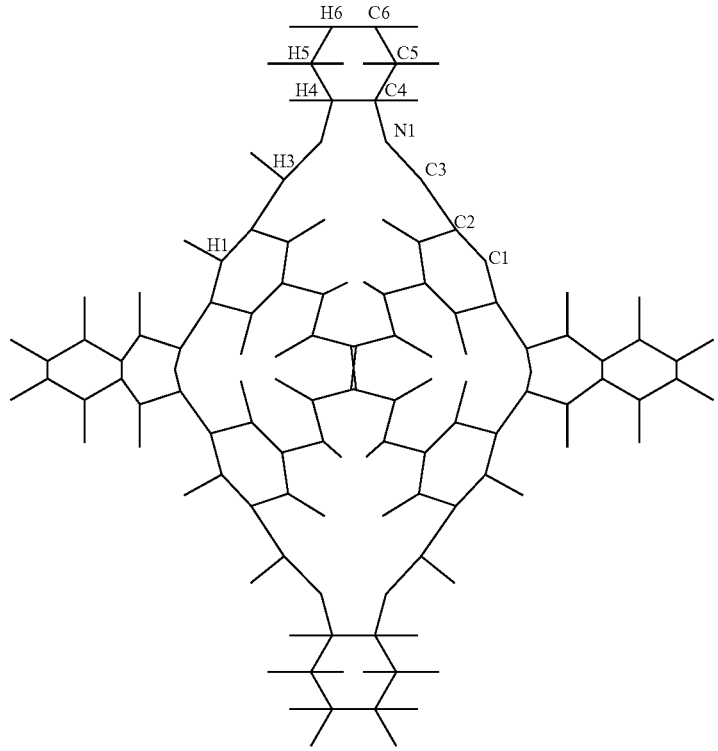

| CC3 atom type | $\varepsilon/k_B$ (K) | $\sigma$ (Å) | q (e) |
|---|---|---|---|
| N1 | 26.83 | 3.2626 | −0.6185 |
| C1 | 32.97 | 3.4730 | −0.3289 |
| C2 | 32.97 | 3.4730 | 0.1870 |
| C3 | 32.97 | 3.4730 | 0.3256 |
| C4 | 32.97 | 3.4730 | 0.2982 |
| C5 | 32.97 | 3.4730 | −0.2024 |
| C6 | 32.97 | 3.4730 | −0.0554 |
| H1 | 5.27 | 2.8464 | 0.1433 |
| H3 | 5.27 | 2.8464 | 0.0195 |

TABLE 5-continued

Force-field parameters for the adsorbates investigated and the CC3 host atoms.[a]

| H4 | 5.27 | 2.8464 | 0.0138 |
| H5 | 5.27 | 2.8464 | 0.0750 |
| H6 | 5.27 | 2.8464 | 0.0339 |

[a]The CAFF parameters (given here) for the CC3 host atoms were used in the MC simulations and not used in the MD simulations.

Figure 5:
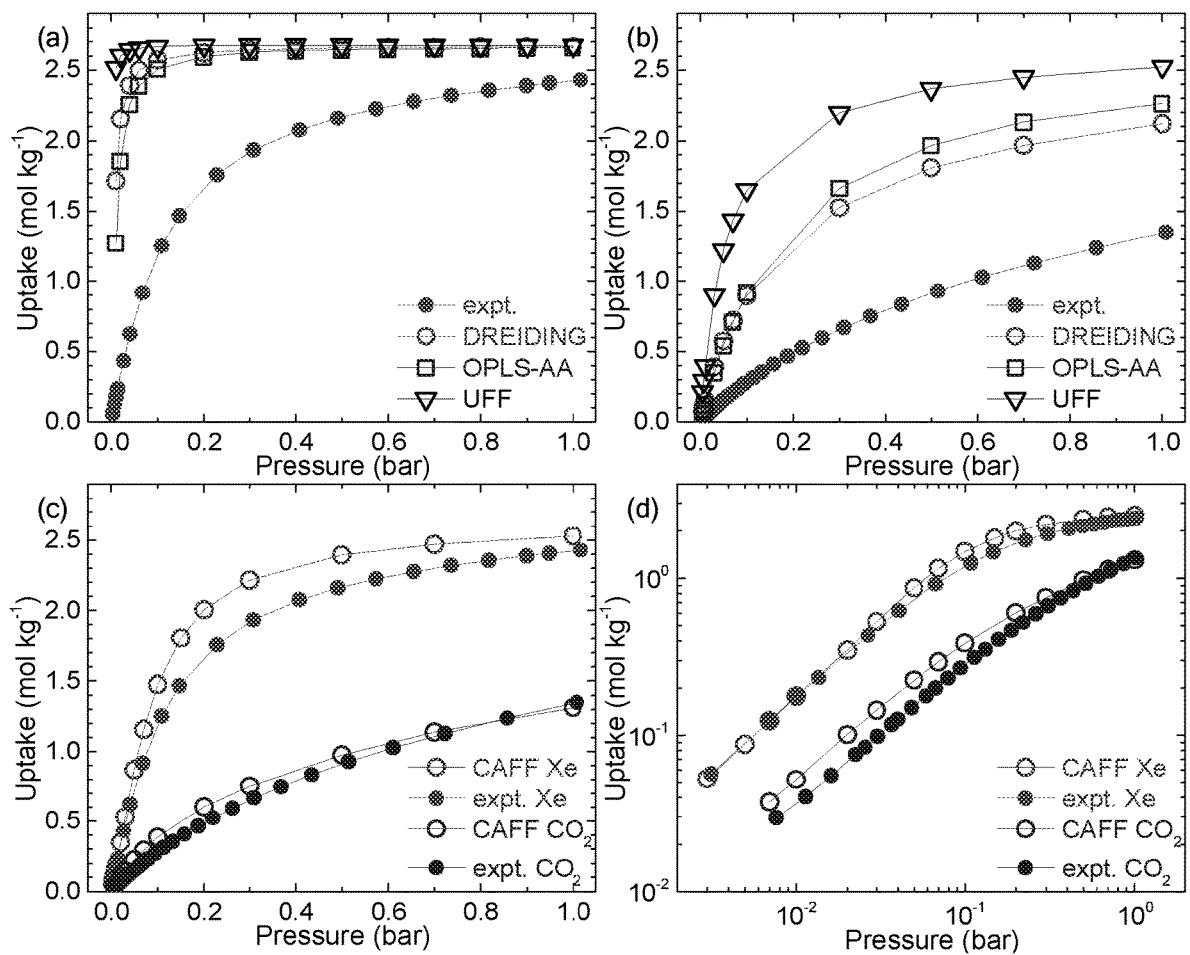
FIGS. 5a, 5b, 5c and 5d show a comparison between simulated and experimental Xe and CO2 adsorption isotherms at 298 K: (a) Xe and (b) CO2 isotherms predicted by three commonly-used literature force fields; (c) and (d), respectively, show linear-linear and log-log representations of the Xe and CO2 isotherms used in this work, based on the Cage Adsorption Force Field (CAFF).

Force Field for CC3. In a preliminary study, we tested the accuracies of five literature force fields—namely, AMBER,[36] CHARMM,[37] DREIDING,[27] OPLS-AA,[38] and UFF[39]—for representing the CC3 host in GCMC simulations. It was found that all of the five force fields yielded substantial overestimations for the adsorption of Xe, Kr, $CO_2$, and $CH_4$ on CC3 when compared to the experimental measurements at the same temperatures. For example, FIG. 5 (a, b) demonstrates the over-predictions of Xe and $CO_2$ uptakes at 298 K: the AMBER- and CHARMM-based isotherms were omitted for clarity, as they are largely identical to the ones given by OPLS-AA. To rationalize these significant discrepancies between simulation and experiment, we calculated binding energies, using the force fields, for a single rare gas atom inside the CC3 bulk crystal structure, and the results are summarized in Table 4. Comparing to the corresponding PBE-D3 binding energies, it is immediately clear that the overestimated sorption predictions are a direct consequence of the force fields overbinding the adsorbates with CC3. In light of this, we introduced one global scaling parameter (0.69) to the original DREIDING E parameters for the CC3 atoms, in order to reduce the host-guest binding strengths. The guest-guest interactions were not modified. With these modified parameters (CAFF), we could accurately reproduce experimental Xe, Kr, $CO_2$, and $CH_4$ adsorption isotherms for temperatures from 263-303 K and for pressures up to 1 bar; see FIG. 5 (c, d) for the examples of Xe and $CO_2$ adsorption at 298 K. This gave us confidence to extrapolate to other gases, such as Rn, where it was not possible to measure adsorption isotherms experimentally. The force-field parameters used to obtain the sorption simulation results reported in this work can all be found in Table 5.

FIGS. 5a, 5b, 5c and 5d show a comparison between simulated and experimental Xe and $CO_2$ adsorption isotherms at 298 K: (a) Xe and (b) $CO_2$ isotherms predicted by three commonly-used literature force fields; (c) and (d), respectively, show linear-linear and log-log representations of the Xe and $CO_2$ isotherms used in this work, based on the Cage Adsorption Force Field (CAFF).

Simulated Capture of Xe and Rn at Low Rare Gas Concentrations.

Figure 33:
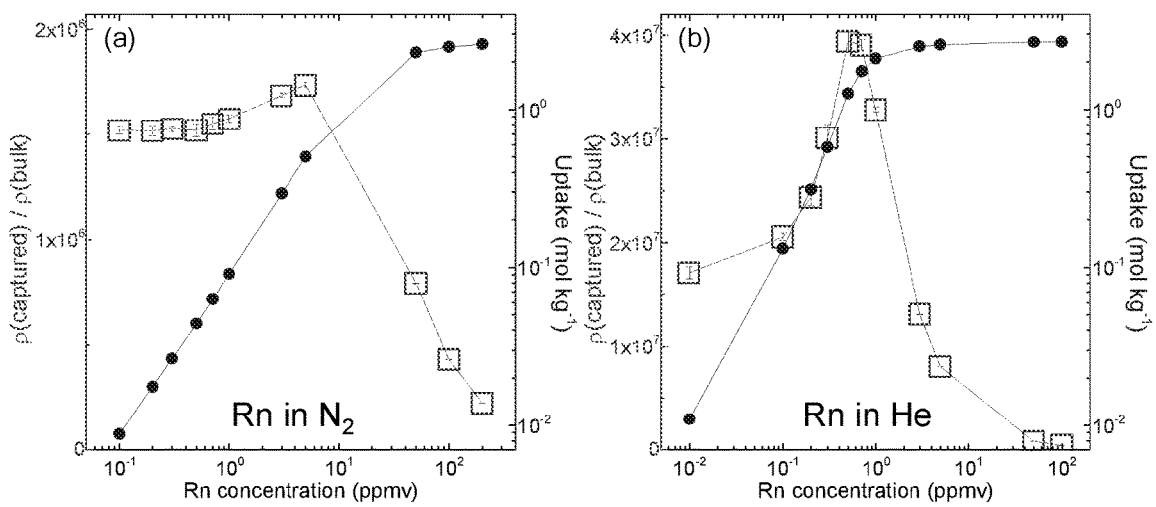
FIGS. 33a and 33b show the simulated removal of low concentrations of Xe and Rn impurities from two binary gas mixtures.

We evaluated the potential of the CC3 crystal for selective removal of low-concentration Xe and Rn from air under ambient conditions (i.e., 298 K and 1 bar) using competitive adsorption simulations. In the simulations, the 'air' was represented by a mixture of $N_2$, $O_2$, Ar, and $CO_2$, having a fixed ratio of 78:21:0.9:0.03. For example, 400 ppmv (0.04%) Xe was balanced by 78.0234% $N_2$, 21.0063% $O_2$, 0.9003% Ar, and 0.0300% $CO_2$. Likewise, 40,000 ppmv (4%) Xe was balanced by 74.9325% $N_2$, 20.1741% $O_2$, 0.8646% Ar, and 0.0288% $CO_2$. At 298 K and 1 bar, the simulated Xe uptake by CC3 for a bulk-phase Xe concentration of 400 ppmv is 0.009 mol kg$^{-1}$, in very good agreement with the experimental value of 0.011 mol kg$^{-1}$ derived from breakthrough experiments. In addition to investigating Rn removal from air, we also simulated the capture of Rn from pure nitrogen at 213 K to compare directly with experiments under those conditions (FIG. 33 and Table 9). We also simulated the capture of Rn from helium at 193 K, under conditions where we have not yet performed experiments. Both cases are of practical importance in particle physics and in astroparticle physics experiments working at low energies. At these lower temperatures, the simulations suggest that the CC3 material readily adsorbs appreciable amounts of Rn at rare gas concentrations as low as 0.01 ppmv Rn.

For each of the simulated separations discussed above, we plotted the volumetric density ratio of the rare gas in the solid adsorbent versus its volumetric density in the gas phase as the function of its concentration in the gas mixture. This is the quantity [ρ(captured)/ρ(bulk)] in FIG. 33 and FIG. 32 (b, c). This quantity is a measure of the ability of CC3 to selectively concentrate these rare gases in the solid state under various conditions. The bulk gas densities of Xe and Rn were calculated using the Peng-Robinson equation of state for given temperatures and pressures. The calculated Xe bulk densities were cross-examined against the experimental values available from the NIST Chemistry WebBook (no Rn data were available). Excellent agreement between the calculations and experimental values was found, with the largest difference being smaller than 0.08%.

Separation of Other Gas Mixtures.

Figure 6:
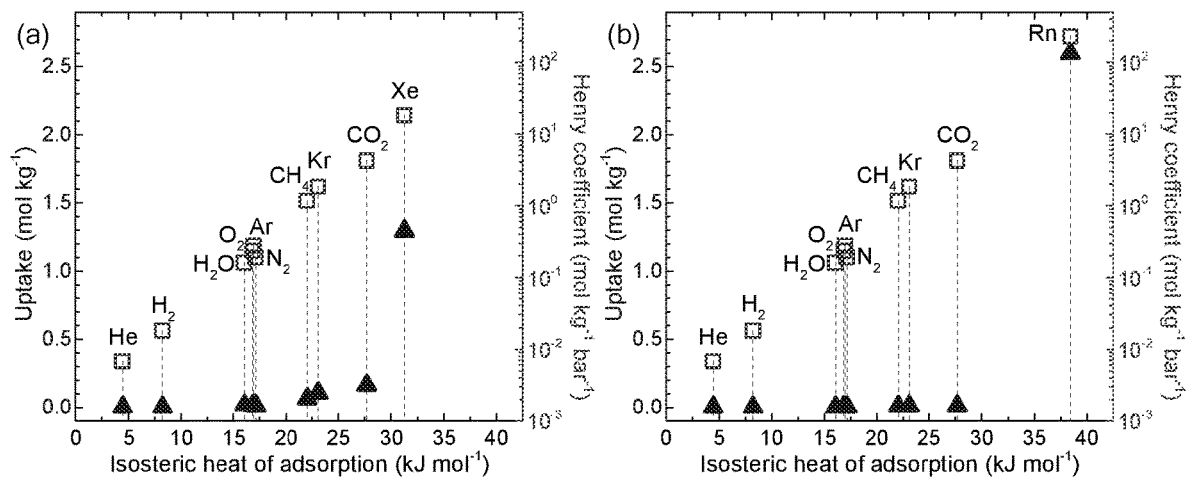
FIGS. 6a and 6b show graphs of additional seperate 10-component simulations for both Xe and Rn, respectively.

FIG. 2d and FIG. 6 report the computed zero-coverage isosteric heats of adsorption and Henry coefficients for 11 gases that include the main constituents of air. In addition to the rare gas separations, these data can also be used to estimate the potential of CC3 for separation of other gas mixtures. In the limit of zero-adsorbate loading, the adsorption selectivity can be inferred from the ratio of the Henry coefficients.[5] For example, we can expect CC3 to separate a binary mixture of $CO_2$ and $H_2$, because there is a big difference between their Henry coefficients (i.e., 4.295 vs. 0.018 mol kg$^{-1}$ bar$^{-1}$). This approach also applies to gas mixtures with more than two components. To further demonstrate that CC3 has potential for separating gas mixtures other than the rare gases, we performed GCMC simulations for competitive adsorption of equimolar binary mixtures of $CO_2/H_2$, $CO_2/N_2$, and $CO_2/CH_4$, all at 298 K and a total pressure of 1 bar. We chose these gas pairs because of the potential technological and industrial importance of these separations (e.g., in pre-combustion carbon capture, post-combustion carbon capture, and natural gas sweetening). From the GCMC simulations, we obtained selectivity values of 351.9, 21.0, and 2.1 for the mixtures of $CO_2/H_2$, $CO_2/N_2$, and $CO_2/CH_4$, respectively. For comparison, the ratios of the Henry coefficients for $CO_2/H_2$, $CO_2/N_2$, and $CO_2/CH_4$, respectively, are 238.6, 22.1, and 3.6. This fair agreement between the full GCMC results and the estimations from the ratios of the Henry coefficients suggests that we might also expect good selectivity, for example, for $CH_4/H_2$ mixtures, or for other gas pairs when there is a big difference in the respective Henry coefficients.

FIGS. 6a and 6b. FIG. 2d shows an 11-component equimolar simulation, which involved both Xe and Rn along with nine more common components of air. FIGS. 6a and 6b show graphs of additional seperate 10- component simulations which were carried out for both Xe and Rn, respectively, with these common air components. These equimolar competitive adsorption simulations were performed at 298 K and a total pressure of 1 bar. The gas uptakes were obtained from multi-component GCMC simulations; the zero-coverage isosteric heats of adsorption and Henry coefficients were computed by the Widom test particle method. As shown by comparison of FIG. 2d and FIG. 6a, the selectivity of CC3 for Xe with respect to the common gases in air is much higher in the absence of competing Rn. FIG. 6b illustrates the very higher selectivity of CC3 for Rn in air, in the absence of competing xenon: none of the other components in air competes effectively with Rn for the sorption sites in CC3, suggesting potential for Rn concentration and detection technologies. This may overcome problems with less ordered porous materials, such as activated carbon, where other guests (e.g., water) can compete for adsorption sites in the material, which unlike CC3 comprises a range of pore sizes, pore shapes, and surface chemical functionalities.

Figure 7:
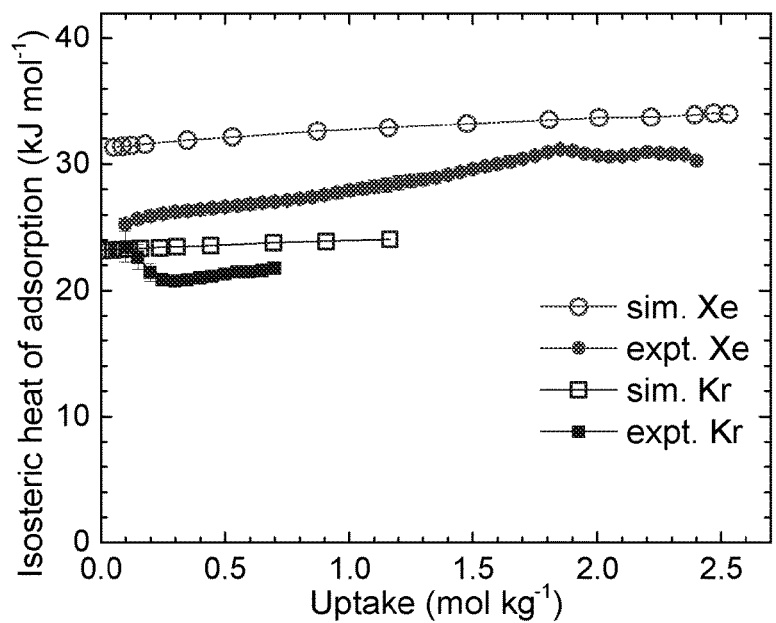
FIG. 7 shows a comparison of experimental and simulated isosteric heats of adsorption for Xe and Kr on CC3.

FIG. 7 shows a comparison of experimental and simulated isosteric heats of adsorption for Xe and Kr on CC3. The simulations were performed at 298 K. The experimental data are the same as those shown separately in FIGS. 14 and 19, along with associated and differential molar heats. The isosteric heat for Xe rises with coverage because of additional Xe . . . Xe interactions that occur at higher gas loadings.

Gas Sorption Analysis.

Xenon (Xe) and krypton (Kr) adsorption/desorption isotherms (FIG. 8) were measured using a Micromeritics ASAP 2020 volumetric adsorption analyser. Carbon dioxide adsorption/desorption isotherms (FIG. 9) were measured using a Micromeritics ASAP 2050 volumetric adsorption analyser. Powder samples were degassed offline at 110° C. for 15 hours under dynamic vacuum ($10^{-5}$ bar) before analysis, followed by degassing on the analysis port under vacuum, also at 110° C. The temperature was controlled by a Haake C40P circulating chiller.

Figure 8:
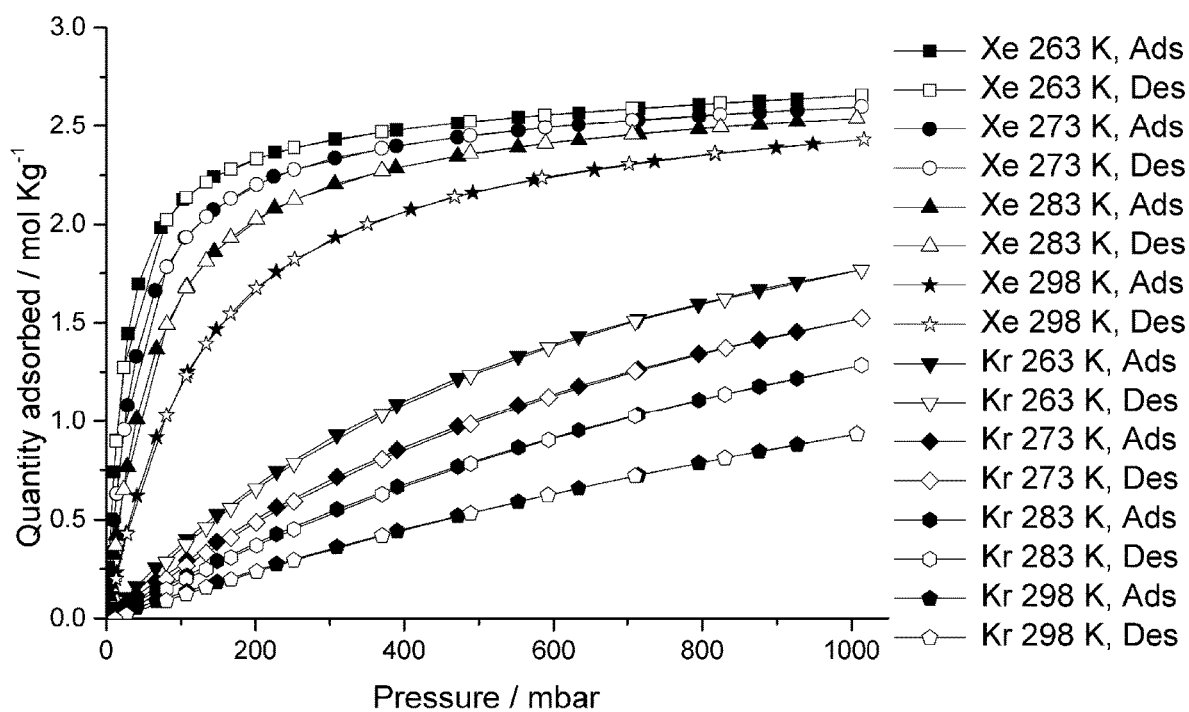
FIG. 8 shows adorption isotherms and desorption isotherms for Xe and Kr on CC3 up to 1 bar pressure and over a range of temperatures between 263 K and 298 K.

FIG. 8 shows adsorption isotherms (solid symbols) and desorption isotherms (open symbols) for Xe and Kr on CC3 up to 1 bar pressure over a range of temperatures between 263 K and 298 K.

Figure 9:
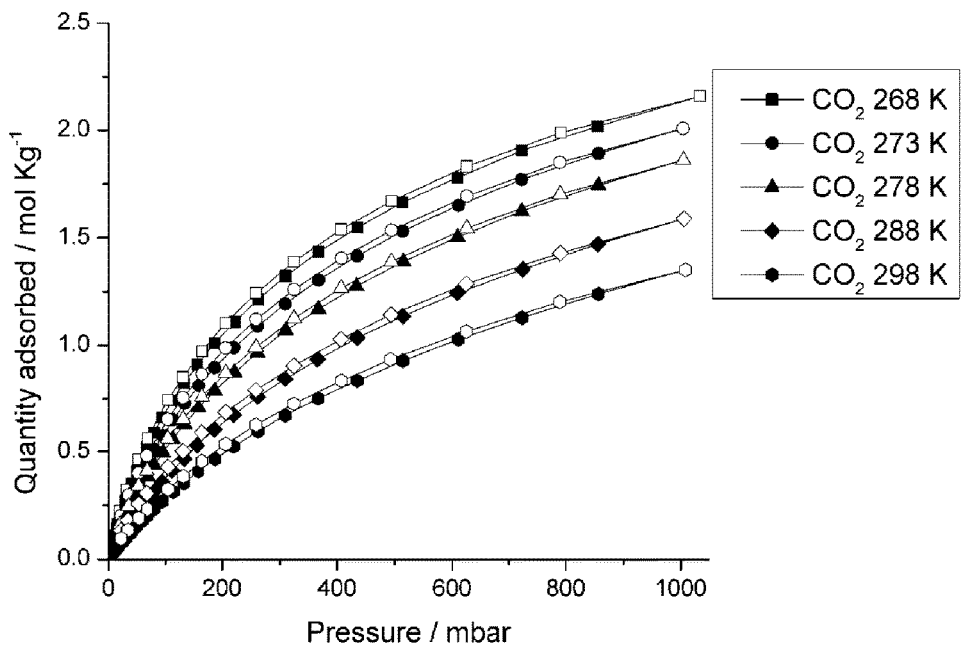
FIG. 9 shows adorption isotherms and desorption isotherms for carbon dioxide on CC3, up to 1 bar pressure and over a range of temperatures between 268 K and 298 K.

FIG. 9 shows adsorption isotherms (solid symbols) and desorption isotherms (open symbols) for carbon dioxide on CC3, up to 1 bar pressure and over a range of temperatures between 268 K and 298 K. Heats of adsorption, determined using the standard calculation routines in the Data-master offline data reduction software (Micromeritics), gave initial, low-coverage $Q_{st}$ values for $CO_2$ of 22-27 kJ mol$^{-1}$ (between 0.04 and 0.1 mol kg$^{-1}$ loading).

Heats of Adsorption.

Gas adsorption isotherms for Xe and Kr (FIGS. 10 and 15) were measured using an IGA gravimetric analyser (Hiden Isochema, IGA-001, Warrington, UK).

This is an ultra-high vacuum (UHV) system comprising a computer-controlled microbalance with both pressure and temperature regulation systems. About 100 mg of CC3 sample was introduced into the IGA for gas sorption measurements. This sample was outgassed to a constant, accurate weight at <$10^{-6}$ Pa and 393 K prior to adsorption measurements. The microbalance had a long-term stability of ±1 µg with a weighing resolution of 0.2 µg. The pressure transducers had ranges of 0-2 mbar, 0-100 mbar and 0-1 bar. The set pressure point was maintained by computer control throughout the course of the experiment. The sample temperature was measured using a thermocouple located 5 mm from the sample. Xe and Kr sorption isotherms were carried out using a circulating water/ethylene glycol bath (268-308 K) and dry ice/acetone (195 K).

Saturated vapor pressures were calculated using the Antoine equation:

$$\log p^0 = A - \frac{B}{T+C}$$

where $p^0$ is the saturated vapor pressure (Torr), T is the temperature (K), and A, B, and C are adsorbate dependent constants. The parameters used for each adsorptive are as follows: Kr (116-209 K) (A) 6.6307, (B) 416.38, (C) 264.45; Xe (161-290 K) (A) 6.64289, (B) 566.282, (C) 2580.660.[56]

Determination of the heat of adsorption at zero surface coverage, which is a fundamental measure of the adsorbate-adsorbent interaction, can be calculated by analysis of the isotherms using the virial equation, which has the form:[56]

$$\ln\left(\frac{n}{p}\right) = A_0 + A_1 n + A_2 n^2 + \ldots$$

where p is pressure, n is the amount adsorbed and $A_0, A_1, A_2$, etc., are virial coefficients. At low surface coverage, $A_2$ and $A_3$ can be neglected. Plotting ln(n/p) gives a straight line graph with the gradient $A_1$ describing adsorbate-adsorbate interactions and the intercept $A_0$ describing adsorbate-adsorbent interactions. At low surface coverage, the virial equation reduces to Henry's Law.[57] However, the $A_1$ parameter for isotherms in the range 198-298 K was very small at low surface and the isotherms were linear following Henry's Law:

$$n = K_H P$$

where n is amount adsorbed, $K_H$ is the Henry's law constant and P is the pressure.

Adherence to Henry's Law is indicative of weak interactions between adsorbate molecules at low surface coverage.

The isostericheat at zero surface coverage was calculated using the following equation:

$$Q_{st,n=0} = RT^2 \left(\frac{\partial (\ln K_H)}{\partial T}\right)_n$$

where $Q_{st, n=0}$ is the isosteric enthalpy of adsorption at zero surface coverage, T is the temperature, R is the universal gas constant and $K_H$ is the Henry constant. Therefore, the gradient of $\ln(K_H)$ vs. 1/T, at constant amount adsorbed, is equal to $Q_{st}/R$.

Figure 11:
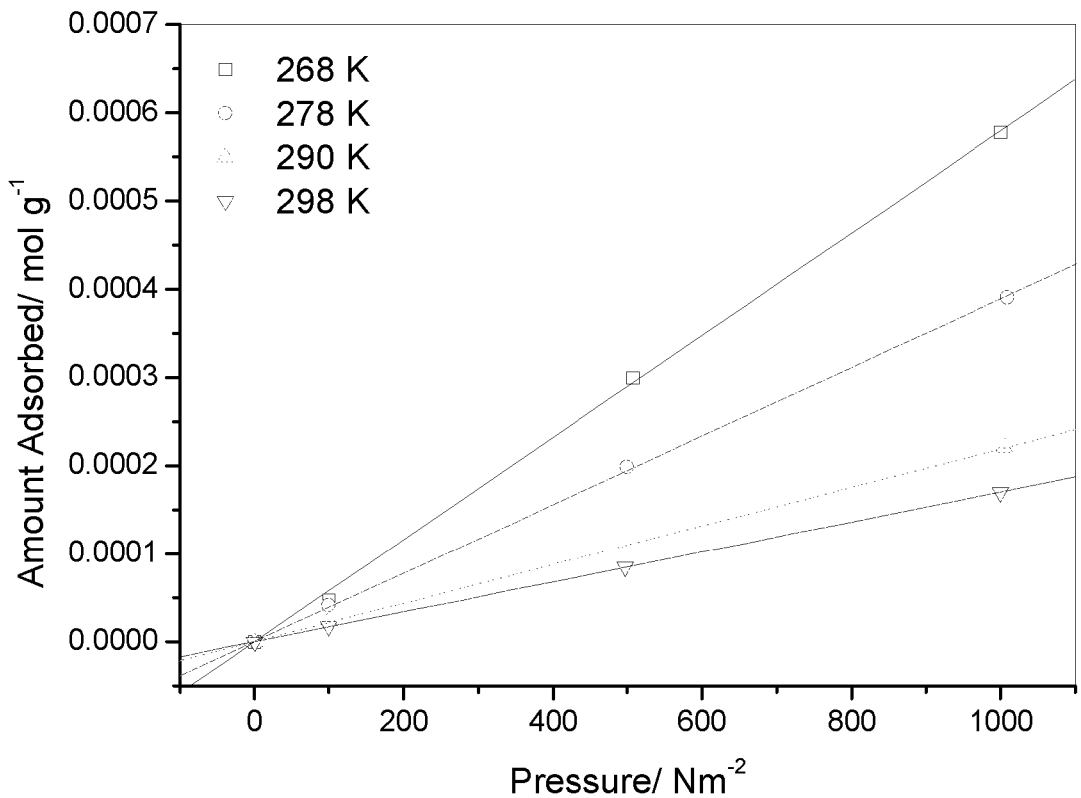
FIG. 11 shows Henry's Law region for the Xe isotherms at 268 K, 278 K, 290 K and 298 K.

The adherence of the xenon isotherms to the Henry's Law region in the temperature range 268-298 K is shown in FIG. 11. The isotherms at 268 K, 278 K, 290 K and 298 K are linear over the range 0-25.0 mbar (0-1000 Pascal). The $K_H$ constants are tabulated in Table 6, which range from 1.70× 10$^{-7}$ g mol$^{-1}$ Pa$^{-1}$ at 298 K to 5.80 g mol$^{-1}$ Pa$^{-1}$ at 268 K. There were insufficient low pressure points in the Henry's Law region for the 198 K isotherm, resulting in the exclusion of the 198 K data from the calculation of $Q_{st}$ at zero surface coverage. Resolution of the Henry's Law region could not be achieved for the 198 K isotherm because addition of low pressure points would prevent isothermal conditions due to the low thermal conductivity of Xe. An isosteric heat at zero surface coverage of 27.80±1.20 kJ mol$^{-1}$ was calculated from the gradient of a graph of ln(K$_H$) vs. 1/T (FIG. 12) for the temperature range 268-298 K.

Figure 13:
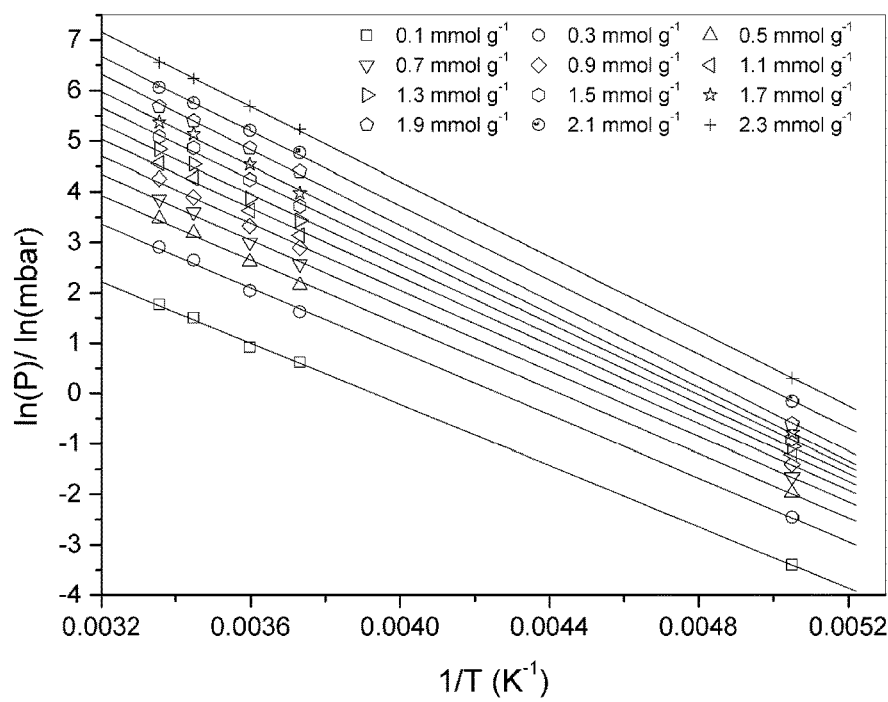
FIG. 13 shows van't Hoff isochore graphs for Xe adsorption on CC3 for temperatures 198 K, 268 K, 278 K, 290 K and 298 K, as a function of the amount adorbed (n) ranging from 0.1-2.3 mmol $g^1$.
Figure 14:
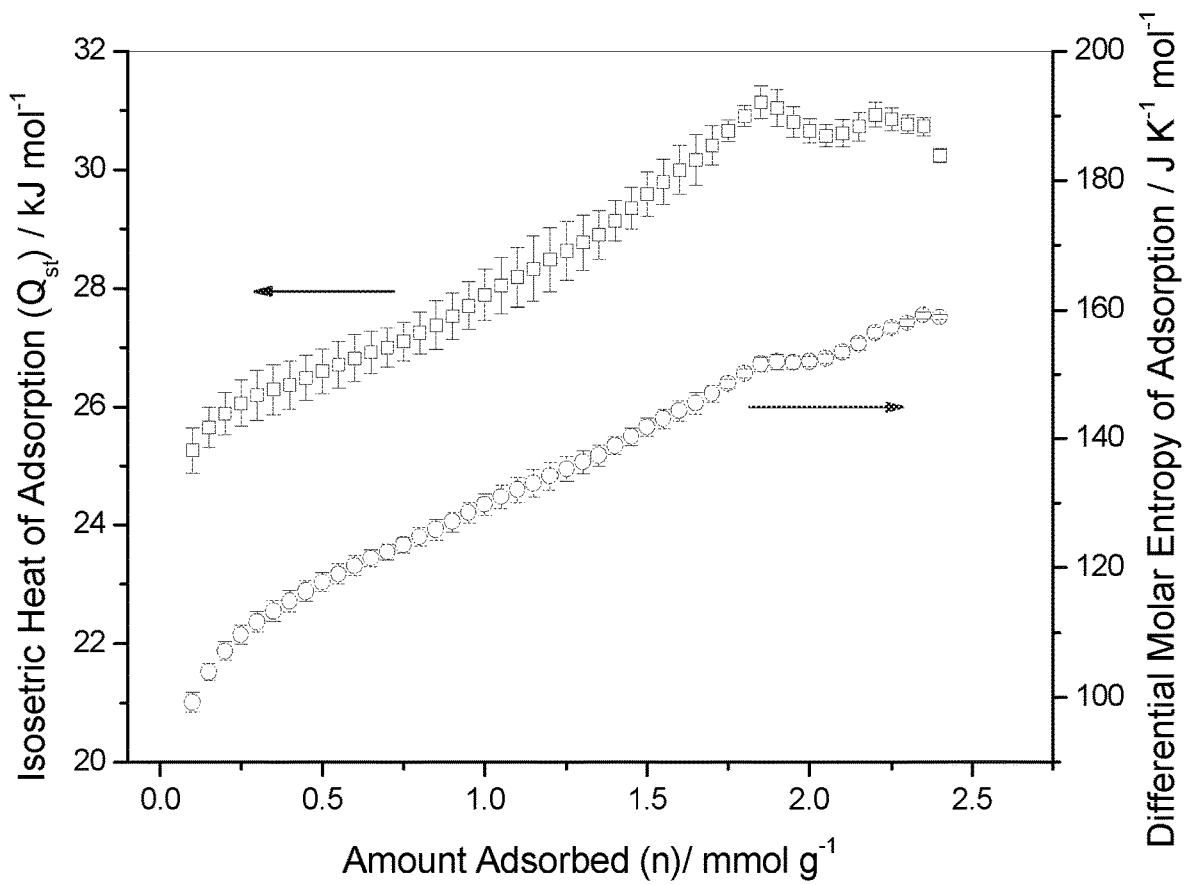
FIG. 14 shows isoteric heat ($Q_{st}$/ kl $mol^{-1}$) and differential molar heat ($\Delta S/J\ K^{-1}mol^{-1}$) of adsorption for Xe as a function of the amount adsorbed (mmol $g^{-1}$) for the temperature range 198-298 K.

Isosteric heats at increasing amounts of gas adsorbed were calculated from Van't Hoff isochores as show in FIG. 13. Since ln(P)=−dH/RT+dS/R, a plot of ln(P) vs 1/T will give a line with a slope of −Q$_{st}$/R and an intercept equal to dS/R. A linear interpolation between isotherm points was used to calculate the pressure for fixed amounts adsorbed in the temperature range 198-298 K. FIG. 14 shows Q$_{st}$ and ΔS vs. the amount adsorbed for the uptake range 0.1-2.4 mmol g$^{-1}$. The Q$_{st}$ increases from 25.26±0.38 kJ mol$^{-1}$ at 0.1 mmol g$^{-1}$ to 31.14±1.48 kJ mol$^{-1}$ at 1.85 mmol g$^{-1}$. From 1.85 to 2.4 mmol g$^{-1}$ Q$_{st}$ varies between 31.14±0.28 kJ mol$^{-1}$ and 30.24±0.12 kJ mol$^{-1}$. This increase is indicative of progressively stronger adsorbate-adsorbate interactions during pore filling. The enthalpy of adsorption at zero surface coverage obtained from plots of K$_H$ VS. 1/T is consistent with differential molar enthalpies calculated at low surface coverage from Van't Hoff isochores.

TABLE 6

Henry's Law constants for Xe adsorption on CC3 at 268, 278, 290 and 298 K.

| Temperature (K) | K$_H$ (×10$^{-7}$ mol g$^{-1}$ Pa$^{-1}$) | Ln (K$_H$) (ln (mol g$^{-1}$ Pa$^{-1}$)) |
|---|---|---|
| 268 | 5.80 | −14.36 |
| 278 | 3.89 | −14.76 |
| 290 | 2.19 | −15.33 |
| 298 | 1.70 | −15.59 |

Figure 10:
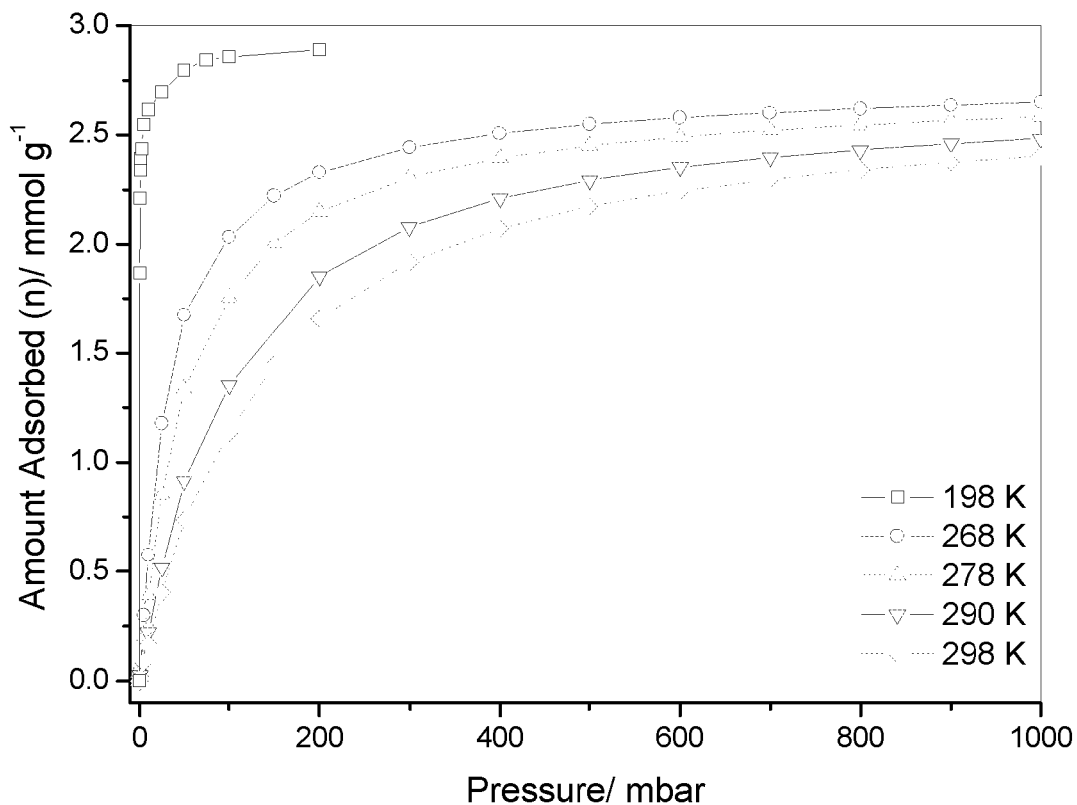
FIG. 10 shows adsorption isotherms for Xe on CC3 at 198 K, 268 K, 278 K, 290 K and 298 K.

FIG. 10 shows adsorption isotherms for Xe on CC3 at 198 K, 268 K, 278 K, 290 K and 298 K.

FIG. 11 shows Henry's Law region, covering the pressure range 0-1000 Pa, for the Xe isotherms at 268 K, 278 K, 290 K and 298 K.

Figure 12:
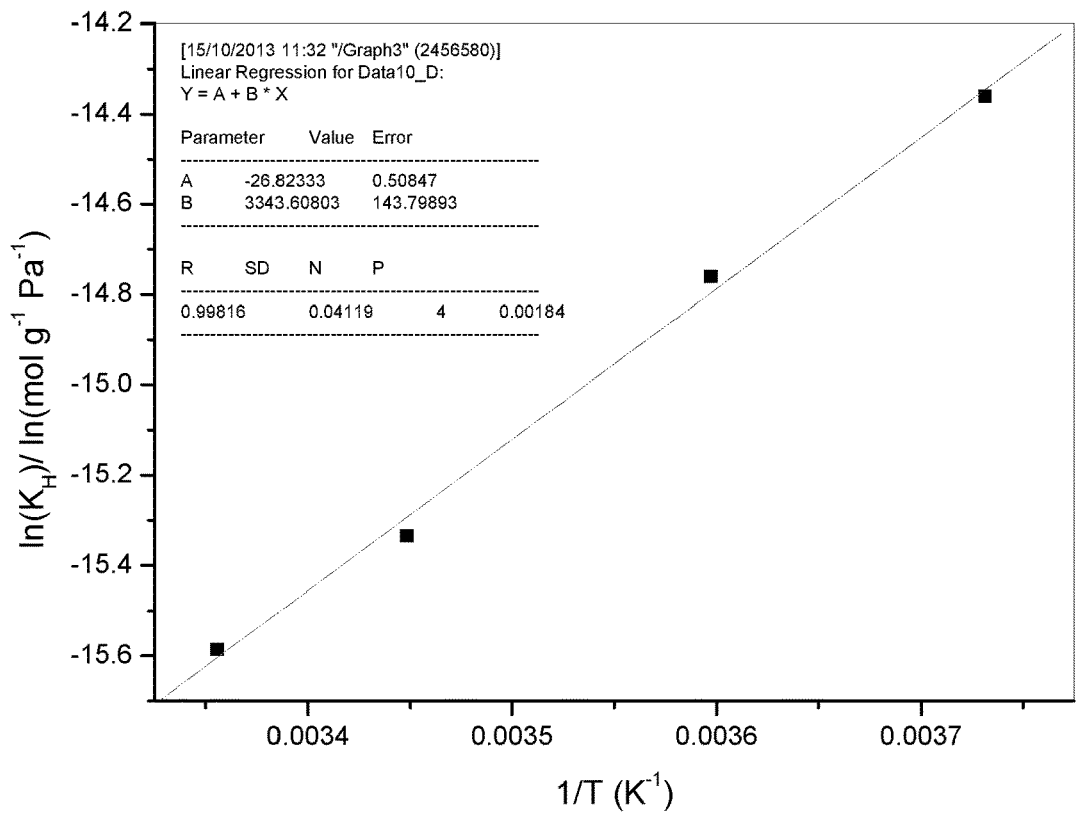
FIG. 12 shows a graph of $\ln(K_h)$ vs. 1/T for calculation of $Q^{st}$ at zero surface coverage for Xe adsorption on CC3.

FIG. 12 shows a graph of ln(K$_H$) vs. 1/T for calculation of Q$_{st}$ at zero surface coverage for Xe adsorption on CC3.

FIG. 13 shows van't Hoff isochore graphs for Xe adsorption on CC3 for temperatures 198 K, 268 K, 278 K, 290 K and 298 K, as a function of the amount adsorbed (n) ranging from 0.1-2.3 mmol g$^{-1}$.

FIG. 14 shows isosteric heat (Q$_{st}$/kJ mol$^{-1}$) and differential molar heat (ΔS/J K$^{-1}$ mol$^{-1}$) of adsorption for Xe as a function of the amount adsorbed (mmol g$^{-1}$) for the temperature range 198-298 K.

Figure 15:
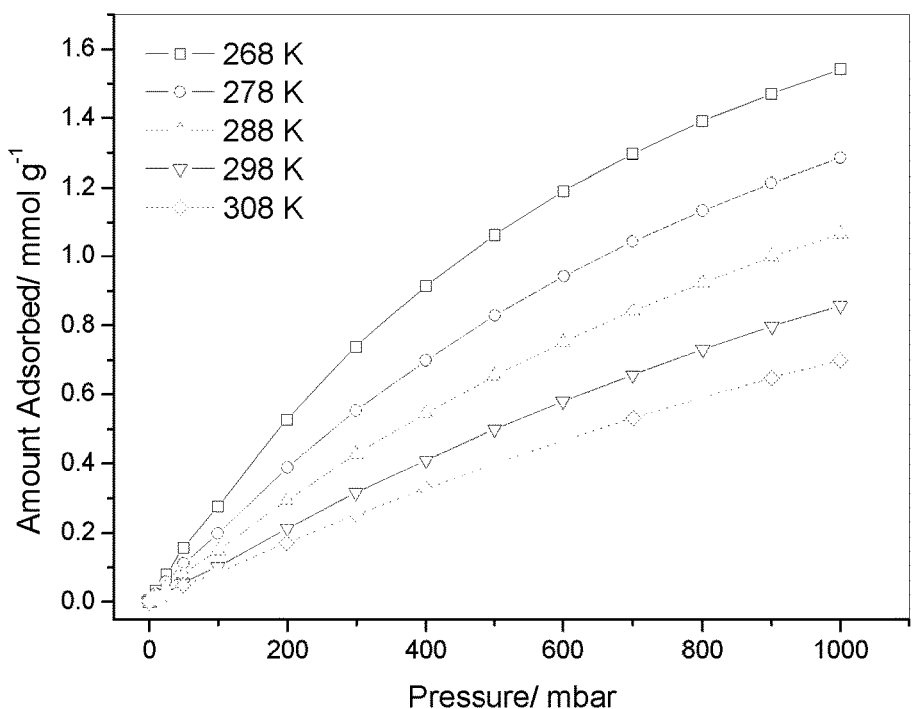
FIG. 15 shows adsorption isotherms for Kr on CC3 at 198 K, 268 K, 278 K, 290 K and 298 K.

FIG. 15 shows adsorption isotherms for Kr on CC3 at 198 K, 268 K, 278 K, 290 K and 298 K.

Figure 16:
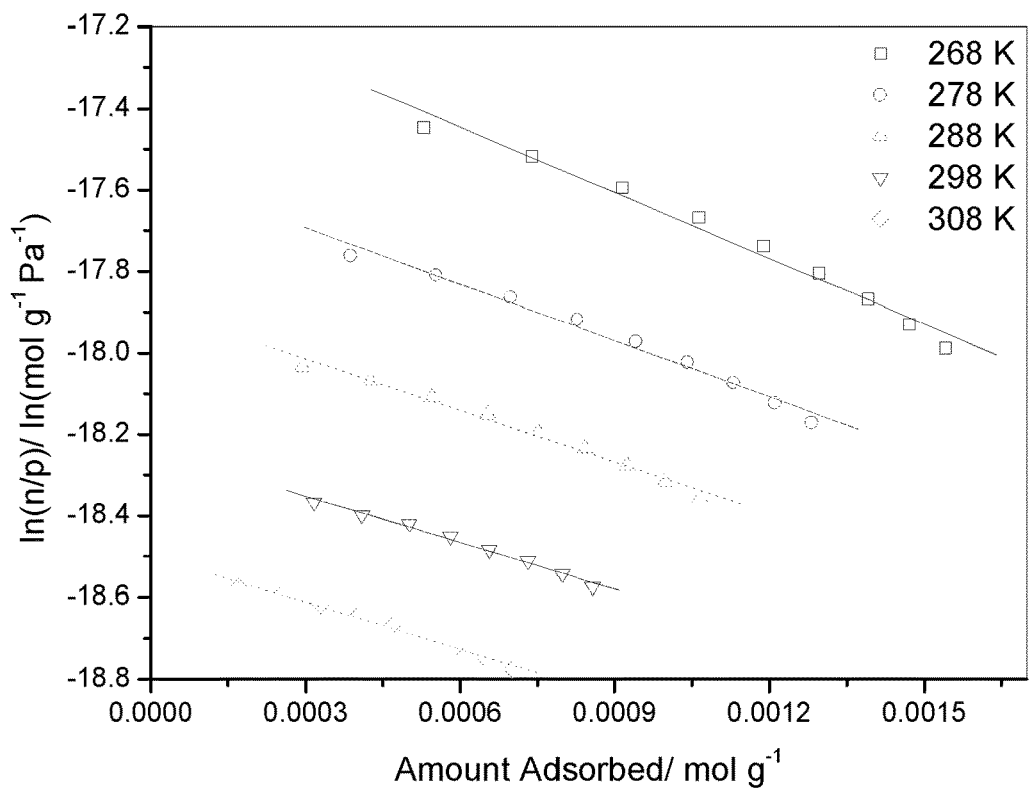
FIG. 16 shows vrial graphs for krypton adsorption on CC3 at 268 K, 278 K, 288 K, 298 K and 308 K.

FIG. 16 shows vrial graphs for krypton adsorption on CC3 at 268 K, 278 K, 288 K, 298 K and 308 K.

Figure 17:
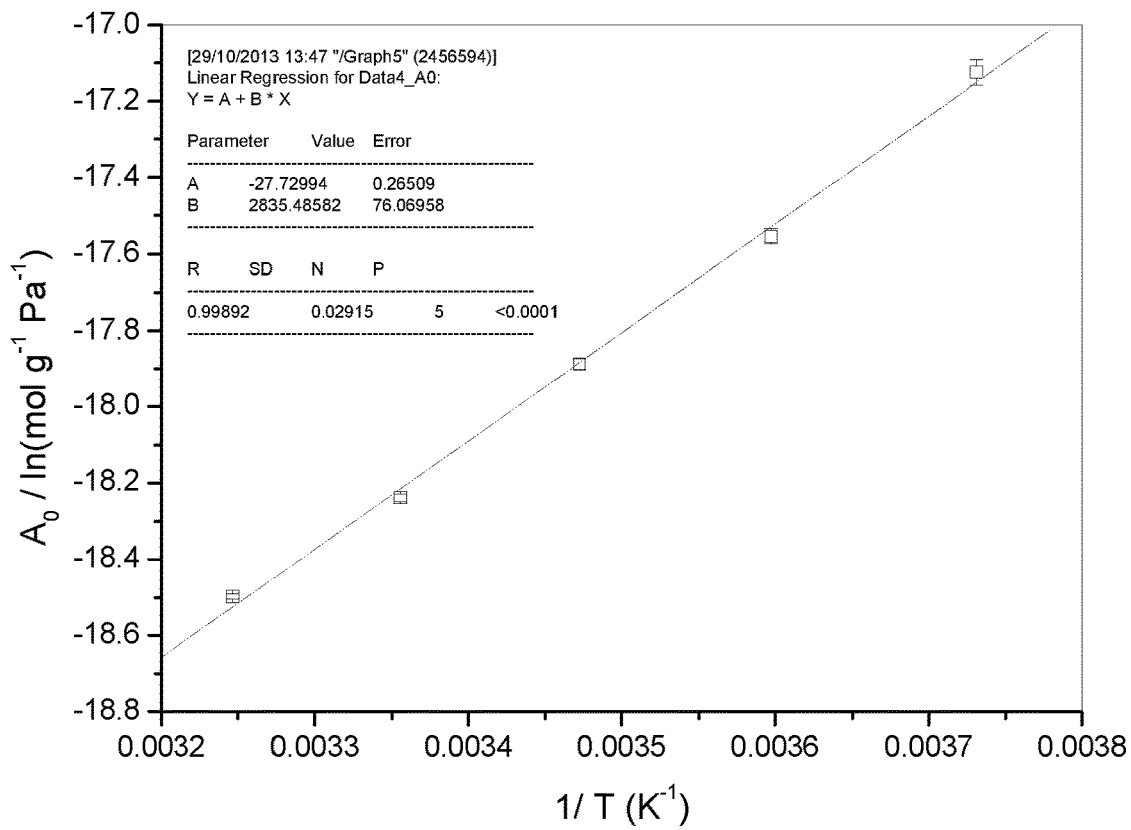
FIG. 17 shows a graph of $A^g$ vs. 1/T for krypton adsorption on CC3 for 268 K, 278 K, 288 K, 298 K and 308 K for calculation of $Q_g$ at zero surface coverage ($Q_{g=}23.57\pm0.63$ kl $mol^{-1}$).

FIG. 17 shows a graph of A$_0$ vs. 1/T for krypton adsorption on CC3 for 268 K, 278 K, 288 K, 298 K and 308 K for calculation of Q$_{st}$ at zero surface coverage (Q$_{st}$=23.57±0.63 kJ mol$^{-1}$).

Figure 18:
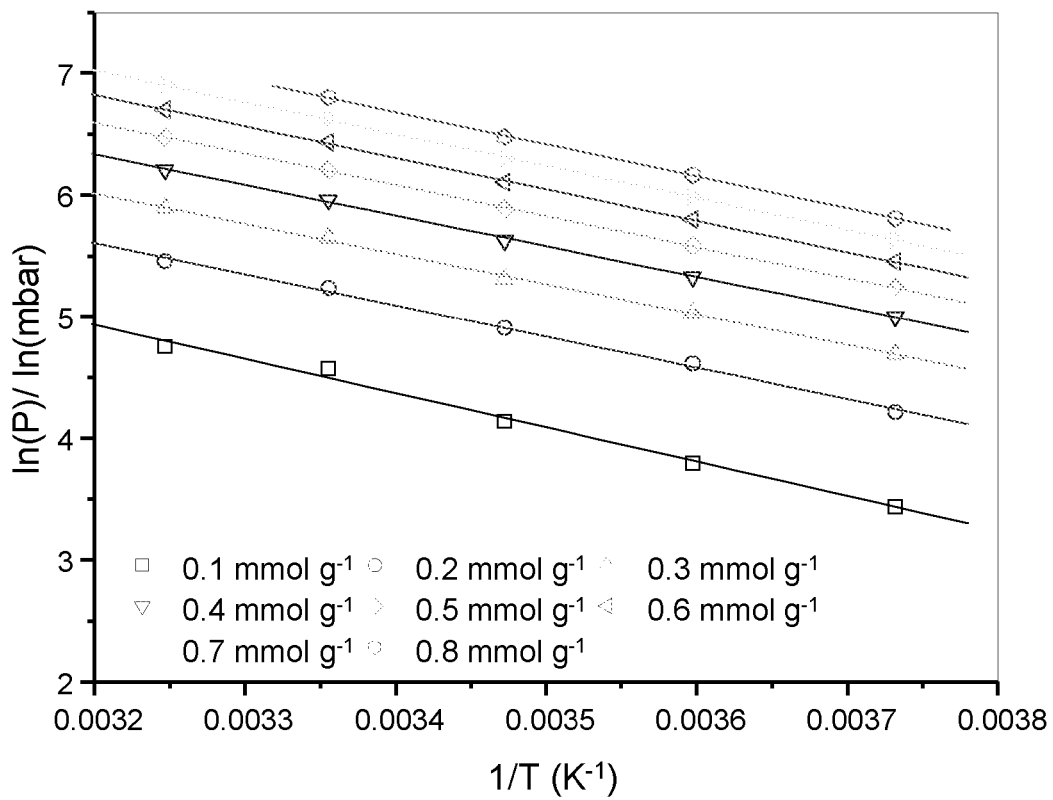
FIG. 18 shows van't Hoff Isochore graphs for Kr adsorption on CC3 at 0.1-0.8 mmol $g^{-1}$ for the temperature range 268-308 K (0.8 mmol $g^{-1}$) for the temperature range 268-308 K.

FIG. 18 shows van't Hoff Isochore graphs for Kr adsorption on CC3 at 0.1-0.8 mmol g$^{-1}$ for the temperature range 268-308 K (0.8 mmol g$^{-1}$ temperature range=268-298 K).

Figure 19:
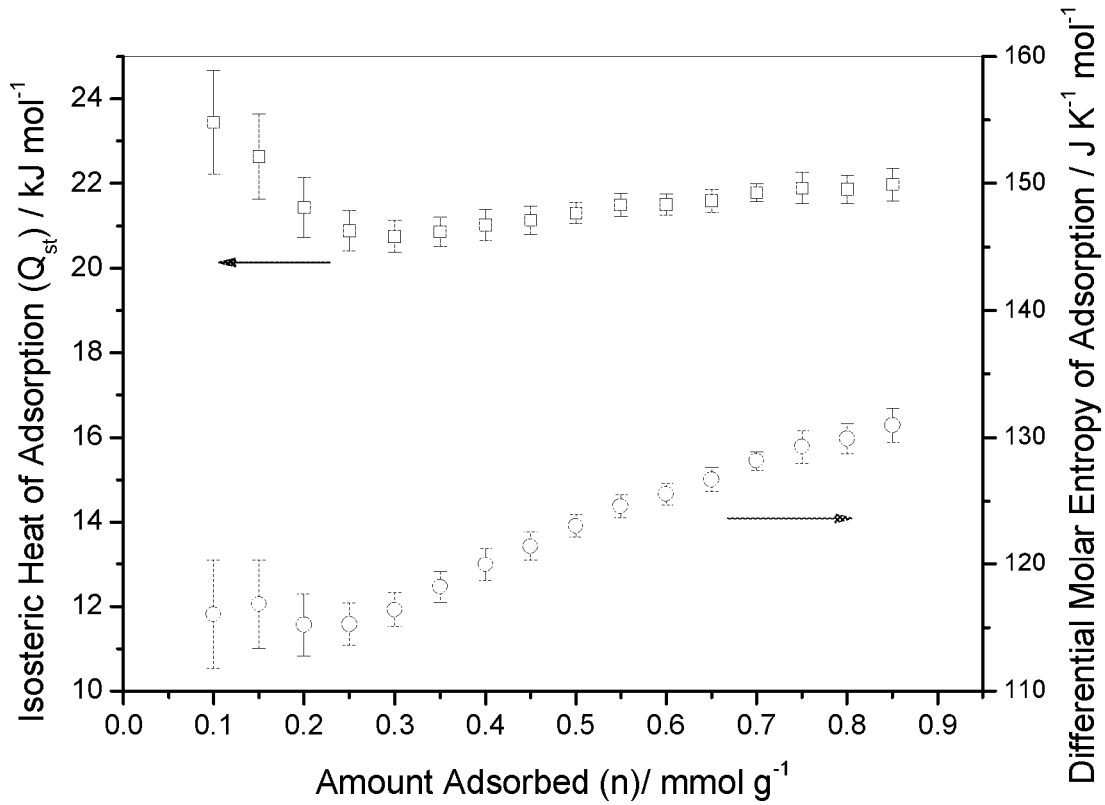
FIG. 19 shows isosteric heat ($Q_g$/ kl mol $^{-1}$) and differential molar heat ($\Delta S/JK^{-1}\ mol^{-1}$) of adsorption for Kr as a function of the amount adsorbed (mmol $g^{-1}$) for the temperature range 268-308 K.

FIG. 19 shows isosteric heat (Q$_{st}$/kJ mol$^{-1}$) and differential molar heat (ΔS/J K$^{-1}$ mol$^{-1}$) of adsorption for Kr as a function of the amount adsorbed (mmol g$^{-1}$) for the temperature range 268-308 K.

Figure 20:
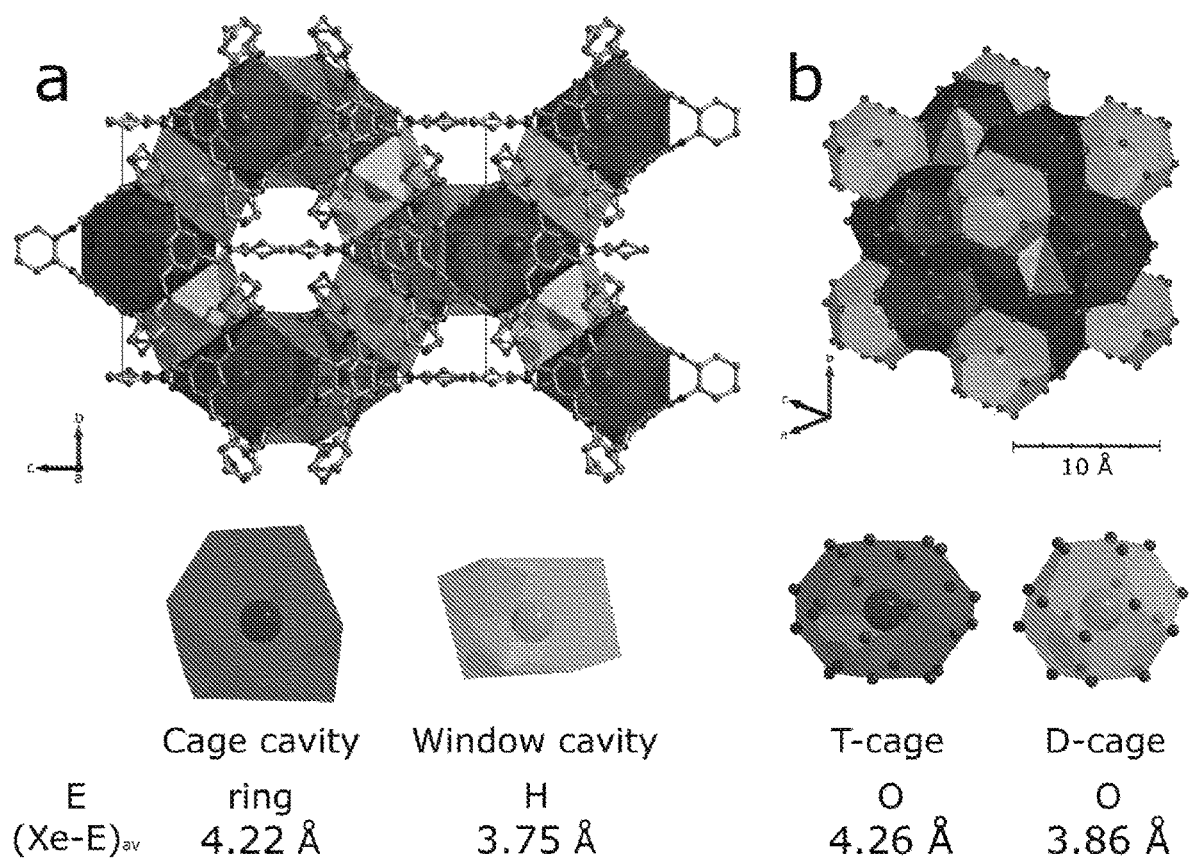
FIGS. 20a and 20b show (a) the structure of CC3 under an excess pressure of xenon (10bar, 295 K) and (B) the structure of a known xenon hydrate.

Powder X-ray diffraction data were used to determine the structure of CC3 under an excess pressure of xenon (10 bar, 295 K, FIG. 20a). FIGS. 20a and 20b show a) the structure of CC3 under an excess pressure of xenon (10 bar, 295 K) and b) the structure of the known xenon hydrate [Yang, L. et al. Synthesis and characterization of a new structure of gas hydrate. *Proc. Natl. Acad. Sci. U.S.A.* 106, 6060-6064, (2009); Ohgaki, K., Sugahara, T., Suzuki, M. & Jindai, H. Phase behavior of xenon hydrate system. *Fluid Phase Equilib.* 175, 1-6, (2000)].

Single xenon atoms were located in the cage cavities (shown dark in FIG. 20) and in the window cavities (light).

At this pressure, the cage cavity is fully occupied, while the window cavity is 88±1% occupied, resulting in a total of 2.8 xenon atoms per cage (1.87 mol kg$^{-1}$, 25 wt. %). A comparison can be made between this pre-structured porous organic clathrate and the known xenon hydrate (FIG. 20b).

At 40 K and 1.01 bar, xenon hydrate adopts a type I clathrate structure in which the polyhedral T-cages and D-cages are 82% and 80% occupied (overall 3.87 mol kg$^{-1}$ Xe, 51 wt. %) with average Xe—O distances of 4.26 Å and 3.86 Å, respectively. In Xe-loaded CC3, the closest atoms from the CC3 molecule form analogous, polyhedral organic cages around the xenon guest (Table 7). The shortest contact distances between the cage molecule and xenon guests are comparable with the xenon hydrate cages: the average Xe . . . phenyl ring centroid distance for the cage cavity is 4.22 Å, while short Xe . . . H contacts with a mean distance of 3.75 Å are present in the window cavity. The volumetric density of enclathrated xenon in CC3 close to saturation is 0.31 g cm$^{-3}$. This is lower than in xenon hydrate (0.85 g cm$^{-3}$) but CC3, unlike the hydrate, is stable to removal of the xenon guest, and retains a preorganised host structure that can capture xenon at low partial gas pressures. The structure of CC3-R Kr-loaded at 9.8 bar was determined by analogous in situ PXRD experiments. This structure indicates that the krypton atoms are hosted in the cage cavity and cage window sites, with a decreased overall occupancy with respect to the xenon-loaded CC3 structure of 2.1±0.1 Kr atoms per cage (1.63 mol kg$^{-1}$, 13 wt. %), reflecting the much lower simulated and measured affinity of Kr for CC3 (FIG. 2c,d).

TABLE 7

Xe-cage contact distances in CC3•2.8Xe.

| C . . . Xe1 | C . . . Xe1/Å |
|---|---|
| C1 . . . Xe1$^i$ | 4.17 (3) |
| C2 . . . Xe1$^i$ | 4.04 (4) |
| C3 . . . Xe1$^i$ | 4.15 (4) |
| C4 . . . Xe1$^i$ | 4.34 (3) |
| C5 . . . Xe1$^i$ | 4.47 (3) |
| C6 . . . Xe1$^i$ | 4.30 (3) |
| C7 . . . Xe1$^i$ | 4.82 (2) |
| C8 . . . Xe1$^i$ | 4.91 (4) |
| C9 . . . Xe1$^i$ | 5.07 (4) |
| Cg1 . . . Xe1$^i$ | 4.02 (2) |
| C10 . . . Xe1$^i$ | 4.62 (3) |
| C11 . . . Xe1$^i$ | 4.57 (4) |
| C12 . . . Xe1$^i$ | 4.65 (4) |
| C13 . . . Xe1$^i$ | 4.70 (4) |
| C14 . . . Xe1$^i$ | 4.65 (3) |
| C15 . . . Xe1$^i$ | 4.56 (3) |
| C16 . . . Xe1$^i$ | 5.33 (3) |
| C17 . . . Xe1$^i$ | 5.18 (4) |
| C18 . . . Xe1$^i$ | 4.93 (4) |
| Cg2 . . . Xe1$^i$ | 4.41 (2) |

| C—H . . . Xe2 | H . . . Xe2/Å | C(—H) . . . Xe2/Å |
|---|---|---|
| C2—H2 . . . Xe2$^i$ | 3.71 (3) | 4.52 (3) |
| C4—H4 . . . Xe2$^{ii}$ | 3.83 (3) | 4.52 (3) |
| C6—H6 . . . Xe2$^{iii}$ | 3.49 (3) | 4.30 (3) |
| C7—H7 . . . Xe2$^i$ | 3.52 (3) | 4.37 (3) |
| C8—H8 . . . Xe2$^{ii}$ | 3.63 (3) | 4.35 (3) |

TABLE 7-continued

Xe-cage contact distances in CC3·2.8Xe.

| | | |
|---|---|---|
| C9—H9 . . . Xe2$^{iii}$ | 3.47 (3) | 4.21 (3) |
| C11—H11 . . . Xe2$^{iii}$ | 3.81 (3) | 4.51 (3) |
| C13—H13 . . . Xe2$^{iv}$ | 3.95 (3) | 4.54 (3) |
| C15—H15 . . . Xe2$^{i}$ | 3.80 (3) | 4.56 (3) |
| C16—H16 . . . Xe2$^{iii}$ | 4.42 (4) | 4.63 (4) |
| C17—H17 . . . Xe2$^{iv}$ | 3.83 (3) | 4.40 (3) |
| C18—H18 . . . Xe2$^{i}$ | 3.49 (3) | 4.37 (3) |

Symmetry codes:
$^{i}$y - ½, 1 - x, z - ¼;
$^{ii}$½ - y, x, z - ¼;
$^{iii}$x, y, z;
$^{iv}$1 - x, 1 - y, z.

Xe1 occupies 4α cage cavity site. Cg1 and Cg2 are ring centroids formed by C1-C6 and C10-C15, respectively. Xe2 resides on general window position.

Powder X-Ray Diffraction.

The gas adsorption of Xe in CC3 was studied in situ using powder diffraction data collected at beamline I11 at the Diamond Light Source. Finely ground samples of slowly-crystallised CC3 were dried in a vacuum oven at 80° C. for 12 hours. These were then packed in 0.7 mm diameter borosilicate capillaries and mounted on the low-pressure capillary gas cell.[40] The sample was exposed to dynamic vacuum (approximately 10$^{-5}$ bar) and heated to 425 K using an Oxford Cryostream Plus to fully evacuate the sample. Data were collected using the Mythen-II position sensitive detector (PSD)[41] at 295 K to obtain an initial powder diffraction profile of guest-free CC3. The sample was rocked through 20° in θ to improve powder averaging; nonetheless, a small number of sharp peaks in some datasets indicated the presence of large crystallites in the exposed sample. Where possible, a new section of the capillary was exposed. Xenon gas was dosed into the system in a number of pressure steps, up to a maximum of 10.1 bar (FIG. 21).

Figure 21:
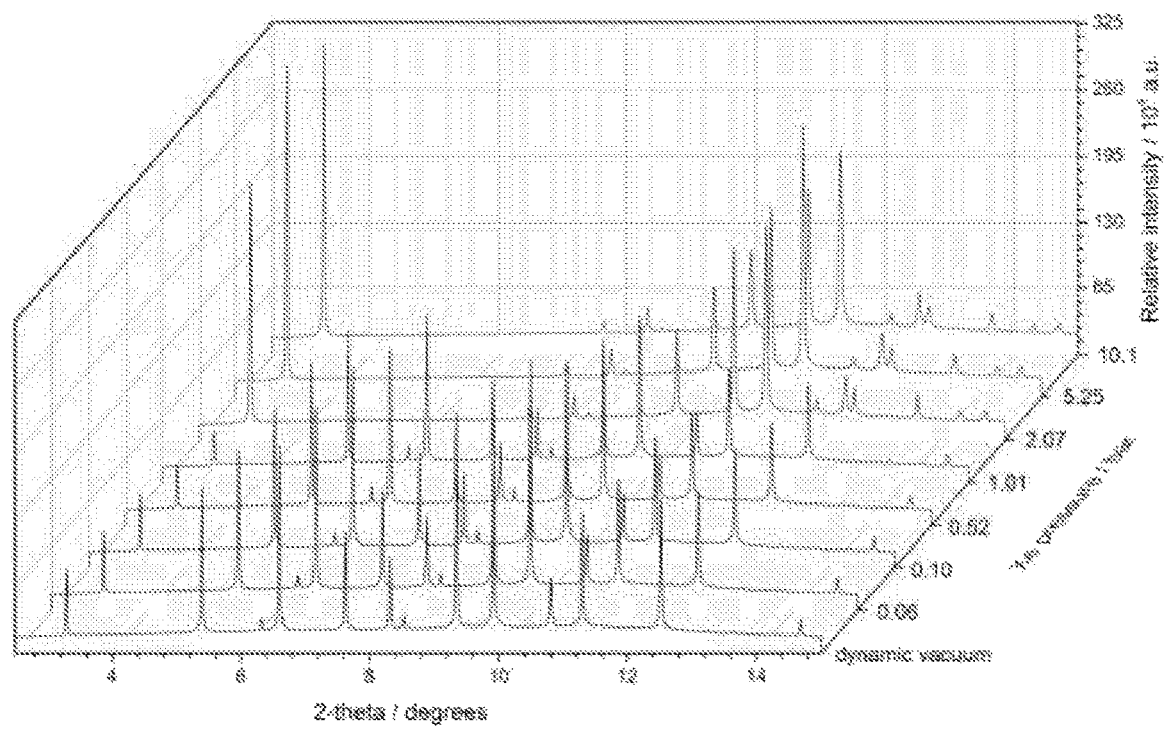
FIG. 21 shows in siu powder diffraction data collected under increasing pressure of xenon up to a maximum of 10 bar (295 K).

FIG. 21 shows In situ powder diffraction data collected under increasing pressure of xenon up to a maximum of 10 bar (295 K). Peak positions remain essentially constant, indicating no expansion of the CC3 structure upon loading with Xe.

The sample was allowed to equilibrate for a minimum of 15 minutes after gas was dosed into the cell. Several datasets were then collected using the PSD to confirm no further observable changes in the diffraction before increasing the pressure of Xe in the system. The pressure of xenon was reduced in steps before evacuating the gas cell under dynamic vacuum to confirm removal of xenon from the pore structure (FIG. 22).

FIG. 22 shows In situ powder diffraction data for loading and removal of xenon into a sample of CC3, demonstrating little change in the peak positions on loading. The original diffraction pattern is reformed when the xenon is completely removed under dynamic vacuum; this is due to a change in symmetry in the crystals.

During loading, the main intensity changes observed in the diffraction profiles occur between 1.01 and 2.07 bar, while the Xe sorption isotherm indicates the structure should be close to saturation at 1 bar. The discrepancy is likely to be due to differences in how equilibration is determined for the diffraction and gas sorption experiments, with the gravimetric sorption measurement being far more sensitive. The diffraction patterns also exhibit a degree of hysteresis between Xe loading and removal that is not observed in the Xe isotherm. The equilibration time for the in situ diffraction experiments was similar on gas loading and removal (15-25 minutes), and the apparent hysteresis may be due in part to the sample not being fully equilibrated. At 1.01 bar on loading, insufficient Xe guest atoms have adsorbed into in the material to result in a ordered guest-loaded structure. The disordered guest is likely to scatter diffusely, consistent with the observed diffraction profile being similar to the evacuated structure. If the sample was allowed to equilibrate for an extended period, it is possible that a higher level of guest loading and guest ordering would be observed, but instrument time did not allow us to test this. From the fully-loaded ordered structure at 10 bar, the pressure was reduced in steps to 1.02 bar. The Xe isotherm indicates the structure should still be close to saturation; that is, the guest is likely to be ordered in the structure. This is consistent with the observed diffraction pattern, which is similar to that observed for the sample loaded under 10 bar of Xe.

Figure 23:
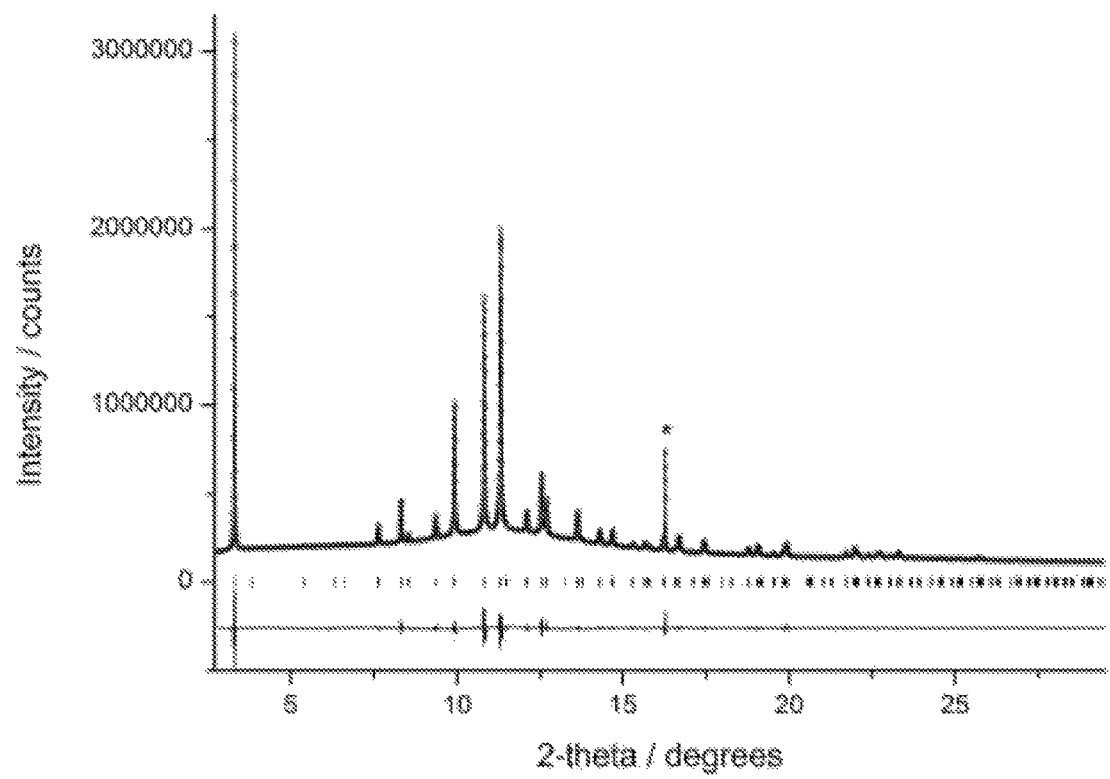
FIG. 23 shows observed (circles), calculated (solid line) and difference (below) X-ray powder diffraction profile (λ=0.827149Å) for the Le Bail refinement of PXRD data of CC3 collected under 10.1 bar of xenon at 295 K ($R^{wp}$=2.35%, $R_p$=1.38%,$\chi^2$=10.6).

Powder diffraction profiles were indexed for (i) the initial guest-free CC3 material at 295 K under vacuum, and (ii) CC3 loaded at 10.1 bar Xe. Le Bail fitting was carried out using TOPAS Academic[42] (FIG. 23). The crystal structure of evacuated CC3 was determined by Rietveld refinement, confirming the known cubic F4$_1$32 structure[11] (a=24.84888 (6) Å, V=15343.4(1) Å$^3$). The PXRD pattern of xenon-loaded CC3 was indexed to give a body-centred tetragonal cell with $V_{Tet} \approx 2V_{Cubic}$, consistent with 0.5 of a CC3 molecule in the asymmetric unit, indicating a lowering of symmetry upon loading with xenon. A set of five simulated annealing optimisations were performed using TOPAS Academic in the chiral space group I4$_1$ with the molecular fragment allowed to rotate freely about the twofold axis and two xenon atoms with variable occupancies translating throughout the unit cell to give an initial structure solution. The occupancies of the Xe atoms were merged dynamically when separated by a distance less than 0.8 Å. The best structure solution shows one xenon atom Xe1 on the 4a Wyckoff position, close to the centre of mass of the CC3 molecule, with approximately full occupancy. The second xenon Xe2 is located on a general position approximately central to two adjacent cage windows. A model was constructed using the CC3 position from the best structure solution and input into JANA2006[43] to generate Fourier difference and maximum entropy maps using BayMEM,[44] which were visualised in VESTA[45] to verify the location of the xenon guest atoms (FIG. 24).

FIG. 23 shows observed (circles), calculated (solid line) and difference (below) X-ray powder diffraction profile (λ=0.827149 Å) for the Le Bail refinement of PXRD data of CC3 collected under 10.1 bar of xenon at 295 K ($R_{wp}$=2.35%, $R_p$=1.38%, $\chi^2$=10.6). Reflection positions are also marked. A large crystallite of CC3 was present in the exposed sample during data collection resulting in a small number of very sharp peaks. The most significant (2θ=16.3, 22.0°) are marked with asterisks (also FIG. 25) and fitted as isolated Lorentzian peaks.

Figure 24:
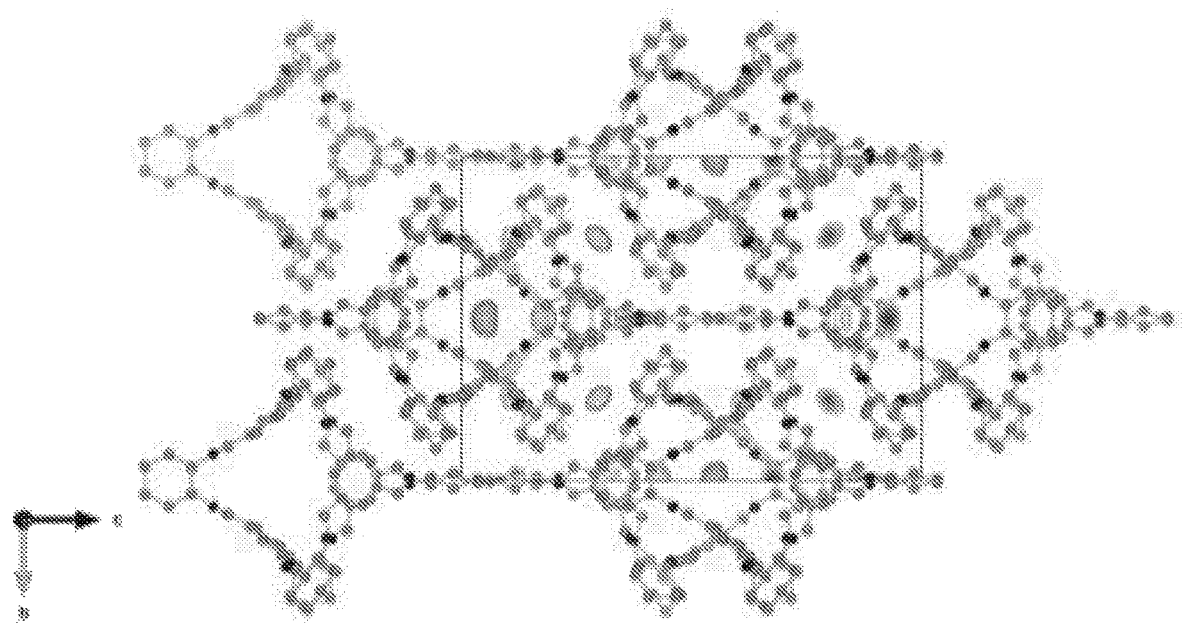
FIG. 24 shows three-dimensional difference Fourier maps indicating positions of the xenon guest atoms (isosurfaces drawn at 2.1 electrons Å$^{-3}$).

FIG. 24 shows three-dimensional difference Fourier maps indicating positions of the xenon guest atoms (isosurfaces drawn at 2.1 electrons Å$^{-3}$).

Figure 25:
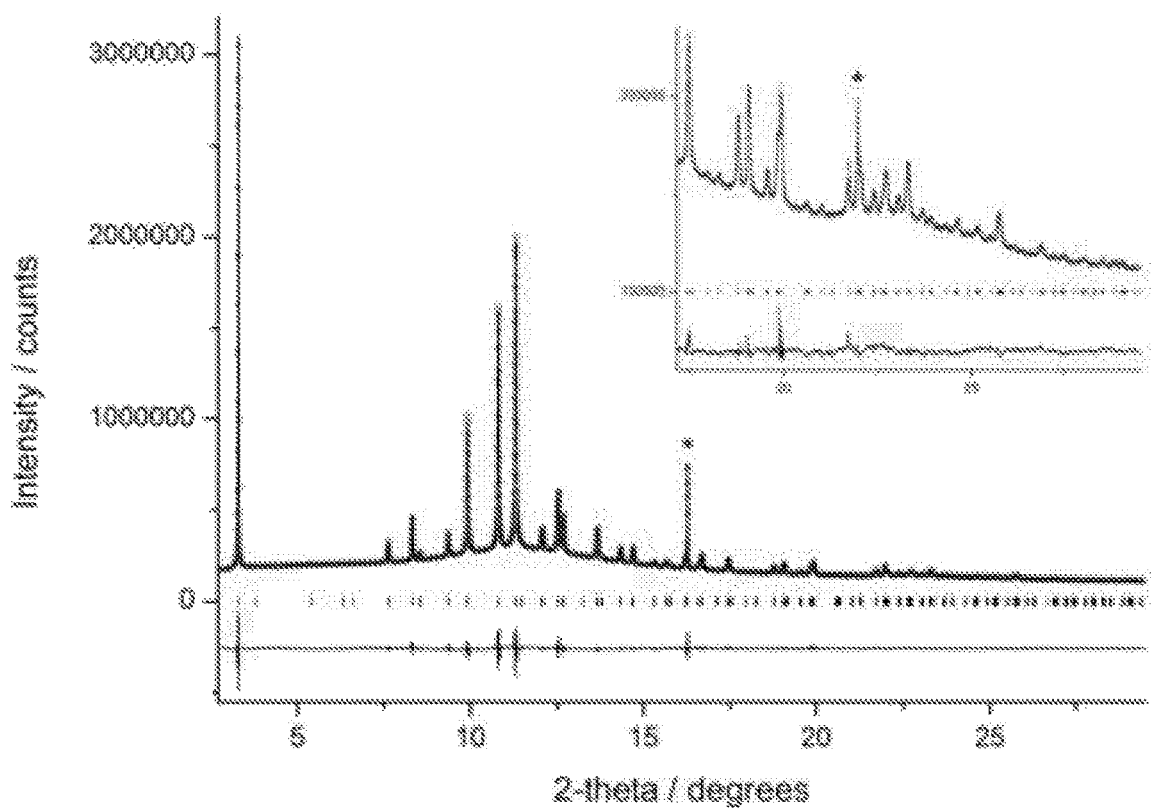
FIG. 25 shows bserved (circles), calculated (solid line) and difference (below) X-ray powder diffraction profile (λ=0.827149 Å) for the Rietveld refinement of PXRD data of CC3 collected under 10.1 bar of xenon at 295 K ($R_{wp}$=2.49%, RP=1.68%, $R_{Bragg}$=1.800%, $\chi^2$=10.8).
Figure 26:
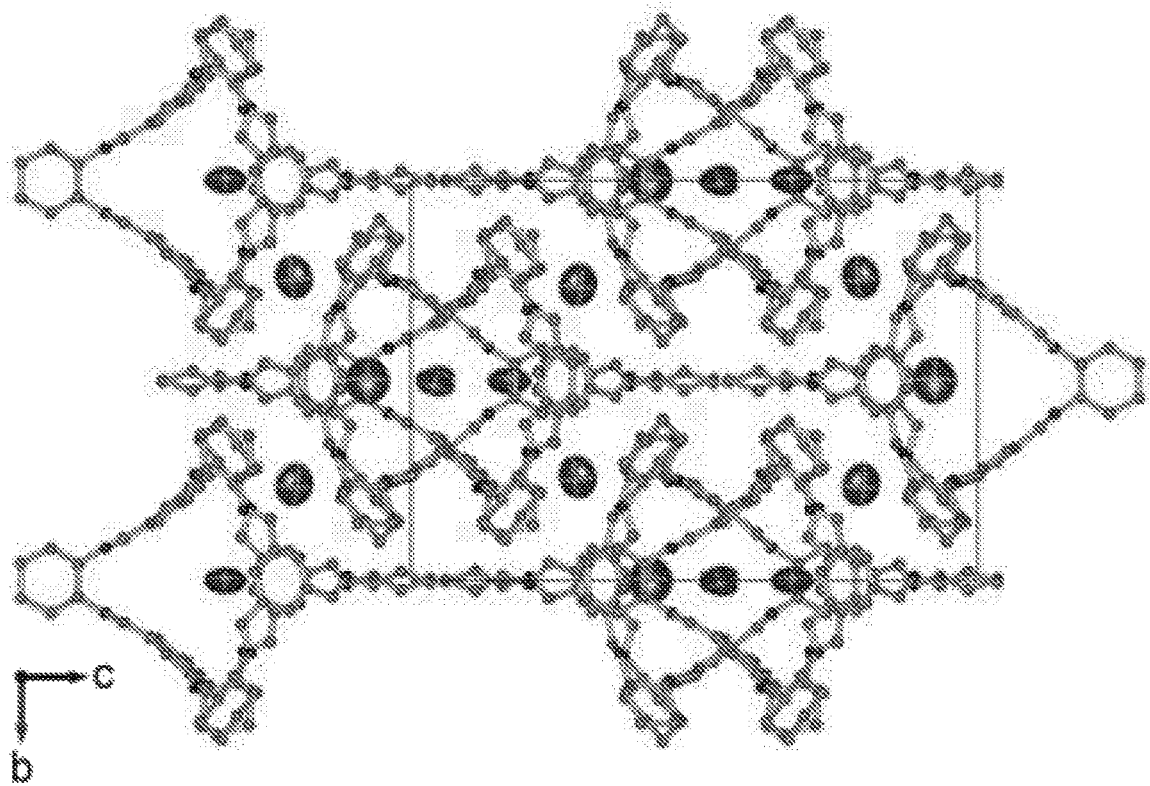
FIG. 26 shows refined structure of xenon-loaded structure, CC3 2.8Xe(a=17.5451(2)Å, c =24.8907(4)Å, V=7662.1(2)Å$^3$, $14_1$).

The best solution, including Xe atoms, was then used as the starting model for Rietveld refinement. The positions of all atoms on general positions and the 4a Xe z-coordinate were varied with geometric restraints on all bond lengths and angles and planarity restraints. All non-H isotropic displacement parameters were refined, constrained by atom type and environment (157 parameters, 116 restraints, 489 reflections, 6676 profile points). Restraint weightings were reduced as the refinement became more stable. The occupancies of both xenon sites were initially refined, but as the special position occupancy consistently refined to approximately unity, it was subsequently fixed. Anisotropic displacement parameters for the xenon atoms were refined in later stages of the refinement. Hydrogen atoms were modelled at standard distances and geometries and refined using the riding model to give the final agreement factors $R_{wp}=2.49\%$, $R_p=1.68\%$, $R_{Bragg}=1.80\%$, $\chi^2=10.8$ (FIGS. 25, 26). Molecular connectivity was maintained with some deformation and no significant improvement in fit when all restraints were removed from the final refined structure.

FIG. 25 shows observed (circles), calculated (solid line) and difference (below) X-ray powder diffraction profile ($\lambda=0.827149$ Å) for the Rietveld refinement of PXRD data of CC3 collected under 10.1 bar of xenon at 295 K ($R_{wp}=2.49\%$, $R_p=1.68\%$, $R_{Bragg}=1.80\%$, $\chi^2=10.8$). Reflection positions are also marked. The inset shows a larger scale plot of the high angle fit.

FIG. 26 shows refined structure of xenon-loaded structure, CC3.2.8Xe (a=17.5451(2) Å, c=24.8907(4) Å, V=7662.1(2) Å$^3$, I4$_1$). Ellipses for xenon are drawn at 50% probability. Hydrogen atoms are omitted for clarity.

There are a small number of relevant entries in the Cambridge Structural Database[46] (CSD) with which the intermolecular Xe . . . cage distances can be compared. These include molecular structures, such as Dianin's compound,[47] calixarenes,[48,49] cucurbiturils,[50] and cryptophanes,[51] as well as metal-organic frameworks.[52] Searches were based on intermolecular distances to non-bonded Xe atoms. Eleven entries in the CSD exhibit short (r=4.0±1.0 Å) Xe . . . phenyl ring centroid (Cg) distances (n=57), with a mean Xe . . . Cg distance of 4.14±0.04 Å, close to the average Xe . . . Cg distance of 4.22 Å for the cage cavity site in CC3.2.8Xe. A search for intermolecular Xe . . . H contacts (r=3.3±1.3 Å) returned thirteen structures (FIG. 27) with a mean separation of 3.71±0.04 Å (n=110). The mean Xe . . . H distance for the CC3.2.8Xe window site is 3.75 Å, which also falls within the distribution of values in the CSD results (FIG. 27).

Figure 27:
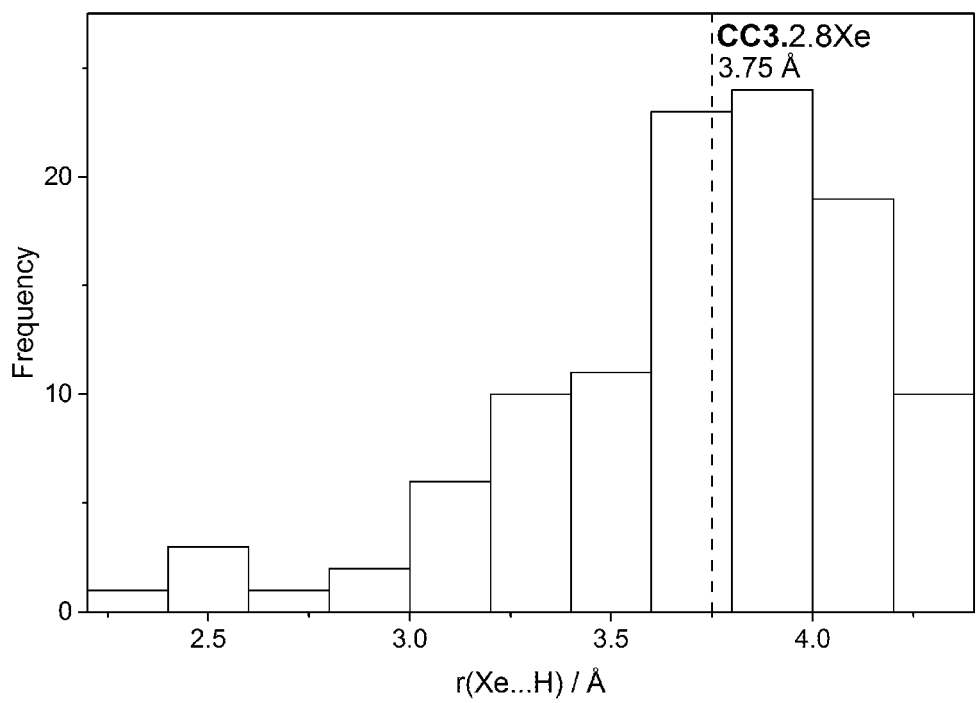
FIG. 27 shows the distribution of intermolecular Xe . . . H distances (r=3.3±1.3 Å).

FIG. 27 shows the distribution of intermolecular Xe . . . H distances (r=3.3±1.3 Å) in relevant entries in CSD database. The mean Xe . . . H contact distance is 3.71±0.04 Å (n=110), which is close to the mean value of 3.75 Å observed for the CC3.2.8Xe window site (line).

Xe . . . Xe separations in previously reported structures were also investigated. The Xe . . . Xe distances in CC3.2.8Xe (5.18(3) and 5.57(3) Å) are considerably longer than in crystalline Xe (4.3 Å).[53] Clearly, the surrounding binding site influences the closest approach of Xe atoms in the host structure. One structure that features direct Xe . . . Xe contacts is a beta-hydroquinone clathrate[54] in which Xe is located in an apparent binding site, yet short Xe . . . Xe contacts of 5.524 Å are present. A similar Xe separation of 5.19(1) Å is observed in HKUST-1 with high loadings of xenon.[55] These distances are comparable with those observed in CC3.2.8Xe. The position adopted by the xenon guests results in a balance between maximizing Xe . . . cage interactions while maintaining Xe . . . Xe contacts. The importance of the Xe . . . Xe interactions may explain the preferential occupancy of the cage cavity site over the window position (100% vs. 88±1%) observed in the crystal structure. The xenon guest atom occupying the cage cavity effectively forms four Xe . . . Xe contacts with tetrahedral geometry, while the linear geometry of the window site only allows two xenon hetero-interactions. Xenon binding in the cage cavity may therefore be favored due to a larger number of these stabilizing interactions. These Xe . . . Xe interactions also explain the fact that the isosteric heat of adsorption for Xe in CC3 increases with increasing Xe loading (FIGS. 7 & 14).

Figure 28:
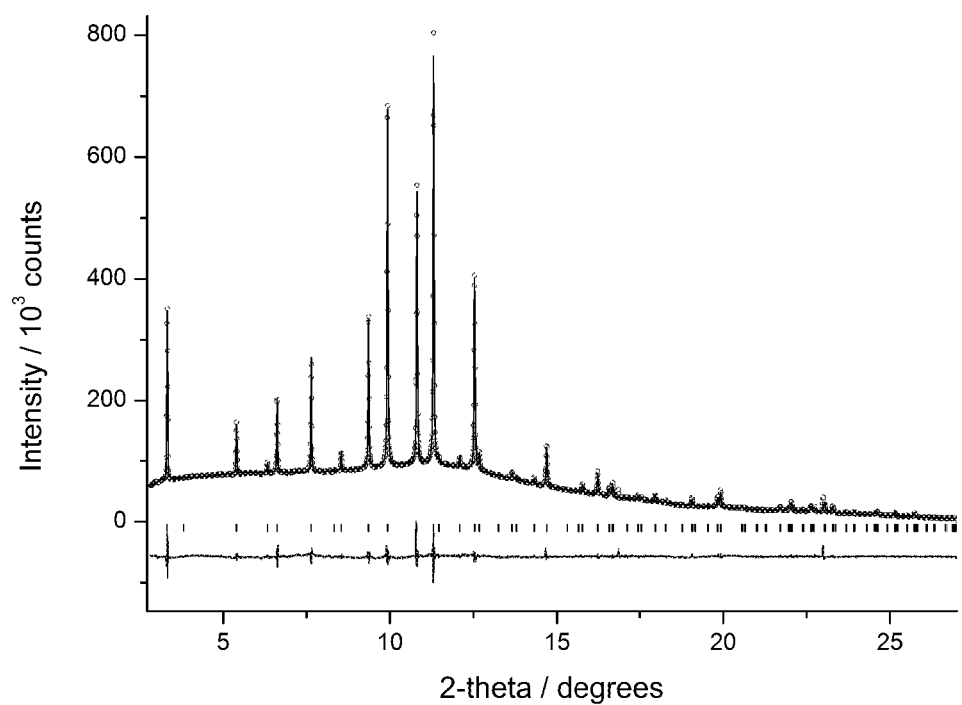
FIG. 28 shows observed (circles), calculated (solid line) and difference (below) X-ray powder diffraction profile (λ=0.826623 Å) for the Le Bail refinement of PXRD data of CC3 collected under 9.8 bar of krypton at 295 K ($R_{wp}$=3.85 %, $R_p$=2.28%, $\chi^2$=8.93).

In situ krypton loading PXRD experiments were carried out under a maximum partial pressure of Kr of 9.8 bar. The PXRD pattern at 9.8 bar was indexed and a refined R-centred trigonal cell (a=17.5700(2) Å, c=42.9530(9) Å, V=11483.3(2) Å$^3$) was obtained by Le Bail fitting ($R_{wp}=3.85\%$, $R_p=2.28\%$, $\chi^2=8.93$; FIG. 28). The symmetry and volume was consistent with ⅓ of two crystallographically independent CC3 molecules in the asymmetric unit. Direct space structure solution was carried out in R3 with the two cage molecular fragments rotating about and translating parallel to the threefold rotation axis and four independent Kr atoms with variable occupancies translating throughout the unit cell. The positions of the Kr atoms from the best of five simulated annealing runs were again compared with the Fourier difference maps generated using the guest-free structure and 9.8 bar PXRD data (FIG. 29) and to verify no further guest atoms were present. As in the xenon-loaded structure, the krypton atoms reside in the centre of the two CC3 molecule cavities. Two further Kr atoms are located in the two intermolecular sites, one of which lies on the threefold axis.

FIG. 28 shows observed (circles), calculated (solid line) and difference (below) X-ray powder diffraction profile ($\lambda=0.826623$ Å) for the Le Bail refinement of PXRD data of CC3 collected under 9.8 bar of krypton at 295 K ($R_{wp}=3.85\%$, $R_p=2.28\%$, $\chi^2=8.93$). Reflection positions are also marked.

Figure 29:
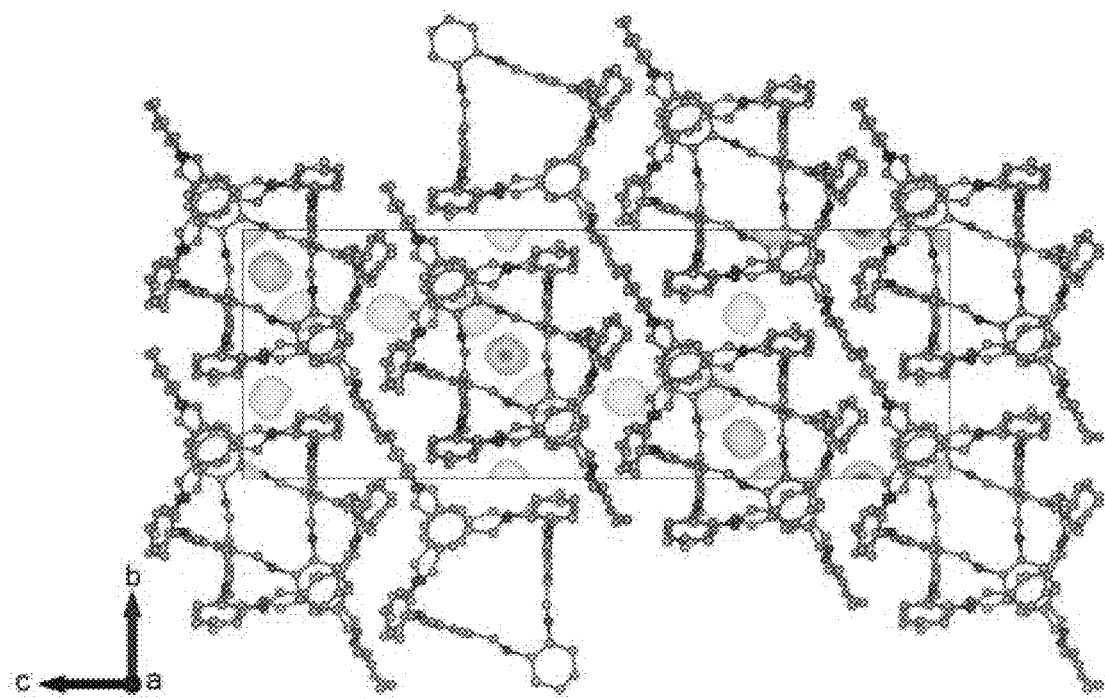
FIG. 29 shows three-dimensional difference Fourier

FIG. 29 shows three-dimensional difference Fourier maps indicating position of the krypton guest atoms (isosurfaces drawn at 0.7 electrons Å$^{-3}$).

Figure 30:
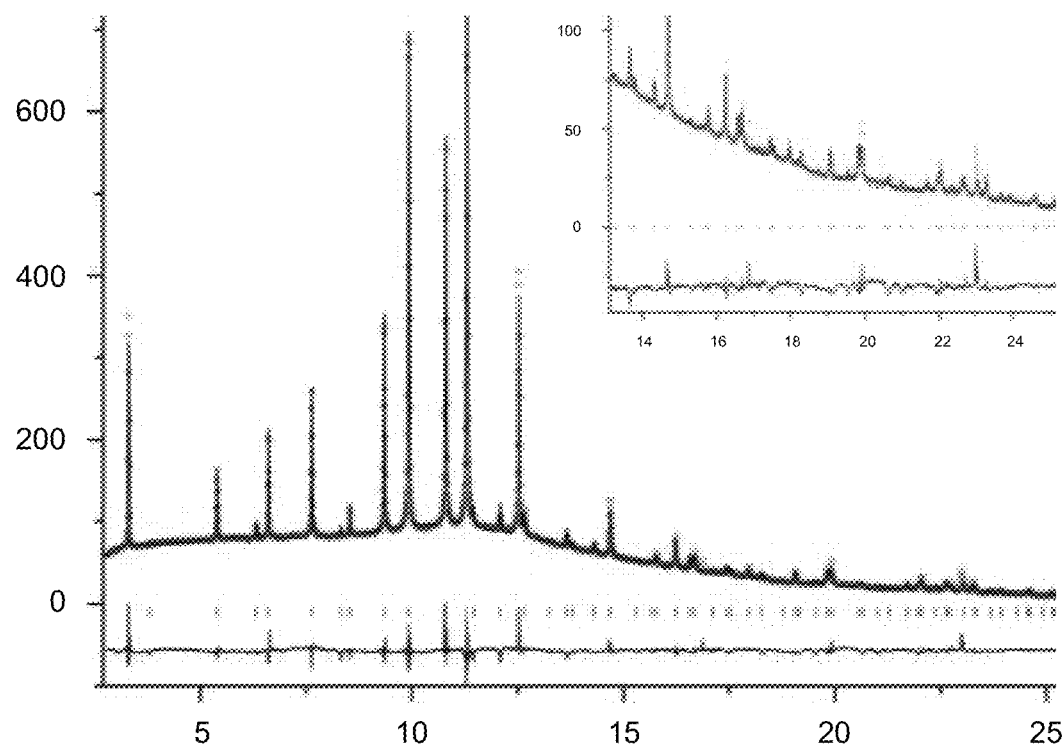
FIG. 30 shows observed (circles), calculated (solid line) and difference (below) X-ray powder diffraction profile (λ=0.826623Å) for the Rietveld refinement of PXRD data of CC3 collected under 9.8 bar of krypton at 295 K ($R_{wp}$=5.04 %, $R_p$=3.02 %, $R_{bragg}$ =2.63 % $X^2$=11.7).
Figure 31:
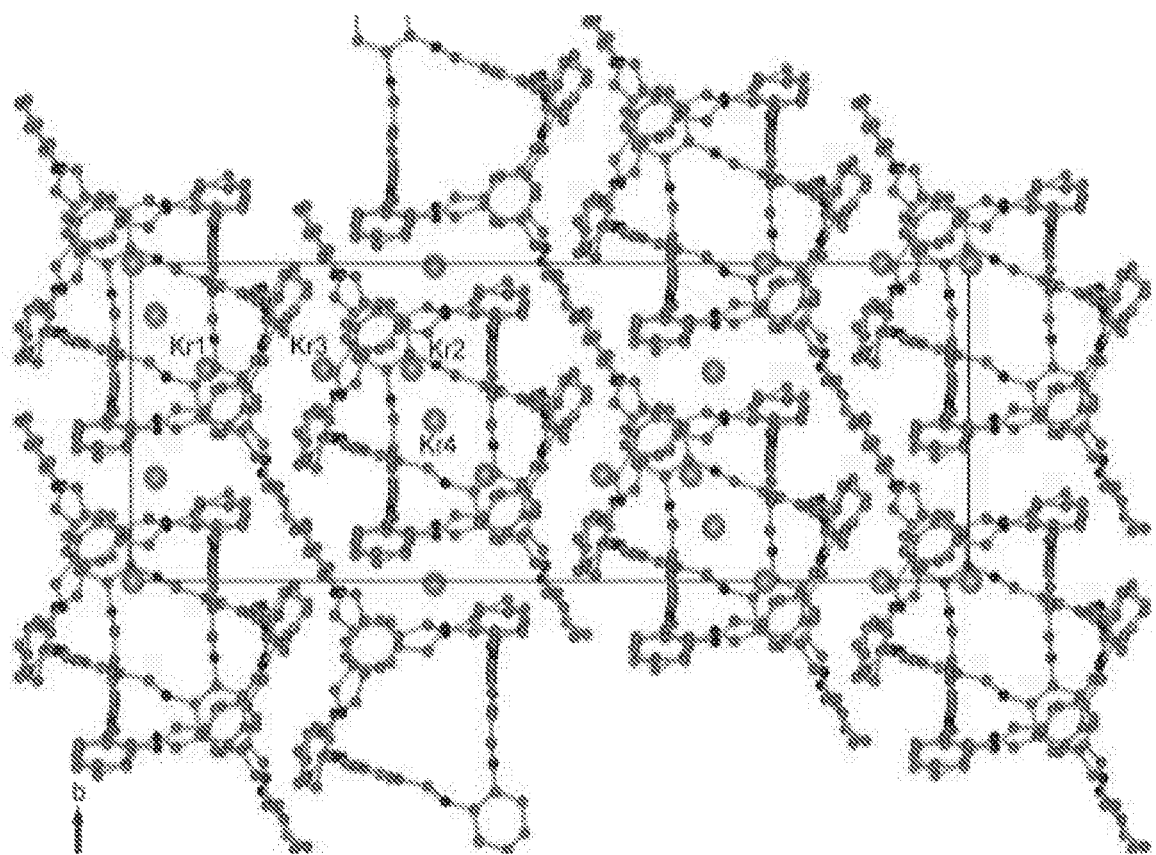
FIG 31 shows refined structure of krypton-loaded structure, $(CC3)_2$•4.2 Kr(a=17.5605(7)Å, c=43.010(3)Å, V=11486(1)Å$^3$, R3).

The best solution was used as the starting model for Rietveld refinement. The positions of all atoms on general positions and the z-coordinates of the three Kr on the threefold rotation axis were varied with geometric restraints on all bond lengths and angles and planarity restraints. An isotropic displacement parameter was refined for each independent CC3 molecule and for individual krypton atoms (389 parameters, 156 restraints, 488 reflections, 3025 profile points). Restraint weightings were reduced as the refinement became more stable. The cyclohexyl vertex functionalities of the CC3 fragments were prone to deformation during refinement, suggesting some disorder of these groups. Relatively heavily weighted restraints were required to maintain connectivity. The occupancies of all krypton sites were initially refined, but as the occupancy of Kr3 consistently refined to approximately unity, it was subsequently fixed. Hydrogen atoms were modelled at standard distances and geometries and refined using the riding model to give the final agreement factors $R_{wp}=5.04\%$, $R_p=3.02\%$, $R_{Bragg}=2.63\%$, $\chi^2=11.7$ (FIGS. 30, 31). No significant improvement in fit was observed when all restraints were removed from the final refined structure.

FIG. 30 shows observed (circles), calculated (solid line) and difference (below) X-ray powder diffraction profile ($\lambda=0.826623$ Å) for the Rietveld refinement of PXRD data of CC3 collected under 9.8 bar of krypton at 295 K ($R_{wp}=5.04\%$, $R_p=3.02\%$, $R_{Bragg}=2.63\%$, $\chi^2=11.7$). Reflection positions are also marked. The inset shows a larger scale plot of the high angle fit.

FIG. 31 shows refined structure of krypton-loaded structure, (CC3)$_2$·4.2Kr (a=17.5605(7) Å, c=43.010(3) Å, V=11486(1) Å$^3$, R3). Hydrogen atoms are omitted for clarity.

The total krypton occupancy was approximately 2.1 krypton atoms per cage (Table 8) averaged over the two crystallographically independent cages, considerably lower than for the xenon-loaded structure. There is an apparent preference for a specific window cavity site in which the krypton atom Kr3 is displaced from the centre of the window cavity. The Fourier difference map shows a small area of electron density between this window site and the adjacent cage cavities. This may be an artefact in the Fourier map. However, during Rietveld refinement, Kr3 was consistently displaced along the threefold rotation axis, towards the more occupied adjacent krypton atom Kr2. This produces a short Kr2-Kr3 distance of 4.6(2) Å, similar to that observed in the krypton-loaded metal organic frameworks HKUST-1[55] and [$Cu_2(O2CPh)_4(pyz)$].[52] Attempts to model possible disorder by splitting the atom over two sites between Kr1 and Kr2 were unsuccessful.

TABLE 8

Position and occupancy of krypton atoms in $(CC3)_2 \cdot 4.2Kr$.

| Atom | Cavity | Fractional coordinates | | | occupancy |
|---|---|---|---|---|---|
| | | x | y | z | |
| Kr1 | Cage | 0 | 0 | 0.243 (1) | 0.66 (2) |
| Kr2 | Cage | 2/3 | 1/3 | 0.331 (1) | 0.70 (2) |
| Kr3 | Window | 0 | 0 | 0.104 (1) | 1 |
| Kr4 | Window | 0.342 (3) | 0.170 (8) | 0.304 (1) | 0.620 (5) |

There are two principal factors that may drive the lowering of symmetry while leaving the overall molecular packing substantively unchanged. The first is that hosting the Xe guest atoms causes small changes in the cage molecular conformation which requires the molecular symmetry to be reduced from that required by the original cubic $F4_132$ space group (1/12th CC3-R molecule in the asymmetric unit) to allow increased flexibility. For example, the tetragonal $I4_1$ Xe-loaded structure contains an asymmetric unit consisting of half of the CC3-R molecule, resulting in a significantly less constrained molecular conformation than the guest-free cubic structure. It also means the window site is formed by two independent cage windows. The second consequence of lowered crystal symmetry is increased degrees of freedom available for guest atoms in terms of position and occupancy and symmetry-allowed anisotropic displacements. In the case of Xe-loaded CC3, the Xe atom occupying the window site is in a general position, unconstrained by symmetry. The Kr-loaded structure appears to have a complex distribution of guest atoms, in terms of both occupancies and positions, and the R3 symmetry allows four independent sites to be modeled to obtain a reasonable fit of the diffraction data.

Breakthrough Experiments

To evaluate CC3 for real separations of noble gases at low concentrations in air, as would be encountered in the reprocessing of spent nuclear fuels, we carried out breakthrough measurements with an adsorption column packed with CC3 crystals.

FIGS. 32a, 32b and 32c show a) graph of breakthrough measurements of noble gases at low concentrations in air, carried out using an adsorption column packed with CC3 crystals; and b) a graph comparing simulated xenon uptake with experimental uptake, comprising the volumetric density of the noble gas in the solid CC3 adsorbent divided by its volumetric density in the bulk gas phase p(captured)/(bulk) (left vertical axis) plotted against its concentration in the gas mixture (squares), and c) a graph of a simulation of the separation of radon from air.

As seen in FIG. 32a, breakthrough measurements show clean separation of krypton (40 ppm) from xenon (400 ppm) when present as low-concentration impurities in simulated air at 298 K (C=concentration of component in column outlet; $C_0$=total concentration of all feed gases). As seen in FIG. 32b, the experimental xenon uptake (400 ppm Xe in simulated air) is also reproduced by simulations; diamond=experimental uptake. The volumetric density of the noble gas in the solid CC3 adsorbent divided by its volumetric density in the bulk gas phase, ρ(captured)/(bulk) (left vertical axis), is plotted against its concentration in the gas mixture (squares), together with the corresponding simulated noble gas uptake (circles, right vertical axis). Other simulations, also at 298 K, predict even higher selectivity for radon separation from air (FIG. 32c), or from pure nitrogen or helium (FIG. 33), as validated by gas adsorption experiments.

Thus, when a mixture of xenon (400 ppm) and krypton (40 ppm) balanced with simulated air was passed through this column, the xenon component was retained for more than 15 minutes, even at a flow rate of 40 $cm^3$ STP $min^{-1}$, which is twice as fast as that used in previous studies for MOFs [Liu, J., Thallapally, P. K. & Strachan, D. Metal-organic frameworks for removal of Xe and Kr from nuclear fuel reprocessing plants. *Langmuir* 28, 11584-11589, (2012)]. By contrast, krypton and the other components ($N_2$, $O_2$, and $CO_2$) broke through almost immediately.

Under these conditions, CC3 adsorbs twice as much xenon as the leading MOF, Ni/DOBDC [Liu, J., Thallapally, P. K. & Strachan, D. Metal-organic frameworks for removal of Xe and Kr from nuclear fuel reprocessing plants. *Langmuir* 28, 11584-11589, (2012)]: around 11 mmol $kg^{-1}$, in good agreement with simulations (FIG. 32b). In addition, the Xe/Kr selectivity for CC3 is almost three times higher than for Ni/DOBDC: 20.4 versus 7.3. Selectivity and capacity are often seen as a trade-off. Here, CC3 shows significant improvements for both of these key parameters with respect to the leading MOF material.

FIGS. 33a and 33b show the simulated removal of low concentrations of Xe and Rn impurities from two binary gas mixtures. In each case, the volumetric density ratio of the rare gas in the solid adsorbent divided by its volumetric density in the bulk gas phase [ρ(captured)/ρ(bulk)] is plotted against its concentration in the gas mixture (left Y axis), together with the corresponding rare gas uptake (right Y axis). Error bars based on a 95% confidence interval are given for the density ratios, and these error bars are generally smaller than the symbols in the plot. (a) Simulated Rn capture from nitrogen at a total pressure of 1 bar at 213 K. These conditions correspond to the lowest-temperature Rn adsorption experiments that we performed (Table 9). (b) Rn capture from helium at a total pressure 1 bar at 193 K. Equilibrium is assumed in these calculations, and hence real, dynamic separations might operate less efficiently than these simulations suggest. However, detailed kinetic measurements show that gas diffusion in CC3 is fast, at least for Kr and Xe, as illustrated by the breakthrough separation shown in FIG. 32a & FIG. 36. The three-dimensional pore structure in CC3 (FIG. 1) might improve the adsorption kinetics with respect to related materials with 1-dimensional pore channels of comparable dimensions.

These breakthrough measurements (FIG. 32a) also prove that the adsorption kinetics are fast enough to allow real separations. This is supported by detailed kinetic measurements for pure Kr and for pure Xe (see below), which show that rare gas diffusion in CC3 is relatively fast (e.g., at 2.0 mbar, 195 K; Kr=$12.7 \times 10^{-3}$ $s^{-1}$ and Xe=$5.76 \times 10^{-3}$ $s^{-1}$). Comparison of activation energies, $E_a$, with the corresponding enthalpies of adsorption, $Q_{st}$, for Kr and Xe show that $E_a$ is lower than $Q_{st}$; therefore, surface diffusion is the rate controlling step for adsorption of both gases on CC3.

There is a near-perfect fit between the cavities in CC3 and the xenon guests. The pore architecture in CC3 has uniform pore channels that are at points too narrow, but at other points just large enough, to accommodate a single xenon atom. There are no larger cavities in CC3 that are a poor fit for xenon, nor any smaller cavities that might competitively adsorb the smaller molecules, such as nitrogen, in the gas mixture.

The organic cage is also an excellent adsorbent for radon gas. The adsorption capacity was evaluated by a dynamic adsorption technique where the radioisotope is mixed at high dilution in a carrier gas, nitrogen. The radon concentration in the gas was 615±17 Bq m$^{-3}$, or 3.8±0.1×10$^{-16}$ mol kg$^{-1}$. The cage crystal adsorbs $^{222}$Rn from the gas phase and concentrates it in the solid state by a volumetric factor of between 5,000 and 1×10$^6$, depending on the adsorption temperature (Table 9). This high selectivity for radon with respect to nitrogen was also predicted at ambient temperature for multicomponent air (FIG. 20c), which includes potentially competing species such as CO$_2$ and water.

TABLE 9

Results obtained for Rn adsorption in CC3 between 20° C. and −50° C.

| T (° C.) | CC3 activity (Bq/kg) | K factor (kg/m$^3$)$^a$ | [Rn] in CC3 (mol/kg) | Volumetric concentration factor, [☐(captured)/☐(bulk)] |
|---|---|---|---|---|
| 20 | 3.6 ± 0.5 · 10$^3$ | 6.0 ± 0.9 | 2.8 ± 0.4 · 10$^{-15}$ | 5,800 |
| 0 | 1.5 ± 0.1 · 10$^4$ | 25.6 ± 2.7 | 1.2 ± 0.1 · 10$^{-14}$ | 25,000 |
| −30 | 5.4 ± 0.2 · 10$^4$ | 89.9 ± 4.6 | 4.2 ± 0.2 · 10$^{-14}$ | 87,000 |
| −50 | 6.0 ± 0.1 · 10$^5$ | 1000.0 ± 32.1 | 4.7 ± 0.1 · 10$^{-13}$ | 978,000 |

$^a$The ratio between the number of atoms of radon trapped in the solid and the radon concentration in the gas, both assumed to be proportional to their respective activity (Bq m$^{-3}$), is given by the equilibrium constant, K:

$$K = \frac{\{A\}}{\{C\}}$$

where {A} is the radon activity in CC3 and {C} is the radon activity in the gas.

Hence, the present invention may be useful for radon removal from air, or from water, or for improving the sensitivity and humidity tolerance of environmental monitoring technologies that use physical adsorption to concentrate the radon gas for detection. Currently, charcoal is used as an adsorbent for short-term radon testing in domestic homes, but its relatively poor selectivity against water vapour can lead to variation in test results with fluctuating humidity. The use of a single pore size that is tailored to adsorb radon offers a solution to this problem.

Experiments with radioisotopes are restricted to specialized laboratories, but radioisotope adsorption is readily studied in silico. For example, we also predict that CC3 could capture $^{222}$Rn from helium at radon concentrations as low as 0.01 ppmv (FIG. 33) with extremely high selectivity (Rn/He=5.4×10$^8$), as relevant in astroparticle physics experiments searching for rare, low-energy events. Our success in calculating the Xe and Kr behaviour relative to experimental results (FIG. 4b) gives us confidence in extrapolating these computational predictions to radon.

Kinetics and Activation Energy.

Kinetics at 195 K: Fitting of Stretched Exponential Model.

Figure 34:
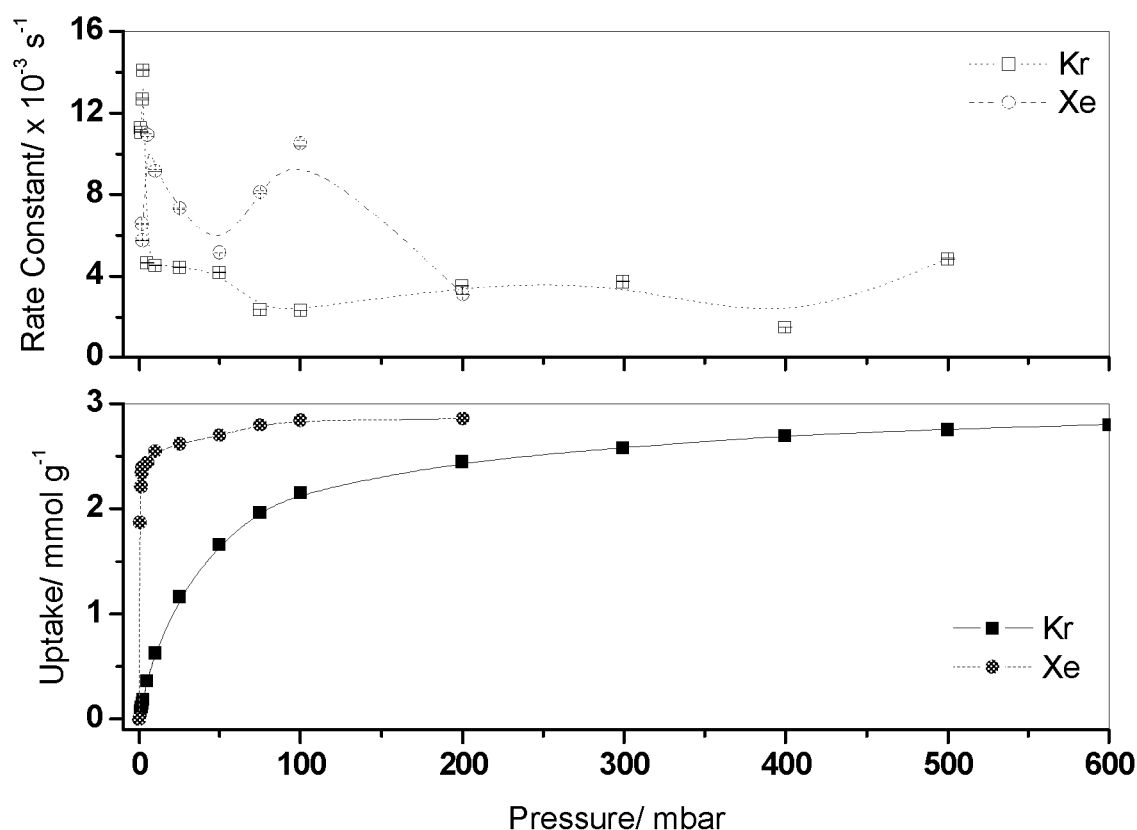
FIG. 34 shows a comparison of streched exponential rate constants for krypton and xenon at 195 K in relation to osition on isotherm.

The stretched exponential (SE) model is described by the following equation:

$$\frac{M_t}{M_e} = 1 - e^{-(kt)^\beta}$$

where $M_t$ is the mass at time t, $M_e$ is the mass at equilibrium, k is the mass transfer rate constant (s$^{-1}$) and t is the time (s). The exponent parameter β is material dependent and reflects the width of the distribution of relaxation times. The SE model is 3-dimensional with a single relaxation time when β=1 (Linear Driving Force (LDF) model) and 1-dimensional with a distribution of relaxation times when β=0.5. Krypton and xenon kinetics follow the stretched exponential model at 195 K. β is in the range 0.6-0.8 for all mass relaxation profiles, which is indicative of two-dimensional diffusion. Comparison of the stretched exponential rate constants for krypton and xenon at 195 K, and position of the rate constant value on the isotherm, are shown in FIG. 34. The rate constants are similar over the pressure range and span the range 2.0×10$^{-3}$-1.4×10$^{-2}$ s$^{-1}$. In the initial low pressure uptake region (up to 2.5 mbar), the krypton kinetics are slightly faster than xenon (e.g., at 2.0 mbar Kr=12.7×10$^{-3}$ s$^{-1}$ and Xe=5.76×10$^{-3}$ s$^{-1}$). This is attributed to the smaller diameter of krypton. The chemical potential gradient increases rapidly due to the very steep uptake with pressure for xenon and the uptake reaches a plateau at low pressure (ca. 95% total predicted uptake at 195 K is achieved at 50 mbar), while krypton is far from the plateau region (95% of the total predicted uptake at 195 K is obtained at 600 mbar). Therefore, xenon kinetics are faster than krypton for pressures greater than 2.5 mbar, hence the differences are attributed to difference in chemical potential gradient associated with varying extents of pore filling. Krypton and xenon adsorption on CC3 at 195 K plateau at 3.00 mmol g$^{-1}$. Based on a formula unit of 1117.548 g mol$^{-1}$ for CC3, this corresponds to 3.35 rare gas atoms per cage.

Figure 35:
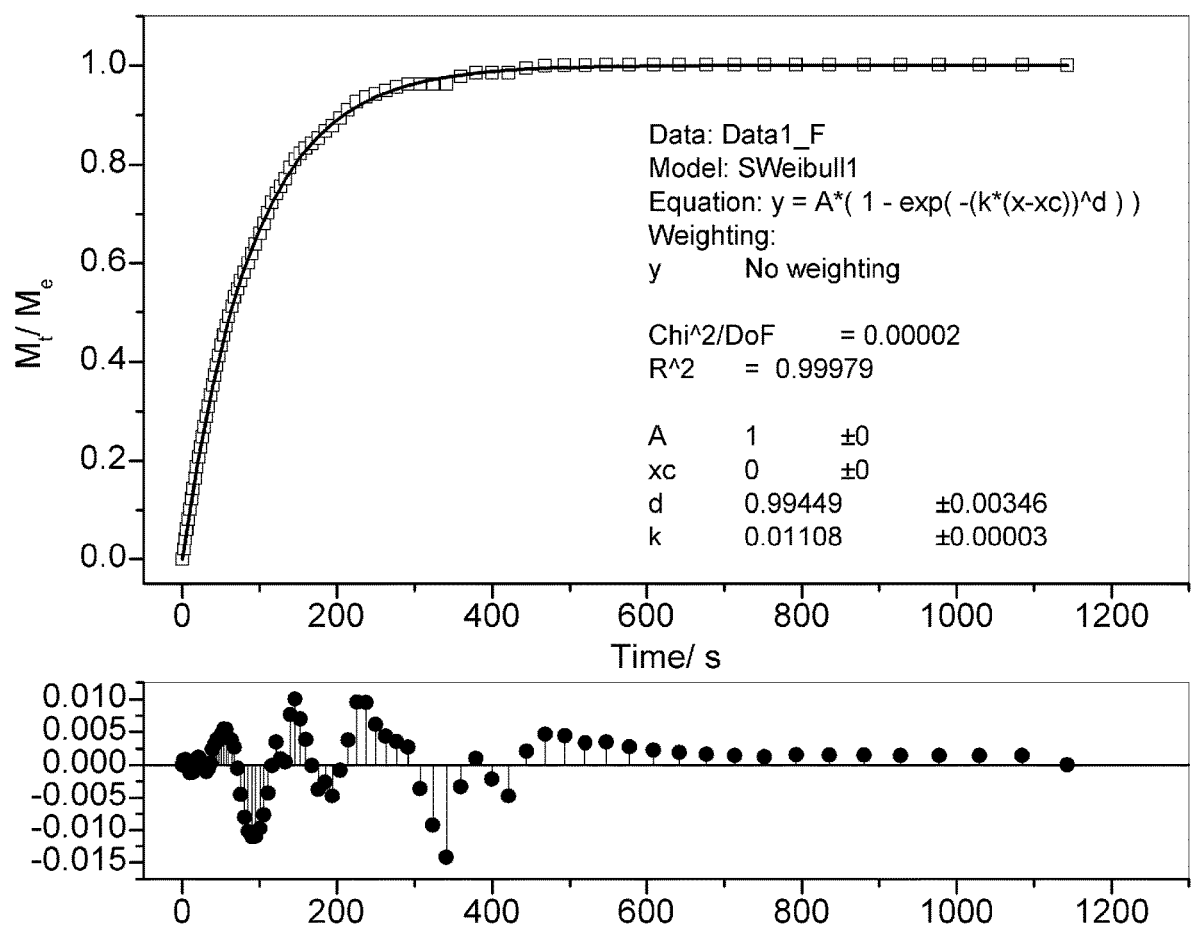
FIG. 35 shows krypton mass relaxation profile and fitting of stretched exponential model for the pressure increment 1.0-1.5 mbar at 195 K.
Figure 36:
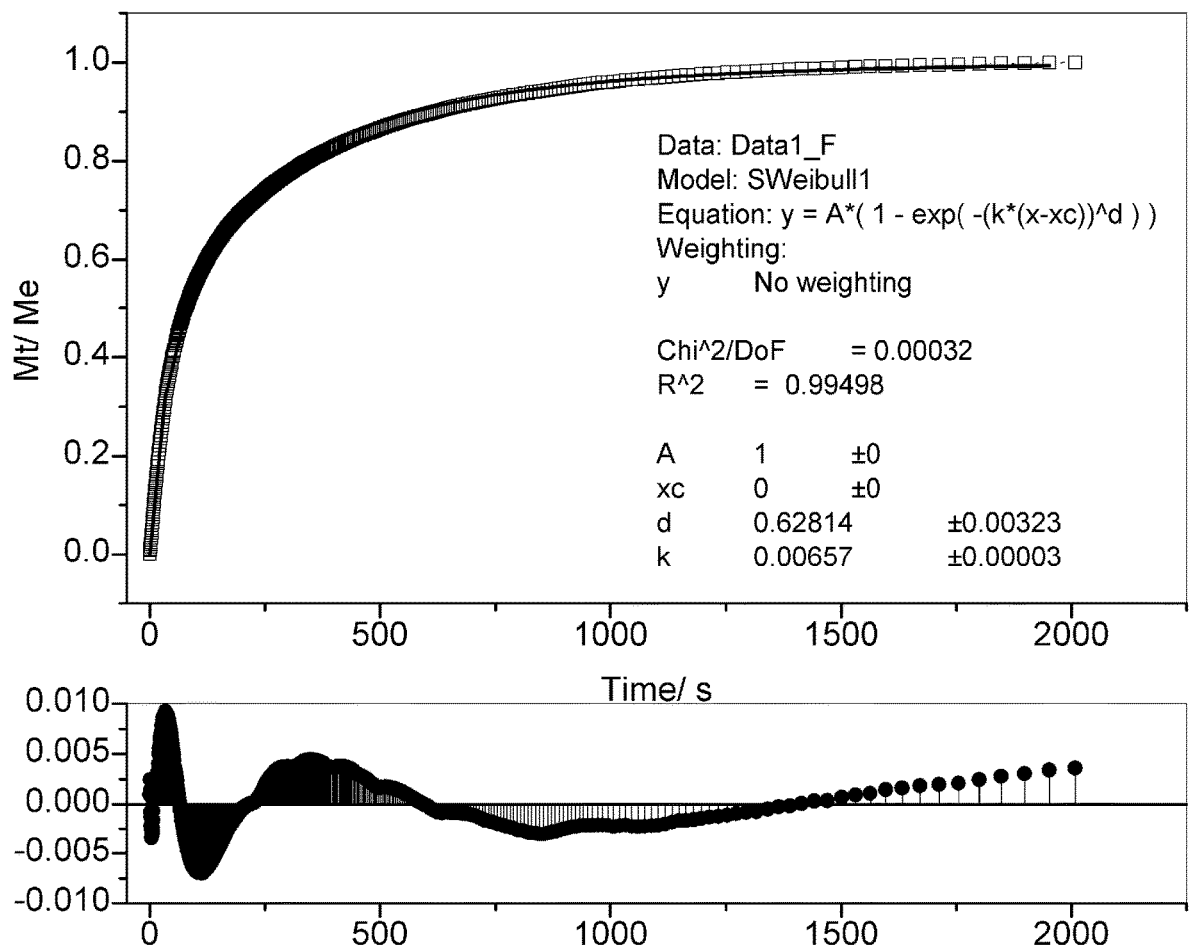
FIG. 36 shows xenon mass relaxion profile and fitting of stretched exponential model for the pressure increment 1.0-1.5 mbar at 195 K.

Typical fits of the stretched exponential model to experimental mass relaxation profiles for krypton and xenon at 195 K are shown in FIGS. 35 and 36, respectively. It is clear that there is a good fit between experimental data and the stretched exponential model with residuals less than 2%.

Equilibration Over the Temperature Range 195-298 K.

Figure 37:
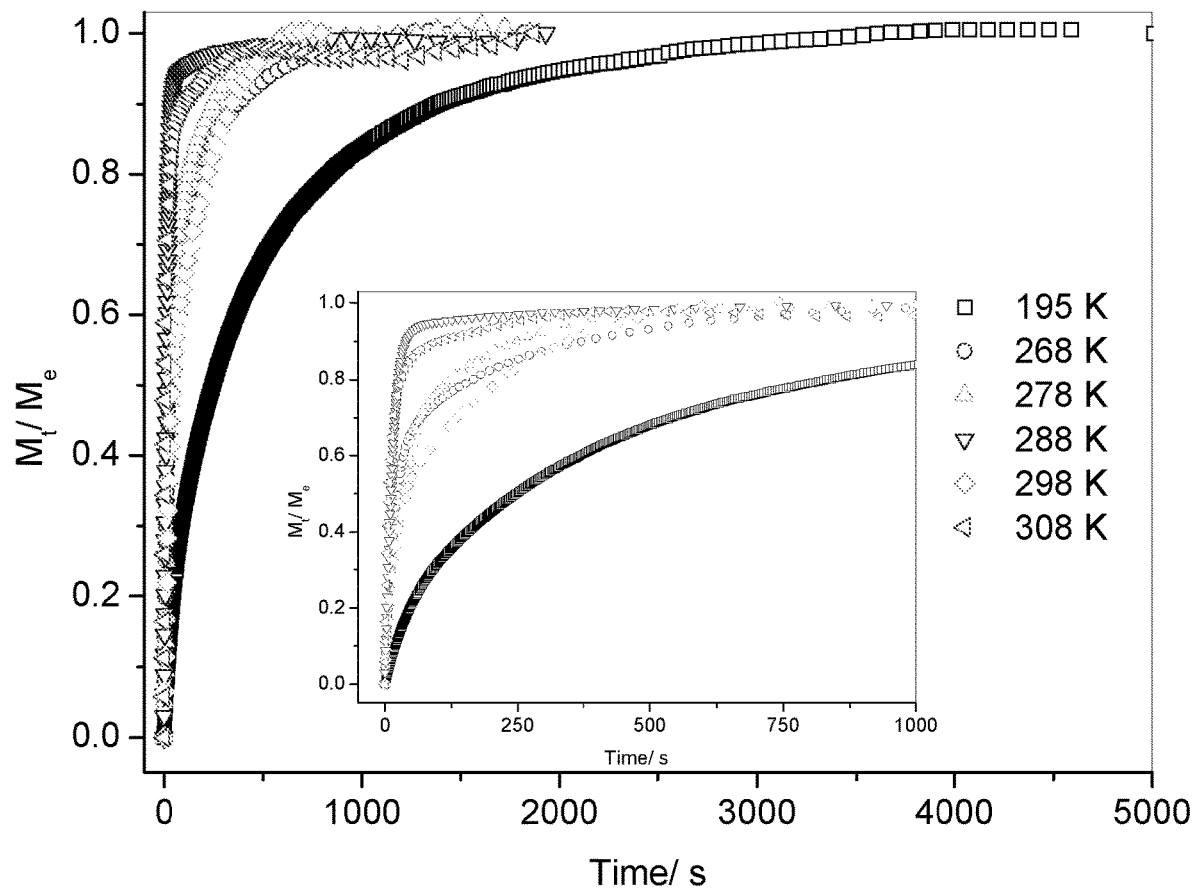
FIG. 37 shows krypton $M_t/M_e$ vs. time graphs in the temperature range 195-298 K for the pressure increment 75-100 mbar for 195 K and 50-100 mbar for 268, 278, 288, 298 and 308 K.
Figure 38:
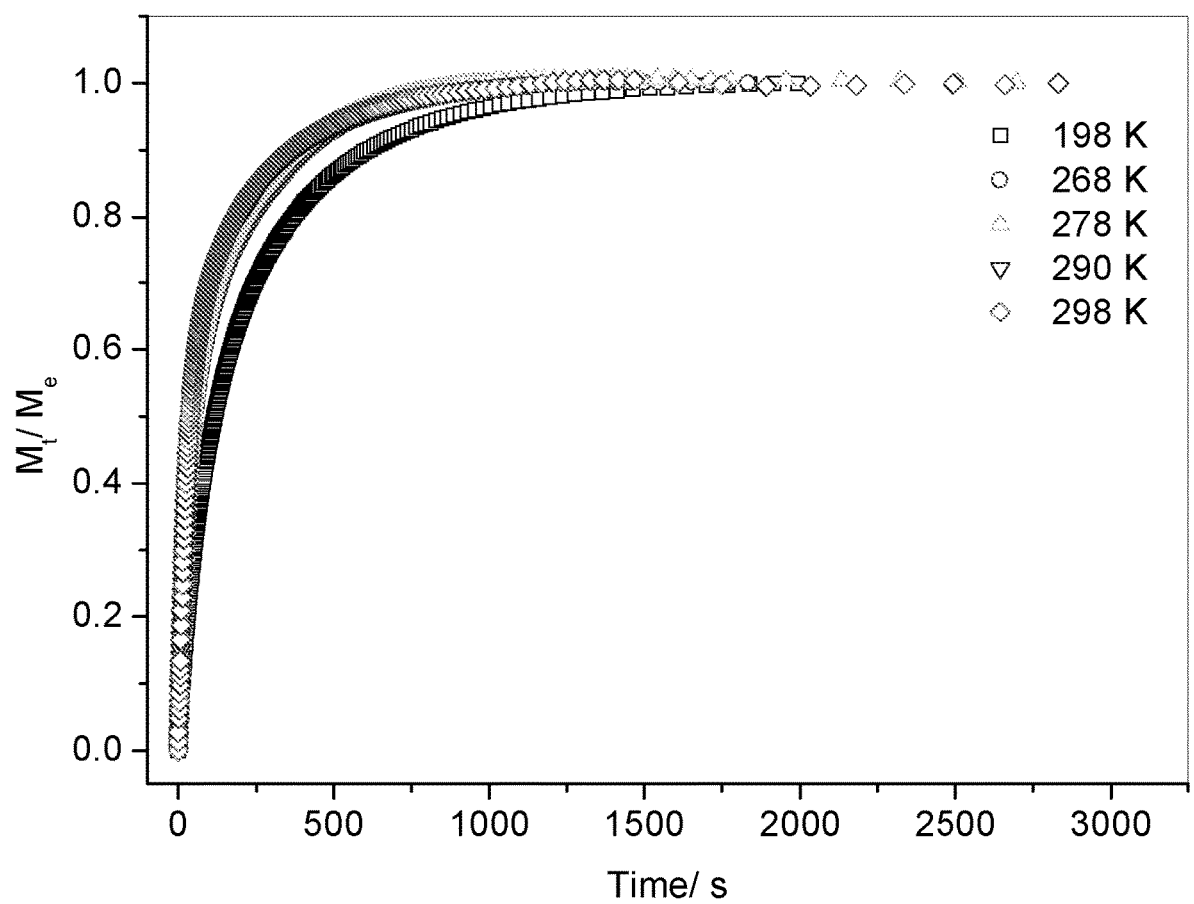
FIG. 38 shows xenon $M_t/M_e$ vs. time graphs in the temperature range 198-298 K for the pressure increment 25-50 mbar.

FIG. 37 shows krypton mass relaxation profiles for the pressure increment 75-100 mbar for 195 K and 50-100 mbar for 268, 278, 288, 298 and 308 K. It is evident that the rate of adsorption is very fast, ranging from 2×10$^{-3}$ to 6×10$^{-2}$ s$^{-1}$. Consequently, there is interference from the pressure set (pressure set time is ca. 30 seconds) at higher temperatures, resulting in a non-monotonic trend in relaxation time with temperature. FIG. 38 shows the mass relaxation profiles for xenon adsorption on CC3 for the pressure increment 25-50 mbar. The rate constants are similar to krypton and are in the range 6×10$^3$ to 1×10$^{-2}$ s$^{-1}$.

Activation Energy.

Activation energies for krypton and xenon adsorption on CC3 were calculated using stretched exponential rate constants in the range 195-308 K and 268-298 K, respectively. Linear interpolation was performed on graphs of ln(k) vs amount adsorbed, at all temperatures, in order to calculate $E_a$ (from graphs of ln(k) vs 1/T) at constant values of amount adsorbed. For krypton, the kinetic barrier increases from 6.4-12.3 kJ mol$^{-1}$ between 0 and 0.8 mmol g$^{-1}$, while xenon increases from 6.0 to 17.5 kJ mol$^{-1}$ between 0 to 2.0 mmol g$^{-1}$. Activation energies for both gases are significantly lower than $Q_{st}$ (22 kJ mol$^{-1}$ for krypton and 28-30 kJ mol$^{-1}$ for xenon (see FIG. 39) over the same uptake range at $Q_{st}$. Therefore, the rate limiting step for adsorption of both species is surface diffusion and not diffusion through constrictions in porosity.

Ideal Adsorbed Solution Theory.

The binary adsorption of xenon and krypton on CC3 was modelled using Ideal Adsorbed Solution Theory. The model requires no equilibrium mixture data only pure component isotherms at equal temperature. The model is based on solving the following set of equations:

$$Py_1 = P_1^0 x_1$$

$$P(1 - y_1) = P_2^0(1 - x_1)$$

$$\int_{P=0}^{P=P_1^0} \frac{n_1^*(P)}{P} dP = \int_{P=0}^{P=P_2^0} \frac{n_2^*(P)}{P} dP$$

$$\frac{1}{n} = \frac{x_1}{n_1^*(P_1^0)} + \frac{x_2}{n_2^*(P_2^0)}$$

where P is the total pressure, $P_i^0$ is the pressure of component i, $y_i$ is the mole fraction of the gas phase for component i, $x_i$ is the adsorbed phase mole fraction of component i. Integration of pure component isotherms, $n_i^0/P_i^0$ vs. $P_i^0$ (the third of the four equations above), was performed numerically using the trapezoid method with constant step size.

Figure 40:
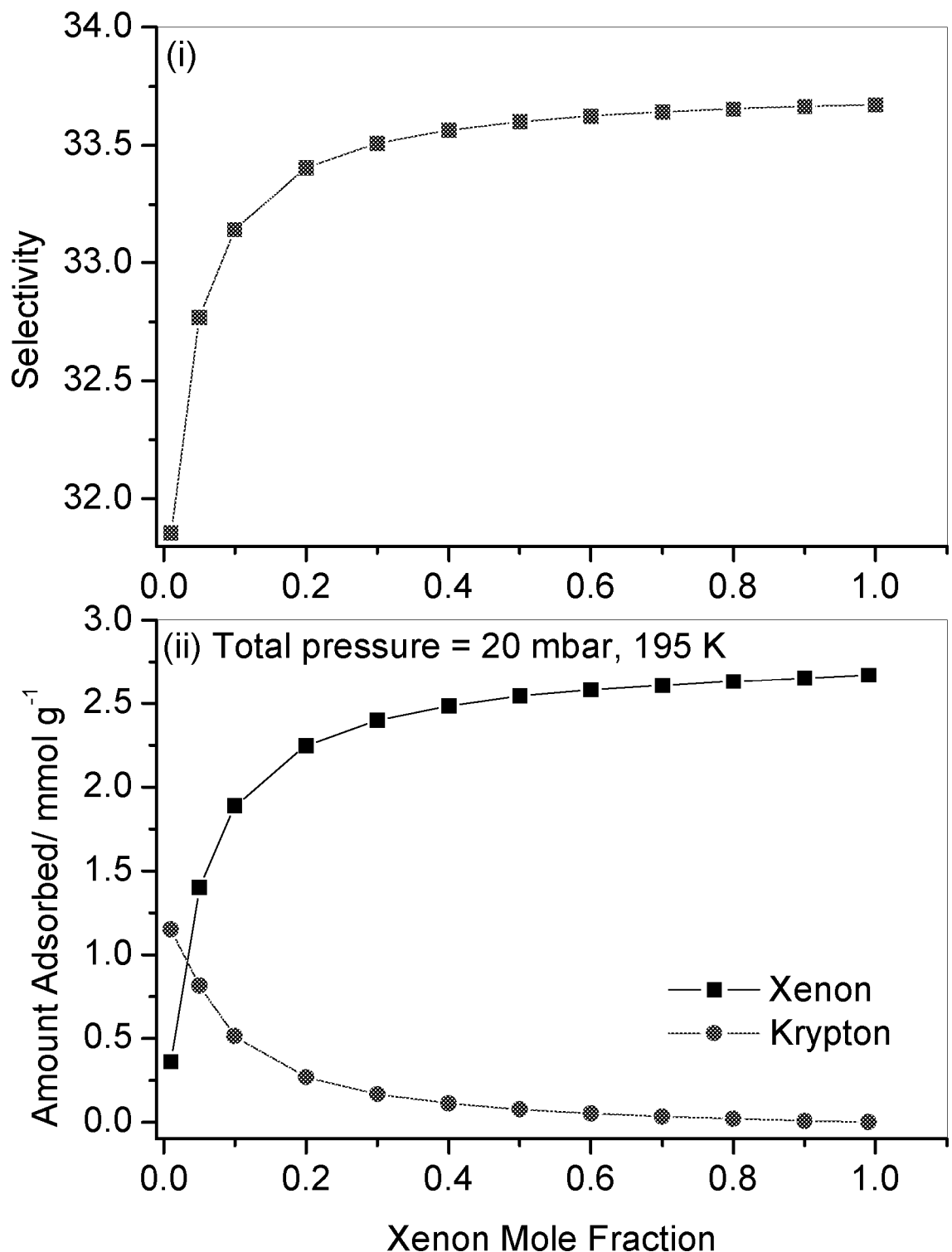
FIG. 40 shows: (I) Xenon/krypton selectivity using ideal Adsorbed Solution Therapy at a total pressure of 20 mbar and 195 K; (II) Amount of xenon/krypton adorbed as a function of xenon mole fraction using Ideal Adsorbed Solution Therapy for a total pressure equal to 20 mbar, at 195 K.

FIG. 40 (ii) shows the amount of xenon and krypton adsorbed (in mmol g$^{-1}$) as a function of xenon mole fraction for a total pressure of 20 mbar and a temperature of 195 K. It is evident that xenon is preferentially adsorbed at very low xenon mole fractions. At a xenon mole fraction equal to 0.2, the amount adsorbed is 2.248 mmol g$^{-1}$ compared to 0.269 mmol g$^{-1}$ for krypton. The selectivity of xenon over krypton is shown in FIG. 40 (i) and increases from 31.5 to 33.5 as the xenon mole fraction tends to one.

FIG. 34 shows a comparison of stretched exponential rate constants for krypton and xenon at 195 K in relation to position on isotherm.

FIG. 35 shows krypton mass relaxation profile and fitting of stretched exponential model for the pressure increment 1.0-1.5 mbar at 195 K.

FIG. 36 shows xenon mass relaxation profile and fitting of stretched exponential model for the pressure increment 1.0-1.5 mbar at 195 K.

FIG. 37 shows krypton $M_t/M_e$ vs. time graphs in the temperature range 195-298 K for the pressure increment 75-100 mbar for 195 K and 50-100 mbar for 268, 278, 288, 298 and 308 K.

FIG. 38 shows xenon $M_t/M_e$ vs. time graphs in the temperature range 198-298 K for the pressure increment 25-50 mbar.

Figure 39:
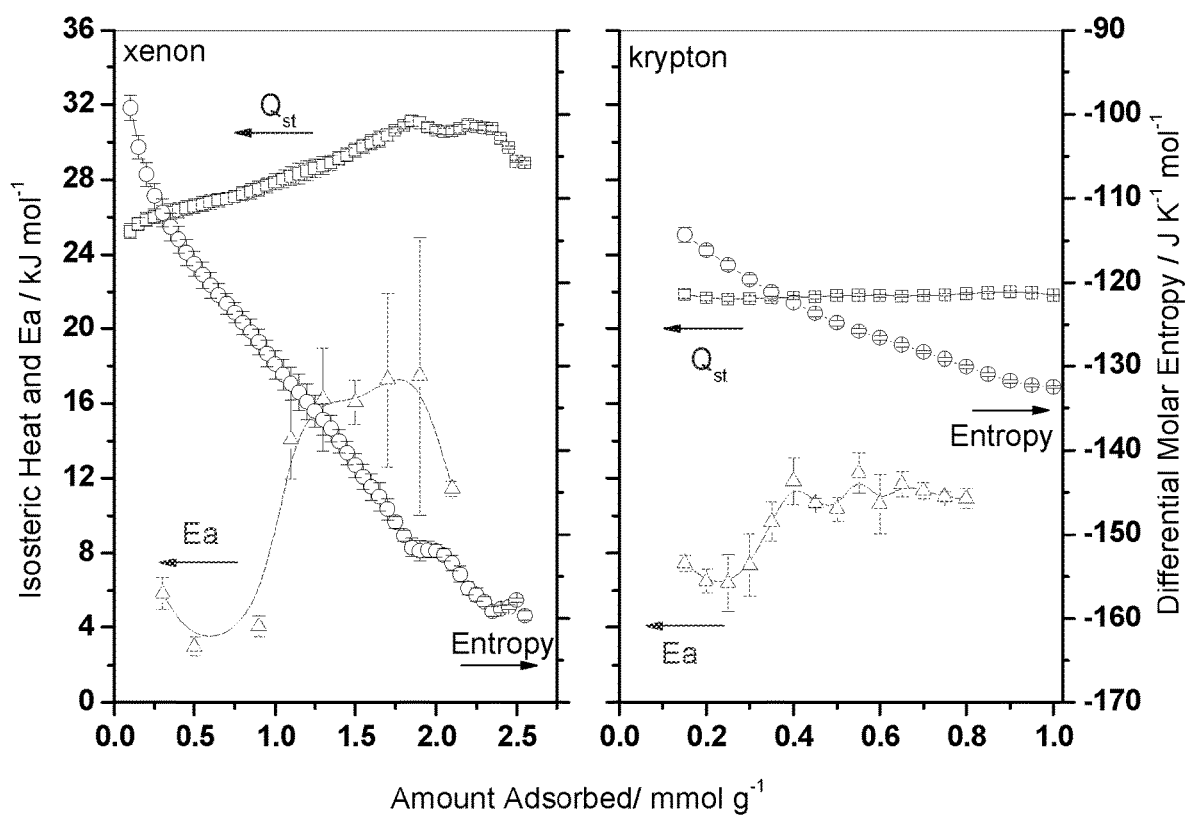
FIG. 39 shows the change of isosteric enthalpy, entropy and activation energy with amount adsorbed for xenon and krypton on CC3.

FIG. 39 shows the change of isosteric enthalpy, entropy and activation energy with amount adsorbed for xenon and krypton on CC3.

FIG. 40 shows: (i) Xenon/krypton selectivity using Ideal Adsorbed Solution Theory at a total pressure of 20 mbar and 195 K; (ii) Amount of xenon/krypton adsorbed as a function of xenon mole fraction using Ideal Adsorbed Solution Theory for a total pressure equal to 20 mbar, at 195 K.

Xe/Kr Breakthrough Measurements.

Breakthrough experiments were carried out to establish the practical potential of CC3 for Xe/Kr separations at low concentrations (<500 ppmv) in air, as would be encountered, for example, in the removal of $^{85}$Kr produced in nuclear reprocessing technologies. To minimise pressure drop and to prevent potential contamination of the main gas pipelines, a pellet sample of CC3 was prepared following a two-step procedure. First, a powder sample was pressed into a disk under 9 MPa for 3 min. The disk was then carefully broken up using a pestle and mortar and the fragments were sieved for 20-30 mesh (600-850 μm) pellets. The two-step procedure was repeated to make more pellets where necessary.

The Xe and Kr breakthrough curves for CC3 were measured using a dynamic sorption analyser (ARBC, Hiden Analytical Ltd., Warrington, U.K.). The cage pellets were packed into an adsorption bed for the breakthrough experiment. With reference to the ARBC system illustrated in a previous paper,[58] the gases were introduced through the bottom inlet of the adsorption bed. The adsorption bed was held between two layers of quartz wool and two sample holders, with frit gaskets installed at both the top and bottom ends of the adsorption bed to further prevent any potential powder contamination of the pipelines. For the separation of Xe (400 ppm in air) and Kr (40 ppm in air) at 298 K, a total flow rate of 40 cm$^3$ STP min$^{-1}$ and a total pressure of 1 bar were used. Prior to the breakthrough experiment, the pellet sample was degassed by heating at 413 K in situ under a helium purge for 10 h. The activated sample weight was determined immediately after unloading the sample and the ideal gas law was used to calculate the moles of gas adsorbed by CC3. Based on the mass balance, the gas adsorption properties can be determined as follows:

$$q = \frac{C_0 V t_s}{22.4 \, W}$$

$$t_s = \int_0^1 \left(1 - \frac{F}{F_0}\right) dt$$

where $t_s$ is the stoichiometric time (min), $C_0$ is the feed gas concentration, $F_0$ and F are the inlet and outlet gas molar flow rates respectively, q is the equilibrium adsorption capacity of gas (mmol g$^{-1}$), t is the adsorption time (min) which is from time zero to time when equilibrium is reached, V is the volumetric feed flow rate (cm$^3$ min$^{-1}$) at standard temperature and pressure (1 atm and 0° C.) and W is the weight of the activated adsorbent (g).[58]

The selectivity was then calculated according to the equation:

$$S_{AB} = \frac{x_A/y_A}{x_B/y_B}$$

where $x_A$ and $x_B$ are the mole fractions of gases A and B in the adsorbed phase and $y_A$ and $y_B$ are the mole fractions of gases A and B in the bulk phase.

Figure 41:
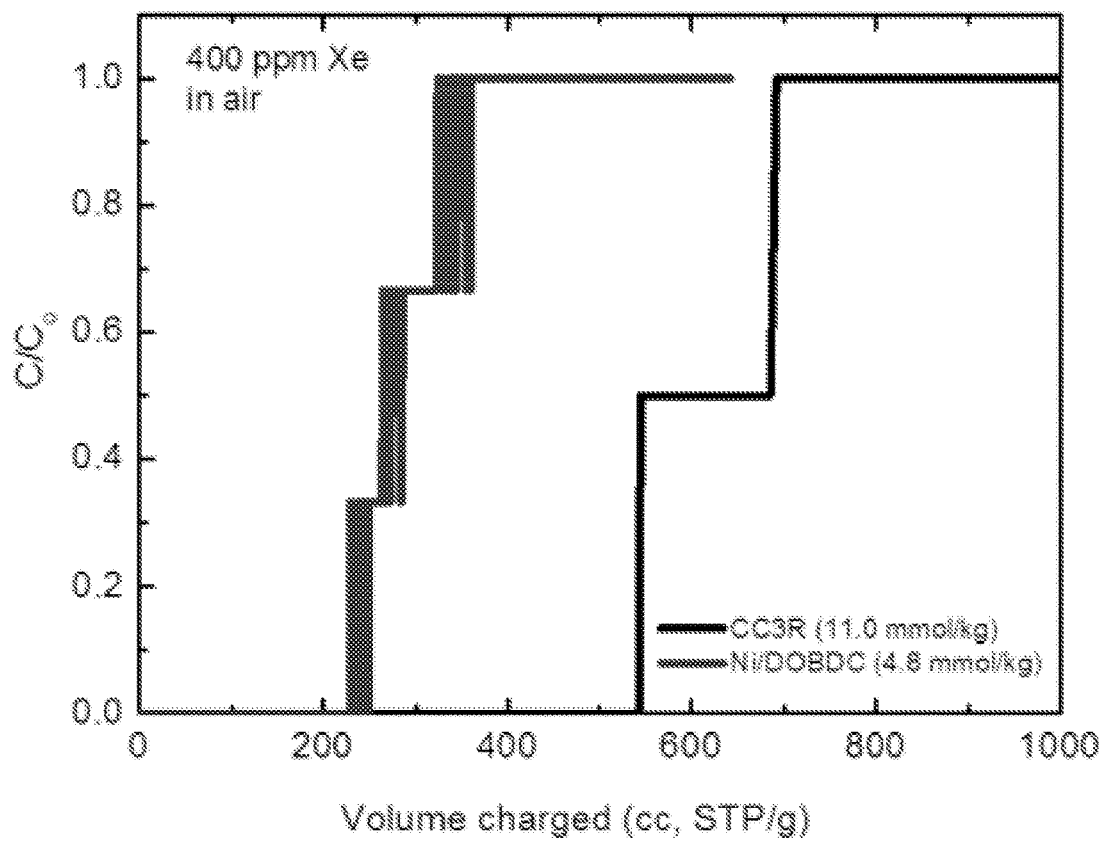
FIG. 41 shows a comparison of breakthrough curves for Xe (400 ppm Xe in air) adsorbed on a metal-organic framework, NI/DOBDC, and a molecular organic cage, CC3, at 298 K.

FIG. 41 shows a comparison of breakthrough curves for Xe (400 ppm Xe in air) adsorbed on a metal-organic framework, Ni/DOBDC, and a molecular organic cage, CC3, at 298 K. The flow rate of the gas mixture was 20 and 40 cm$^3$ STP min$^{-1}$, respectively, in the two experiments. That is, the flow rate was twice as high for the CC3 experiments compared to the experiments with the nickel MOF. Despite this faster flow rate, the Xe gas is retained more than twice as long by CC3. The value (C/C$_0$) is outlet Xe concentration divided by the inlet Xe concentration.

These breakthrough data demonstrate that the kinetics of adsorption of Xe in CC3 are sufficiently fast to allow effective separations, even though the diameter of Xe is at the edge of the pore limiting envelope for CC3 (FIG. 2 *a,b*). The kinetics may be aided by the three-dimensional, diamondoid pore structure in CC3. This contrasts with many organic molecular crystals, such as tris(o-phenylenedioxy) phosphonitrile (TPP),[59] which tend to have 1-dimensional, linear pore channels.

Comparison of Xe/Kr Separation Performance for CC3 with Other Porous Solids.

Figure 32:
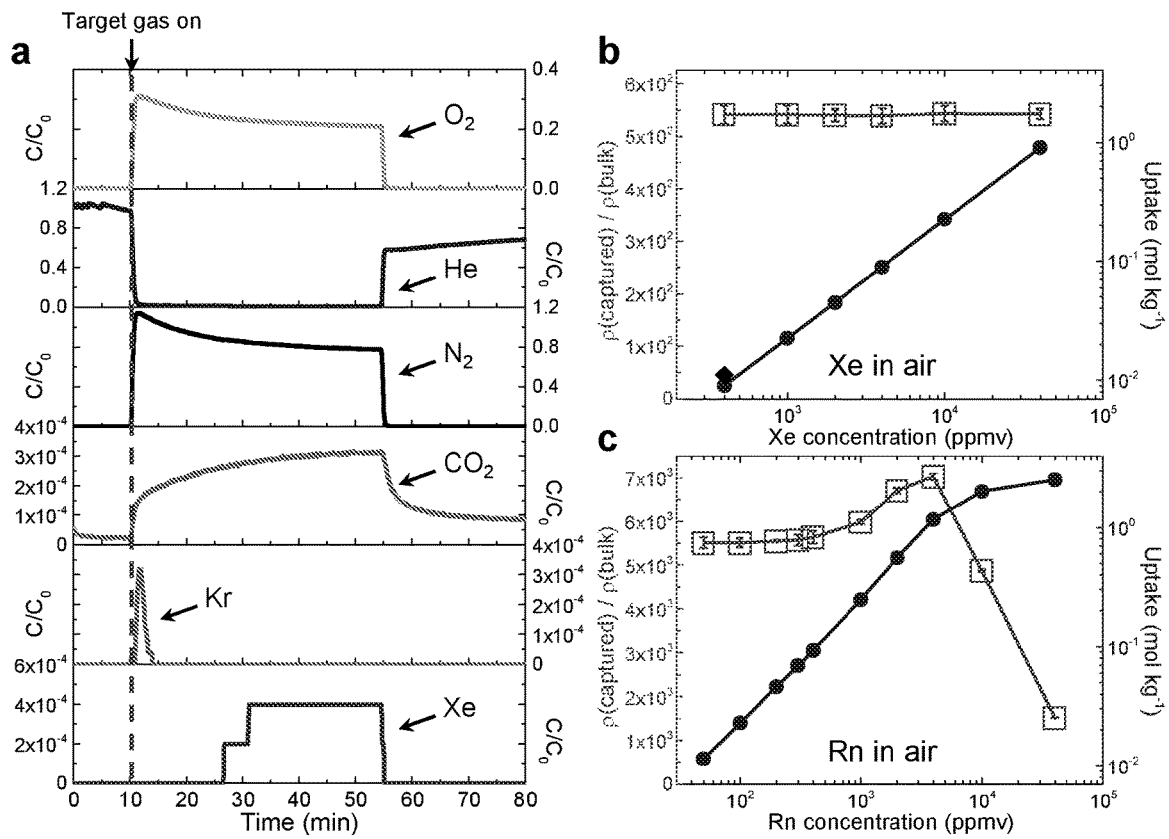
FIGS. 32a, 32b and 32c show (a) a graph of breakthrough measurements of noble gases at low concentrations in air, using an adsorption column packed with CC3 crystals; and (b) a graph comparing simulated xenon uptake with experimental uptake, comprising the volumetric density density of the noble gas in the solid CC3 adsorbent divided by its volumetric density in the bulk gas phase plotted against its concentration in the gas mixture; and (c) a graph of a simulation of the separation of radon from air.

While a number of experimental and simulation papers have been published in the area of MOFs for xenon and krypton adsorption, a far smaller number of papers have reported the separation of Xe and Kr at realistic, low concentrations in air, as would be relevant in processing of spent nuclear fuel (e.g., FIG. 32).

Table 10, below, gives an overview of the experimental adsorption capacities, the isosteric heats (Q$_{st}$), and the Xe/Kr selectivities for a range of porous materials at room temperature and 1 bar pressure. By far the majority of the selectivities reported in Table S10 were calculated from pure gas adsorption isotherms, rather than by competitive adsorption studies involving mixed gases. The exceptions are MOF-505, Cu(HFIPBB), and Co$_3$(HCOO)$_6$. For MOF-505, Cu(HFIPBB) and Co$_3$(HCOO)$_6$, the experimental breakthrough selectivities were calculated using 20/80 or 50/50 Xe/Kr mixtures. This is relevant to Xe/Kr separation for gas mixtures arising from oxygen distillation, but does not necessarily reflect separation performance for these gases at <500 ppm concentrations. For nuclear re-processing applications, porous solids need to selectively remove Xe and Kr in parts per million (ppm) levels in the presence of other competing gases such as CO$_2$, N$_2$, O$_2$, Ar, and water. Materials such as MOFs, which often contain polar binding sites, might selectively adsorb water and/or CO$_2$ under such conditions. Based on earlier studies at the Oakridge National Laboratory, the concentrations of Xe and Kr in nuclear re-processing plants were found to be 400 ppm (Xe) and 40 ppm (Kr) in air consisting of N$_2$, 78%, O$_2$, 21%, Ar, 0.9%; CO$_2$, 0.03%, etc. However, with the exception of MOF-74, none of the MOFs listed in Table 10 was tested in such gas mixtures.

Both the Xe selectivity and the Xe uptake of CC3 are significantly higher than MOF-74Ni (Table 11), even when tested at higher flow-rate. Comparable data for Xe at 1000 ppm mixed in air are shown in Table 12 for MOF-74Ni, activated carbon, and HKUST-1.

TABLE 10

Xenon uptake and xenon/krypton selectivity at room temperature and 1 bar on selected adsorbents.

| Sorbent | Xe uptake (mmol g$^{-1}$) | Xe Q$_{st}$ (kJ mol$^{-1}$) | Xe/Kr Selectivity |
|---|---|---|---|
| MOF-5 | 1.98 | 15 | — |
| MOF-74Ni | 4.2 | 9.5 | 5 |
| Ag@MOF-74Ni | 4.6 | 11 | 6.8 |

TABLE 10-continued

Xenon uptake and xenon/krypton selectivity at room temperature and 1 bar on selected adsorbents.

| Sorbent | Xe uptake (mmol g$^{-1}$) | Xe Q$_{st}$ (kJ mol$^{-1}$) | Xe/Kr Selectivity |
|---|---|---|---|
| MIL-53-Al | 3 | — | — |
| Cu(HFIPBB) | — | 15 | 2 |
| MFU-4 | 1.8 | 20 | 4.7 |
| HKUST-1 | 3.3 | 26.9 | 8.4 |
| MOF-505 | 2.2 | — | 8 |
| CO$_3$(HCOO)$_6$ | 2 | 28 | 6 |
| Activated Carbon | 4.2 | — | 4 |

TABLE 11

Xenon uptake and selectivity at room temperature from gas mixtures containing 400 ppm Xe, 40 ppm Kr in Air on MOF-74 Ni and CC3.

| Sorbent | Xe uptake (mmol kg$^{-1}$) | Xe/Kr Selectivity |
|---|---|---|
| MOF-74Ni | 4.8 | 7.3 |
| CC3 | 11 | 20.4 |

TABLE 12

Xenon uptake and selectivity at room temperature from gas mixtures containing 1000 ppm Xe, 1000 ppm Kr in Air on MOF-74 Ni, HKUST-1, and Activated Carbon.

| Sorbent | Xe uptake (mmol kg$^{-1}$) | Xe/Kr Selectivity |
|---|---|---|
| MOF-74Ni | 9.3 | 5.3 |
| HKUST-1 | 8.5 | 5.0 |
| Activated Carbon | 8.4 | 4.9 |

Radon Measurements.

Figure 42:
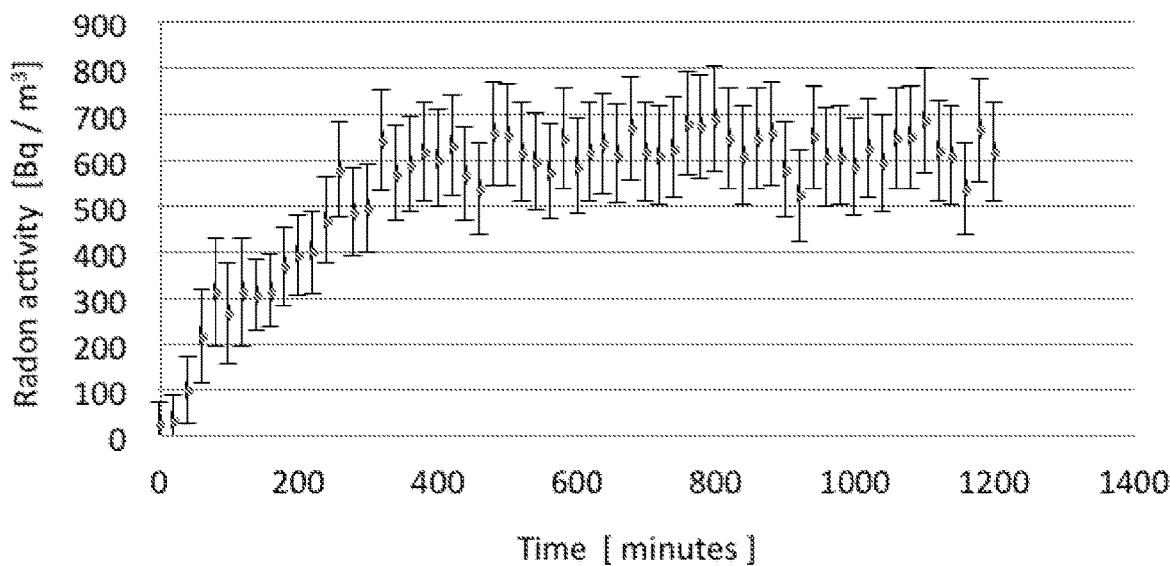
FIG. 42 shows a saturation curve for Rn (at high dilution in $N_2$) adsorbed on CC3.

The radon adsorption capability of CC3 was evaluated using a dynamic adsorption technique. $^{222}$Rn is a short time-period isotope, and it must be diluted in a carrier gas at a very low concentration. The carrier gas, with a fixed concentration of radon, is then injected into an adsorbent trap. Adsorption equilibrium is attained when the breakthrough curve reaches a constant value (FIG. 42). Under such conditions, the ratio between the number of atoms of radon trapped and the radon concentration in the gas, both assumed to be proportional to their respective activity (Bq m$^{-3}$), is given by the equilibrium constant, K:

$$K = \frac{\{A\}}{\{C\}}$$

where {A} is the radon activity in CC3 and {C} is the radon activity in the gas.

Figure 43:
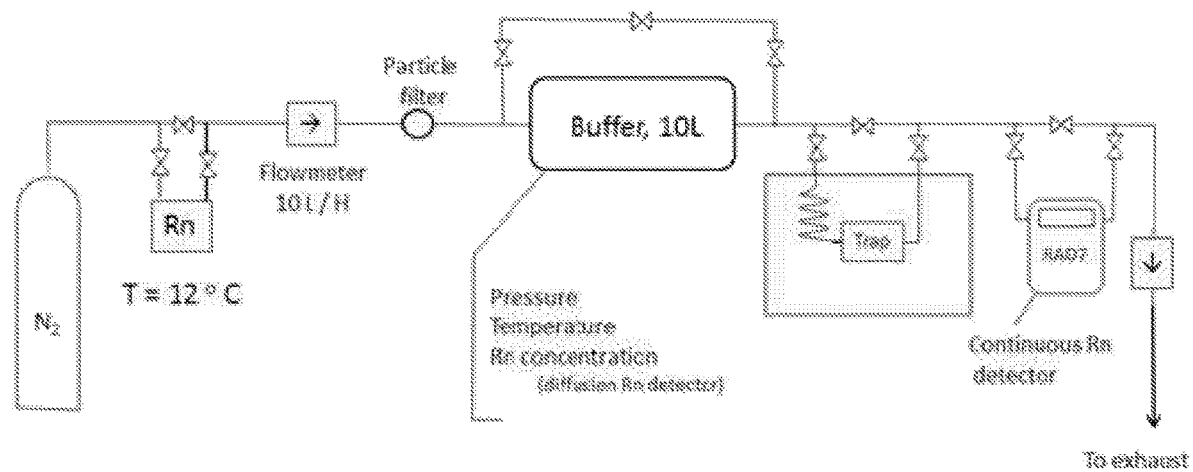
FIG. 43 is a scheme showing apparatus used for Rn adsorption measurements.

The experimental setup is illustrated in FIG. 43. The nitrogen carrier gas is radonised in the radon source by emanation from a metal plate coated with a thin radium layer and maintained at a fixed temperature (12° C.). The mean radon concentration in the carrier gas is 615±17 Bq m$^3$ (3.8±0.1·10$^{-1}$ mol kg$^{-1}$). The gas is introduced into a buffer tank in which the radon concentration (C), the temperature, and the pressure are controlled. Thereafter, the carrier gas, with a well-defined amount of radon, is introduced into the column trap, which is located in a freezer. In order to define the equilibrium capture in the radon trap, the output gas is measured with a commercial RAD7 detector calibrated for a continuous nitrogen flow. Once equilibrium is reached, the trap is disconnected from the gas circuit and the $^{222}$Rn activity of the CC3 sample is measured by gamma spectrometry in a germanium detector from the main gamma lines of radon progeny (352 keV from $^{214}$Pb and 609 keV from $^{214}$Bi).

FIG. 42 shows a saturation curve for Rn (at high dilution in N$_2$) adsorbed on CC3.

FIG. 43 is a scheme showing apparatus used for Rn adsorption measurements.

Enantioselective Separation

Porous organic cages can also be used to separate molecules other than rare gases.

Figure 44:
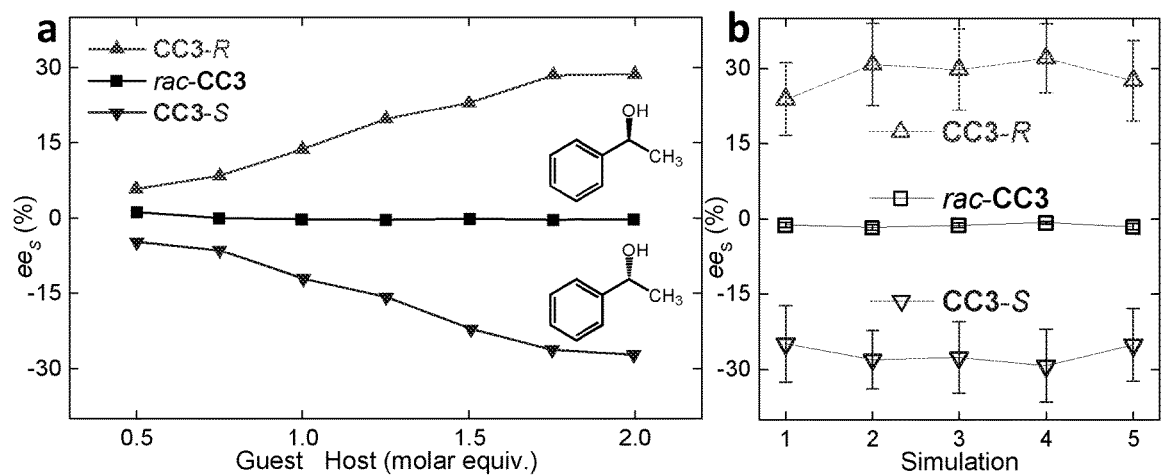
FIGS. 44a and 44b show experimental (a) and simulated (b) enantiomeric excess (ee) fr 1-phenylethanol.

Chiral molecules are important pharmaceutical feedstocks and there is a need for their effective separation. CC3 can be prepared in homochiral form by synthesizing the cage from either the (R,R) or (S,S) enantiomer of 1,2-cyclohexanediamine [Hasell, T. et al. Porous organic cage nanocrystals by solution mixing. *J. Am. Chem. Soc.* 134, 588-598, (2012)]. We therefore explored homochiral CC3 for chiral separations. Homochiral crystals of CC3 were found to adsorb a chiral alcohol, 1-phenylethanol, with selectivity for the enantiomer with opposite chirality to that of the cage (FIG. 44a). This results from more favourable intermolecular interactions between the 1-phenylethanol guest and the CC3 cage of the opposite chirality. The racemic cage crystal, rac-CC3, showed no enantioselectivity for this alcohol. However, rac-CC3 does show size selectivity for achiral guests, such as xenon and radon, much as found for the homochiral forms of CC3. Hence, rac-CC3 is size selective, whereas homochiral CC3 is both size selective and enantioselective.

Chiral Selectivity Measurements.

The enantioselectivity of CC3-R, CC3-S, rac-CC3, and a chiral conglomerate of CC3 (an equimolar mixture of CC3-R and CC3-S) was measured for rac-1-phenylethanol. Solutions of rac-1-phenylethanol in 1-tert-butyl-3,5-dimethylbenzene (ca. 1 cm$^3$) were exposed to the CC3 host (ca. 30 mg) and allowed to reach equilibrium (18 h). The solvent, 1-tert-butyl-3,5-dimethylbenzene, was chosen such that it is size- and shape excluded from the cage cavities.[60] The resulting slurry was then filtered to yield a guest-adsorbed CC3 phase and guest-depleted filtrate. The quantity of each enantiomer of 1-phenylethanol adsorbed in the CC3 host was then be measured by chiral GC analysis. The chemical and phase purity of the CC3 before and after guest adsorption was examined using $^1$H NMR and PXRD. This experiment was repeated at various guest:host ratios to generate the plot shown in FIG. 44a.

Materials.

rac-1-Phenylethanol and bromomesitylene were purchased from Sigma-Aldrich and used as received. 1-tert-Butyl-3,5-dimethylbenzene was purchased from Sigma-Aldrich, purified by vacuum distillation (55° C., 1.7 mbar), and stored over 4 Å molecular sieves. Acetonitrile, methanol, and chloroform were purchased from Fisher Scientific and used as received. Finely ground CC3-R, CC3-S, and rac-CC3 were prepared according to methods described previously.[1] A chiral conglomerate of CC3, was prepared by accurately weighing equal amounts of solid CC3-R and CC3-S into a vial (average particle size approx. 0.5-200 micro-m) followed by gentle shaking to mix the particles. In contrast to the homochiral and chiral conglomerate cages, the average particle size of rac-CC3 was smaller, approximately 0.5-50 micro-m.

Gas Chromatography (GC) Analysis.

GC measurements were carried out using a Thermo Scientific TRACE 1310 instrument configured with an FID detector and a 2,3-di-O-methyl-6-O-TBDMS-β-cyclodextrin capillary column (Supelco Beta DEX 325; 30 m×0.25 mm×0.25 μm). Samples were analysed using either headspace or liquid injections. Headspace injections were performed by incubating the sample at 100° C. for 30 minutes followed by sampling 1 mL of the samples headspace. Liquid injections were taken by directly injecting 2 μL of the sample. The following GC method was used, regardless of the injection technique. A temperature gradient was used to achieve the desired separation; the oven was programmed from 95° C. with 35 min hold and 10° C. min$^{-1}$ increments to 150° C. with 4 min hold, the total run time was 44.5 min; injection temperature 300° C.; detection temperature 300° C. with hydrogen, air, and make-up flow-rates of 35, 350, and 35 mL min$^{-1}$ respectively; helium (carrier gas) flow-rate 1 mL min$^{-1}$. The samples were injected in the split mode (5:1 for headspace and 25:1 for liquid injections). Numeric integration of the resulting peaks was performed using the supplied Chromeleon 7.1.2.1478 (Thermo Scientific Corporation) software package.

FIGS. 44a and 44b show experimental (FIG. 44a) and simulated (FIG. 44b) enantiomeric excess (ee) for 1-phenylethanol. Enantiomeric excess of the S enantiomer (ee$_S$) of 1-phenylethanol adsorbed in CC3 was measured over a range of guest:host ratios. Equal and opposite ee$_S$ is observed for homochiral CC3-R (upper line) and CC3-S (lower line) crystals because of preferential adsorption of the 1-phenylethanol enantiomer with opposite chirality. The racemic cage crystal, rac-CC3 (middle line), is not enantioselective. Simulated ee$_S$ were obtained from advanced configurational-bias Monte Carlo simulations for 1-phenylethanol in the CC3 host. All simulations were carried out at ambient temperature and pressure. Simulated maximum guest loadings and ee$_S$ for 1-phenylethanol in the CC3 host correspond closely with experimental observations at a guest:host ratio of 2. Five independent simulations were performed in each case. A parallel mole-fraction grand-canonical Monte-Carlo simulation was used [Dubbeldam, D., Torres-Knoop, A. & Walton, K. S. On the inner workings of Monte Carlo codes. *Mol. Simul.* 39, 1253-1292, (2013)].

Figure 46:
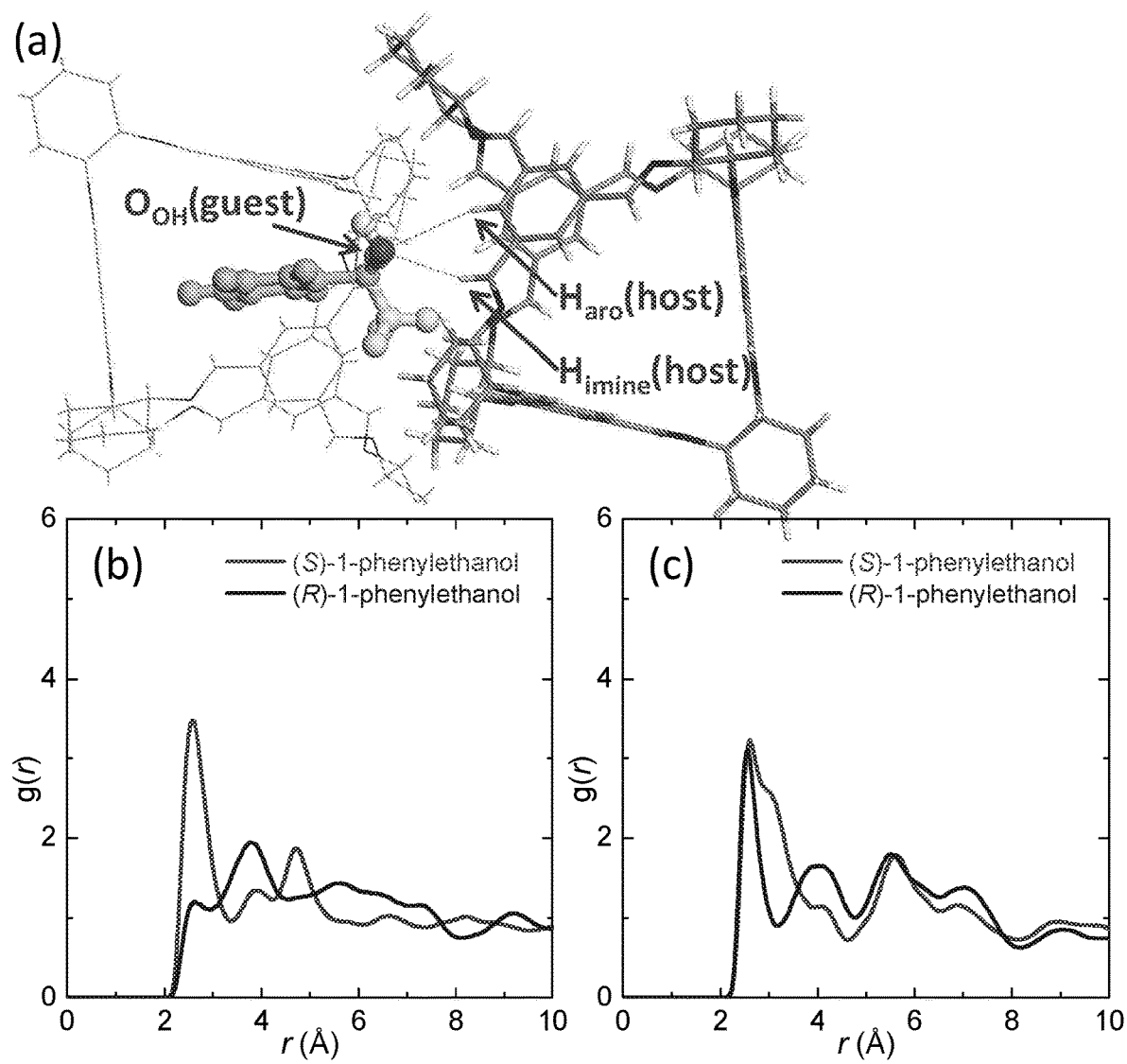
FIGS. 46a, 46b and 46c show a molecular configuration showing the hydroxyl oxygen atom of an (S)-1-phenylethanol [OOH(guest)] in close proximity of the hydrogen atom bonded to an imine carbon atom [Himine(host)] and an aromatic hydrogen [Haro(host)]of the CC3-R cage (a); radial distribution functions of the OOH(guest) . . . Himine (host) pair (b) and the OOH(guest) . . . Haro(host) pair (c) for the S and R enantiomers in the CC3-R crystal structure computed over 1.0-ns NPT MD simulations.
Figure 47:
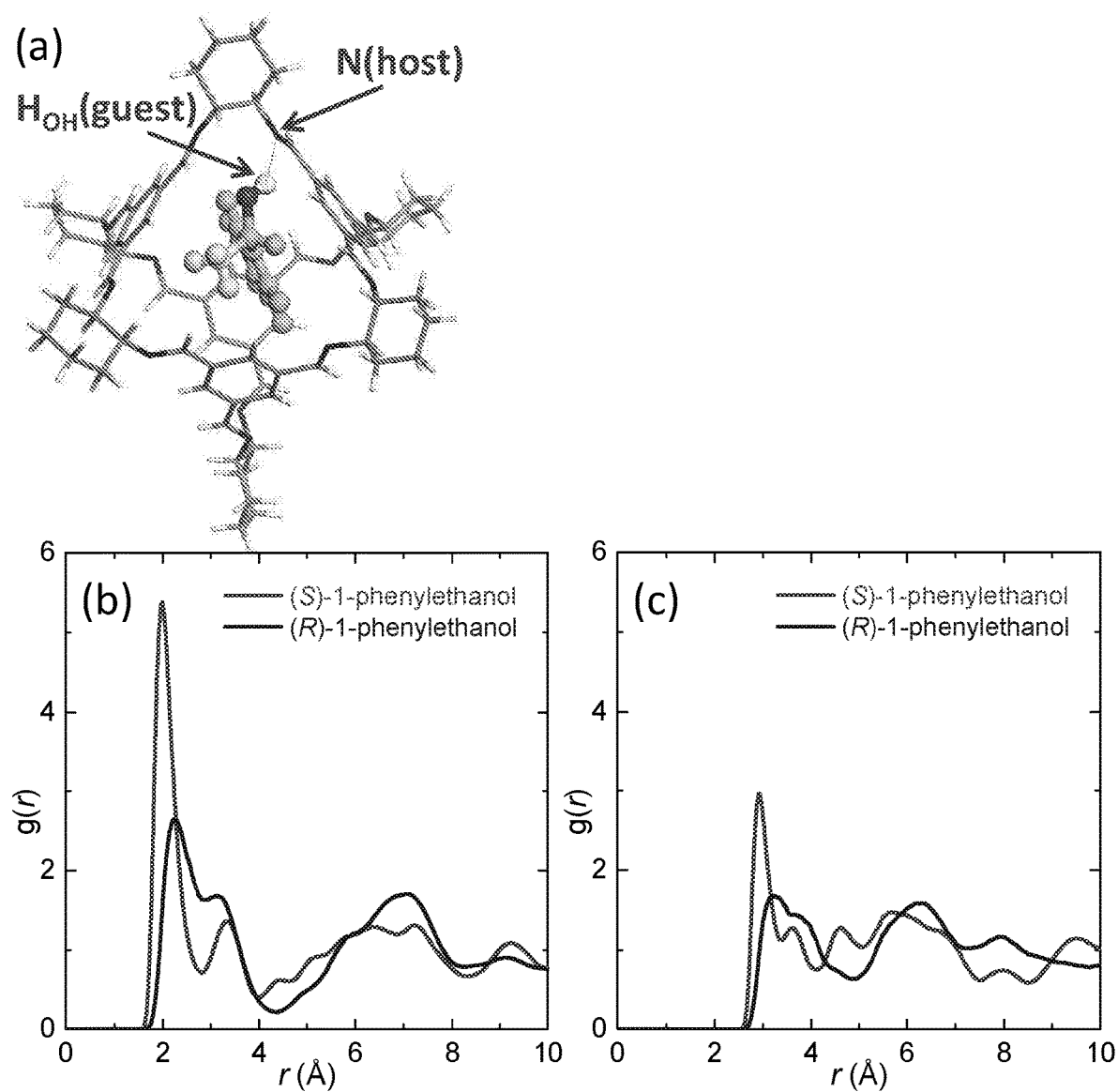
FIGS. 47a, 47b, and 47c show a molecular configuration showing the hydroxyl hydrogen atom of an (S)-1-phenylethanol molecule [HOH(guest] in close proximity of a nitrogen atom of the CC3R cage [N(host)](a).
Figure 48:
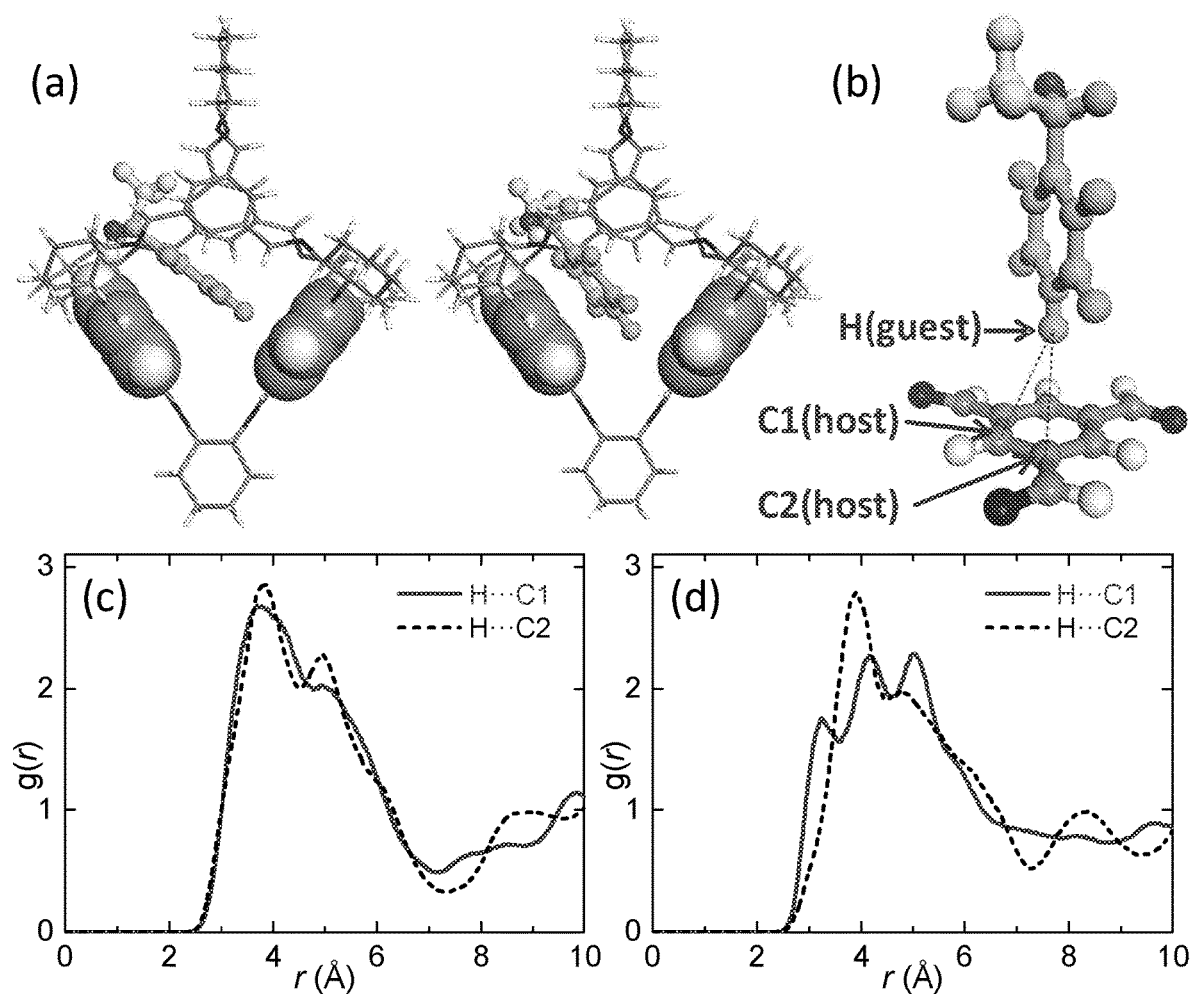
FIGS. 48a, 48b, 48c and 48d show that (S)-1-Phenylethanol is a better firt with the cavity of the CC3-R cage in comparison with (R)-1-phenylethanol is a better fit with the cavity of the CC3-R cage in comparison with (R)-1-phenylethanol.

Single crystal X-ray diffraction shows that the 1-phenylethanol guests are disordered over several sites in the pores of CC3. The electron density is too diffuse to be modelled accurately, but molecular simulations suggest that the chiral selectivity stems from a specific interaction between the hydroxyl group in the alcohol and the nitrogen atom in the imine of CC3 (FIG. 45a), supported by π-π interactions between aryl groups in the cage and in the alcohol. This conformation is predicted to be common for (S)-1-phenylethanol in CC3-R, but is much less apparent in CC3-S, as illustrated by radial distribution function plots (FIGS. 46-48). This leads to a predicted difference in host-guest binding energy for (S)-1-phenylethanol and (R)-1-phenylethanol in CC3-R of around 28.5±4.0 kJ mol$^{-1}$, which explains the observed enantioselectivity.

Figure 45:
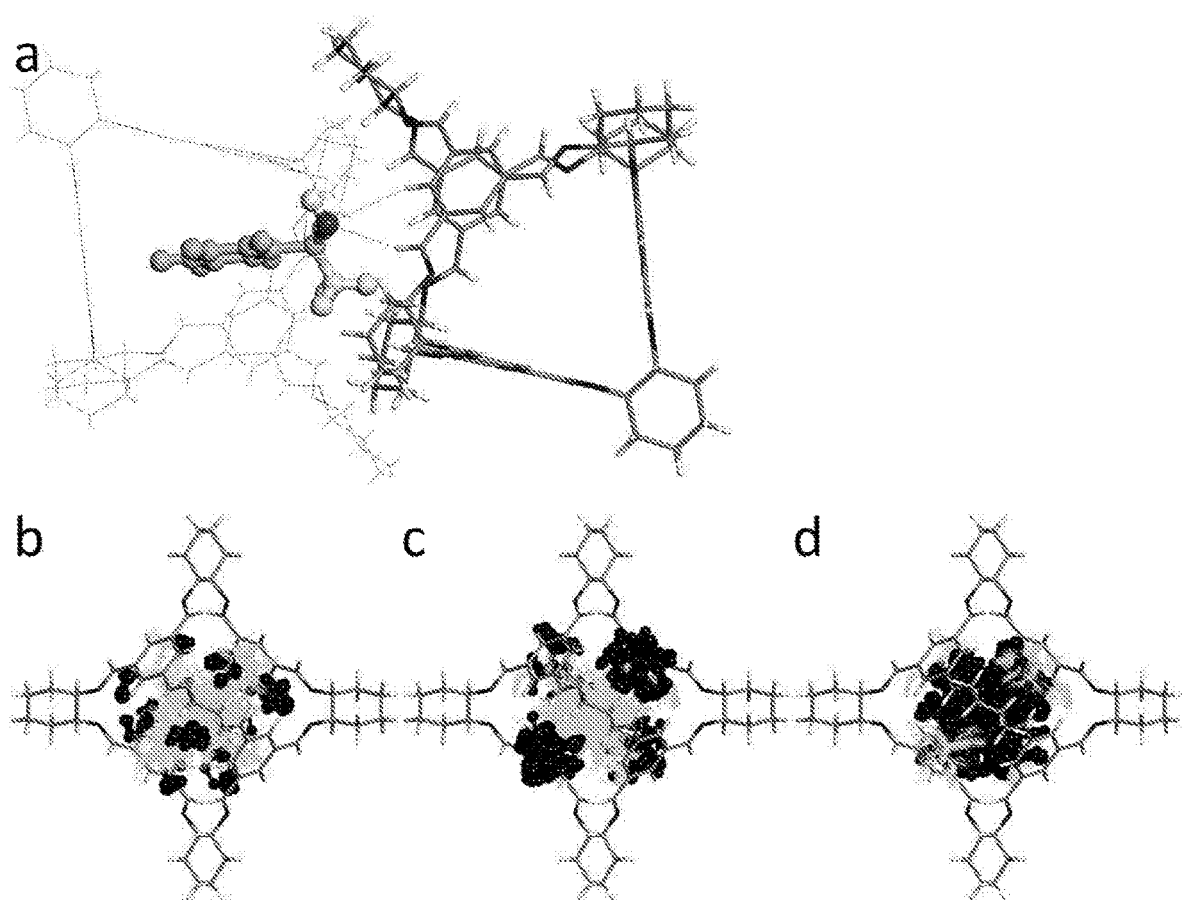
FIGS. 45a, 45b, 45c and 45d show simulated molecular configurations of (S)-1-phenylethanol in the pores of CC3-R.

FIGS. 45a, 45b, 45c and 45d show simulated molecular configurations of (S)-1-phenylethanol in the pores of CC3-R. FIG. 45a shows a frequently observed conformation where the hydroxyl oxygen atom of (S)-1-phenylethanol is in close proximity to the hydrogen atom (2.57 Å), bonded to an imine carbon atom, and to an aryl hydrogen atom (2.61 Å), both of CC3-R. FIG. 45b is an overlay of one hundred snapshots of (S)-1-phenylethanol in the CC3-R cage molecule. The alcohol groups (FIG. 45b: hydroxyl group of 1-phenylethanol in ball-and-stick representation and colored as black) and the methyl groups (FIG. 45c: methyl group of 1-phenylethanol in ball-and-stick representation and coloured as black) of (S)-1-phenylethanol occupy the cage windows, pointing toward neighboring cages; the phenyl ring (FIG. 45d: phenyl rings of 1-phenylethanol in ball-and-stick representation and coloured as black) is located inside the cage cavity. The predicted disordered orientation of (S)-1-phenylethanol inside the CC3-R cage is consistent with experimental single crystal observations.

FIGS. 46a, 46b and 46c show a molecular configuration showing the hydroxyl oxygen atom of an (5)-1-phenylethanol [$OO_H$(guest)] in close proximity of the hydrogen atom bonded to an imine carbon atom [$H_{imine}$(host)] and an aromatic hydrogen [$H_{aro}$(host)] of the CC3-R cage (a); radial distribution functions of the $O_{OH}$(guest) . . . $H_{imine}$ (host) pair (b) and the $OO_H$(guest) . . . $H_{aro}$(host) pair (c) for the S and R enantiomers in the CC3-R crystal structure computed over 1.0-ns NPT MD simulations.

FIGS. 47a47b and 47c show a molecular configuration showing the hydroxyl hydrogen atom of an (S)-1-phenylethanol molecule [$H_{OH}$(guest)] in close proximity of a nitrogen atom of the CC3-R cage [N(host)] (a). Radial distribution functions (RDFs) of the $H_{OH}$(guest) . . . N(host) pair for the S and R enantiomers in the CC3-R crystal structure computed over 1.0-ns NPT MD simulations (b), and the corresponding RDFs for the $OO_H$(guest) . . . N(host) pair (c), which indicate a characteristic Donor-Hydrogen-Acceptor (O—H—N) distance of 2.97 Å and 3.23 Å for the S and R enantiomers of the alcohol, respectively.

FIGS. 48a, 48b, 48c and 48d show that (S)-1-Phenylethanol is a better fit with the cavity of the CC3-R cage in comparison with (R)-1-phenylethanol. (a) The phenyl ring of the S-enantiomer can form two near π-π stacking conformations (one "sandwich" and the other "T-shaped") with two phenyl rings of the CC3-R cage (left), whereas these conformations are less apparent in the case of the R-enantiomer in the CC3-R cage (right). (b) Atom definition for the radial distribution functions (RDFs) shown in (c) and (d); atom type C1(host) corresponds to all of the cage aromatic carbon atoms bonded to a hydrogen atom while atom type C2(host) corresponds to the rest of the aromatic carbon atoms that are bonded to an imine group. The RDFs of (S)-1-phenylethanol in CC3-R suggest formation of the T-shaped π stacking (c), while the RDFs of (R)-1-phenylethanol in CC3-R do not (d).

Powder X-Ray Diffraction (PXRD) Analysis.

Laboratory PXRD data were collected in transmission geometry on a Bruker D8 Advance diffractometer with Ge-monochromated Cu $K\alpha_1$ radiation and a LynxEye PSD on samples held between Mylar film. Data were collected in the range $4 \leq 2\theta \leq 50°$ with a step size of 0.013° over 2 hours. Le Bail fitting was carried out using TOPAS Academic.

Figure 49:
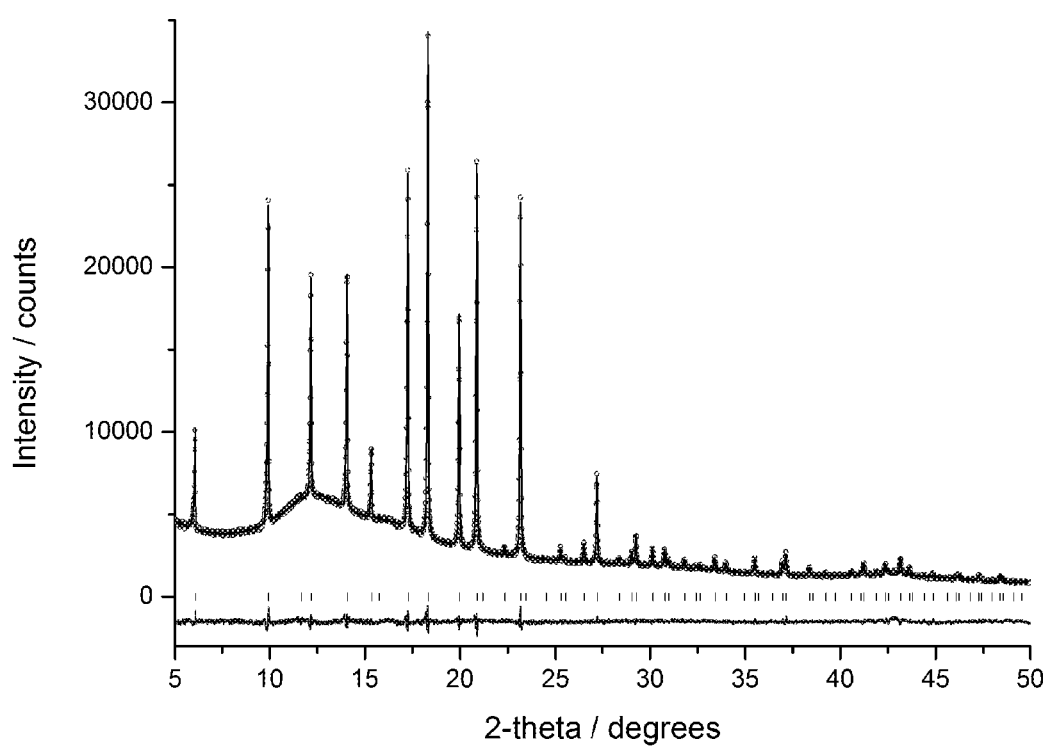
FIG. 49 shows final observed (circles), calculated (line) and difference (below) PXRD profiles for Le Bail refinement of bulk CC3-R (a=25.1302(1)Å, V=15870.5(2)Å$^3$, $F4_132$) used for chiral selectivity measurements ($R_{wp}$=2.85%, $R_p$=2.10%,$X^2$=1.57).
Figure 50:
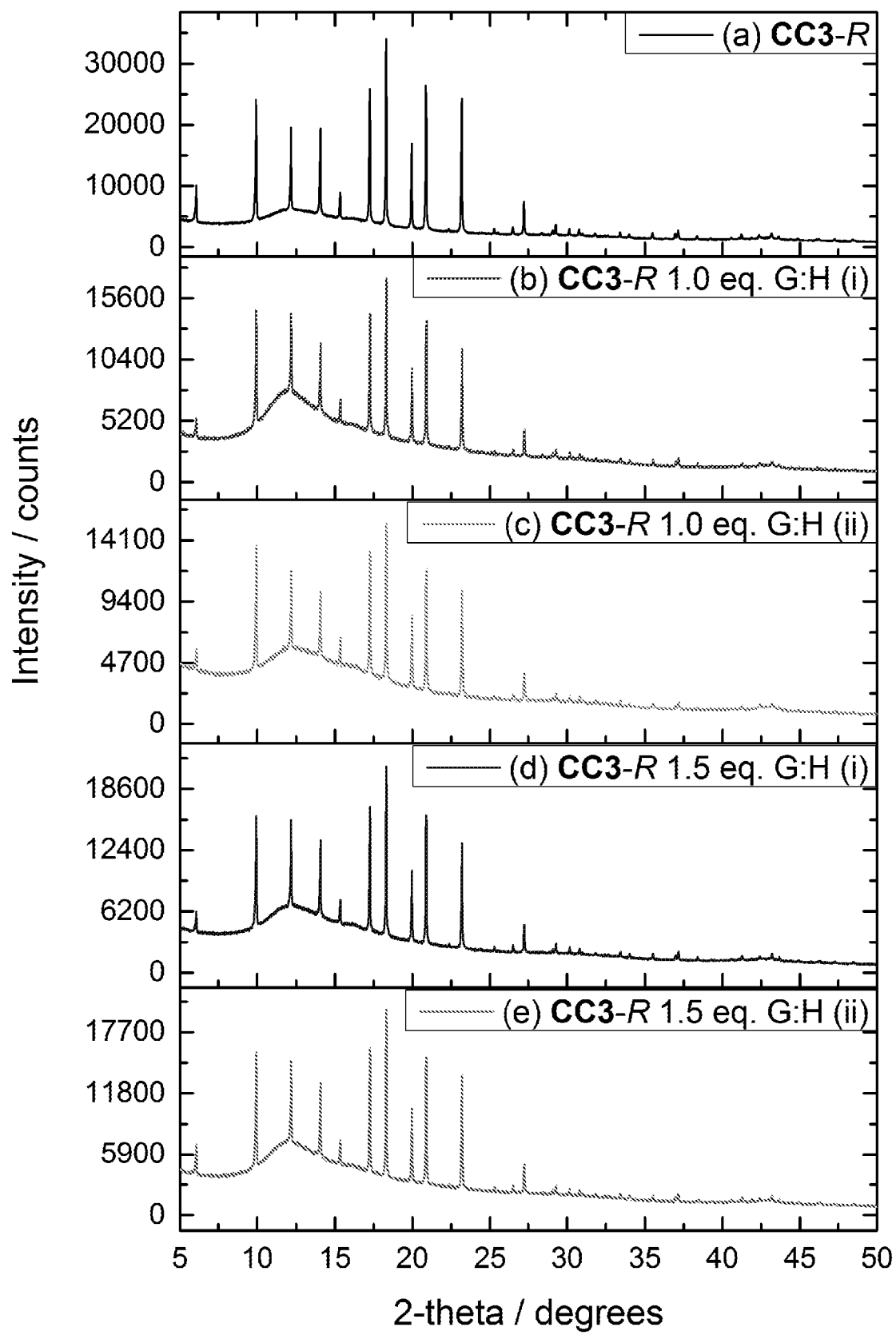
FIG. 50 shows PXRD patterns of CC3-R samples (a) prior to separation experiments; (b) post rac-1-phenylethanol separations in the presence of a guest:host (G:H) ratio of 1.0 equivalents and exposed to vacuum, and (c) post guest-washout and exposed to vacuum; (d) postsepearation In the presence of a 1.5 equivalents G:H ratio and exposed to vacuum, and (e) post guest-washout and exposed to vacuum.

Initial phase purity of the bulk CC3-R sample used for the GC measurements was confirmed by Le Bail fitting of the PXRD data (FIG. 49). Powder data were subsequently collected for solid samples (i) after GC analysis and exposure to vacuum at 60° C., and then (ii) post-guest washout with acetonitrile and drying under vacuum at 60° C., which show the PXRD patterns are largely unchanged throughout the separation process (FIG. 50). Le Bail fitting for a representative evacuated sample after 1-phenylethanol separation (FIG. 51a) and after guest-washout (FIG. 51b) confirmed the persistence of the cubic structure.

FIG. 49 shows final observed (circles), calculated (line) and difference (below) PXRD profiles for Le Bail refinement of bulk CC3-R (a=25.1302(1) Å, V=15870.5(2) Å$^3$, F4$_1$32) used for chiral selectivity measurements ($R_{wp}$=2.85%, $R_p$=2.10%, $\chi^2$=1.57). Reflection positions are also shown.

FIG. 50 shows PXRD patterns of CC3-R samples (a) prior to separation experiments; (b) post rac-1-phenylethanol separation in the presence of a guest:host (G:H) ratio of 1.0 equivalents and exposed to vacuum, and (c) post guest-washout and exposed to vacuum; (d) post-separation in the presence of a 1.5 equivalents G:H ratio and exposed to vacuum, and (e) post guest-washout and exposed to vacuum. The patterns remain largely unchanged throughout the process, indicating no change in cage packing was induced by the loading and exchange of the guest.

Figure 51:
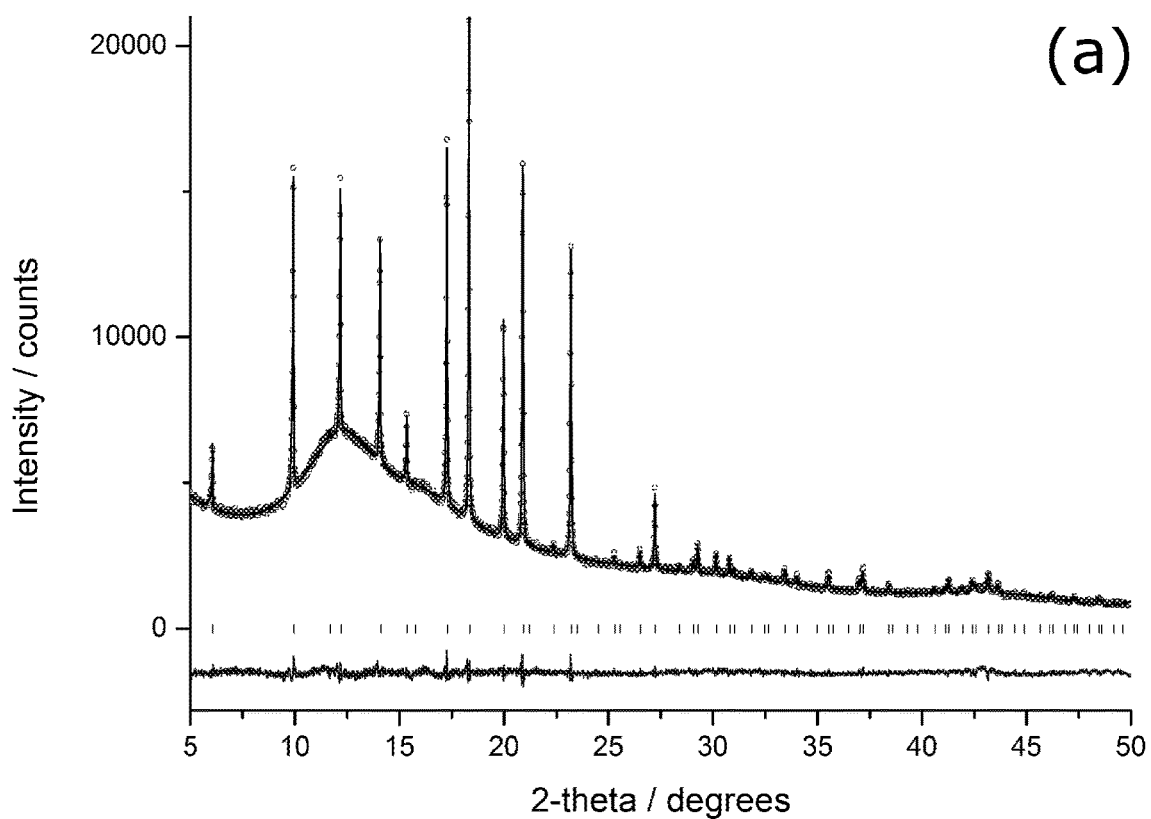
FIGS. 51a and 51b show final observed (circles), calculated (line) and difference (below) PXRD profiles for Le Bail refinement of CC3-R (a) after separation of rac-1-phenylethanol (1.5 guest: host ratio) and subsequent vacuum exposure (a=25.1087(4)Å, V=15829.6(8)Å$^3$, $F4_132$; $R^{wp}$=2.79 %,$R_p$=2.05%,, $X^2$=1.50) and (b) after washing out of guest using acetonitrille and drying by vacuum (a=25.1117(5)Å, V=15835.4(9)Å$^3$, $F4_132$; $R_{wp}$=2.71%, $R_p$=2.02%, $X^2$=1.47)
Figure 51:
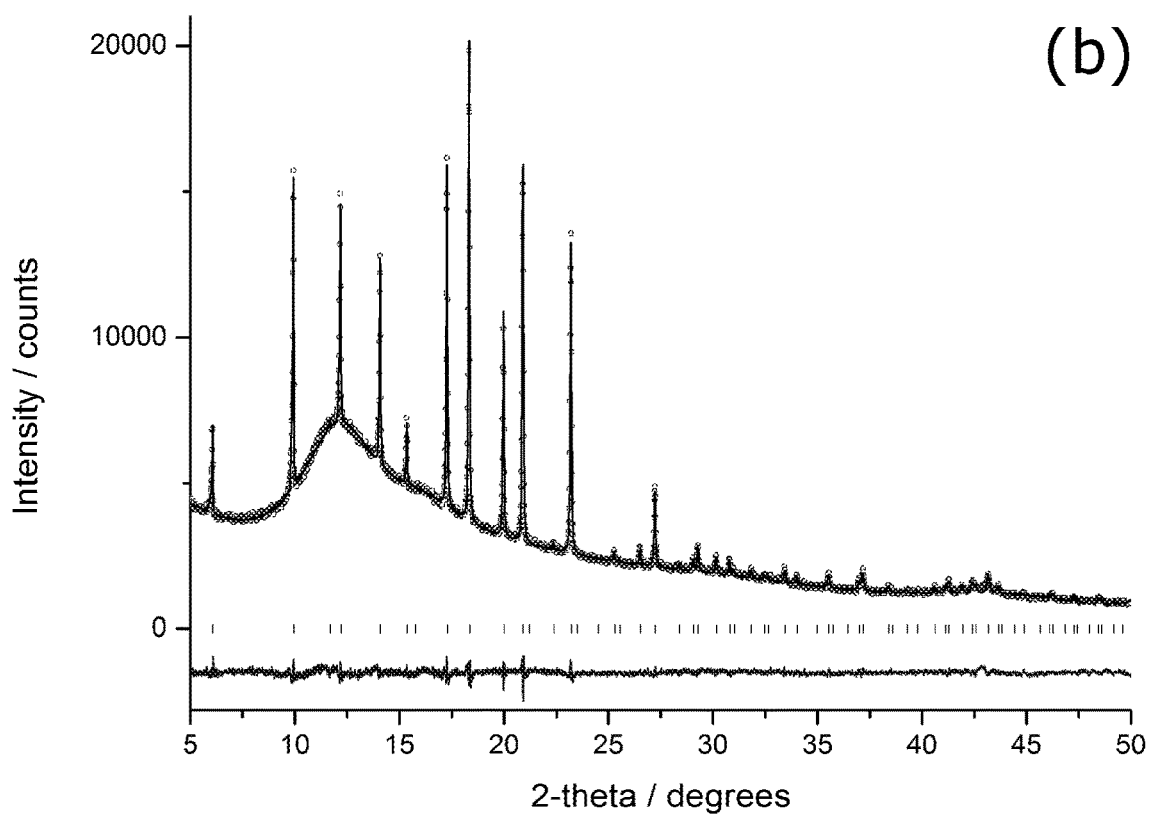

FIGS. 51a and 51b show final observed (circles), calculated (line) and difference (below) PXRD profiles for Le Bail refinement of CC3-R (a) after separation of rac-1-phenylethanol (1.5 guest:host ratio) and subsequent vacuum exposure (a=25.1087(4) Å, V=15829.6(8) Å$^3$, F4$_1$32; $R_{wp}$=2.79%, $R_p$=2.05%, $\chi^2$=1.50) and (b) after washing out of guest using acetonitrile and drying by vacuum (a=25.1117 (5) Å, V=15835.4(9) Å$^3$, F4132; R, =2.71%, $R_p$=2.02%, $\chi^2$=1.47). Reflection positions are also marked.

NMR Spectroscopy.

Solution $^1$H NMR spectra were recorded in deuterated chloroform at 400.13 MHz using a Bruker Avance 400 NMR spectrometer.

Chiral Separation Procedure.

A stock solution of bromomesitylene in 1-tert-butyl-3,5-dimethylbenzene (ca. 3 mg mL$^{-1}$) was made. Seven solutions of rac-1-phenylethanol in the stock were made at different accurate concentrations: 56.67, 49.87, 42.50, 35.70, 28.34, 21.25, and 15.59 μmol mL$^{-1}$. These were then used for both the host:guest exchange process and for GC calibration. Each concentration was chosen to produce the desired guest:host ratio in the later experimental steps; for example, the 56.67 μmol mL$^{-1}$ solution is used to produce 2:1 guest:host ratio slurries. This means that, for all guest:host equivalents, the overall slurry volume does not greatly differ. In addition, four lower-concentration solutions were made by serial dilution for exclusive use in GC calibration: 7.79, 3.90, 1.95, and 0.97 μmol mL$^{-1}$. The bromomesitylene solution was also used as a blank injection, which allows us to correct for any impurities present in the reaction solvent.

1-tert-Butyl-3,5-dimethylbenzene was chosen as the solvent both because CC3 is very poorly soluble in it, and it is unable to fit within the pores of CC3 and hence disturb the host:guest exchange process.[60] Likewise, bromomesitylene was chosen as the internal standard because it is unable to fit within the pores of CC3. GC calibration samples and the analysis samples were prepared in triplicate. Additional samples were prepared in parallel for PXRD and $^1$H NMR analyses at various stages to check phase and chemical purity. Approximately 30 mg of CC3 hosts were placed into pre-weighed vials and activated in a vacuum oven for 18 h at 90° C. Once cooled, the filled vials were weighed in order to accurately calculate the moles of CC3 in each vial. Based on the desired guest:host ratio, the suitable guest solution was accurately added to each of the CC3 samples. For example, a sample containing 27.56 μmol of CC3 with a target guest:host ratio of 2 would require 0.97 mL of the 56.67 μmol mL$^{-1}$ stock solution.

The resulting slurries were vortexed at 200 rpm for 18 h, and then filtered through a glass-fiber disc. The guest-depleted filtrates were analysed as static headspace injections by GC in order to obtain the quantity of guest adsorbed by the CC3. Guest-adsorbed solids had 1 mL of acetonitrile added to them (a large excess), followed by the same vortex mixing and filtration procedure, to extract the guest from the CC3 solid. The filtrates were analysed by liquid injection to obtain the enantiomeric excess of the 1-phenylethanol desorbed from the CC3. Again, the cage solids were analysed to ensure they were still chemically and phase pure after acetonitrile extraction.

Post-Exchange Filtrate Analysis.

Figure 52:
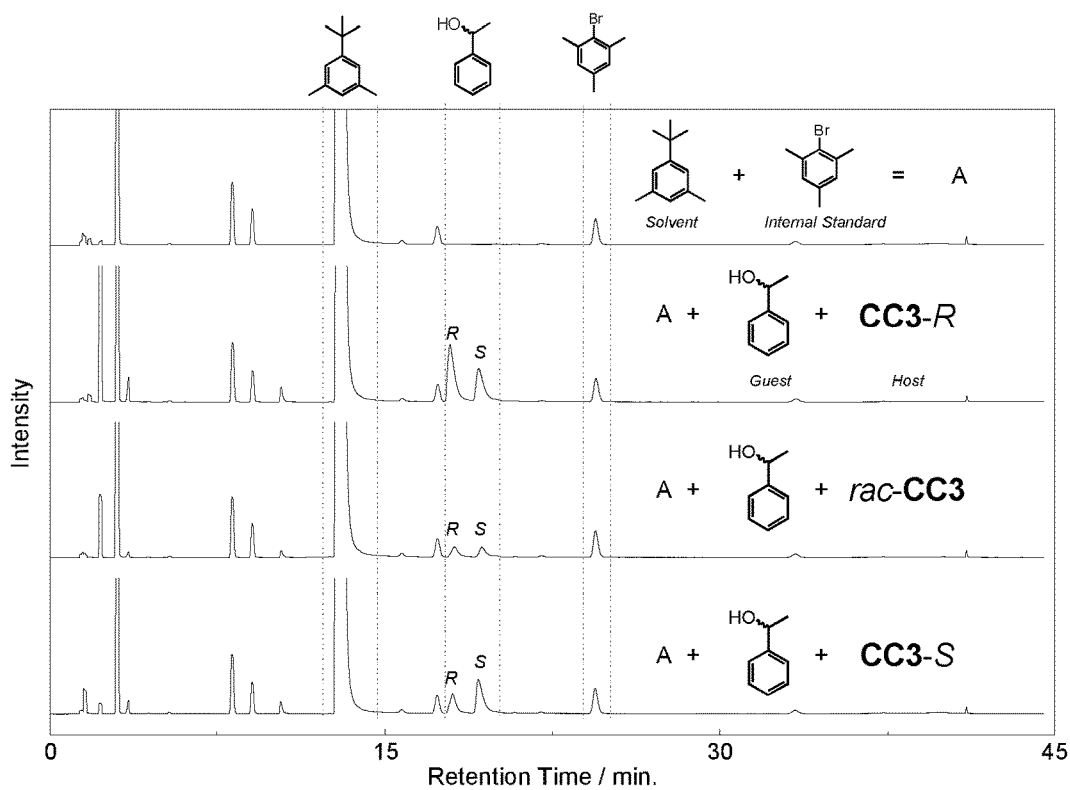
FIG. 52 shows representative full GC-FID (static headspace) chromatograms of guest-depleted filtrates collected after mixing a 1-phenylethanol solution with CC3-R, rac-CC3, and CC3-S.
Figure 53:
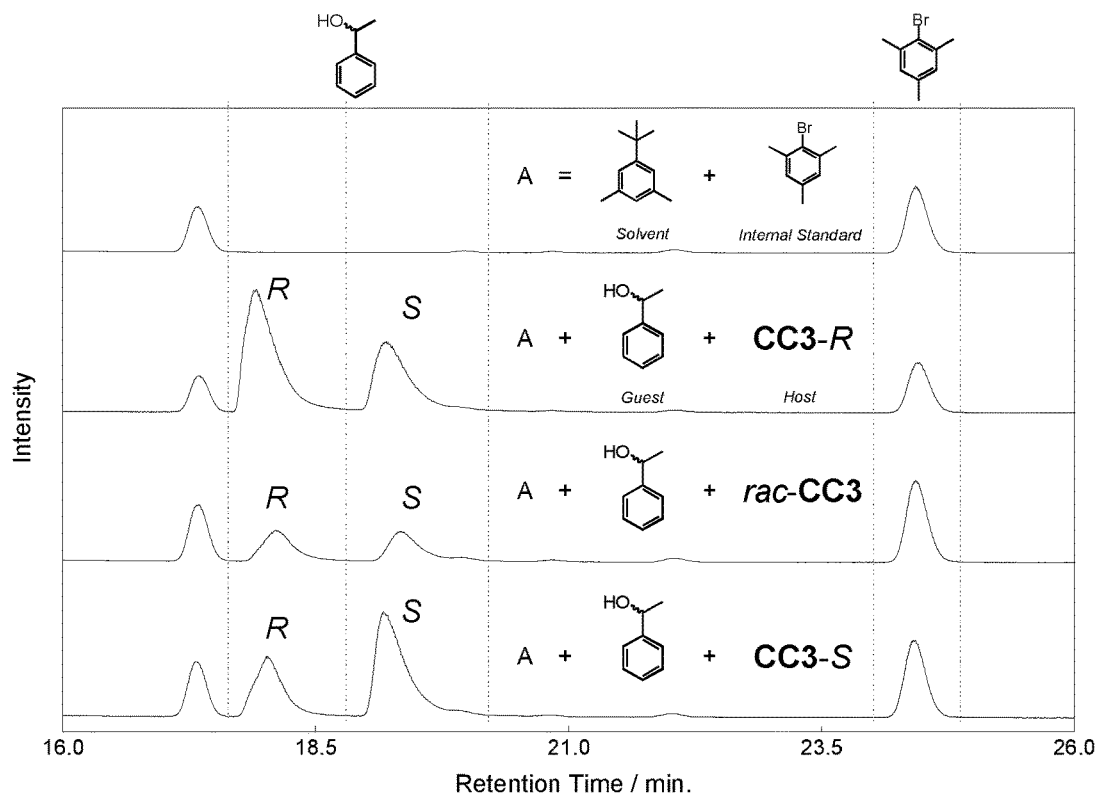
FIG. 53 shows the 16-26 min. region of FIG. 52.

FIGS. 52 and 53 show representative chromatograms produced from guest-depleted 1-tert-butyl-3,5-dimethylbenzene filtrates. rac-1-Phenylethanol calibrations show the expected 50:50 peak area ratio. By contrast, upon exposure to homochiral CC3-R or CC3-S, a chiral imbalance is observed in the solution. Calibration chromatograms were collected. The peak areas for the 1-phenylethanol enantiomers ($A_{R/S}$) and for bromomesitylene ($A_{BrMes}$) were recorded for each calibration point. The response factor for each enantiomer ($f_{i(R/S)}$) was calculated (according to the equation below)[61] and plotted against half the stock concentration $$\left(\frac{c_{rac}}{2} = c_{R/S}\right).$$

Quadratic fits of these plots yielded a relationship between chromatographically measured $f_i$ values and sample (R/S)-1-phenylethanol concentrations. Y-intercepts of the fits were set to $f_i$ values measured for blank (c=0) samples to accommodate for trace impurities present in the solvent. Quadratic fits were used in preference to linear fits due to the large 1-phenylethanol concentration range between stock solutions and post-adsorption solutions.

$$f_{i(R/S)} = \frac{A_{R/S}}{A_{BrMes}}.$$

Using this relationship, in combination with the known values for the concentration and volume of added stock, the adsorbed moles of (R/S)-1-phenylethanol was calculated from the guest-depleted filtrate samples. This is plotted as a dotted line in FIG. 56. Values calculated in this manner compare well with $^1$H NMR analysis of the 1-phenylethanol contained within guest-adsorbed CC3-R (GC: 1.00, $^1$H NMR: 0.98 equivalents of 1-phenylethanol for a representative sample).

FIG. 52 shows representative full GC-FID (static headspace) chromatograms of guest-depleted filtrates collected after mixing a 1-phenylethanol solution with CC3-R, rac-CC3, and CC3-S. The bromomesitylene stock solution is included at the top as a calibration standard. The chromatograms are collected for 1.5 guest:host equivalent slurries.

FIG. 53 shows the 16-26 min. region of FIG. 52. The 1-phenylethanol in these plots is representative of what is left in the solution phase after adsorption into CC3. Equal and opposite enantiomeric excess is seen for CC3-R and CC3-S. Rac-CC3 gives no enantiomeric excess. Due to the presence of an internal standard, the number of moles of (R)-1-phenylethanol and (S)-1-phenylethanol present in these samples can be calculated and, as the number of moles added is known, the number of adsorbed moles can be also be calculated. Adsorbed equivalents is plotted as a dotted line in FIG. 56.

Filtrate Analysis after Guest Extraction.

Figure 54:
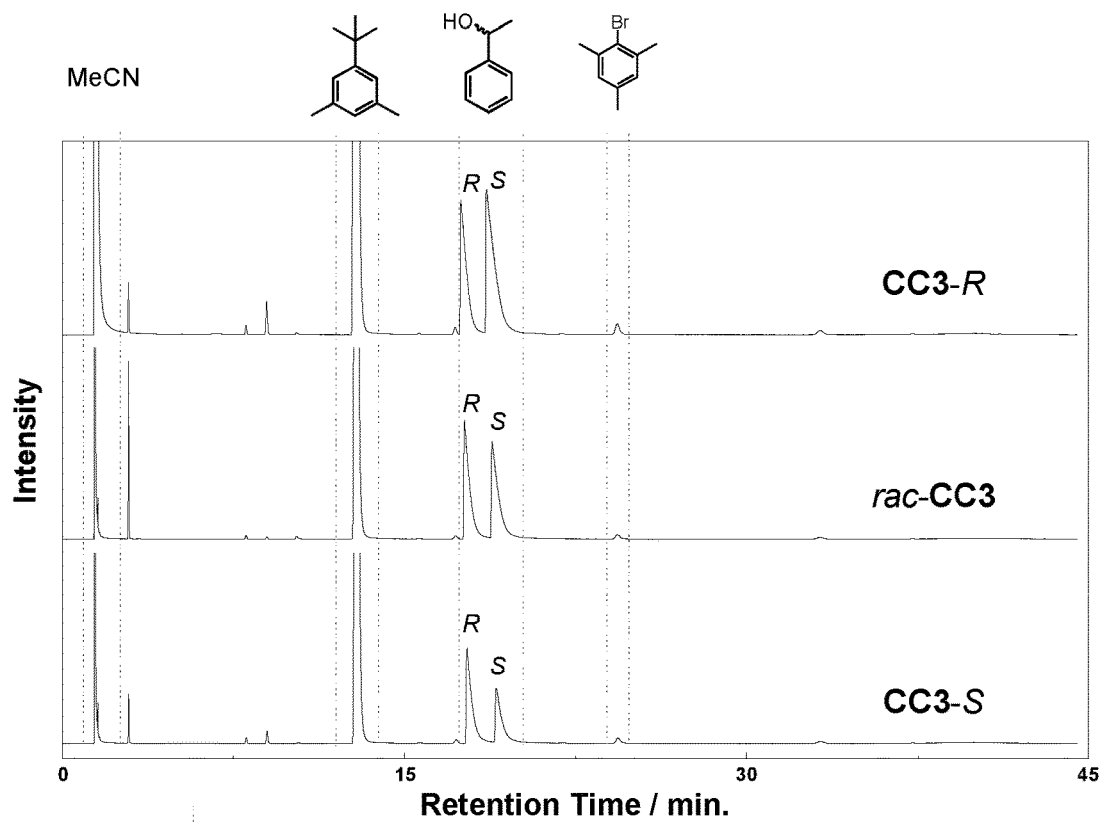
FIG. 54 shows representativ full GD-FID (liquid injection) of evicted-guest-containing filtrates collected after washing CC3 samples woth 1 mL acetonitrile.
Figure 55:
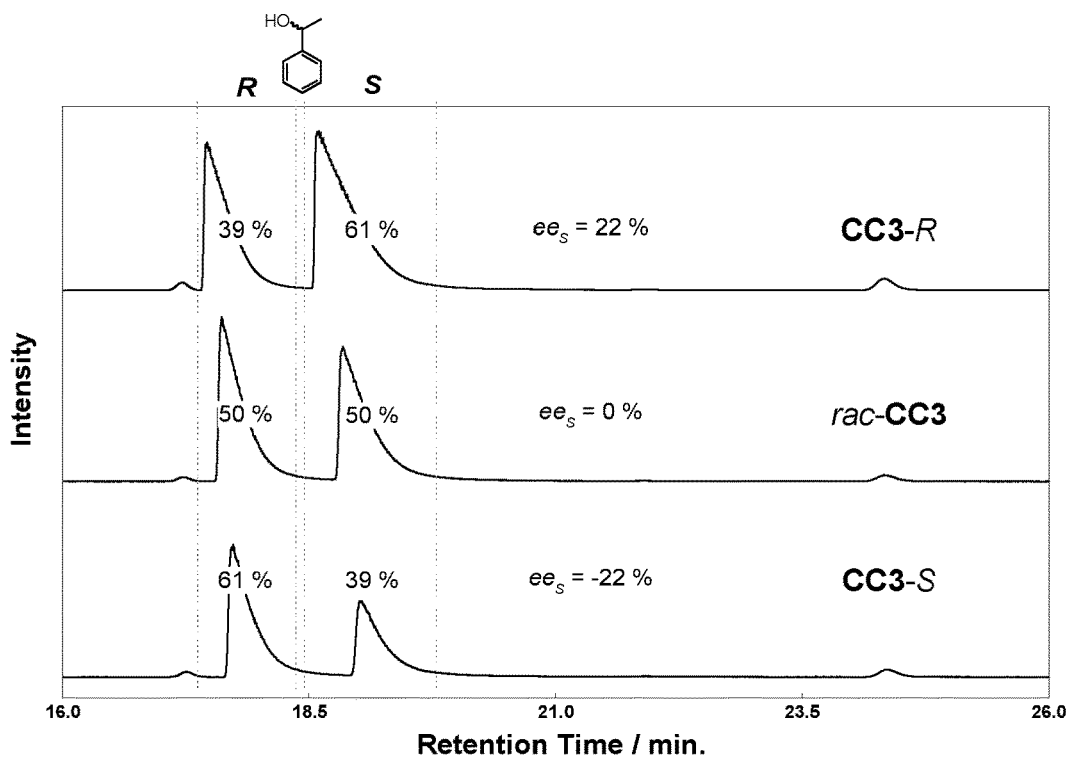
FIG. 55 shows the 16-26 min. region of FIG. S48.

FIGS. 54 and 55 are representative GC chromatograms of the filtrates produced after extracting guest-adsorbed CC3 with acetonitrile. Unlike 1-tert-butyl-3,5-dimethyl benzene, acetonitrile can enter the cage cavity and it readily displaces adsorbed 1-phenylethanol within CC3 when used in large excess. Therefore, these plots show the adsorbed, post-exchange, contents of CC3. By contrast, FIGS. 52 and 53 show what is left in the solution phase.

Figure 57:
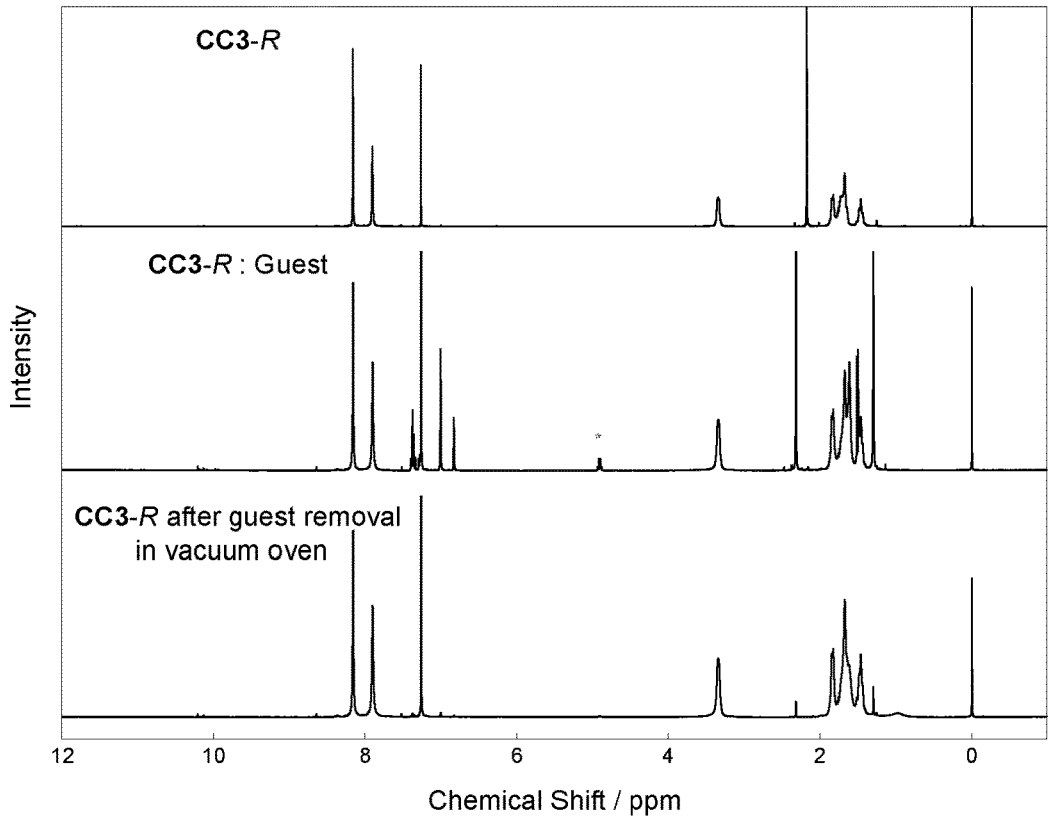
FIG. 57 shows $^1$H NMR (CDCl$_3$) spectra of CC3-R samples. 1.5 guest:host equivalents were present for the exchange process of these representative samples.

Due to the multi-step nature of the sample preparation and the volatility of acetonitrile, only the relative areas of peaks within the chromatogram were analysed; these values could then be used to calculate the enantiomeric excess of the 1-phenylethanol adsorbed by the CC3. Bromomesitylene, visible in FIGS. 54 and 55, stems from residual solvent on the solids after the first filtration step, and hence it may not be used as an internal standard for this data. Removing residual 1-tert-butyl-3,5-dimethyl-benzene and bromomesitylene from the surface of guest-adsorbed CC3 required vacuum oven drying or solvent washing; however, both techniques were also observed to readily displace the guest from within CC3 (FIG. 57).

The ee of each sample was calculated from the relative peak areas in the chromatograms. These values are in-line with predictions from atomistic simulations (GC: 29%, simulated: 24-32%; see FIG. 44).

FIG. 54 shows representative full GC-FID (liquid injection) of evicted-guest-containing filtrates collected after washing CC3 samples with 1 mL acetonitrile. Samples were gently dried in the filter funnel to prevent guest-desorption resulting in the presence of some residual 1-tert-butyl-3,5-dimethylbenzene (ca. 14 min.) and bromomesitylene (ca. 22 min.) adsorbed on the surface of the crystals.

FIG. 55. 16-26 min. region of FIG. S48. Peak annotations indicate the measured relative area. Acetonitrile washes the majority of guest adsorbed in CC3 into the solution phase. The 1-phenylethanol in these plots is representative of adsorbed guest after host:guest equilibration. As indicated, equal and opposite enantiomeric excess are observed for CC3-R and CC3-S. Enantiomeric excess ($ee_z$) were measured in this manner for a variety of guest:host equivalents with CC3-R, CC3-S, rac-CC3, and CC3-RS hosts. The measured values are plotted as solid lines in FIG. 550.

Figure 56:
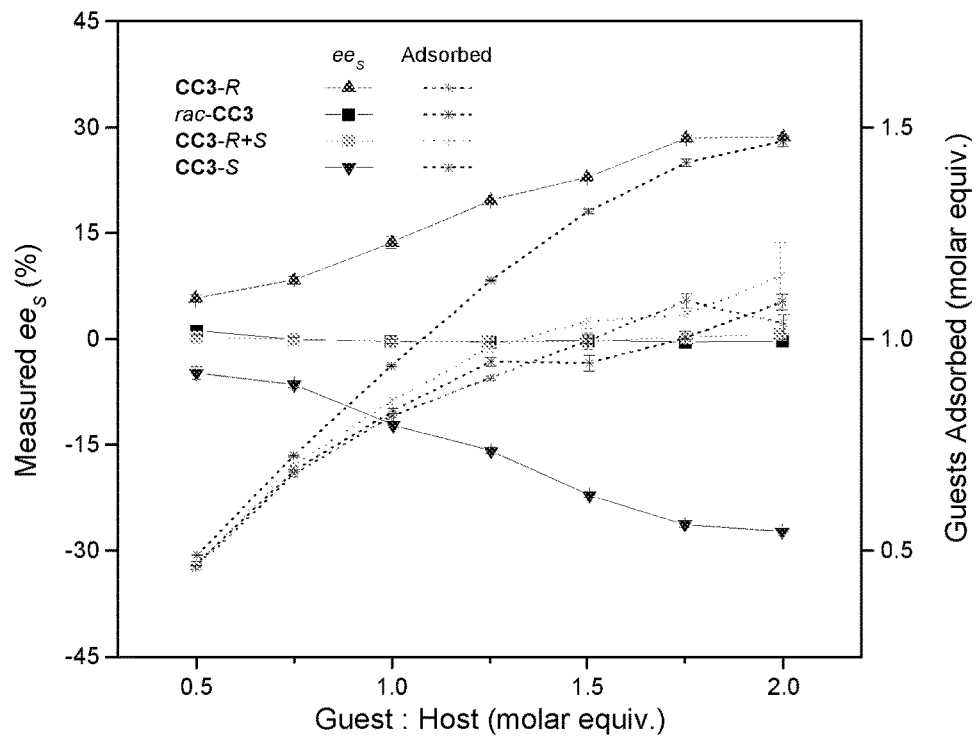
FIG. 56. Solid Lines: Meausred enantiomeric excess of the S enantiomer ($^{ees}$) of 1-phenylethanol wihtin CC3 hosts with respect to the guest: host equivalents present during the exchange mechanism.

FIG. 56. Solid Lines: Measured enantiomeric excess of the S enantiomer ($ee_s$) of 1-phenylethanol within CC3 hosts with respect to the guest:host equivalents present during the exchange mechanism. Dotted Lines: Calculated equivalents of 1-phenylethanol adsorbed into each CC3 host. Four hosts were analyzed: CC3-R (red lines), CC3-S(blue lines), rac-CC3 (black lines), and CC3-RS (green lines). Approximately equal, opposite, and non-zero excess values are seen for CC3-R/S. Near-zero excess values are observed for rac-CC3 and CC3-R+S. A similar level of guest adsorption is observed for the homochiral phases CC3-R and CC3-S and the chiral conglomerate, CC3-R+S. The racemic phase rac-CC3 shows a reproducibly higher level of 1-phenylethanol uptake. This difference is likely due to the increased surface area of the racemic phase, which arises from both the smaller particle size and an increased level of voids/defects produced in this racemate from the more rapid crystallisation process, as described previously.[1]

FIG. 57 shows $^1$H NMR ($CDCl_3$) spectra of CC3-R samples. 1.5 guest:host equivalents were present for the exchange process of these representative samples. CC3-R, 1-tert-butyl-3,5-dimethylbenzene (residual on solid) and 1-phenylethanol are observed after mixing (middle). Vacuum oven treatment of the guest-adsorbed CC3-R removes the guest and solvent with no observable chemical change (bottom). The exchange process does not chemically alter CC3-R. Integration of the CH peak of 1-phenylethanol (4.9 ppm) against the CH=N peak of CC3-R (8.2 ppm)

shows a ratio of 0.98:1 guest:host. This compares well with the ratio of 1.00:1.00 guest:host obtained from GC measurements (FIG. 56).

Single Crystal Studies of CC3 Hosts Loaded with 1-Phenylethanol.

A number of loading conditions were investigated in an attempt to load a single crystal of CC3 with the 1-phenylethanol guest, and hence to confirm its location in the pores. Only one enantiomer of CC3, CC3-R, was used in these single crystal studies. Suitable quality single crystals of CC3-R were prepared by dissolving CC3-R in $CH_2Cl_2$ at a concentration of 5 mg $mL^{-1}$. Vapour diffusion of acetone over a 24-48 hour period afforded phase pure single crystals of CC3-R (space group $F4_132$), which were evacuated in a vacuum oven at 80° C. for 24 hours to remove all of the crystallization solvent. In its native form (space group $F4_132$), CC3-R packs window-to-window, resulting in an interconnected diamondoid pore network, as discussed in the main text. For this crystalline phase, the asymmetric unit is comprised of 1/12 of a CC3 fragment.

(S)-1-Phenylethanol Uptake in CC3-R Single Crystals.

Initially, two data sets were recorded at room temperature without the use of a nitrogen gas flow to prevent $N_2$ condensing in the diamondoid pore network of CC3, or evaporation of the guest. One collection was recorded on an evacuated CC3 sample that had been left to stand in air for 24 hours, and a second on the same batch of crystalline CC3 material that had instead been immersed in neat (S)-1-phenylethanol for 24 hours. The structure of the air-standing CC3 sample was solved and refined in chiral cubic space group $F4_132$ (unit cell parameters; a=24.869(5) Å, V=15381 (5) Å$^3$, CCDC #998365). For this structure, no notable electron density was found in the diamondoid pore network (highest q-peak=0.24 e·Å$^{-3}$). After 24 hours of being immersed in neat (S)-1-phenylethanol, a single crystal of CC3 was selected and a full data set was recorded. This structure was solved and refined in the cubic space group $F4_132$ (unit cell parameters; a=24.88(1) Å, V=15402(12) Å$^3$, CCDC #998362). In this structure, there was clear evidence of electron density in the pore network (highest q-peak=1.07 e·Å$^{-3}$), however this electron density was too diffuse to be accurately modelled as (5)-1-phenylethanol. This could be indicative of the (S)-1-phenylethanol guest adopting a number of possible conformers inside the CC3 cavity, as suggested by molecular simulations (FIG. 45b). An approximate number of electrons contained within the pore network was calculated using a solvent masking routine in OLEX2.[62] This indicated that there were 632 electrons contained within a 3376 Å$^3$ void. For comparison, the SQUEEZE routine in Platon,[63] removed a total of 589 electrons from a 3159 Å$^3$ interconnected void. Both values are in good agreement and indicate that there are approximately 1.2 (S)-1-phenylethanol molecules per CC3 molecule adsorbed in the crystal lattice.

A second set of experiments was performed at low collection temperatures (T=100 K) to improve data quality. In this second study, neat (S)-1-phenylethanol (0.1 mL) was added onto an evacuated crystalline sample of CC3 (20 mg) kept under vacuum. The vacuum was gradually released and the crystals were kept immersed in (S)-1-phenylethanol. After 24 hours a full single crystal data set was recorded at 100 K. The structure was solved and refined in the chiral cubic space group $F4_132$ (unit cell parameters; a=24.923(6) Å, V=15480(7) Å$^3$, CCDC #998364). There was again clear evidence of electron density in the pore network (highest q-peak=0.9 e·Å$^{-3}$), however again it was too diffuse to accurately model. A solvent masking routine performed in OLEX2 was used during the final stages of refinement. This routine removed a total of 642 electrons from an interconnected 3287 Å void, or ca. 1.25 (S)-1-phenylethanol molecules per CC3. From the same sample vial and after 2 weeks of being immersed in (S)-1-phenylethanol, only one cubic phase was evident. A second crystal of this phase was selected and a full data set was recorded. The structure was solved and refined in the chiral cubic space group $F4_132$ (unit cell parameters; a=24.951(3) Å, V=15533(3) Å$^3$, CCDC #998363). There was again clear evidence of electron density in the pore network structure (highest q-peak=1.2 e·Å$^{-3}$), also too diffuse to accurately model. Residual electron density was masked in OLEX2, which indicated: there were 561 electrons contained within a 3358 Å$^3$ void, or ca. 1.10 (S)-1-phenlyethanol molecules per CC3. As such, all three procedures suggest disordered guests, and a concentration of approximately 1.2 (S)-1-phenylethanol molecules per CC3 molecule adsorbed in the crystal lattice.

Figure 58:
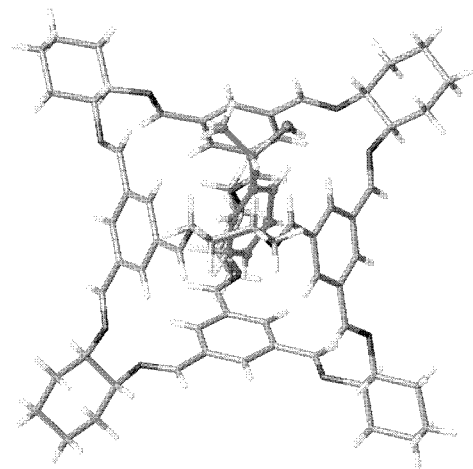
FIG. 58 shows guest (S)-1-phenylethanol positioned in the CC3 cavity from the single crystal structure 3(CC3-R) 20((S)-1-phenylethanol).

The experiments above show that solid CC3-R does not change its cubic crystal packing when immersed in (S)-1-phenylethanol, even for long periods. By contrast, when CC3 is crystallized from a homogeneous solution in $CH_2Cl_2$ containing the (S)-1-phenylethanol guest, then we found that (S)-1-phenylethanol directs CC3-R to pack in a new, non-native crystalline packing. This previously unknown solvate, 3(CC3-R).20((S)-1-phenylethanol), crystallizes from a $CH_2Cl_2$/(S)-1-phenylethanol solution in the chiral monoclinic space group C2 (unit cell parameters; a=36.665(3) Å, b=22.696(2) Å, c=21.875(2) Å, V=17831(3) Å$^3$, CCDC #998359). The asymmetric unit for this phase comprises one crystallographically distinct CC3 molecule and one half of a crystallographically distinct CC3 molecule centred on a twofold rotation axis. In addition, nine (S)-1-phenylethanol molecules refined with site occupancies of 100%, and three partially-occupied (S)-1-phenylethanol molecules refined with site occupancies of 25, 50, and 75% to make up the asymmetric unit. For one of the crystallographically distinct CC3 molecules, one (S)-1-phenylethanol molecule has its phenyl ring positioned within the cage cavity with the alcohol group located in the cage window site (FIG. 58). There is clear evidence of a hydrogen bond between the alcohol group of (S)-1-phenylethanol and one of the imine nitrogen atoms CC3 (O—H—N distance 3.004(8) Å). A comparable distance of 2.97 Å, measured by the first peak in the radial distribution function for the atom pair [FIG. 47 (c)], was found in a molecular dynamics simulation of CC3-R loaded with (S)-1-phenylethanol. For 3(CC3-R).20 ((S)-1-phenylethanol), the other (S)-1-phenylethanol molecules are located in extrinsic positions, between cages.

FIG. 58 shows guest (S)-1-phenylethanol positioned in the CC3 cavity from the single crystal structure 3(CC3-R).20((S)-1-phenylethanol). Carbon atoms of (S)-1-phenylethanol highlighted.

(R)-1-Phenylethanol Uptake in CC3-R Single Crystals.

Onto an evacuated crystalline sample of CC3 (20 mg), kept under vacuum, neat (R)-1-phenylethanol (0.1 mL) was added. The vacuum was gradually released and the crystals were kept immersed in (R)-1-phenylethanol. After 24 hours, the crystals were irradiated with polarised light; both a cubic and a non-cubic single crystal phase were evident. Data collections were recorded on each of these two phases. The first phase was solved and refined in the chiral cubic space group $F4_132$ (unit cell parameters; a=24.938(5) Å; V=15509 (5) Å$^3$, CCDC #998360). Diffuse electron density was found in the pore network (highest q-peak=1.09 e·Å$^{-3}$), but no chemically accurate model that represented (R)-1-phenylethanol was found. A solvent masking routine calculated in OLEX2 was applied during the final stages of refinement. This routine removed a total of 589 electrons from a 3412 Å$^3$ void, or 1.15 (R)-1-phenylethanol molecules per CC3.

The second non-cubic crystalline phase was solved and refined in the trigonal space group R3 (unit cell parameters; a=17.681(4) Å, c=43.55(1) Å; V=11790(4) Å$^3$, CCDC #998361) as CC3-R.1.29((R)-1-phenylethanol). The asymmetric unit for this phase is comprised of two ⅓ CC3 fragments from two crystallographically distinct cage molecules, each of which is centred on threefold rotation axis and a (R)-1-phenylethanol molecule, refined with a combined site occupancy factor of 0.69 and modelled over two positions. The (R)-1-phenylethanol guest molecule is located in the interstitial window site between two CC3 molecules. The crystal packing of CC3 in this structure is reminiscent of the native window-to-window packing mode of CC3, with a cage centre distance (calculated using the central point of the four aromatic rings as a reference) of 10.7-10.9 Å, as compared to 10.8 Å for the native phase when refined in the space group F4$_1$32.

The presence of ordered (R)-1phenylethanol in the crystal lattice results in a single-crystal to single-crystal transformation, lowering the crystal symmetry (F4$_1$32 to R3). Well ordered (R)-1-phenylethanol is positioned in three of the four CC3 windows (FIG. 553); in the fourth cage window, the electron density was too diffuse to accurately model. A solvent mask was therefore applied during the final stages of refinement. This removed a 46 electrons from three 184 Å$^3$ voids, per unit cell, or ca. 0.5 additional (R)-1-phenylethanol molecules per void. Each void is positioned between two CC3 molecules, hence this guest would be shared. For analysis purposes, a solvent masking routine performed in OLEX2 was used to remove electrons from the whole network structure before assigning the well-ordered (R)-1-phenylethanol guest. This masking routine removed a total of 412 electrons from a 2740 Å$^3$ void, or ca. 1.1 (R)-1-phenylethanol molecules per CC3, in reasonably good agreement with the refined formula unit.

Figure 59:
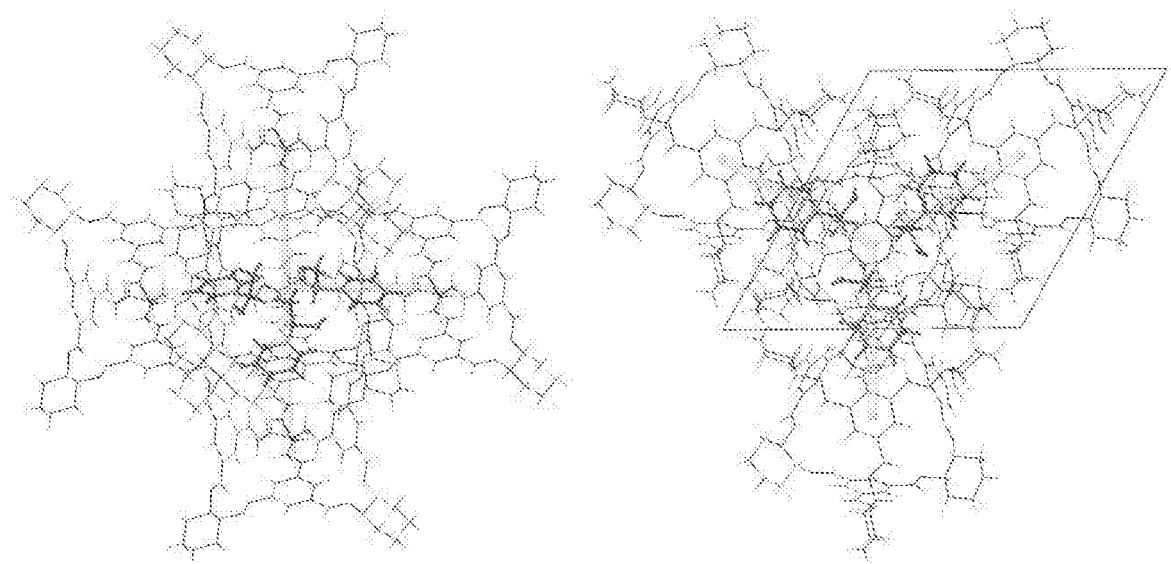
FIG. 59 shows crystal packing from the single crystal structure CC3-R•1.29((R)-1-phenylethanol) showing window positioned (R)-1-phenylethanol highlighted.

FIG. 59 shows crystal packing from the single crystal structure CC3-R.1.29((R)-1-phenylethanol) showing window positioned (R)-1-phenylethanol highlighted. Diamondoid network shown (left); perspective view [001] (right). Only one (R)-1-phenylethanol position shown for clarity.

Single Crystal X-Ray Diffraction Refinement Details.

Single crystal X-ray data were measured on a Rigaku MicroMax-007 HF rotating anode diffractometer (Mo-Kα radiation, λ=0.71073 Å, Kappa 4-circle goniometer, Rigaku Saturn724+ detector), or if stated at beamline I19, Diamond Light Source, Didcot, UK using silicon double crystal monochromated synchrotron radiation (λ=0.6889 Å).[64] Empirical absorption corrections using equivalent reflections were performed with the program SADABS.[65] Structure were solved with SHELXD,[66] or by direct methods using SHELXS,[66] and reined by full-matrix least squares on F$^2$ by SHELXL,[66] interfaced through the programme OLEX2. Unless stated all non-H atoms were refined anisotropically and H atoms were fixed in geometrically estimated positions using the riding model. In the absence of heavy scatters Friedel pairs were merged.

Crystal data for CC3-R (CCDC #998365). Formula $C_{72}H_{84}N_{12}$; M=1117.51 g·mol$^{-1}$; cubic space group F4$_1$32, colourless crystal; a=24.869(5) Å; V=15381(5) Å$^3$; ρ=0.965 g·cm$^{-3}$; μ=0.058 mm$^{-3}$; F (000)=4800; crystal size=0.32× 0.21×0.20 mm$^3$; T=293(2) K; 13036 reflections measured (2.32<Θ<26.34°), 1315 unique ($R_{int}$=0.0439), 917 (I>2σ (I)); $R_1$=0.0965 for observed and $R_1$=0.1208 for all reflections; $wR_2$=0.2872 for all reflections; max/min residual electron density=0.240 and −0.127 e·Å$^{-3}$; data/restraints/parameters=1315/1/64; GOF=1.092. Slight disorder was evident on the cyclohexyl ring; one C—C bond restraint (DFIX in SHELX) was used during refinement. A displacement ellipsoid plot for this structure is shown in FIG. 60.

Figure 60:
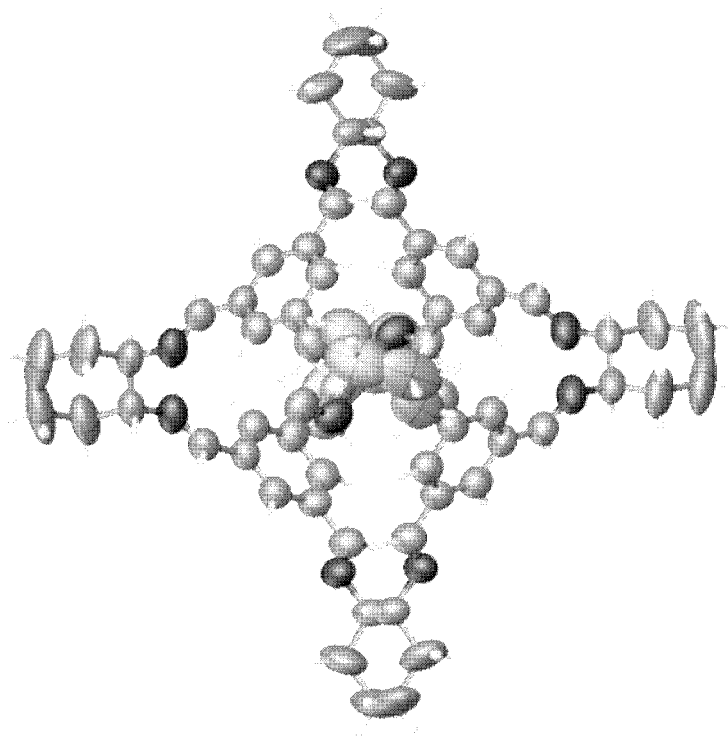
FIG. 60 shows a displacement ellipsoid plot of the asymmetric unit from the single crystal structure CC3-R (CCDC#998365).

FIG. 60. shows a displacement ellipsoid plot of the asymmetric unit from the single crystal structure CC3-R (CCDC #998365). Ellipsoids displayed at 50% probability level.

Crystal data for CC3-R.1.2((S)-1-phenylethanol) (CCDC #998362). Formula $C_{81.6}H_{96}N_{12}O_{1.2}$; M=1264.10 g·mol$^{-1}$; cubic space group F4$_1$32, colourless crystal; a=24.88(1) Å; V=15402(12) Å$^3$; ρ=1.090 g·cm$^{-3}$; μ=0.066 mm$^{-3}$; F (000)= 5434; crystal size=0.17×0.12×0.11 mm$^3$; T=293(2) K; 12035 reflections measured (2.32<Θ<26.38°), 1327 unique ($R_{int}$=0.0412), 768 (I>2σ(I)); $R_1$=0.0946 for observed and $R_1$=0.1219 for all reflections; $wR_2$=0.3118 for all reflections; max/min residual electron density after masking solvent=0.233 and −0.218 e·Å$^{-3}$; data/restraints/parameters=1327/16/64; GOF=1.124. A solvent masking routine performed in OLEX2, removed a total of 632.5 electrons from an interconnected 3376 Å$^3$ void. The solvent mask was used during the final stages of refinement. Slight disorder was evident on the cyclohexyl ring; one bond restraint (DFIX in SHELX) was used during refinement. In addition the carbon atoms of the cyclohexyl ring were refined with anisotropic displacement parameter restraints (SIMU and DELU in SHELX). The approximate numbers of (S)-1-phenylethanol solvent molecules removed during solvent masking routine were included in the refined formula unit. For a displacement ellipsoid plot see FIG. 61.

Figure 61:
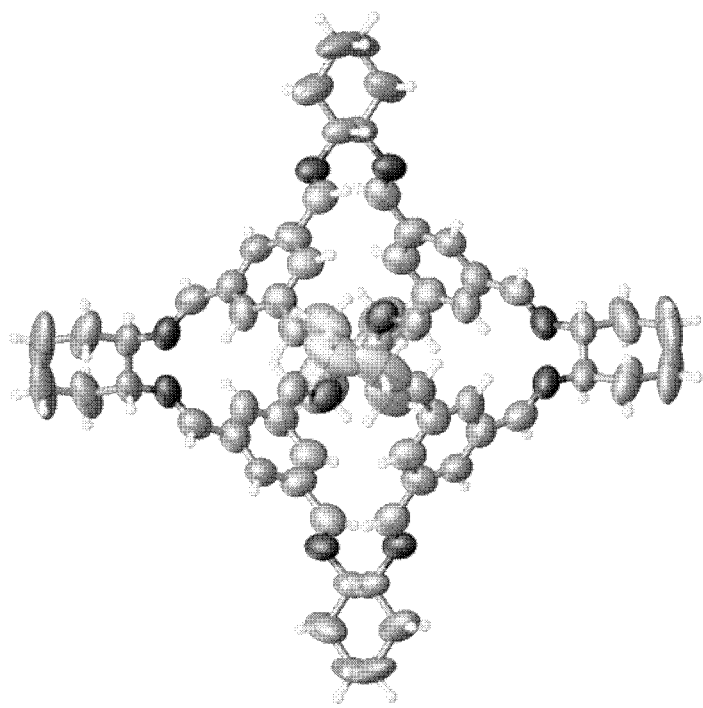
FIG. 61 shows a displacement ellipsoid plot from the single crystal structure CC3-R•1.2((S)-1-phenylethanol) (CCDC#998362).

FIG. 61 shows a displacement ellipsoid plot from the single crystal structure CC3-R.1.2((S)-1-phenylethanol) (CCDC #998362). Ellipsoids displayed at 50% probability level.

Crystal data for CC3-R.1.25((S)-1-phenylethanol) (CCDC #998364): Formula $C_{82}H_{96.5}N_{12}O_{1.25}$; M=1270.21 g·mol$^{-1}$; cubic space group F4$_1$32, colourless crystal; a=24.923(6) Å; V=15480(7) Å$^3$; ρ=1.090 g·cm$^{-3}$; μ=0.066 mm$^3$; F (000)=5460; crystal size=0.12×0.11×0.07 mm$^3$; T=100(2) K; 12607 reflections measured (2.31<Θ<26.34°), 1324 unique ($R_{int}$=0.0449), 779 (I>2σ(I)); $R_1$=0.1491 for observed and $R_1$=0.1750 for all reflections; $wR_2$=0.4205 for all reflections; max/min residual electron density after solvent mask had been applied=0.275 and −0.323 e·Å$^{-3}$; data/ restraints/parameters=1324/16/64; GOF=1.652. A solvent masking routine performed in OLEX2, removed a total of 645 electrons from an interconnected 3287 Å$^3$ void. The solvent mask was used during the final stages of refinement. Slight disorder was evident on the cyclohexyl ring; one bond restraint (DFIX in SHELX) was used during refinement. In addition the carbon atoms of the cyclohexyl ring were refined with anisotropic displacement parameter restraints (SIMU and DELU in SHELX). The numbers of (S)-1-phenylethanol solvent molecules removed during solvent masking routine were included in the refined formula unit. For a displacement ellipsoid plot see FIG. 62.

Figure 62:
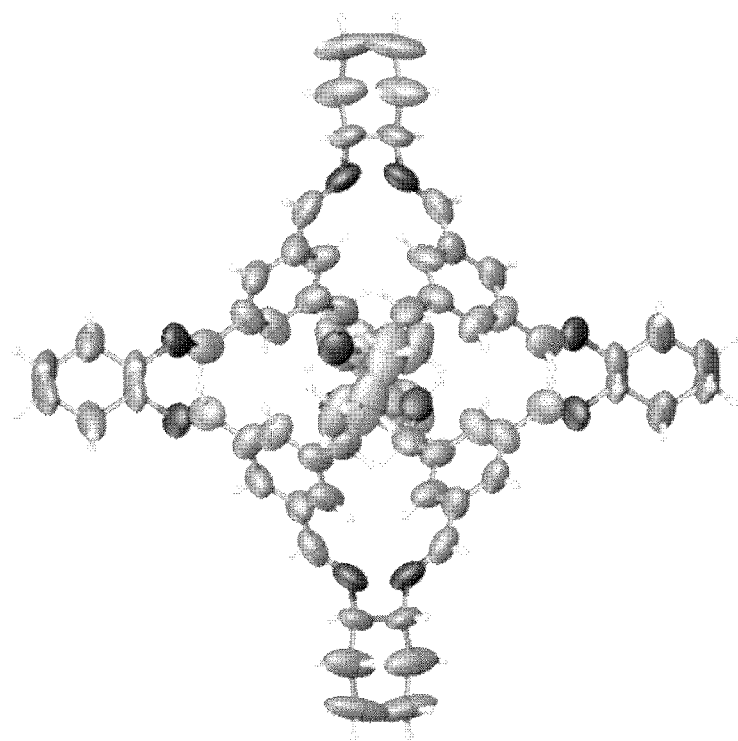
FIG. 62 shows a displacement ellipsoid plot from the single crystal structure CC3R•1.25((S)-1-phenylethanol) (CCDC#998364).

FIG. 62 shows a displacement ellipsoid plot from the single crystal structure CC3-R.1.25((S)-1-phenylethanol) (CCDC #998364). Ellipsoids displayed at 50% probability level.

Crystal data for CC3-R.1.1((S)-1-phenylethanol) (CCDC #998363): Formula $C_{80.9}H_{95}N_{12}O_{1.1}$; M=1251.89 g·mol$^{-1}$; cubic space group F4$_1$32, colourless crystal; a=24.951(3) Å; V=15533(3) Å$^3$; ρ=1.071 g·cm$^{-3}$; μ=0.065 mm$^3$; F (000)= 5381; crystal size=0.22×0.22×0.14 mm$^3$; T=100(2) K; 13735 reflections measured (2.31<Θ<26.34°), 1348 unique ($R_{int}$=0.0361), 1092 (I>2σ(I)); $R_1$=0.0963 for observed and $R_1$=0.1042 for all reflections; $wR_2$=0.3064 for all reflections; max/min residual electron density after solvent mask had been applied=0.205 and −0.168 e·Å$^{-3}$; data/restraints/parameters=1348/16/64; GOF=1.094. A solvent masking routine performed in OLEX2, removed a total of 561 electrons from an interconnected 3358 Å$^3$ void. The solvent mask was used during the final stages of refinement. Slight disorder was evident on the cyclohexyl ring; one bond restraint (DFIX in SHELX) was used during refinement. In addition the carbon atoms of the cyclohexyl ring were refined with anisotropic displacement parameter restraints (SIMU and DELU in SHELX). The numbers of (S)-1-phenylethanol solvent molecules removed during solvent masking routine were included in the refined formula unit. For a displacement ellipsoid plot see FIG. 63.

Figure 63:
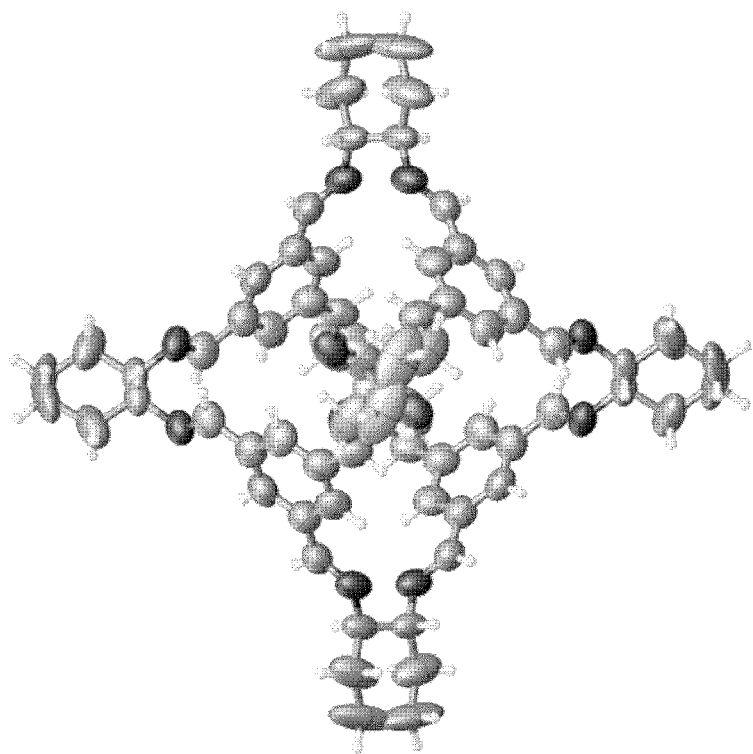
FIG. 63 shows a displacement ellipsoid plot from the single crystal structure CC3-R•1.1((S)-1-phenylethanol) (CCDC#998363).

FIG. 63 shows a displacement ellipsoid plot from the single crystal structure CC3-R.1.1((S)-1-phenylethanol) (CCDC #998363). Ellipsoids displayed at 50% probability level.

Crystal data for 3(CC3-R).20((S)-1phenylethanol) (CCDC #998359), collected using synchrotron radiation. Formula $C_{376}H_{452}N_{36}O_{20}$; M=5795.74 g·mol$^{-1}$; monoclinic space group C2, colourless crystal; a=36.665(3), b=22.696(2), c=21.875(2) Å; β=101.611(1)°; V=17831(3) Å$^3$; ρ=1.079 g·cm$^{-3}$; μ=0.063 mm$^3$; F (000)=6240; crystal size=0.12×0.09×0.09 mm$^3$; T=100(2) K; 88230 reflections measured (0.92<Θ<25.53°), 35127 unique ($R_{int}$=0.0630), 31393 (I>2σ(I)); $R_1$=0.0901 for observed and $R_1$=0.0984 for all reflections; $wR_2$=0.2608 for all reflections; max/min residual electron density=1.178 and −1.482 e·Å$^{-3}$; data/restraints/parameters=35127/186/1845; GOF=1.062. For the crystallographically distinct CC3-R molecules no restraints were used during refinement; however a number of S-phenylethanol molecules were disordered and refined with restraints or constraints on atomic coordinates and/or displacement parameters. Nine (S)-1-phenylethanol molecules were refined with rigid-body constraints (AFIX 66). One of these was particularly disordered, the atoms for which were refined as part of a group EADP. Two (S)-1-phenylethanol molecules were centred on twofold rotation axis for these two molecules C—C bond distance restraints (DFIX in SHELX) and planarity restraints (FLAT in SHELX) were used during refinement and the atoms were refined as part of a group EADP. For a displacement ellipsoid plot of the asymmetric unit see FIG. 64.

Figure 64:
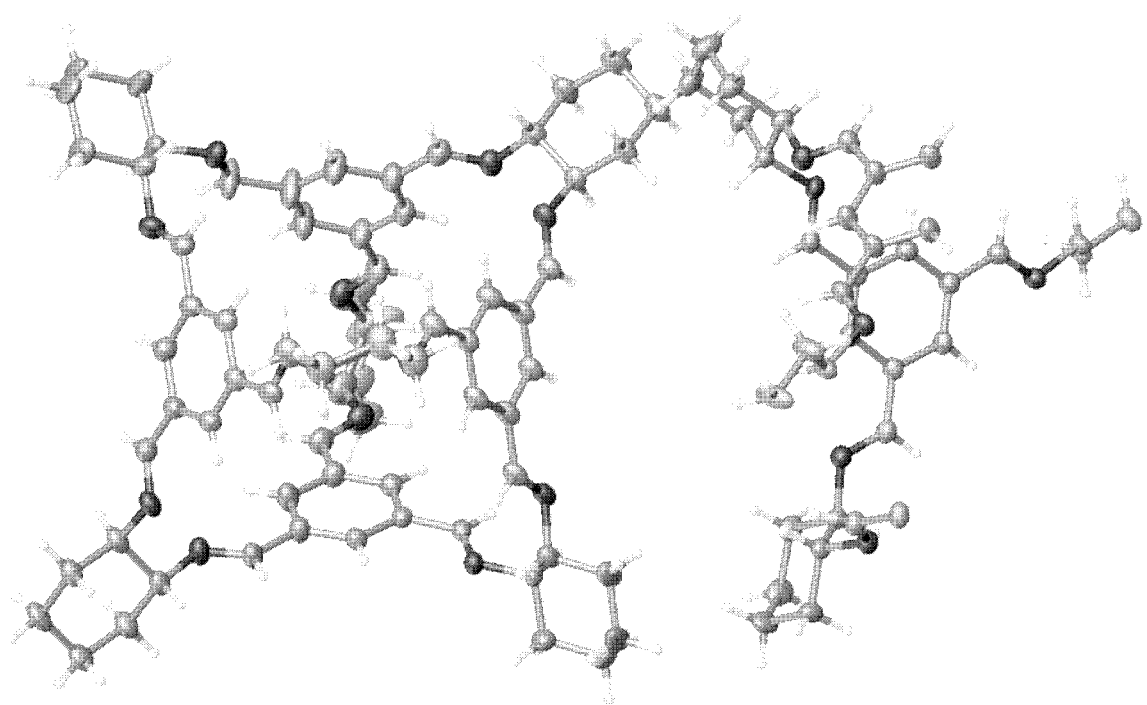
FIG. 64 shows a displacement ellipsoid plot from the single crystal structure 3(CC3-R)•20((S)-1-phenylethanol) (CCDC#998359).

FIG. 64 shows a displacement ellipsoid plot from the single crystal structure 3(CC3-R).20((S)-1-phenylethanol) (CCDC #998359). (S)-1-Phenylethanol solvent omitted for clarity. Ellipsoid displayed at 50% probability level.

Crystal data for CC3-R.1.15((R)-1-phenylethanol) (CCDC #998360): Formula $C_{81.2}H_{95.5}N_{12}O_{1.15}$; M=1258 g·mol$^{-1}$; cubic space group F4$_1$32, colourless crystal; a=24.938(5) Å; V=15509(5) Å$^3$; ρ=1.078 g·cm$^{-3}$; μ=0.065 mm$^3$; F (000)=5407; crystal size=0.15×0.10×0.09 mm$^3$; T=100(2) K; 13282 reflections measured (2.31<Θ<26.38°), 1347 unique ($R_{int}$=0.0423), 892 (I>2σ(I)); $R_1$=0.1293 for observed and $R_1$=0.1498 for all reflections; $wR_2$=0.4223 for all reflections; max/min residual electron density after solvent mask had been applied=0.220 and −0.279 e·Å$^{-3}$; data/restraints/parameters=1347/16/64; GOF=1.649. A solvent masking routine performed in OLEX2, removed a total of 589 electrons from an interconnected 3412 Å$^3$ void. The solvent mask was used during the final stages of refinement. Two C—C bonds of the cyclohexyl ring were refined with restraints (DFIX in SHELX); in addition the atomic displacement parameters for this group were restrained during refinement (SIMU and DELU in SHELX). For a displacement ellipsoid plot see FIG. 65.

Figure 65:
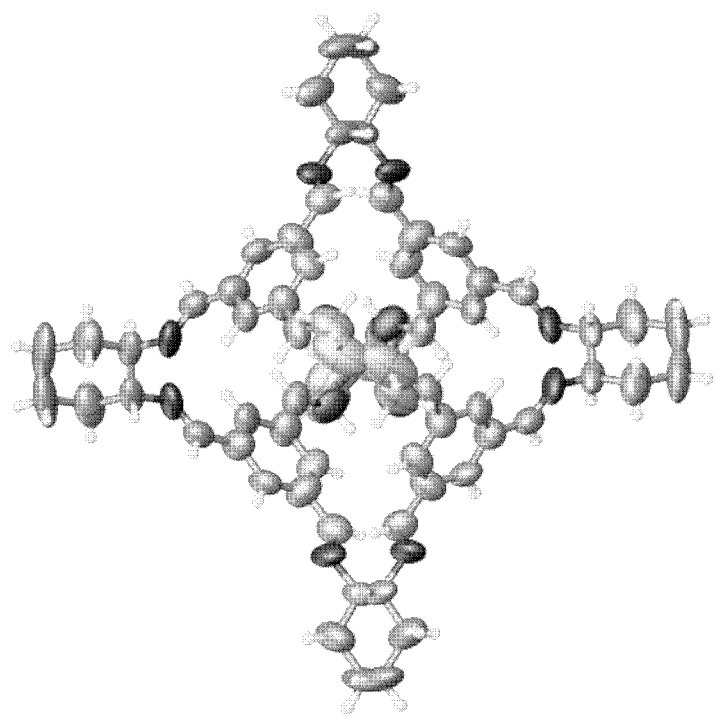
FIG. 65 shows a displacement ellipsoid plot from the single crystal structure CC3-R•1.15((R)-1-phenylethanol) (CCDC#998360).

FIG. 65 shows a displacement ellipsoid plot from the single crystal structure CC3-R.1.15((R)-1-phenylethanol) (CCDC #998360). Ellipsoids displayed at 50% probability level.

Crystal data for CC3-R.1.29((R)-1-phenylethanol) (CCDC #998361): Formula $C_{82.29}H_{96.86}N_{12}O_{1.29}$; M=1274.67 g·mol$^{-1}$; trigonal space group R3, colourless crystal; a=17.681(4), c=43.55(1) Å; V=11790(4) Å$^3$; ρ=1.077 g·cm$^{-3}$; μ=0.065 mm$^{-3}$; F (000)=4109; crystal size=0.24×0.17×0.16 mm$^3$; T=100(2) K; 39692 reflections measured (1.63<Θ<24.71°), 8887 unique ($R_{int}$=0.0745), 8319 (I>2σ(I)); $R_1$=0.1273 for observed and $R_1$=0.1304 for all reflections; $wR_2$=0.3710 for all reflections; max/min residual electron density after solvent mask had been applied=0.568 and −0.350 e·Å$^{-3}$; data/restraints/parameters=8319/54/553; GOF=1.664. For one of the crystallographically distinct CC3-R molecules a cyclohexyl ring was refined with restraints on anisotropic displacement parameters (SIMU and DELU in SHELX). The (R)-1-phenylethanol molecule located in the difference map was modelled over two positions; for each part the site occupancies were determined using group $F_{VAR}$ during refinement. For each (R)-1-phenylethanol the aromatic rings were refined with a rigid-bond constraint (AFIX 66 in SHELX) and the C—CH$_3$ and C—O bond distances were refined with restraints (DFIX in SHELX). Each (R)-1-phenylethanol molecules was refined with constrained atomic displacement parameters (EADP in SHELX). A solvent masking routine performed in OLEX2, removed a total of 35 electrons from three 184 Å$^3$ voids. The solvent masked reflections file was used during the final stages of refinement. The approximate number (R)-1-phenylethanol molecules removed during this routine were included in the refined formula unit. For a displacement ellipsoid plot see FIG. 66.

Figure 66:
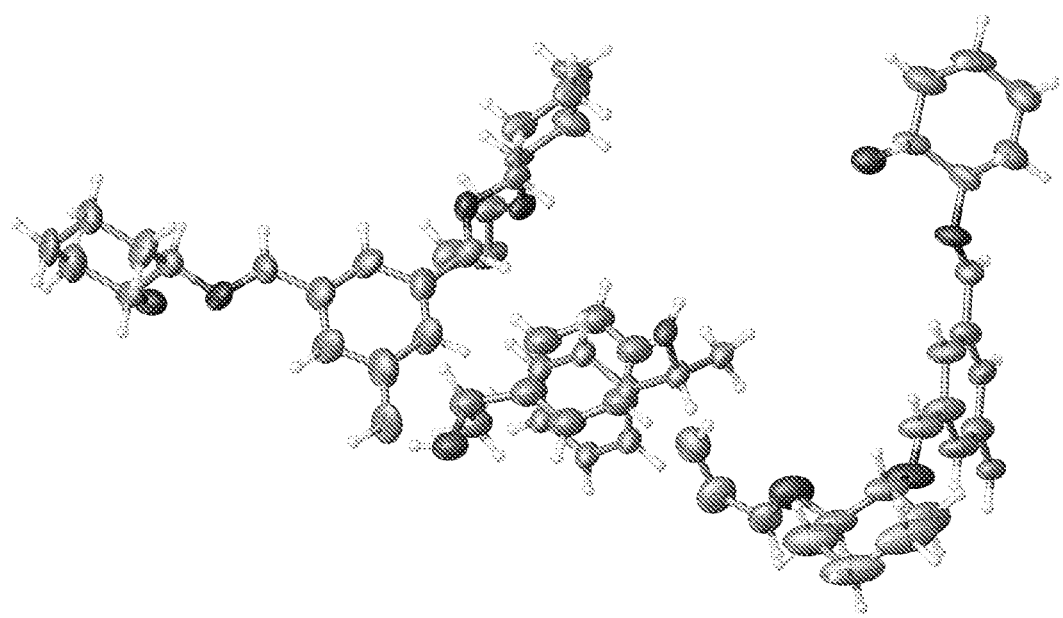
FIG. 66 shows a displacement ellipsoid plot of the asymmetric unit from the single crystal structure CC3-R•1.29 ((R)-1-phenylethanol) (CCDC#998361).

FIG. 66 shows a displacement ellipsoid plot of the asymmetric unit from the single crystal structure CC3-R.1.29((R)-1-phenylethanol) (CCDC #998361). Ellipsoids displayed at 50% probability level.

Simulations of the Enantioselective Adsorption of Chiral 1-Phenylethanol in CC3.

In adsorption studies, the amount of guest molecules adsorbed under a given temperature and pressure is of central interest. Monte Carlo simulations in the grand-canonical ensemble (or GCMC simulations) mimic this situation by attempting to insert and delete molecules into and from the system; the property that is computed is the average number of adsorbed molecules per unit of volume.[25] The adsorbate density inside the adsorbent has a strong impact on the efficiency of the adsorption simulation. Toward saturation of adsorbate molecules in the available pore volume, the probability that an insertion or a deletion is accepted becomes increasingly low. It is, however, important to ensure the statistical reliability and accuracy of a GCMC simulation by achieving appreciable successful insertions and deletions. In this respect, adsorption simulations of chiral molecules can be challenging because the molecules are normally liquids under the conditions of interest. In liquid-phase simulations, the adsorbent pores are filled with adsorbate molecules and the acceptance ratios for insertion and deletion become vanishingly small. To increase the number of successfully inserted molecules, the configurational-bias Monte Carlo (CBMC) technique is usually called for.[67] Instead of attempting to insert the molecule as a whole, CBMC grows the molecule segment-by-segment so that energetically unfavourable configurations—for example, where the molecule overlaps with the host and/or other guests—are largely avoided. When it comes to simulating multi-component adsorption at high adsorbate densities, improving the insertion and deletion efficiencies constitutes only part of the solution to the slow ergodicity experienced by the simulation. Under saturation conditions, it is almost impossible to insert an additional molecule, and it is also energetically extremely unfavourable to delete an adsorbed one. With mixture simulations, we are interested in the ratio of components in the adsorbed phase; identity-change Monte Carlo moves are therefore usually necessary to enhance the sampling. Simulating chiral separation can be even more challenging, as the left- and right-handed enantiomers are so similar that differentiation can be very difficult. Hence, significantly prolonged simulations may be needed for equilibration and production of results; even then, the conventional CBMC simulations can still be prone to statistical errors.[68]

To overcome the aforementioned difficulties in the GCMC simulations of enantioselective adsorption, we adopted a replica-exchange method, namely, the parallel mole-fraction Monte Carlo (PMF MC) scheme by van Erp et al.[69] In a PMF GCMC simulation, the system of interest is simulated parallel to its replicas, with each of them having a different chemical composition of the adsorbing mixture. In other words, all the replica systems, including the original system, have the same temperature and total external pressure but differ in mole fractions of the mixture components. A chain of systems is constructed in a way that the mole fraction of component A varies from 0% to 100%, while the mole fraction of component B varies accordingly from 100% to 0%, in the case of a binary mixture. These grand-canonical systems are simulated in parallel and neighbouring systems are swapped at a defined frequency. During the system-swap moves, the molecular configurations of adjacent replicas are exchanged subject to certain acceptance rules; i.e., the moves may be accepted or rejected. By exchanging replicas, the presence of metastable states and entropic barriers can be better dealt with compared to conventional GCMC simulation. PMF GCMC simulations have been demonstrated to be a powerful tool for studying enantioselective adsorption in porous materials.[69-71]

Computational Details.

The molecular dimensions of the chiral (R, S)-1-phenylethanol molecules were determined by inspection of the shape of the molecules combined with consideration of the van der Waals radii of the atom (FIG. 67).[70] Different orientations were considered, allowing the maximum dimension that would have to traverse the window cross-section to be determined. For (S)-1-phenylethanol, the maximum dimension of 5.4 Å corresponds to the width of the arene ring; this is considerably larger than the upper limit of the proposed PLE for the empty host CC3 structure of ca. 4.6 Å (FIG. 2*a*;). We have previously observed, both in adsorption experiments and MD simulations, that para-xylene,[60] of similar dimensions to (S)-1-phenylethanol, is able to diffuse through CC3, albeit much more slowly than smaller gas molecules such as Xe. We presume that the window can expand the additional 0.8 Å, either through the effect of loading or through cooperative effects between the guest and host.

Figure 67:
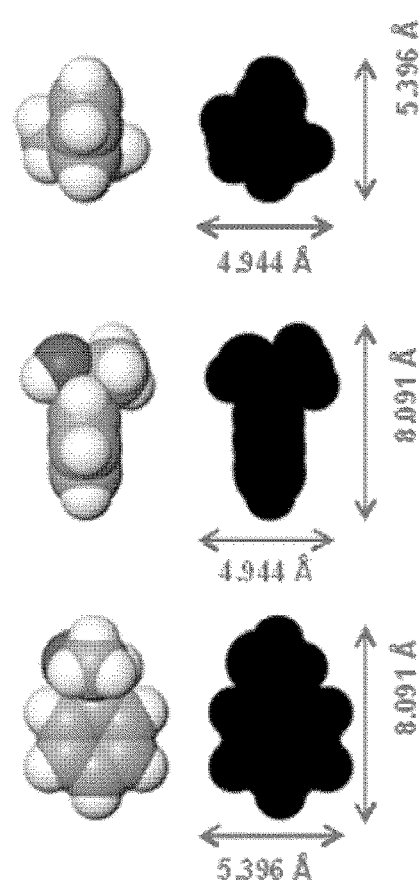
FIG. 67 shows three different orientations of (S)-1-phenylethanol.

FIG. 67 shows three different orientations of (S)-1-phenylethanol, showing the molecular dimensions of the chiral molecule.

The two homochiral CC3 crystal structures (namely, CC3-R and CC3-S) and the racemate (rac-CC3) were all modelled as rigid hosts in the adsorption simulations. The atomistic representation of CC3-R was taken directly from the experimental CC3-R crystal structure loaded with (S)-1-phenylethanol (see above). Prior to simulation, the (S)-1-phenylethanol molecules were deleted; the CC3-R atoms were kept fixed at their crystallographic positions during the simulation. Chiral inversion of all of the R cage molecules in this CC3-R crystal structure gave the CC3-S structure used in the corresponding simulations (the unit-cell parameters and the symmetry, of course, remained unchanged). To obtain a structure of rac-CC3 for simulation, two steps were taken, starting from the aforementioned experimental CC3-R structure with the adsorbed (S)-1-phenylethanol removed. In the first step, half of the R cages were chirally inverted such that R and S cages alternate in the crystal lattice, with each cage surrounded by four partner cages of the opposite chirality. In the second step, the newly generated rac-CC3 structure was optimized by density functional theory (DFT) using the PBE-D3 method, in conjunction with the MOLOPT-DZVP basis set and an energy cutoff of 600 Ry, as implemented in the CP2K package. The optimization was performed on both the unit-cell dimensions and the atomic positions. The structure was considered to be optimized when the maximum geometry change, root-mean-square geometry change, maximum force, and root-mean-square force converged to the values of $3.0 \times 10^{-3}$ Bohr, $1.5 \times 10^{-3}$ Bohr, $4.5 \times 10^{-4}$ Hartree/Bohr, and $3.0 \times 10^{-4}$ Hartree/Bohr, respectively. The resulting rac-CC3 structure has a cubic F d-3 unit cell with a cell length of 24.7040 Å. Compared to the CC3-R cell dimension of 24.9261 Å (which was the starting value in the optimization), the contraction in the computed rac-CC3 cell is consistent with the experimental observation that the unit cell of rac-CC3 is smaller than that of CC3-R (opposite enantiomers can pack together more tightly).[1]

To describe the repulsive and dispersive interactions of the host-guest and guest-guest pairs, the standard (12-6) Lennard-Jones (LJ) potential was used, together with a real-space cutoff of 12.0 Å. Each simulation box consisted of one unit cell of CC3 crystal structure, with periodic boundary conditions exerted in three dimensions. The force-field parameters for the CC3 hosts were assigned by the CHARMM General Force Field (CGenFF),[37] using the ParamChem webserver.[72,73] The adsorbates, (R, S)-1-phenylethanol, were modelled as flexible molecules using the all-atom version of the OPLS force field (OPLS-AA). The Lorentz-Berthelot combining rules were used to calculate the host-guest U cross-parameters, while the guest-guest cross-parameters were determined via geometric means (as adopted by OPLS-AA). The partial atomic charges for the CC3 hosts and those for the (R, S)-1-phenylethanol molecules were taken from the corresponding chosen force fields. Electrostatic interactions were handled by the Ewald summation technique with the relative precision set to $10^{-6}$.

As mentioned above, the enantioselective adsorption of (R, S)-1-phenylethanol by CC3 crystals was studied by parallel mole-fraction GCMC simulations (i.e., PMF GCMC). The system of interest, where a racemic mixture of (R, S)-1-phenylethanol was simulated, and its replicas having different guest mole fractions were run in parallel, with swaps of molecular configurations between adjacent systems at regular intervals. The simulation chain was comprised of nine systems, each of which was a binary adsorption (CBMC) simulation performed at 298 K and a total pressure of 1 bar but with the mole fraction of the R enantiomer varying from 0.1 to 0.9 in steps of 0.1. Translation and rotation MC moves were used, in combination with configurational-biased insertion, deletion and reinsertion, for thermalization. Identity-change moves were performed, in which attempts were made to change a randomly selected 1-phenylethanol molecule to its opposite enantiomer. Each simulation included $1 \times 10^6$ cycles for equilibration, followed by $1 \times 10^6$ cycles for production of results. One cycle consisted of N MC moves and N was the number of adsorbed molecules with a minimum value of 20. For each CC3 crystal structure, five PMF GCMC simulations were run independently, all starting with an empty host and with different random numbers, to ensure proper sampling of the phase space. Errors were estimated by dividing the production run into five 'blocks' and calculating the standard deviation of the block averages; error bars were determined as the 95% confidence interval.

Modelling Results.

Here, we report only the simulation results for the racemic mixtures of (R, S)-1-phenylethanol, as direct comparison with the chiral chromatography experiments can be made. This means that the replicating systems with the different mole ratios of the R and S enantiomers (i.e., other than a 50/50 ratio), involved in the PMF GCMC simulations, are not discussed hereafter. The chiral selectivity of CC3 is reported in the form of the enantiomeric excess (ee), which characterizes the excess of one enantiomer over the other inside the adsorbent and is calculated from the binary mixture as $$ee(\%) = \frac{S-R}{S+R} \times 100$$

where S and R are the amounts of the left- and right-handed enantiomers adsorbed, respectively. In this definition, an ee value greater than zero means preferential adsorption toward the S enantiomer.

Figure 68:
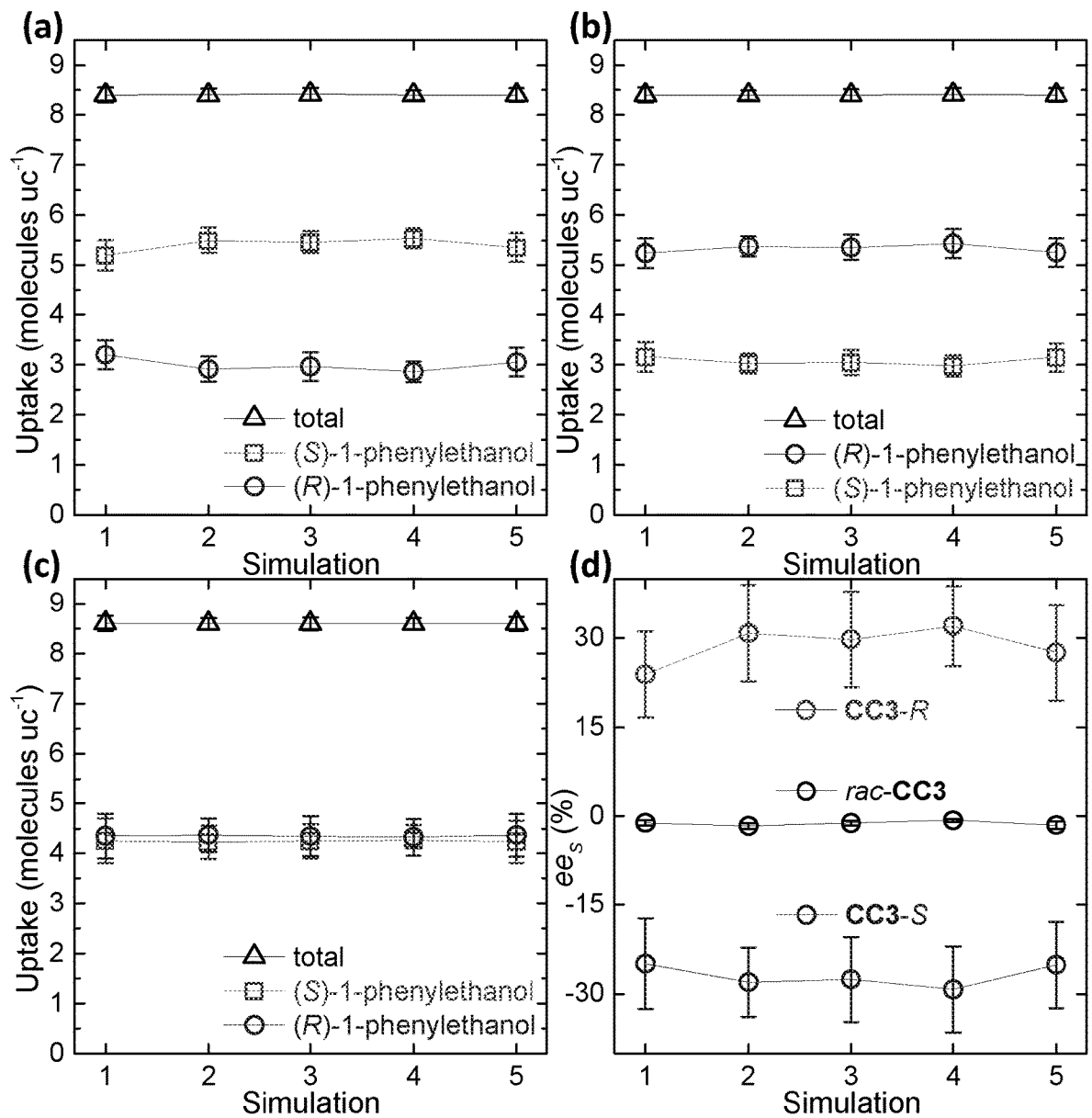
FIG. 68a, 68b, 68c and 68d show parallel-mole fraction (PMF) GCMC simulation results for enantioselective adsorption of the racemic (R,S)-1-phenylethanol mixtures by CC3-R (a), CC3-S (b), and rac-CC3 (c), all at 298 K and a total pressure of 1 bar.

FIG. 68 reports the PMF GCMC simulation results for the enantioseparation of (R, S)-1-phenylethanol by the CC3-R, CC3-S, and rac-CC3 crystal structures, all obtained at 298 K and a total pressure of 1 bar. FIG. S62 shows that the CC3 crystals exhibit a marked capability of discriminating the left- and right-handed 1-phenylethanol molecules. CC3-R was predicted to have an ee value of ca. 30% toward 5-1-phenylethanol, while an ee of ca. −30% was predicted for CC3-S(i.e., CC3-S showed a similar degree of selectivity but toward R-1-phenylethanol over its opposite enantiomer). In line with this, the rac-CC3 crystal structure was found to display no preferential uptake for either enantiomer in (R, S)-1-phenylethanol. In the rac-CC3 simulations, we observed that the adsorbed 1-phenylethanol molecules predominantly occupy the cage cavities with the opposite chirality. These simulated enantioselective adsorption of (R, S)-1-phenylethanol by the bulk CC3 crystals are in good agreement with our chiral chromatography experiments (FIG. 5, main text), performed under similar conditions.

FIGS. 68*a*, 68*b*, 68*c* and 68*d* show parallel-mole fraction (PMF) GCMC simulation results for enantioselective adsorption of the racemic (R, S)-1-phenylethanol mixtures by CC3-R (a), CC3-S(b), and rac-CC3 (c), all at 298 K and a total pressure of 1 bar. For each CC3 crystal structure, five independent PMF GCMC simulations were performed. For each simulation, the amounts of (S)- and (R)-1-phenylethanol adsorbed and the corresponding total uptake are reported, together with error bars. Enantiomeric excess values are summarized in (d) for all three forms of crystalline CC3, as from their respective five independent simulations.

To rationalize the enantioselective discrimination of 1-phenylethanol by CC3, as established by both experiment and computation, we extracted molecular-level structural and energetic information from the simulations to understand the separation mechanism.

Radial distribution functions (RDFs) were used to characterize time-resolved conformational changes of the adsorbed 1-phenylethanol molecules with respect to the CC3 host. For a consistent comparison, we generated the RDF data reported here by running two parallel simulations: one was CC3-R loaded with eight (S)-1-phenylethanol molecules and the other was CC3-R loaded with eight (R)-1-phenylethanol molecules. We used configurational-biased insertions to place eight S or R enantiomers inside one unit cell of the CC3-R crystal structure, followed by $1 \times 10^6$ MC cycles (including translation, rotation, and reinsertion moves) for equilibration. The final configuration from the MC simulation was further equilibrated by an isobaric-isothermal (NPT) molecular dynamics (MD) simulation, ran for 0.5 nanosecond, before the RDF data were generated over the following 1.0 nanosecond of the NPT MD simulation. In the MD simulations, the flexible CC3-R host was modelled by CGenFF while OPLS-AA was used for the flexible 1-phenylethanol molecules.

At a loading of one 1-phenylethanol per cage (i.e., eight guests per host unit-cell), for both the S and R enantiomers, we observed that each CC3-R cage accommodated one 1-phenylethanol molecule. Regardless of the chirality, the phenyl ring of the 1-phenylethanol molecule is located inside the cage cavity while the alcohol group and the methyl "tail" were positioned at the interstitial site between two neighbouring cages; see FIG. 46*a* for an example of (S)-1-phenylethanol in CC3-R. Several strong host-guest interactions could be identified as (main) contributors to the observed enantioselectivity of CC3-R toward (5)-1-phenylethanol.

First, the hydroxyl oxygen atom of S-1-phenylethanol was situated in close proximity to the hydrogen atoms bonded to the imine carbon atoms and/or the aromatic hydrogen atoms on the window of a cage adjacent to the cage in which the aryl ring of the guest resides (FIG. 46*a*). Evidence for the formation of electron donor-acceptor (EDA) complexes between the (S)-1-phenylethanol molecules and CC3-R is apparent from the RDFs shown in FIG. 46*b,c*. The characteristic distance between the hydroxyl oxygen of (S)-1-phenylethanol and the hydrogen atom bonded to an imine carbon of CC3-R, $O_{OH}$(guest) . . . $H_{imine}$(host), is 2.57 Å, measured by the first distinct peak of the RDF for the pair [FIG. 46 (*b*)]. Such a short distance suggests a strong, directional hydrogen bonding between the two monomers. Similarly, the RDF plotted for the $O_{OH}$ (guest) . . . $H_{aro}$(host) pair (FIG. 46*c*) points to another hydrogen bonding, formed between the hydroxyl oxygen and the aromatic hydrogen of CC3-R, by displaying the first peak at 2.61 Å. In contrast, the (R)-1-phenylethanol molecules did not exhibit obvious hydrogen bonding with the $H_{imine}$(host) atoms (FIG. 46*b*). Furthermore, its hydrogen bonding to the host aromatic hydrogen atoms was also slightly less frequent, compared to that of the S enantiomer, and the narrower first RDF peak indicates that the EDA complex was more easily disrupted (FIG. 46*c*).

Second, the (S)-1-phenylethanol molecules adsorbed inside the CC3-R pores additionally formed a hydrogen bond with an imine nitrogen atom of the cage through its hydroxyl hydrogen atom (FIG. 47). This EDA conformation, $H_{OH}$(guest) . . . N(host), can be confirmed by the characteristic RDF peak centred at 1.98 Å (FIG. 47*b*). Again, hydrogen bonding of the kind was considerably weaker in the case when the 1-phenylethanol molecule and the cage molecule had the same chirality (FIG. 47b).

Third, FIG. 48 demonstrates that there is a better shape match between (S)-1-phenylethanol and the CC3-R cage compared to that between the R guest and the R cage. The phenyl ring of (S)-1-phenylethanol was predicted to be able to adopt an energetically favourable conformation with two out of the four phenyl rings of the cage molecule. In this conformation, the guest phenyl ring orients in such a way that it pi-stacks, nearly in the so-called "sandwich" configuration, with one of the three cage phenyl rings forming the window where its alcohol group sits. Moreover, the guest phenyl ring, at the same time, forms a T-shaped π-π stacking with the fourth cage phenyl ring, opposite to the cage window. By contrast, the orientations of the (R)-1-phenylethanol molecules inside the CC3-R cages were found to be markedly different. It is clear from FIG. 48 that the two types of π-π stacking, as observed for (S)-1-phenylethanol are less well established for the (R)-1-phenylethanol . . . CC3-R complex or, at least, were less frequently sampled in the simulation. This suggests that a less optimal fit would arise when the guest and the host are of the same chirality. There was also evidence, from the simulations, that the methyl group of (S)-1-phenylethanol is situated at around the centre of cage window, while the methyl group of the R enantiomer is positioned such that it clashes sterically with the window edge; see FIG. 48a.

Simulations demonstrate, therefore, that the CC3-R . . . (S)-1-phenylethanol pair is able to afford a proper host-guest shape matching, both in energetic and in steric terms. This shape match, however, is disturbed when the host-guest complex involves two molecules of the same chirality.

To investigate the preferential binding between 1-phenylethanol and CC3 having the opposite chirality, as indicated by the force-field-based modelling, we performed further DFT calculations to determine binding energies for the CC3-R crystal structure loaded with (S)- or (R)-1-phenylethanol. One 1-phenylethanol molecule was placed into one unit cell of CC3-R, with its position and conformation sampled by MC moves. After equilibration, five simulation snapshots, separated by 1×10$^6$ MC cycles, were extracted for each case (i.e., CC3-R loaded with one S or one R enantiomer). The molecular configurations of the snapshots were geometry-optimized with density functional based tight binding (DFTB) methods. DFTB in the self-consistent-charge parameterization was used in combination with a UFF dispersion correction.[74,75] Using these DFTB-optimized configurations, host-guest binding energies were computed, following the same procedure adopted for determining the binding energies for the rare gases with CC3. Briefly, we used the PBE-D3 density functional, together with the MOLOPT-DZVP basis set and an energy cutoff of 700 Ry. We further corrected basis set superposition errors by using the counterpoise procedure. The resulting binding energies for (S, R)-1-phenylethanol with the bulk CC3-R crystal structure are summarized in FIG. 69. Clearly, CC3-R was found to bind more strongly with (S)-1-phenylethanol than with the R enantiomer, corroborating the above described enantioselective adsorption of 1-phenylethanol by CC3.

Figure 69:
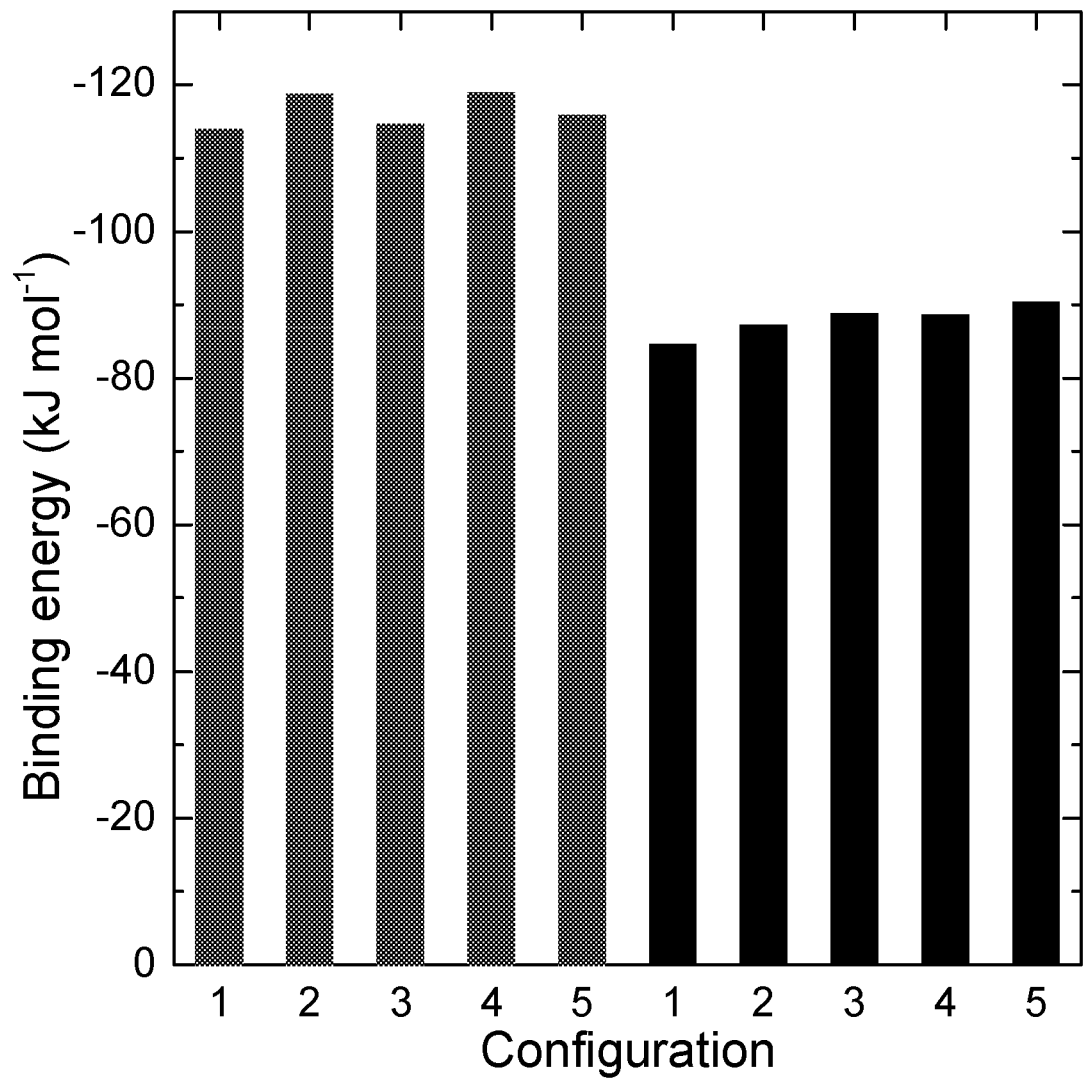
FIG. 69 shows host-guest binding energies for one (S)-1-phenylethanol (left-hand five bars) or (R)-1-phenylethanol (right-hand five bars) molecule per unit cell of the bulk CC3-R crystal structure, as determined by the DFT (PBE-D3/DZVP) calculations.
Figure 70:
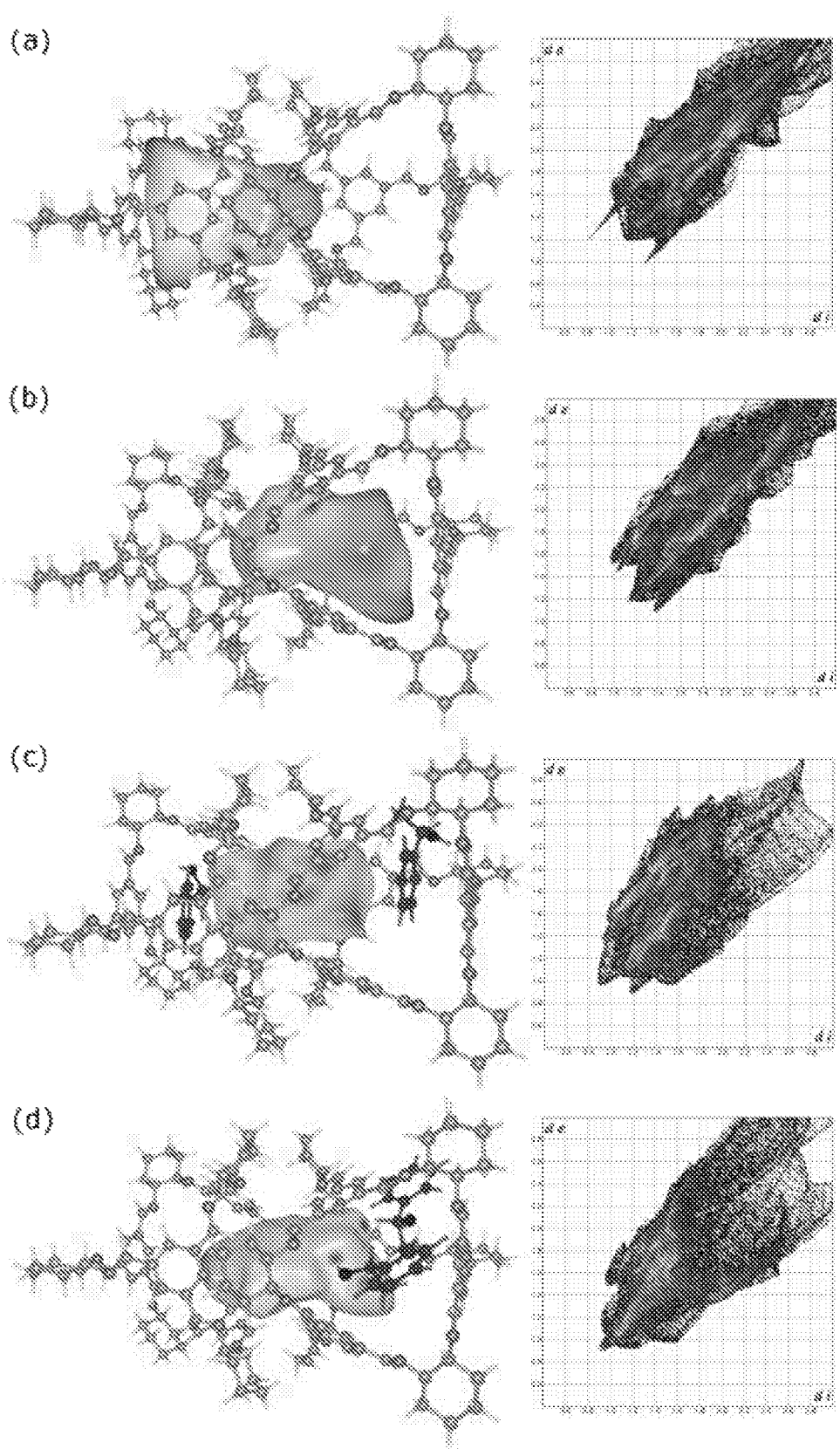
FIG. 70a, 70b, 70c and 70d show Hirshfeld surfaces mapped with $d_{norm}$ (left) and fingerprint plots (right) for simulated and experimental CC3-R structures containing 1-phenylethanol.

FIG. 69 shows host-guest binding energies for one (S)-1-phenylethanol (left-hand five bars) or (R)-1-phenylethanol (right-hand five bars) molecule per unit cell of the bulk CC3-R crystal structure, as determined by the DFT (PBE-D3/DZVP) calculations.

FIGS. 70a, 70b, 70c and 70d show Hirshfeld surfaces mapped with $d_{norm}$ (left) and fingerprint plots (right) for simulated and experimental CC3-R structures containing 1-phenylethanol.[76] (a) Snapshot of (S)-1-phenylethanol in CC3-R simulation exhibits distinct $d_{norm}$ peaks and fingerprint 'horns' for O—H . . . N and phenyl C—H . . . O hydrogen bond. π-π stacking between host and guest is also apparent. (b) Hirshfeld analysis of a snapshot of (R)-1-phenylethanol in CC3-R simulation shows features corresponding to weaker a O—H . . . N H-bond, and additional guest to host phenyl C—H . . . N and C—H . . . r interactions. (c) Hirshfeld plots for a simulation snapshot with three (S)-1-phenylethanol guest molecules in CC3-R suggests that the (5)-1-phenylethanol guest can interact with its CC3-R host via a bifurcated O—H . . . N hydrogen bond and a range of weaker C—H . . . N, O and π and weak hydrophobic H—H contacts (several dense areas in red on the Hirshfeld surface), with reduced contact between guest molecule limited to a single C—H . . . π. (d) In contrast, the experimental crystal structure of (R)-1-phenylethanol in CC3-R shows significant peaks for O—H . . . O hydrogen bonding and additional C—H . . . O and hydrophobic contacts between guest molecules, with only limited C—H . . . O and hydrophobic interaction with the cage host.

Therefore porous organic cage solids can be used for analytical chiral separations, or preparative separations given the scalability and hydrothermal stability of CC3 and its derivatives. Porous organic cage materials have specific advantages. In particular, unlike extended frameworks, they can be highly soluble in organic solvents, and this allows direct solution deposition in practical formats such as capillary columns, thus avoiding problems that can be encountered with slurries of insoluble porous frameworks.

Separation of Further Compounds

As discussed above, GC columns may be prepared by filling an organic molecular host material into a GC column.

Chiral GC columns may be prepared by for example filling chiral CC3-R or -S into a blank GC column. One group of compounds which the columns exhibit selectivity towards are alcohol containing compounds, and the columns also exhibit enantiomeric selectivity in respect of these. The present invention is capable of performing difficult separations in a short time.

Materials and Methods—Preparation of GC Columns

Two types of column were prepared, one containing rac-CC3, and the other containing CC3-R.

Dichloromethane, SP-2100 GC, and blank, intermediate polarity, fused-silica capillary columns were purchased from Sigma Aldrich and used as received. CC3-R was synthesized as described previously [Hasell, T., Chong, S. Y., Jelfs, K. E., Adams, D. J. & Cooper, A. I. Porous Organic Cage Nanocrystals by Solution Mixing. *J. Am. Chem. Soc.* 134, 588-598 (2012)]. A suspension of rac-CC3 nanoparticles in dichloromethane was synthesized as described therein. As a summary, two 5 mg mL$^{-1}$ solutions of CC3-R and CC3-S were rapidly combined, with stirring, at −78° C. The resulting suspension of rac-CC3 nanoparticles was warmed to room temperature and used in the preparation. The same column preparation was used to load both CC3-R and rac-CC3 onto the column surface. However, different loading solutions are used. For the CC3-R column, a 3 mg mL$^{-1}$ solution of CC3-R in dichloromethane was loaded into the column. For rac-CC3 columns, a 5 mg mL$^{-1}$ suspension of rac-CC3 nanoparticles was diluted to 1 mg mL$^{-1}$ with dichloromethane and SP-2100 was added until its concentration was 2.5 mg mL$^{-1}$. SP-2100 is used to adhere rac-CC3 nanoparticles to the inner wall of the capillary column. Control experiments where only SP-2100 was coated on the column surface observed no separation at equivalent conditions. The preparation of a GC column involves several steps. A blank fused-silica capillary column is cut open on both ends. One end of the column is immersed into the loading solution while the other end is exposed to a vacuum to pull the solution through. Once droplets are observed at the vacuumed end the vacuum is released and one end of the column is flame sealed closed. The column is immersed in a water bath set to 30° C. and its open end is exposed to a vacuum to begin the removal of volatile solvent. Finished columns are conditioned on the gas chromatograph by heating to 40° C. for 20 min. raising the temperature to 180° C. at 10° C. min$^{-1}$ and maintaining that temperature for a further 30 min under a 1 mL min$^{-1}$ helium flow.

Materials and Methods—GC Analyses

GC analyses were carried out using a Thermo Scientific TRACE 1310 instrument configured with an FID detector. Analytes were loaded onto the column using a static headspace injection with no solvent. Samples were incubated at 40° C. for 10 min. and a 5 uL sample of the headspace vapor was taken. Injection temperature 300° C.; detection temperature 300° C. with hydrogen, air, and make-up flow-rates of 35, 350, and 35 mL min$^{-1}$ respectively; helium (carrier gas) flow-rate 1.2 mL min$^{-1}$. Samples were injected in the split mode.

The columns have been observed to have excellent lifetimes. The columns have endured over 200 injections with no measurable loss of selectivity.

Separation of Mixtures of Enantiomers, and Separation of Mixtures of Alkanes

The following mixtures have been separated using the columns:

| Compound Mixture | Column Used |
| --- | --- |
| Pentane, hexane, heptane, and octane | rac-CC3 |
| All five isomers of hexane | |
| Xylenes | |
| rac-1-Phenylethanol | CC3-R |
| rac-2-Butanol | |
| rac-3-Methyl-2-butanol | |
| rac-2-Ethyl-1,3-hexanediol | |
| rac-3-Buten-2-ol | |
| rac-1-Pentyn-3-ol | |
| rac-1-Penten-3-ol | |
| rac-2-Pentanol | |
| rac-3-Hydroxytetrahydrofuran | |
| rac-2-Hexanol | |
| rac-1-Phenyl-2-propanol | |
| rac-2-Heptanol | |
| rac-1,3-Butanediol | |

Mixtures wherein components have similar boiling points can be difficult to separate completely by distillation. The present invention is effective in separating such mixtures, e.g. in achieving complete separation of all five structural isomers of hexane. This is believed to be the first example of the use of organic cages for the separation of hexane isomers.

Figure 71:
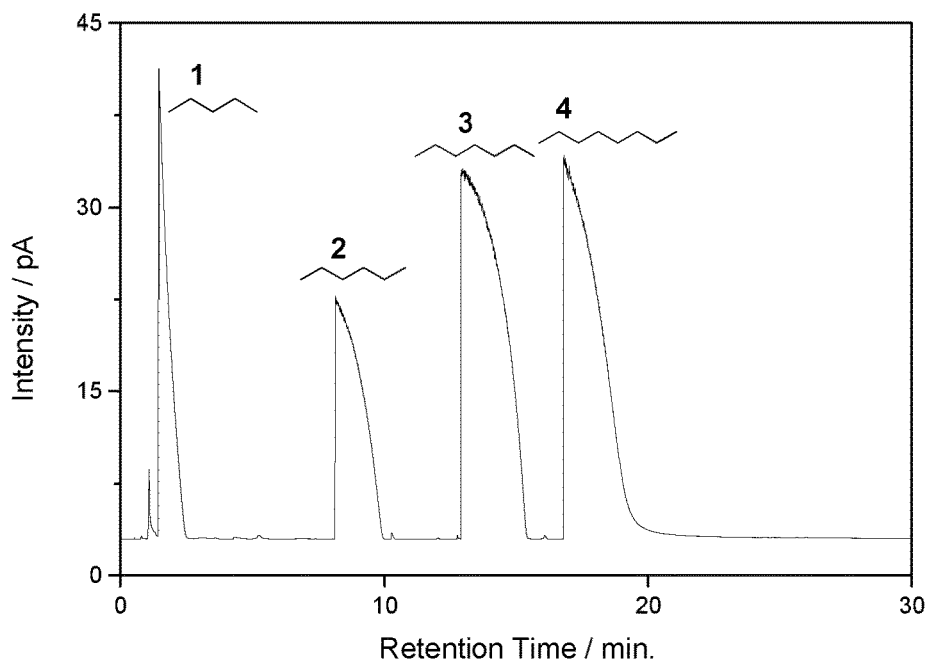
FIG. 71 shows a GC-FID chromatogram of a mixture of alkanes separated on the rac-CC3 column.

FIG. 71 shows a GC-FID chromatogram of a mixture of alkanes separated on the rac-CC3 column. 1—n-pentane, 2—n-hexane, 3—n-heptane, 4—n-octane. A temperature gradient was used to achieve the desired separation; the oven was programmed from 40° C. with a 3.5 min. hold followed by raising to 160° C. at 5° C. min$^{-1}$ with a 4.5 min. hold. 250:1 injection split ratio.

Figure 72:
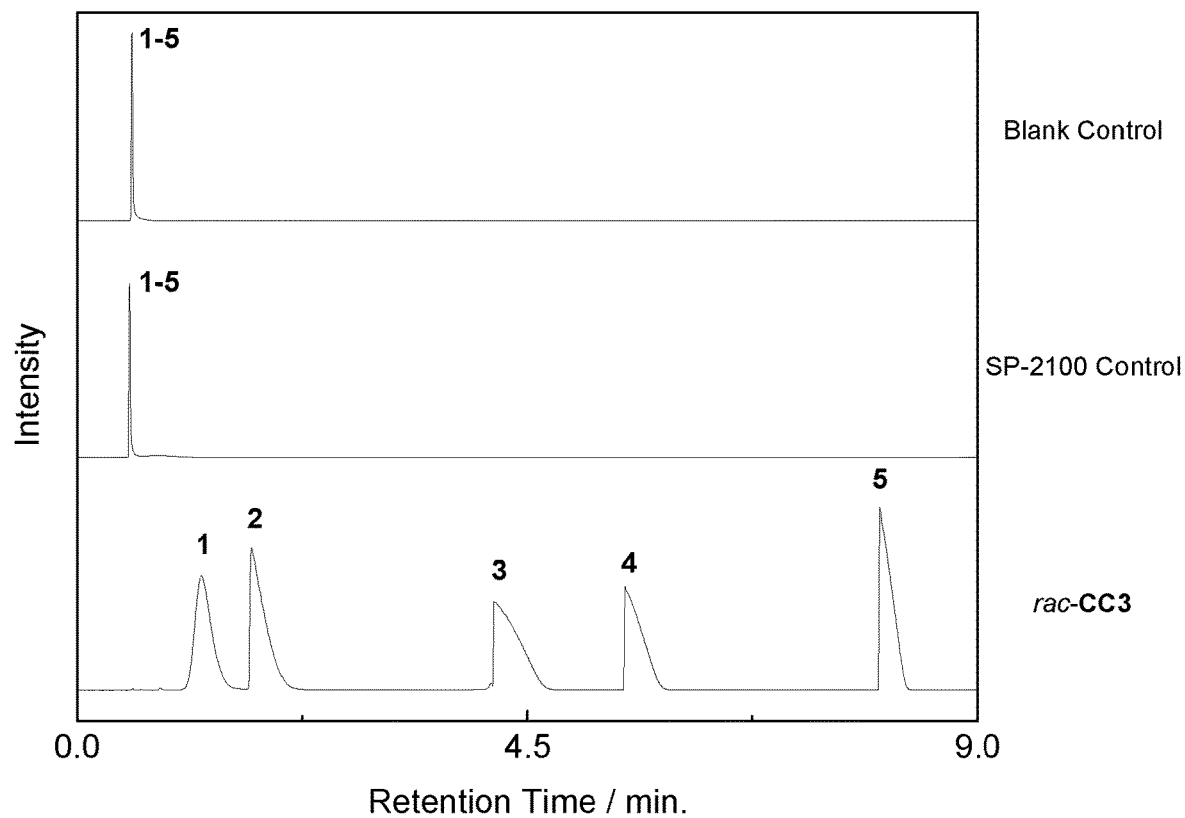
FIG. 72 shows GC-FID chromatograms of a mixture of all hexane isomers eluted through two control (top, middle) and rac-CC3 (bottom) columns.

FIG. 72 shows GC-FID chromatograms of a mixture of all hexane isomers eluted through two control (top, middle) and rac-CC3 (bottom) columns. Top: blank, as purchased, fused-silica capillary column. Middle: a SP-2100 coated fused-silica capillary column. Bottom: rac-CC3 and SP-2100 coated fused-silica capillary column. SP-2100 is used to adhere rac-CC3 nanoparticles to the inner wall of the column. 1-2,2-dimethylbutane; 2—2,3-dimethylbutane; 3—3-methylpentane; 4—2-methylpentane; 5—n-hexane. A temperature gradient was used to achieve the desired separation; the oven was programmed from 40° C. with a 3.5 min. hold followed by raising to 100° C. at 10° C. min$^{-1}$. 250:1 injection split ratio.

Figure 73:
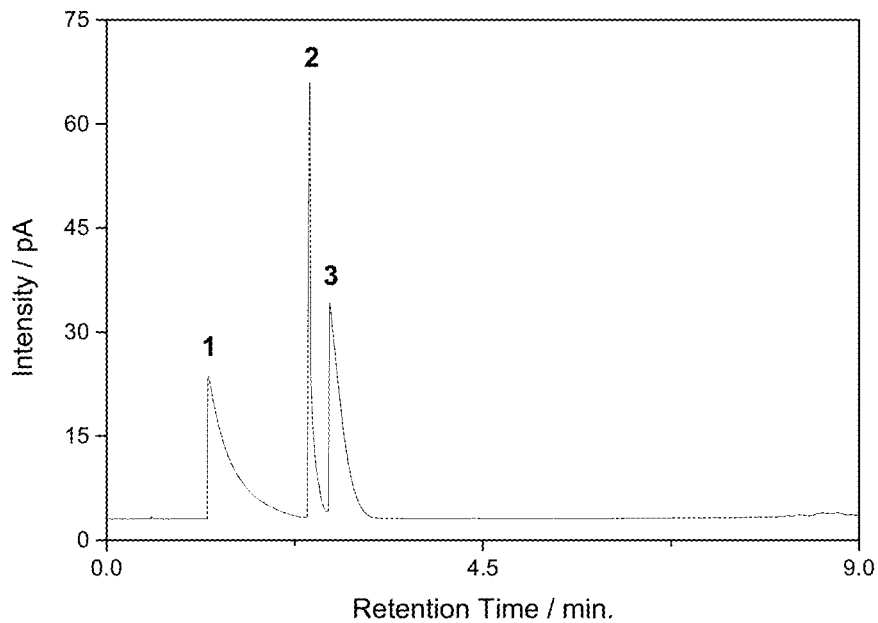
FIG. 73 shows a GD-FID chromatogram of a micture of xylenes eluted through the rac-CC3 column.

FIG. 73 shows a GC-FID chromatogram of a mixture of xylenes eluted through the rac-CC3 column. 1—o-xylene, 2—m-xylene, 3—p-xylene. A temperature gradient was used to achieve the desired separation; the oven was programmed from 50° C. followed by raising to 140° C. at 10° C. min$^{-1}$. 100:1 injection split ratio.

Figure 74:
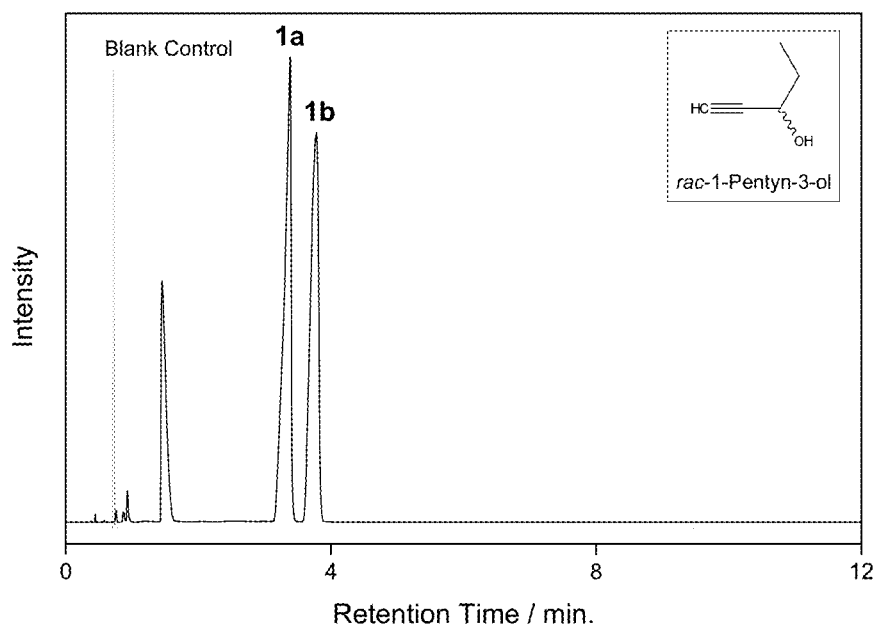
FIG. 74 shows a GD-FID chromatogram of rac-1-pentyn-3-ol eluted through the CC3-R column.

FIG. 74 shows a GC-FID chromatogram of rac-1-pentyn-3-ol eluted through the CC3-R column. The two labelled peaks indicate each chiral enantiomer of the racemic mixture. A chromatogram obtained from a blank column used as an experimental control is overlaid for comparison. A temperature gradient was used to achieve the desired separation; the oven was programmed from 60° C. followed by raising to 180° C. at 10° C. min$^{-1}$. 100:1 injection split ratio.

Figure 75:
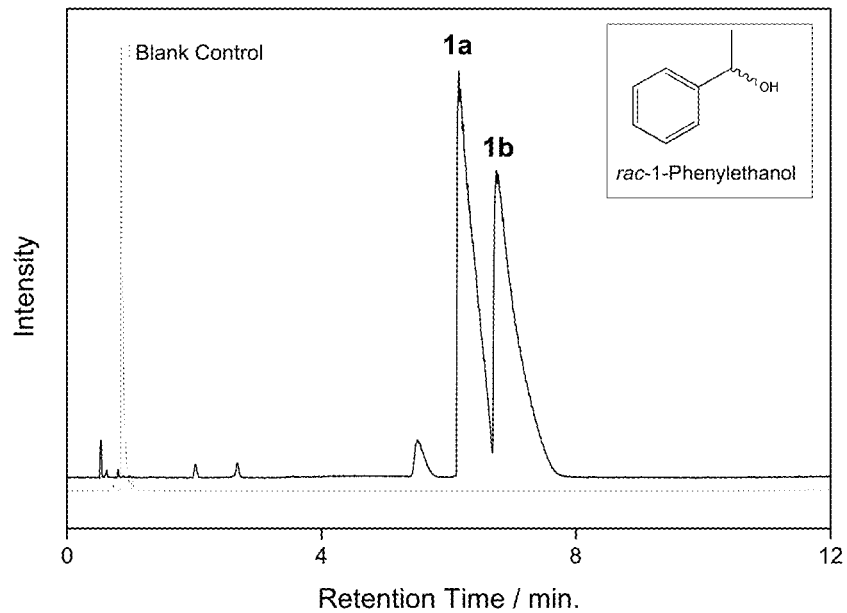
FIG. 75 shows a GC-FIG chromatogram of rac-1-phenylethanol separated on the CC3-R column.

FIG. 75 shows a GC-FID chromatogram of rac-1-phenylethanol separated on the CC3-R column. The two labelled peaks (1a & 1b) indicate each chiral enantiomer of the racemic mixture. A chromatogram obtained from a blank column used as an experimental control is overlaid for comparison. A temperature gradient was used to achieve the desired separation; the oven was programmed from 60° C. followed by raising to 180° C. at 10° C. min$^{-1}$. 100:1 injection split ratio.

Figure 76:
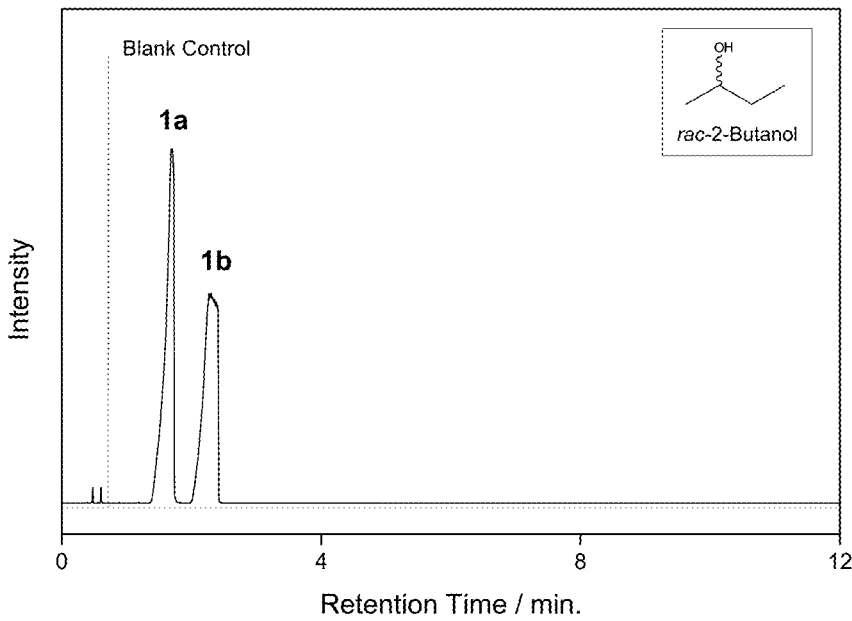
FIG. 76 shows a GD-FID chromatogram of rac-2-butanol separated on the CC3-R column, Labelled peaks 1a & 1b indicate each chiral enantiomer of the racemic mixture.

FIG. 76 shows a GC-FID chromatogram of rac-2-butanol separated on the CC3-R column. The two labelled peaks (1a & 1b) indicate each chiral enantiomer of the racemic mixture. A chromatogram obtained from a blank column used as an experimental control is overlaid for comparison. A temperature gradient was used to achieve the desired separation; the oven was programmed from 60° C. followed by raising to 180° C. at 10° C. min$^{-1}$. 100:1 injection split ratio.

Figure 77:
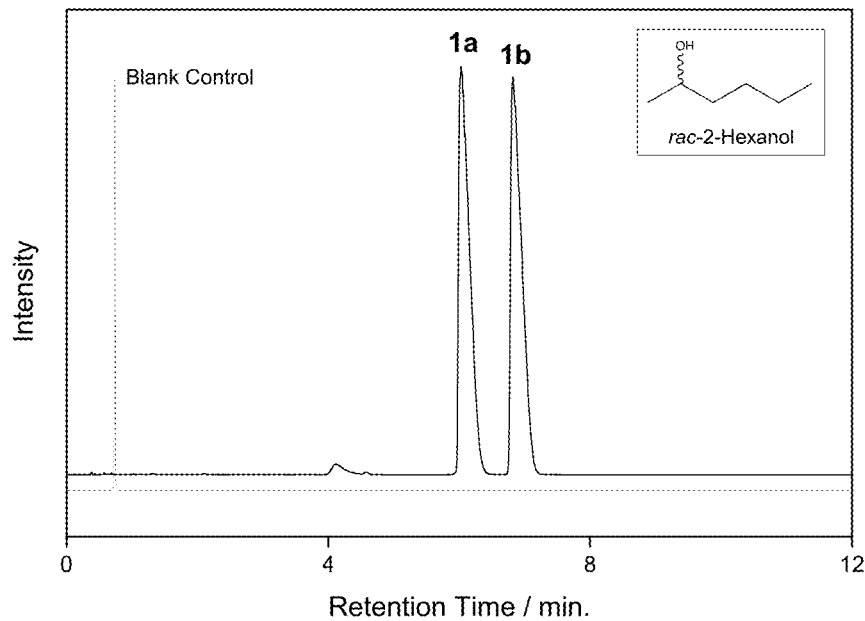
FIG. 77 shows a GD-FID chromatogram of rac-2-hexanol separated on the CC3-R column.

FIG. 77 shows a GC-FID chromatogram of rac-2-hexanol separated on the CC3-R column. The two labelled peaks (1a & 1b) indicate each chiral enantiomer of the racemic mixture. A chromatogram obtained from a blank column used as an experimental control is overlaid in light-gray for comparison. A temperature gradient was used to achieve the desired separation; the oven was programmed from 60° C. followed by raising to 180° C. at 10° C. min$^{-1}$. 100:1 injection split ratio.

Figure 78:
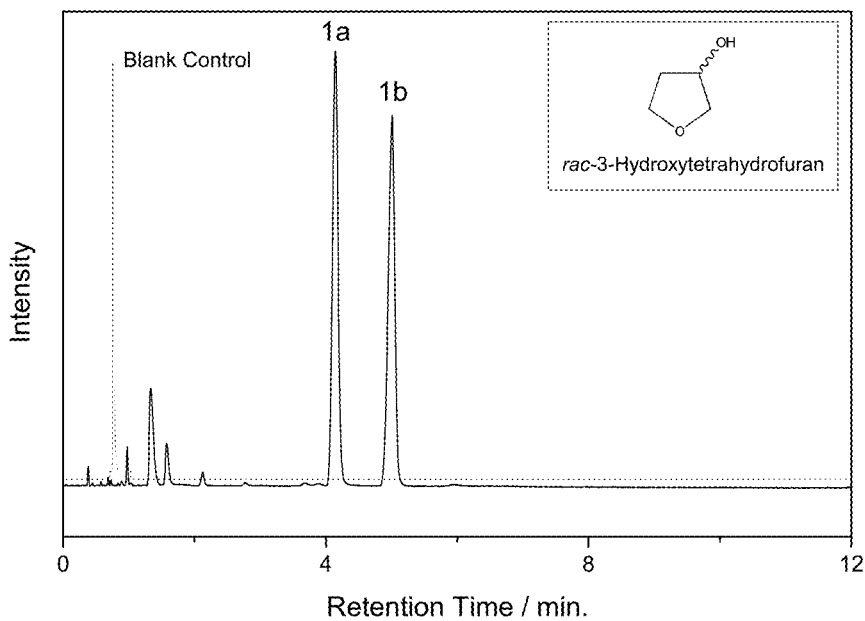
FIG. 78 shows a GD-FID chromatogram of rac-3-hydroxytetrahydrofuran seperated on the CC3-R column.

FIG. 78 shows a GC-FID chromatogram of rac-3-hydroxytetrahydrofuran separated on the CC3-R column. The two labelled peaks (1a & 1b) indicate each chiral enantiomer of the racemic mixture. A chromatogram obtained from a blank column used as an experimental control is overlaid for comparison A temperature gradient was used to achieve the desired separation; the oven was programmed from 60° C. followed by raising to 180° C. at 10° C. min$^{-1}$. 100:1 injection split ratio.

Figure 79:
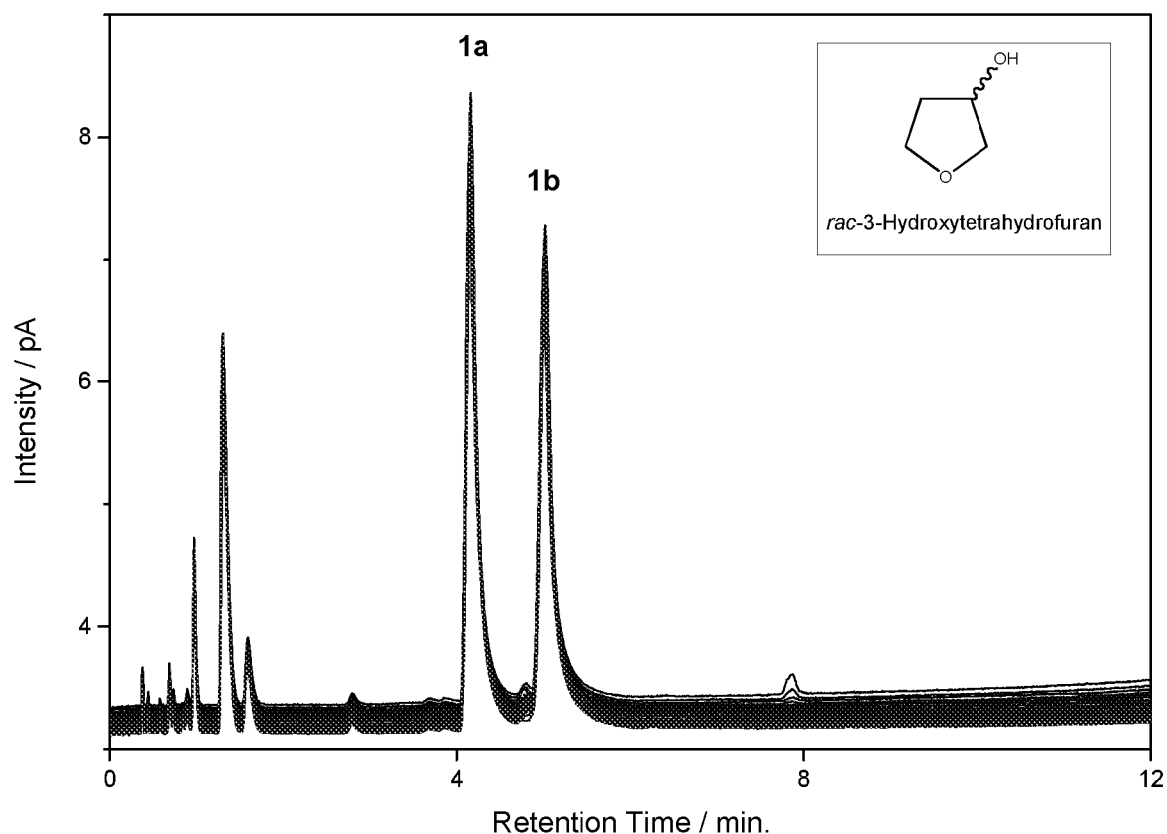
FIG. 79 shows overlaid GD-FID chromatograms of 36 repeat injections of rac-3-hydroxytetrahydrofuran on CC3-R.

FIG. 79 shows overlaid GC-FID chromatograms of 36 repeat injections of rac-3-hydroxytetrahydrofuran on CC3-R. The two labelled peaks (1a & 1b) indicate each chiral enantiomer of the racemic mixture. A chromatogram obtained from a blank column used as an experimental control is overlaid for comparison A temperature gradient was used to achieve the desired separation; the oven was programmed from 60° C. followed by raising to 180° C. at 10° C. min$^{-1}$. 100:1 injection split ratio.

In summary, porous organic cages have unprecedented selectivity for various separations including rare gas separations at low rare gas concentrations, and are also useful for other separations including chiral separations and alkane separations.

REFERENCES

1 Hasell, T. et al. Porous organic cage nanocrystals by solution mixing. *J. Am. Chem. Soc.* 134, 588-598, (2012).
2 Willems, T. F. et al. Algorithms and tools for high-throughput geometry-based analysis of crystalline porous materials. *Microporous Mesoporous Mater.* 149, 134-141, (2012).
3 http://www.ccdc.cam.ac.uk/products/csd/radii.
4 Shrake, A. & Rupley, J. A. Environment and exposure to solvent of protein atoms. Lysozyme and insulin. *J. Mol. Biol.* 79, 351-371, (1973).
5 Van Heest, T. et al. Identification of metal-organic framework materials for adsorption separation of rare gases: applicability of ideal adsorbed solution theory (IAST) and effects of inaccessible framework regions. *J. Phys. Chem. C* 116, 13183-13195, (2012).
6 Martin, M. G. & Siepmann, J. I. Transferable potentials for phase equilibria. 1. United-atom description of n-alkanes. *J. Phys. Chem. B* 102, 2569-2577, (1998).
7 Roberts, D. L., Abraham, L. C., Blum, Y. & Way, J. D. Gas separation with glass membranes. Final report. Report No. DOE/MC/25204-3133 (1992).
8 Holden, D. et al. Bespoke force field for simulating the molecular dynamics of porous organic cages. *J. Phys. Chem. C* 116, 16639-16651, (2012).
9 http://theory.chem.cf.ac.uk/dave/soft_intro.html.
10 Smith, W. & Forester, T. R. DL_POLY_2.0: A general-purpose parallel molecular dynamics simulation package. *J. Mol. Graph.* 14, 136-141, (1996).
11 Tozawa, T. et al. *Porous organic cages. Nat. Mater.* 8, 973-978, (2009).
12 Melchionna, S., Ciccotti, G. & Lee Holian, B. Hoover NPT dynamics for systems varying in shape and size. *Mol. Phys.* 78, 533-544, (1993).
13 VandeVondele, J. et al. Quickstep: Fast and accurate density functional calculations using a mixed Gaussian and plane waves approach. *Comp. Phys. Commun.* 167, 103-128, (2005).
14 Lippert, G., Hutter, J. & Parrinello, M. A hybrid Gaussian and plane wave density functional scheme. *Mol. Phys.* 92, 477-488, (1997).
15 VandeVondele, J. & Hutter, J. Gaussian basis sets for accurate calculations on molecular systems in gas and condensed phases. *J. Chem. Phys.* 127, 114105, (2007).
16 Goedecker, S., Teter, M. & Hutter, J. Separable dual-space Gaussian pseudopotentials. *Phys. Rev. B* 54, 1703-1710, (1996).
17 Hartwigsen, C., Goedecker, S. & Hutter, J. Relativistic separable dual-space Gaussian pseudopotentials from H to Rn. *Phys. Rev. B* 58, 3641-3662, (1998).
18 Krack, M. Pseudopotentials for H to Kr optimized for gradient-corrected exchange-correlation functionals. *Theor. Chem. Acc.* 114, 145-152, (2005).
19 Klimes, J. & Michaelides, A. Perspective: Advances and challenges in treating van der Waals dispersion forces in density functional theory. *J. Chem. Phys.* 137, 120901, (2012).
20 Grimme, S., Antony, J., Ehrlich, S. & Krieg, H. A consistent and accurate ab initio parametrization of density functional dispersion correction (DFT-D) for the 94 elements H—Pu. *J. Chem. Phys.* 132, 154104, (2010).
21 Perdew, J. P., Burke, K. & Ernzerhof, M. Generalized gradient approximation made simple. *Phys. Rev. Lett.* 77, 3865-3868, (1996).
22 Vydrov, O. A. & Van Voorhis, T. Nonlocal van der Waals density functional: The simpler the better. *J. Chem. Phys.* 133, (2010).
23 Sabatini, R., Gorni, T. & de Gironcoli, S. Nonlocal van der Waals density functional made simple and efficient. *Phys. Rev. B* 87, 041108, (2013).
24 Simon, S., Duran, M. & Dannenberg, J. J. How does basis set superposition error change the potential surfaces for hydrogen-bonded dimers? *J. Chem. Phys.* 105, 11024-11031, (1996).
25 Frenkel, D. & Smit, B. *Understanding Molecular Simulation: from algorithms to applications*. (Academic Press, San Diego, Calif. 92101-4495, USA, 2002).
26 Vlugt, T. J. H. et al. Computing the heat of adsorption using molecular simulations: the effect of strong coulombic interactions. *J. Chem. Theor. Comput.* 4, 1107-1118, (2008).
27 Mayo, S. L., Olafson, B. D. & Goddard, W. A. DREIDING: a generic force field for molecular simulations. *J. Phys. Chem.* 94, 8897-8909, (1990).
28 Gaussian 09 v. AM64L-G09RevB.01 (Gaussian, Inc., Wallingford Conn., 2009).
29 van Loef, J. J. On the thermophysical properties of liquid radon-222. *Physica B+C* 103, 362-364, (1981).
30 Pellenq, R. J. M. & Nicholson, D. Intermolecular potential function for the physical adsorption of rare gases in silicalite. *J. Phys. Chem.* 98, 13339-13349, (1994).
31 Hirschfelder, J. O., Curtiss, C. F. & Bird, R. B. *Molecular Theory of Gases and Liquids*. (Wiley, New York, 1964).
32 Potoff, J. J. & Siepmann, J. I. Vapor-liquid equilibria of mixtures containing alkanes, carbon dioxide, and nitrogen. *AIChE J.* 47, 1676-1682, (2001).
33 Zhang, L. & Siepmann, J. I. Direct calculation of Henry's law constants from Gibbs ensemble Monte Carlo simulations: nitrogen, oxygen, carbon dioxide and methane in ethanol. *Theor. Chem. Acc.* 115, 391-397, (2006).
34 Levesque, D., Gicquel, A., Darkrim, F. L. & Kayiran, S. B. Monte Carlo simulations of hydrogen storage in carbon nanotubes. *J. Phys.: Condens. Matter* 14, 9285, (2002).
35 Rick, S. W. A reoptimization of the five-site water potential (TIP5P) for use with Ewald sums. *J. Chem. Phys.* 120, 6085-6093, (2004).
36 Wang, J. et al. Development and testing of a general amber force field. *J. Comput. Chem.* 25, 1157-1174, (2004).
37 Vanommeslaeghe, K. et al. CHARMM general force field: A force field for drug-like molecules compatible with the CHARMM all-atom additive biological force fields. *J. Comput. Chem.* 31, 671-690, (2010).
38 Jorgensen, W. L., Maxwell, D. S. & Tirado-Rives, J. Development and testing of the OPLS all-atom force field on conformational energetics and properties of organic liquids. *J. Am. Chem. Soc.* 118, 11225-11236, (1996).
39 Rappe, A. K. et al. UFF, a full periodic table force field for molecular mechanics and molecular dynamics simulations. *J. Am. Chem. Soc.* 114, 10024-10035, (1992).
40 Parker, J. E. et al. In situ gas supply system on the powder diffraction beamline I11 at Diamond Light Source. *Mater. Sci. Forum* 706-709, 1707-1712, (2012).

41 Thompson, S. P. et al. Fast X-ray powder diffraction on I11 at Diamond. *J. Synchr. Rad.* 18, 637-648, (2011).
42 TOPAS Academic version 4.1 (Coelho Software, Brisbane, Australia, 2007).
43 JANA2006. The crystallographic computing system (Institute of Physics, Praha, Czech Republic, 2006).
44 van Smaalen, S., Palatinus, L. & Schneider, M. The maximum-entropy method in superspace. *Acta Cryst. Sect. A* 59, 459-469, (2003).
45 Momma, K. & Izumi, F. VESTA 3 for three-dimensional visualization of crystal, volumetric and morphology data. *J. Appl. Crystallography* 44, 1272-1276, (2011).
46 Allen, F. The Cambridge Structural Database: a quarter of a million crystal structures and rising. *Acta Cryst. Sect. B* 58, 380-388, (2002).
47 Lee, F., Gabe, E., Tse, J. S. & Ripmeester, J. A. Crystal structure, CP/MAS xenon-129 and carbon-13 NMR of local ordering in Dianin's compound clathrates. *J. Am. Chem. Soc.* 110, 6014-6019, (1988).
48 Enright, G. D., Udachin, K. A., Moudrakovski, I. L. & Ripmeester, J. A. Thermally programmable gas storage and release in single crystals of an organic van der Waals host. *J. Am. Chem. Soc.* 125, 9896-9897, (2003).
49 Brouwer, D. H. et al. Guest loading and multiple phases in single crystals of the van der Waals host p-tert-butyl-calix[4]arene. *Cryst. Growth Des.* 8, 1878-1885, (2008).
50 Miyahara, Y., Abe, K. & Inazu, T. "Molecular" molecular sieves: Lid-free decamethylcucurbit[5]uril absorbs and desorbs gases selectively. *Angew. Chem. Int. Ed.* 41, 3020-3023, (2002).
51 Taratula, O. et al. Crystallographic observation of 'induced fit' in a cryptophane host-guest model system. *Nat. Commun.* 1, 148, (2010).
52 Ueda, T. et al. Local structure and xenon adsorption behavior of metal-organic framework system $[M_2(O_2CPh)_4(pyz)]_n$ (M=Rh and Cu) as studied with use of single-crystal X-ray diffraction, adsorption isotherm, and xenon-129 NMR. *J. Phys. Chem. C* 111, 1524-1534, (2007).
53 Sears, D. R. & Klug, H. P. Density and expansivity of solid xenon. *J. Chem. Phys.* 37, 3002-3006, (1962).
54 Ilczyszyn, M., Selent, M. & Ilczyszyn, M. M. Participation of xenon guest in hydrogen bond network of β-hydroquinone crystal. *J. Phys. Chem. A* 116, 3206-3214, (2012).
55 Hulvey, Z. et al. Rare gas adsorption in copper trimesate, HKUST-1: An experimental and computational study. *J. Phys. Chem. C* 117, 20116-20126, (2013).
56 Cole, J. H. et al. Thermodynamics of the high temperature adsorption of some permanent gases by porous carbons. *J. Chem. Soc., Farad. Trans. 1: Phys. Chem. Cond. Phases* 70, 2154-2169, (1974).
57 Rouquerol, J., Rouquerol, F. & Sing, K. *Adsorption by Powders and Porous Solids.* (Academic Press, London, 1999).
58 Liu, J., Thallapally, P. K. & Strachan, D. Metal-organic frameworks for removal of Ke and Kr from nuclear fuel reprocessing plants. *Langmuir* 28, 11584-11589, (2012).
59 Siegel, L. A. & van den Hende, J. H. The crystal structure of molecular inclusion compounds of tris(o-phenylenedioxy)phosphonitrile trimer. *J. Chem. Soc. A: Inorg., Phys. Theor.*, 817-820, (1967).
60 Mitra, T. et al. Molecular shape sorting using molecular organic cages. *Nat. Chem.* 5, 276-281, (2013).
61 Poole, C. F. *Gas Chromatography* Ch. 17. (Elsevier, Oxford, Oxford, 2012).
62 Dolomanov, O. V. et al. OLEX2: a complete structure solution, refinement and analysis program. *J. Appl. Crystallography* 42, 339-341, (2009).
63 Spek, A. PLATON, An integrated tool for the analysis of the results of a single crystal structure determination. *Acta Cryst. Sect. A* 46, c34, (1990).
64 Nowell, H. et al. 119, the small-molecule single-crystal diffraction beamline at Diamond Light Source. *J. Synchr. Rad.* 19, 435-441, (2012).
65 Sheldrick, G. M. SADABS. *University of Göttingen, Germany,* (2008).
66 Sheldrick, G. A short history of SHELX. *Acta Cryst. Sect. A* 64, 112-122, (2008).
67 Siepmann, J. I. & Frenkel, D. Configurational bias Monte Carlo: a new sampling scheme for flexible chains. *Mol. Phys.* 75, 59-70, (1992).
68 Dubbeldam, D., Torres-Knoop, A. & Walton, K. S. On the inner workings of Monte Carlo codes. *Mol. Simul.* 39, 1253-1292, (2013).
69 van Erp, T. S. et al. Effective Monte Carlo scheme for multicomponent gas adsorption and enantioselectivity in nanoporous materials. *J. Phys. Chem. Lett.* 1, 2154-2158, (2010).
70 Caremans, T. P. et al. Enantioselective adsorption characteristics of aluminum-substituted MFI zeolites. *Chem. Mater.* 22, 4591-4601, (2010).
71 Qiao, Z. et al. Advanced Monte Carlo simulations of the adsorption of chiral alcohols in a homochiral metal-organic framework (DOI: 10.1002/aic.14415). *AIChE J.*, (2014).
72 Vanommeslaeghe, K. & MacKerell, A. D. Automation of the CHARMM General Force Field (CGenFF) I: Bond perception and atom typing. *J. Chem. Inf. Model.* 52, 3144-3154, (2012).
73 Vanommeslaeghe, K., Raman, E. P. & MacKerell, A. D. Automation of the CHARMM General Force Field (CGenFF) II: Assignment of bonded parameters and partial atomic charges. *J. Chem. Inf. Model.* 52, 3155-3168, (2012).
74 Elstner, M. et al. Self-consistent-charge density-functional tight-binding method for simulations of complex materials properties. *Phys. Rev. B* 58, 7260-7268, (1998).
75 Zhechkov, L. et al. An efficient a posteriori treatment for dispersion interaction in density-functional-based tight binding. *J. Chem. Theor. Comput.* 1, 841-847, (2005).
76 Spackman, M. A. & Jayatilaka, D. Hirshfeld surface analysis. *CrystEngComm* 11, 19-32, (2009).

The invention claimed is:
1. Use of a host material for the separation of elements or compounds,
wherein the host material is an organic molecular solid with suitable cavities for accommodating a guest material to be separated, and with interconnections between the cavities to allow the guest material to diffuse through the host material,
wherein said interconnections are closed for a proportion of the time,
wherein the host comprises molecular cages prepared by the condensation of aldehydes and amines in a cycloimination reaction; and
wherein said use is effective for the separation of rare gases, or
wherein said use is effective for enantioselective separation, or
wherein said use is effective for the separation of alkane isomers or mixtures of different alkanes.

2. The use as claimed in claim 1 wherein said interconnections are closed for the majority of the time.

3. The use as claimed in claim 2 wherein said interconnections are only open for 10% or less of the time.

4. Use of a host material for the separation of rare gases,
wherein the host material is an organic molecular solid with suitable cavities for accommodating a guest material to be separated, and with interconnections between the cavities to allow the guest material to diffuse through the host material,
wherein said interconnections have a static pore limiting diameter which is smaller than the static dimension of the guest material,
wherein the host comprises molecular cages prepared by the condensation of aldehydes and amines in a cycloimination reaction, and
wherein said use is effective for the separation of rare gases.

5. The use as claimed in claim 4 wherein the host has a regular structure with one or two repeating cavities.

6. The use as claimed in claim 4 wherein the number of interconnections to each cavity is at least three.

7. The use as claimed in claim 4 wherein the host has a tetrahedral symmetry.

8. The use as claimed in claim 4 wherein the host comprises molecular cages prepared by the reaction of a compound having at least three aldehyde groups with a compound having at least two amine groups.

9. The use as claimed in claim 4 wherein the host comprises molecular cages prepared by the reaction of a compound having three aldehyde groups with a compound having two amine groups.

10. The use as claimed in claim 4 wherein the host comprises molecular cages prepared by a [4+6] cycloimination reaction.

11. The use as claimed in claim 10 wherein the host material comprises a cage material (CC3) which is made from four 1,3,5triformylbenzene molecules and six 1, 2-diaminocyclohexane molecules.

12. The use as claimed in claim 11 wherein the host material is CC3-R or CC3-S, or racemic CC3.

13. The use as claimed in claim 4 for the separation and concentration of radon gas from air to facilitate its detection.

14. Use of a host material for the enantioselective separation of compounds,
wherein the host material is an organic molecular solid with suitable cavities for accommodating a guest material to be enantiomerically separated, and with interconnections between the cavities to allow the guest material to diffuse through the host material,
wherein said interconnections have a static pore limiting diameter which is smaller than the static dimension of the guest material,
wherein the host comprises molecular cages prepared by the condensation of aldehydes and amines in a cycloimination reaction, and
wherein said use is effective for enantioselective separation;
or,
use of a host material for the separation of alkanes,
wherein the host material is an organic molecular solid with suitable cavities for accommodating a guest material to be separated, and with interconnections between the cavities to allow the guest material to diffuse through the host material,
wherein said interconnections have a static pore limiting diameter which is smaller than the static dimension of the guest material,
wherein the host comprises molecular cages prepared by the condensation of aldehydes and amines in a cycloimination reaction, and
wherein said use is effective for the separation of alkane isomers or mixtures of different alkanes.

15. The use as claimed in claim 14 for the enantioselective separation of chiral alcohols.

16. The use as claimed in claim 14 for the separation of hexane isomers.

17. The use as claimed in claim 4 wherein the host material is crystalline.

18. A method of chemical separation, or of preparative separation, or of analytical separation, comprising the use of claim 4.

19. The use of claim 14 wherein said mixture of alkanes is selected from different $C_5$-$C_8$ alkanes.

20. The use as claimed in claim 1 wherein the host has a regular structure with one or two repeating cavities, and wherein the number of interconnections to each cavity is at least three.

21. The use as claimed in claim 1 wherein the host comprises molecular cages prepared by the reaction of a compound having at least three aldehyde groups with a compound having at least two amine groups.

22. The use as claimed in claim 1 wherein the host comprises molecular cages prepared by a [4+6] cycloimination reaction, wherein the host material comprises a cage material (CC3) which is made from four 1,3,5triformylbenzene molecules and six 1, 2-diaminocyclohexane molecules, and wherein the host material is CC3-R or CC3-S or racemic CC3.

23. A method of chemical separation, or of preparative separation, or of analytical separation comprising the use of claim 1.

24. The use as claimed in claim 14 wherein the host has a regular structure with one or two repeating cavities, and wherein the number of interconnections to each cavity is at least three.

25. The use as claimed in claim 14 wherein the host comprises molecular cages prepared by the reaction of a compound having at least three aldehyde groups with a compound having at least two amine groups.

26. The use as claimed in claim 14 wherein the host comprises molecular cages prepared by a [4+6] cycloimination reaction, wherein the host material comprises a cage material (CC3) which is made from four 1,3,5-triformylbenzene molecules and six 1, 2-diaminocyclohexane molecules, and wherein the host material is CC3-R or CC3-S.

27. A method of chemical separation, or of preparative separation, or of analytical separation comprising the use of claim 14.

* * * * *